US006858422B2

(12) United States Patent
Giver et al.

(10) Patent No.: US 6,858,422 B2
(45) Date of Patent: Feb. 22, 2005

(54) LIPASE GENES

(75) Inventors: Lorraine J. Giver, Santa Clara, CA (US); Jeremy Minshull, Menlo Park, CA (US); Kurt Vogel, Palo Alto, CA (US)

(73) Assignee: Codexis, Inc., Redwood City, CA (US)

( * ) Notice: Subject to any disclaimer, the term of this patent is extended or adjusted under 35 U.S.C. 154(b) by 0 days.

(21) Appl. No.: 09/905,666

(22) Filed: Jul. 13, 2001

(65) Prior Publication Data

US 2003/0096390 A1 May 22, 2003

Related U.S. Application Data

(60) Provisional application No. 60/300,378, filed on Jun. 21, 2001, and provisional application No. 60/217,954, filed on Jul. 13, 2000.

(51) Int. Cl.[7] .................................. C12N 9/20
(52) U.S. Cl. ................ 435/198; 435/197; 435/196; 435/195
(58) Field of Search ................ 435/195–198, 435/252.3, 252.33, 320.1; 536/23.2, 23.7

(56) References Cited

U.S. PATENT DOCUMENTS

| | | | |
|---|---|---|---|
| 5,427,936 A | 6/1995 | Moeller et al. | 435/198 |
| 5,512,463 A | 4/1996 | Stemmer | 435/91.2 |
| 5,514,588 A | 5/1996 | Varadaraj et al. | 435/262 |
| 5,605,793 A | 2/1997 | Stemmer | 435/6 |
| 5,763,239 A | 6/1998 | Short et al. | 435/6 |
| 5,789,228 A | 8/1998 | Lam et al. | 435/209 |
| 5,811,238 A | 9/1998 | Stemmer et al. | 435/6 |
| 5,814,473 A | 9/1998 | Warren et al. | 435/15 |
| 5,824,469 A | 10/1998 | Horwitz et al. | 435/6 |
| 5,830,696 A | 11/1998 | Short | 435/69.1 |
| 5,830,721 A | 11/1998 | Stemmer et al. | 435/489 |
| 5,834,252 A | 11/1998 | Stemmer et al. | 435/91.1 |
| 5,837,458 A | 11/1998 | Minshull et al. | 435/6 |
| 5,866,363 A | 2/1999 | Pieczenik | 435/69.1 |
| 5,876,997 A | 3/1999 | Kretz | 435/196 |
| 5,925,749 A | 7/1999 | Mathur et al. | 536/23.1 |
| 5,928,905 A | 7/1999 | Stemmer et al. | 435/91.1 |
| 5,939,250 A | 8/1999 | Short | 435/4 |
| 5,939,300 A | 8/1999 | Robertson et al. | 435/192 |
| 5,942,430 A | 8/1999 | Robertson et al. | 435/197 |
| 5,948,666 A | 9/1999 | Callen et al. | 435/194 |
| 5,958,672 A | 9/1999 | Short | 435/4 |
| 5,958,751 A | 9/1999 | Murphy et al. | 435/208 |
| 5,962,258 A | 10/1999 | Mathur et al. | 435/69.1 |
| 5,962,283 A | 10/1999 | Warren et al. | 435/128 |
| 5,965,408 A | 10/1999 | Short | 435/91.1 |
| 5,985,646 A | 11/1999 | Murphy et al. | 435/252.3 |
| 6,001,574 A | 12/1999 | Short et al. | 435/6 |
| 6,004,788 A | 12/1999 | Short | 435/183 |
| 6,030,779 A | 2/2000 | Short | 435/6 |
| 6,054,267 A | 4/2000 | Short | 435/6 |
| 6,057,103 A | 5/2000 | Short | 435/6 |
| 6,096,548 A | 8/2000 | Stemmer | 435/440 |
| 6,117,679 A | 9/2000 | Stemmer | 435/440 |
| 6,132,970 A | 10/2000 | Stemmer | 435/6 |
| 6,165,793 A | 12/2000 | Stemmer | 435/440 |
| 6,168,919 B1 | 1/2001 | Short | 435/6 |
| 6,171,820 B1 | 1/2001 | Short | 435/69.1 |
| 6,174,673 B1 | 1/2001 | Short et al. | 435/6 |
| 6,180,406 B1 | 1/2001 | Stemmer | 435/440 |
| 6,238,884 B1 | 5/2001 | Short et al. | 435/69.1 |

FOREIGN PATENT DOCUMENTS

| | | |
|---|---|---|
| EP | 0 243 338 | 10/1997 |
| EP | 0911396 A2 | 4/1999 |
| EP | 0911396 A3 | 5/1999 |
| EP | 0934999 A1 | 8/1999 |
| WO | WO 97/07205 | 2/1997 |
| WO | WO 97/20078 | 6/1997 |
| WO | WO 97/25410 | 7/1997 |
| WO | WO 97/35957 | 10/1997 |
| WO | WO 97/35966 | 10/1997 |
| WO | WO 97/44361 | 11/1997 |
| WO | WO 97/48416 | 12/1997 |
| WO | WO 97/48717 | 12/1997 |
| WO | WO 97/48794 | 12/1997 |
| WO | WO 98/00526 | 1/1998 |
| WO | WO 98/01581 | 1/1998 |
| WO | WO 98/13485 | 4/1998 |
| WO | WO 98/13487 | 4/1998 |
| WO | WO 98/24799 | 6/1998 |
| WO | WO 98/27230 | 6/1998 |
| WO | WO 98/28416 | 7/1998 |
| WO | WO 98/31837 | 7/1998 |
| WO | WO 98/36080 | 8/1998 |
| WO | WO 98/41622 | 9/1998 |
| WO | WO 98/41623 | 9/1998 |
| WO | WO 98/41653 | 9/1998 |
| WO | WO 98/42832 | 10/1998 |
| WO | WO 98/48034 | 10/1998 |
| WO | WO 98/58085 | 12/1998 |
| WO | WO 99/07837 | 2/1999 |

(List continued on next page.)

OTHER PUBLICATIONS

Dartois, V, et al., "Cloning, nucleotide sequence and expression in *Escherichia coli* of a lipase gene from *Bacillus subtilis* 168", Biochimica et Biophysica Acta 1131:253–260, (1992).

Kouker, G., et al., "Specific and sensitive plate assay for bacterial lipases", Appl. Environ. Microbiol. 53:211–213, (1987).

Jaeger, K., et al., *FEMS Microbiology Reviews* (1994) 15:29–63.

(List continued on next page.)

*Primary Examiner*—Nashaat T. Nashed
(74) *Attorney, Agent, or Firm*—Sharon M. Fujita; Quine Intellectual Property Law Group; Norman J. Kruse

(57) ABSTRACT

New lipase enzymes (both nucleic acids and polypeptides) are provided. Compositions which include these polypeptides, proteins, nucleic acids, recombinant cells, as well as methods involving the enzymes, antibodies to the enzymes, and methods of using the enzymes are also provided

31 Claims, 25 Drawing Sheets

FOREIGN PATENT DOCUMENTS

| WO | WO 99/08539 | 2/1999 |
|---|---|---|
| WO | WO 99/10472 | 3/1999 |
| WO | WO 99/10539 | 3/1999 |
| WO | WO 99/19518 | 4/1999 |
| WO | WO 99/21979 | 5/1999 |
| WO | WO 99/23107 | 5/1999 |
| WO | WO 99/23236 | 5/1999 |
| WO | WO 99/29902 | 6/1999 |
| WO | WO 99/41368 | 8/1999 |
| WO | WO 99/41369 | 8/1999 |
| WO | WO 99/41383 | 8/1999 |
| WO | WO 99/41402 | 8/1999 |
| WO | WO 99/45154 | 9/1999 |
| WO | WO 91/16422 | 10/1999 |
| WO | WO 99/57128 | 11/1999 |
| WO | WO 99/65927 | 12/1999 |
| WO | WO 00/42560 | 7/2000 |
| WO | WO 00/42561 | 7/2000 |
| WO | WO 00/53744 | 9/2000 |
| WO | WO 00/58517 | 10/2000 |

OTHER PUBLICATIONS

Jensen, R., et al., *LIPIDS* (1983) 18(9):650–657.
Jette, J., et al., *Analytical Biochem.* (1994) 219:256–260.
Kunst, F., et al., *Nature* (1997) 390(6657):249–256.
Misset, O., et al., *Protein Engineering* (1994) 7(4):523–529.
Nthangeni, M., et al., *Enzyme & Microbial. Tech.* (2001) 28:705–712.
Pandey, A., et al., *Biotechnol. Appl. Biochem.* (1999) 29:119–131.
Roloff, J., et al., *Acta Pathol. Microbiol. Immunol. Scand.* [*B*] 92(3):155–158.
Rua, M., et al., *Appl. Microbiol. Biotechnol.* (1998) 49(4):405–410.
Schmidt–Dannert, C., et al., *Biochim et Biophys Acta* (1996) 1301(1–2):105–114.
Schmidt–Dannert, C., et al., *Methods in Enzymol.* (1997) 284:194–220.
Schmidt–Dannert, C., et al. *Ann NY Acad Sci.* (1998) 864:14–22.
Thomson, C., et al., *Crt. Ref. Food Sci. Nutr.* (1999) 39(2):165–187.
Ulitzur, S., *Biochim Biophys Acta.* (1979) 572(2):211–217.
Yamamoto, H., et al., *Gene* (1996) 181:147–151.
Chang, C., et al. (1999) "Evolution of a cytokine using DNA family shuffling." *Nature Biotechnology* 17:793–797.
Christians, F.C. et al., (1999) "Directed evolution of thymidine kinase for AZT phosphorylation using DNA family shuffling." *Nature Biotechnology* 17:259–264.
Coco et al., (2001) "DNA shuffling method for generating highly recombined genes and evolved enzymes" *Nature Biotechnology* vol. 19 pp. 354–359.

Crameri et al., (1993) "10(20)–Fold aptamer library amplification without gel purification," *Nuc. Acids Res.* 21(18):4410.
Crameri, A. & Stemmer W.P.C. (1995) "Combinatorial multiple cassette mutagenesis creates all the permutations of mutant and wildtype cassettes." *Biotechniques* 18:194–195.
Crameri, A. et al. (1996) "Improved green fluorescent protein by molecular evolution using DNA shuffling." *Nature Biotechnology* 14:315–319.
Crameri, A. et al. (1996) "Construction and evolution of antibody–phage libraries by DNA shuffling." *Nature Medicine* 2:100–103.
Crameri, A. et al., (1997) "Molecular evolution of an arsenate detoxification pathway by DNA shuffling." *Nature Biotechnology* 15:436–438.
Crameri, A. et al., (1998) "DNA shuffling of a family of genes from diverse species accelerates directed evolution," *Nature* 391:288–291.
Gates, C.M. et al., (1996) "Affinity selective isolation of ligands from peptide libraries through display on a lac repressor headpiece dimer". *Journal of Molecular Biology* 255:373–386.
Minshull, J., Stemmer, W.P.C. (1999) "Protein evolution by molecular breeding." *Current Opinion in Chemical Biology* 3:284–290.
Ness, J. et al., (1999) "DNA shuffling of subgenominc sequences of subtilisin." *Nature Biotechnology* 17:893–896.
Patten, P.A. et al., (1997) "Application of DNA Shuffling to Pharmaceuticals and Vaccines." *Current Opinion in Biotechnology* 8:724–733.
Pelletier, Joelle N., (2001) "A Rachitt for our toolbox" *Nature Biotechnology* vol. 19, p. 314–315.
Stemmer, W.P.C. (1994) "DNA Shuffling by random fragmentation and reassembly: In vitro recombination for molecular evolution." *PNAS* 91:10751.
Stemmer, W.P.C. (1994) "Rapid evolution of a protein in vitro by DNA shuffling." *Nature* 370:389–391.
Stemmer, W.P.C. (1995) "The Evolution of Molecular Computation." *Science* 207:1510.
Stemmer, W.P.C. (1995) "Searching Sequence Space." *Bio/ Technology* 13:549–553.
Stemmer, W.P.C. (1996) "Sexual PCR and Assembly PCR." In: *The Encyclopedia of Molecular Biology*. VCH Publishers, New York. pp. 447–457.
Stemmer, W.P.C. & Soong, N.W. (1999) "Molecular breeding of viruses for targeting and other clinical properties." *Tumor Targeting* 4:59–62.
Zhang, J. et al., (1997) "Directed evolution of an effective fucosidase from a galactosidase by DNA shuffling and screening." *Proceedings of the National Academy of Sciences, USA* 94:4504–4509.

| Clone name | SEQ ID NO | Enantioselectivity for Neryl Butyrate (N) or Geranyl Butyrate (G) |
|---|---|---|
| 1f15(G2) | 21 | G |
| 3C12 | 22 | G |
| 3N19(G2) | 23 | G |
| G2.2 | 24 | G |
| 2C3 | 25 | G |
| 2F11 | 26 | G |
| KV11(6C7) | 27 | N |
| KV6(3A1) | 28 | N |
| KV2(2D1) | 29 | N |
| N2.5 | 30 | N |
| KV5(2H6) | 31 | N |
| 3E5 | 32 | G |
| G2.1 | 33 | G |
| 3H24(G2) | 34 | G |
| KV10(4G6) | 35 | N |
| KV12(6D4) | 36 | N |
| N2.2 | 37 | N |
| N2.3 | 38 | N |
| N2.1 | 39 | N |
| KV4(2E12) | 40 | N |
| KV9(4C6) | 41 | N |
| 7D6 | 42 | G |
| 3F3 | 43 | G |
| 2D11(G2) | 44 | G |
| 3C23(G2) | 45 | G |
| G2.3 | 46 | G |
| 2A3 | 47 | G |
| 2F4 | 48 | G |
| 2B9(G2) | 49 | G |
| 2C5 | 50 | G |
| KV1(2A6) | 51 | N |
| 2D13(G2) | 52 | G |
| 3C8 | 53 | G |
| 2D5 | 54 | G |

FIGURE 1

| Clone Name | E value for Neryl Butyrate | E value for Geranyl Butyrate |
|---|---|---|
| Exemplar (sgc2 and sgd2) | --- | 2.1 |
| Exemplar (2h6) | 1.4 | --- |
| Exemplar (14g14) | 1.8 | --- |
| Exemplar (3f19a11) | 2.2 | (not tested) |
| Exemplar (3e5) | --- | 3.0 |
| Exemplar (3n19) | --- | 3.8 |

FIGURE 2

| | | 1 | | | 75 |
|---|---|---|---|---|---|
| SEQ: 001 | (1) | ------ATGAAATTTGTAAAAGAAGGATCATTGCA-----CTTGTAACAATTTGGTGCTG-TCAGTCACATCGC |
| SEQ: 002 | (1) | ------ATGAAATTTGTAAAAGAAGGATCATTGCA-----CTTGTAACAATTTGGTGCTG-TCAGTCACATCGC |
| SEQ: 003 | (1) | ------ATGAAATTTGTAAAAGAAGAAGGATCATTGCA-----CTTGTAACAATTTGATGCTG-TCTGTTACATCGC |
| SEQ: 004 | (1) | ------ATGAAATTTGTAAAAGAAGAAGGATCATTGCA-----CTTGTAACAATTTGGTGCTG-TCAGTCACATCGC |
| SEQ: 005 | (1) | ------ATGAAATTTGTATAAAGAAGGATCATTGCA-----CTTGTAACAATTTGGTGCTG-TCAGTCACATCGC |
| SEQ: 006 | (1) | ------ATGAAATTTGTAAAAGAAGAAGGATCATTGCA-----CTTGTAACAATTTGGTGCTG-TCAGTCACATCGC |
| SEQ: 007 | (1) | ------ATGAAATTTGTAAAAGAAGAAGGATCATTGCA-----CTTGTAACAATTTGGTGCTG-TCAGTCACATCGC |
| SEQ: 008 | (1) | ------ATGAAATTTGTAAAAGAAGAAGGATCATTGCA-----CTTGTAACAATTTGGTGCTG-TCAGTCACATCGC |
| SEQ: 009 | (1) | ------ATGAAATTTGTAAAAGAAGAAGGATCATTGCA-----CTTGTAACAATTTGATGCTG-TCAGTCACATCGC |
| SEQ: 010 | (1) | ------ATGAAATTTGTAAAAGAAGAAGGATCATTGCA-----CTTGTAACAATTTGATGCTG-TCTGTTACATCGC |
| SEQ: 011 | (1) | ATGAAAGTGATTTTTGTTAAAAGAAAAGGAGT-TTGCAAATTCTTGTTGCCCTTAGTGCTAGTTCAATAGC |
| SEQ: 012 | (1) | ATGAAAGTGATTTTTGTTAAGAAAAAGAAGGAGT-TTGCAAATTCTTGTTGCTTGCATTGGTGATGGTTCAATGGC |
| SEQ: 013 | (1) | ATGAAAGTGATTTTTGTTAAGAAAAAGAAGGAGT-TTGCAAATTCTTGTTGCTTGCATTGGTGATTGGTTCAATGGC |
| SEQ: 014 | (1) | ------ATGAAATTTGTAAAAGAAGAAGGATCATTGCA-----CTTGTAACAATTTGATGCTG-TCTGTTACATCGC |
| SEQ: 015 | (1) | ------ATGAAATTTGTAAAAGAAGAAGGATCATTGCA-----CTTGTAACAATTTGATGCTG-TCTGTTACATCGC |
| SEQ: 016 | (1) | ------ATGAAATTTGTAAAAGAAGAAGGATCATTGCA-----CTTGTAACAATTTGATGCTG-TCTGTTACATCGC |
| SEQ: 017 | (1) | ------ATGAAATTTGTAAAAGAAGAAGGATCATTGCA-----CTTGTAACAATTTGATGCTG-TCTGTTACATCGC |
| SEQ: 018 | (1) | ------ATGAAATTTGTAAAAGAAGAAGGATCCTTGCA-----CTTGTAACAATTTGATGCTG-TCTGTTACATCGC |
| SEQ: 019 | (1) | ATGAAAGTGATTTTTGTTAAGAAAAAGAAGGAGT-TTGCAAATTCTTGTTGCCCTTAGTGCTAGGTTCAATGGC |
| SEQ: 020 | (1) | ------ATGAAATTTGTAAAAGAAGAAGGATCATTGCA-----CTTGTAACAATTTGATGCTG-TCTGTTACATCGC |

FIGURE 3a

```
                              (Signal peptide                    (Mature
                              coding region)                     coding region)
                    76                                       |                                              150
SEQ: 001  (65)  TGTTTGCGATGCAGCCGTCAGCAAAAGCCGCT|GAACACAATCCAGTTGTTATGGTTCAC-GGTATCGGAGGAGCT
SEQ: 002  (65)  TGTTTGCGTTGCAGCCGTCAGCAAAAGCCGCT|GAACACAATCCAGTCGTTATGGTTCAC-GGTATTGGAGGGGCA
SEQ: 003  (65)  TGTTTGCGATGCAGCCGTCAGCAAAAGCCGCT|GA-CACACAATCCAGTTGTTATGGTTCACTGGTATCGGAGGAGCT
SEQ: 004  (65)  TGTTTGCGATGCAGCCGTCAGCAAAAGCCGCT|GAACACAATCCAGTTGTTATGGTTCAC-GGTATCGGAGGAGCT
SEQ: 005  (65)  TGTTTGCGATGCAGCCGTCAGCAAAAGCCGCT|GAACACAATCCAGTTGTTATGGTTCAC-GGTATCGGAGGAGCT
SEQ: 006  (65)  TGTTTGCGATGCAGCCGTCAGCAAAAGCCGCT|GAACACAATCCAGTTGTTATGGTTCAC-GGTATCGGAGGAGCT
SEQ: 007  (65)  TGTTTGCGATGCAGCCGTCAGCAAAAGCCGCT|GAACACAATCCAGTCGTTATGGTTCAC-GGTATCGGAGGAGCT
SEQ: 008  (65)  TGTTTGCGATGCAGCCGTCAGCAAAAGCCGCT|GAACACAATCCAGTCGTTATGGTTCAC-GGTATCGGAGGAGCT
SEQ: 009  (65)  TGTTTGCGATGCAGCCGTCAGCAAAAGCCGCT|GAACACAATCCAGTTGTTATGGTTCAC-GGTATCGGAGGAGCT
SEQ: 010  (65)  TGTTTGCGTTGCAACCGTCAGCAAAAGCCGCT|GAACACAATCCAGTCGTTATGGTTCAC-GGTATTGGAGGGGCA
SEQ: 011  (75)  CTTCATCCAGCCAACCGTCAGCAAAAGCCAAA-GCGGCT|GAACACAATCCAGTCCGTTGTGTAATGGTGCAT-GGCATGGGCGGTGCG
SEQ: 012  (75)  CTTCATCCAGCCAACCGTCAGCAAAAGCCAAA-GCGGCT|GAGCATAATCCGGTTGTGATGGTACAT-GGCATGGGCGGTGCG
SEQ: 013  (75)  GTTTATCCAGCCAACCGTCAGCAAAGAGAGG-GCGGCT|GAGCATAATCCGGTTGTGATGGTGCAT-GGCATTGGCGGTGCC
SEQ: 014  (65)  TGTTTGCGTTGCAACCGTCAGCAAAAGCCGCT|GAACACAATCCAGTCGTTATGGTTCAC-GGTATTGGAGGGGCA
SEQ: 015  (65)  TGTTTGCGTTGCAACCGTCAGCAAAAGCCGCT|GAACACAATCCAGTCGTTATGGTTCAC-GGTATTGGAGGGGCA
SEQ: 016  (65)  TGTTTGCGTTGCAACCGTCAGCAAAAGCCGCT|GAACACAATCCAGTCGTTATGGTTCAC-GGTATTGGAGGGGCA
SEQ: 017  (65)  TGTTTGCGTTGCAACCGTCAGCAAAAGCCGCT|GAACACAATCCAGTCGTTATGGTTCAC-GGTATTGGAGGGGCA
SEQ: 018  (65)  TGTTTGCGTTGCAACCGTCAGCAAAAGCCGCT|GAACACAATCCAGTCGTTATGGTTCAC-GGTATTGGAGGGGCA
SEQ: 019  (75)  CTTCATCCAGCCAAAAGCCAAAGAAATCAAA-AGCAGCT|GAGCACAATCCGGTTGTGATGGTACAT-GGTATTGGAGGAGCG
SEQ: 020  (65)  TGTTTGCGTTGCAACCGTCAGCAAAAGCCGCT|GAACACAATCCAGTCGTTATGGTTCAC-GGTATTGGAGGGGCA
```

```
                        226                                                              300
SEQ: 001   (214)  TTTTGGGACAAGACAGGACGAATTATAACAATGGCCCGGTATTATCACGATTTGTGCAAAAGGTTTTAGACGAA
SEQ: 002   (214)  TTTTGGGACAAGACAGGACACAAATTATAACAATGGACCGGTATTACCACGATTTGTGCAAAAGGTTTTAGATGAA
SEQ: 003   (214)  TTTTGGGACAAGACAGGACAGGACGAATTATAACAATGGCCCGGTATTATCACGATTTGTGCAAAAGGTTTTAGACGAA
SEQ: 004   (214)  TTTTGGGACAAGACAGGACAGGACGAATTATAACAATGGCCCGGTATTATCACGATTTGTGCAAAAGGTTTTAGACGAA
SEQ: 005   (214)  TTTTGGGACAAGACAGGACAGGACGAATTATAACAATGGCCCGGTATTATCACGATTTGTGCAAAAGGTTTTAGACGAA
SEQ: 006   (214)  TTTTGGGACAAGACAGGACAGGACGAATTATAACAATGGCCCGGTATTATCACGATTTGTGCAAAAGGTTTTAGACGAA
SEQ: 007   (214)  TTTTGGGACAAGACAGGACAGGACGAATTATAACAATGGCCCGGTATTATCACGATTTGTGCAAAAGGTTTTAGACGAA
SEQ: 008   (214)  TTTTGGGACAAGACAGGACAGGACGAATTATAACAATGGCCCGGTATTATCACGATTTGTGCAAAAGGTTTTAGACGAA
SEQ: 009   (214)  TTCAAGGACAAGACAGGACACAGGACGAATTATAACAATGGCCCGGTATTATCACGATTTGTGCAAAAGGTTTTAGACGAA
SEQ: 010   (214)  TTCTAAGACAAAACAGGACACAGGAATAACGCAACAATTAAACAATAACCGTCGAGATTCGTCAAGATGTTAGACAAA
SEQ: 011   (223)  TTCATAGACAAAACAGGCAATAACAGGCAATAACAGCAATAAACAATAACCGTCGAGATTCGTGAAAGACTACTAGCCAAA
SEQ: 012   (223)  TTCATAGACAAAACAGGCAATAACAGGCAATAACAGCAATAAACAATAACCGTCGAGATTCGTCAAGATGCTAGCCAAA
SEQ: 013   (223)  TTCATAGACAAAACAGGAACAGGAAATAACAACGCAACAATGGTCCGATTCGTCAAGATGGTTAGACAAA
SEQ: 014   (214)  TTCAGGGACAAGACAGGCAATAACAACTAAACAACGGTCCAGTATTATCGCGTTTCGTGAAAAGGTATTAGATGAA
SEQ: 015   (214)  TTCTGGGATAAGACAGGCAATAACAACTAAACAACGGTCCAGTATTATCGCGTTTGTGAAAAGGTATTAGATGAA
SEQ: 016   (214)  TTTAGTGACAAAACAGGCAATAACAACGGTCCAGTATTATCGCGTTTGTGAAAAGGTATTAGATGAA
SEQ: 017   (214)  TTCAAAGACAAGACAGGAATAACCGCAACAATGGTCCGCGTCTATCGAGATTCGTCAAAGATGTGTTAGACAAA
SEQ: 018   (214)  TTCATTGACAAGACAGGAAATAACCGCACAATGGTCCGCGTCTATCGAGATTCGTCAAAGATGTGTTAGACAAA
SEQ: 019   (223)  TTCATAGACAAAACAGGAATAACCGCAACAATGGTCCTCGTTTATCTAGATTCGTCAAAGATGCTAGACAAA
SEQ: 020   (214)  TTCAGGGACAAGACAGGAAATAACCGCAACAATGGTCCGCGTCTATCTAAATTCGTCAAAGATGTGTTAGACAAA
```

FIGURE 3d

```
             301                                                                          375
SEQ: 001 (289) ACGGGTGCGAAAAAGTGGATATTGTCGCTCACAGTATGGGTGGCGCGAACACACCTTACTACACATAAAAAATCTG
SEQ: 002 (289) ACGGGTGCGAAAAAGTGGATATTGTCGCTCACAGTATGGGTGGCGCGAACACACTTTACTACACATAAAAAATCTG
SEQ: 003 (289) ACGGGTGCGAAAAAGTGGATATTGTCGCTCACAGCATGGGTGGCGCGAACACACTTTACTACACATAAAAAATCTG
SEQ: 004 (289) ACGGGTGCGAAAAAGTGGATATTGTCGCTCACAGCATGGGTGGCGCGAACACACTTTACTACACATAAAAAATCTG
SEQ: 005 (289) ACGGGTGCGAAAAAGTGGATATTGTCGCTCACAGCATGGGTGGCGCGAACACACTTTACTACACATAAAAAATCTG
SEQ: 006 (289) ACGGGTGCGAAAAAGTGGATATTGTCGCTCACAGCATGGGTGGCGCGAACACACTTTACTACACATAAAAAATCTG
SEQ: 007 (289) ACGGGTGCGAAAAAGTGGATATTGTCGCTCACAGCATGGGTGGCGCGAACACACTTTACTACACATAAAAAATCTG
SEQ: 008 (289) ACGGGTGCGAAAAAGTGGATATTGTCGCTCACAGCATGGGTGGCGCGAACACACTTTACTACACATAAAAAATCTG
SEQ: 009 (289) ACGGGTGCGAAAAAGTGGATATTGTCGCTCACAGCATGGGGGCGCGAACACACTTTACTACACATAAAAAATCTG
SEQ: 010 (289) ACGGGTGCCAAAAAGTAGATATTGTGGCTCATGTATGGGTGGAGCGGTGCGAACACACGCTATATCTATAAAACCTA
SEQ: 011 (298) ACGGGCGCCAAAAAGTAGATATTGTGGCTCATGTATGGGTGGAGCGGTGCGAACACACGCTATATCTATATTAAGAATCTA
SEQ: 012 (298) ACAGGTGCCAAAAAGTTGATATTGTGGCTCATGTATGGGTGGAGCGGTGCGAACACACGCTATACTATATTAAGAATCTA
SEQ: 013 (298) ACGGGTGCCAAAAAGTAGATATTGTGGCTCATGTATGGGTGGAGCGGTGCGAACACACGCTATATCTATATTAAGAATCTA
SEQ: 014 (289) ACCGGTGCGAAAAAGTAGATATTGTCGCTCACAGCATGGGCGGCGCGCTAACACACGCTTTACTACACATAAAAATTTG
SEQ: 015 (289) ACCGGTGCCAAAAAGTGGATATTGTCGCTCACAGCATGGGCGGCGCGCTAACACACGCTTTACTACACATAAAAATTTG
SEQ: 016 (289) ACCGGTGCGAAAAAGTGGATATTGTCGCTCACAGCATGGGCGGCGCGCTAACACACGCTTTACTACACATAAAAATTTG
SEQ: 017 (298) ACAGGAGCCAAAAAGTAGATAGTATTGTGGCTCATGTATGGGCGGAGCGAACACATTATACTATATTAAGAATCTA
SEQ: 018 (289) ACAGGAGCCAAAAAGTAGATAGTATTGTGGCTCATGTATGGGCGGAGCGAACACATTATACTATATTAAGAATCTA
SEQ: 019 (298) ACGGGTGCCAAAAAGTAGATAGTATTGTGGCTCATGTATGGGCGGGGCGAACACGCTATACTATATTAAGAATCTA
SEQ: 020 (289) ACGGGTGCCAAAAAGTAGATAGTATTGTGGCTCATGTATGGGCGGGGCGAACACGCTATACTATATTAAGAATCTA
```

FIGURE 3e

```
                 376                                                                              450
SEQ: 001  (364)  GACGGCGGAAATAAAATTGAAAACGTCGTAACGCTTGGCGGCGGCGAACCGTTCGACGACAAGCAAGGCGCTTCCG
SEQ: 002  (364)  GACGGCGGAAATAAAATTGCAAACGTCGTGACGCTTGGCGGCGGCGAACCGTTTGACGACAAGCAAGGCGCTTCCG
SEQ: 003  (364)  GACGGCGGAAATAAAGTTGCAAACGTCGTCGTGACGCTTGGCGGCGGCGAACCGTTCGACGACAAGCAAGGCGCTTCCG
SEQ: 004  (364)  GACGGCGGAAATAAAATTGAAAACGTCGTAACGCTTGGCGGCGGCGAACCGTTCGACGACAAGCAAGGCGCTTCCG
SEQ: 005  (364)  GACGGCGGAAATAAAATTGAAAACGTCGTAACGCTTGGCGGCGGCGAACCGTTCGACGACAAGCAAGGCGCTTCCG
SEQ: 006  (364)  GACGGCGGAAATAAAATTGAAAACGTCGTAACGCTTGGCGGCGGCGAACCGTTTGACGACAAGCAAGGCGCTTCCG
SEQ: 007  (364)  GACGGCGGAAATAAAATTGAAAACGTCGTAACGCTTGGCGGCGGCGAACCGTTTGACGACAAGCAAGGCGCTTCCG
SEQ: 008  (364)  GACGGCGGAAATAAAATTGAAAACGTCGTAACGCTTGGCGGCGGCGAACCGTTTGACGACAAGCAAGGCGCTTCCG
SEQ: 009  (364)  GACGGCGGAAATAAAATTGAAAACGTCGTGACGCTTGGCGGCGGCGAACCGTTTGACGACAAGCAAGGCGCTTCCG
SEQ: 010  (364)  GACGGCGGAAATAAAATTGAAAACGTCGTGACGCTTGGCGGCGGCCAACCGTTTGACGACAAACGACTCGTTTCAAGCAGAGCATTACCA
SEQ: 011  (373)  GATGGCGGCGATAAAATTGAGAACGTTGTCACATTGGTGGAGCAAACGACTCGTTTCAAGCAGAGCATTACCA
SEQ: 012  (373)  GACGTGGAGATAAAATTGAAAACGTCGTCACATTGTTACTGGTGGAGCAAACGACTCGTATCACTCAGAGCATTACCA
SEQ: 013  (373)  GACGCGGCGATAAAATAGAAAACGTCGTGTTACACTTGGTGGAGCGAAACGACTCGTTTCACTCAGAGCATTACCA
SEQ: 014  (364)  GATGGCGGCGATAAAATTGAGAACGTCGTCACAATTGGTGGAGCGAAACGACTCGTCTTGTGACAGGCAAGGCGCTTCCG
SEQ: 015  (364)  GATGGCGGCGGTAATAAAATTGAAAACGTCGTAACACTTGGCGCGGCGAATCGTCTGTGACAGGCAAGGCGCTTCCG
SEQ: 016  (364)  GATGGCGGCGGTAATAAAATTGAAAACGTCGTAACACTTGGCGCGGCGAATCGTCTTGTGACAGGCAAGGCGCTTCCG
SEQ: 017  (364)  GATGGCGGCGGTAATAAAATTGAAAACGTCGTAACACTTGGCGCGGCGAATCGTCTTGTAACAGGCAAGGCGCTTCCG
SEQ: 018  (364)  GATGGTGGCGATAAAATTGTCACAATTGTCACAATTGTCACAATTGGTGGAGCAAACGACTCGTTTCAAGCAGAGCATTACCA
SEQ: 019  (373)  GATGGCGGCGATAAAATTGAAAACGTCGTCACCATTGGTGGAGCAAACGACTCGTTTCACTCAGAGCATTACCA
SEQ: 020  (364)  GATGGCGGCGATAAAATTGAGAACGTTGTCACAATTGGCGGAGCAAACGACTCGTTTCAAGCAGAGCATTACCA
```

FIGURE 3f

```
       451                                                                                          525
SEQ: 001 (439) GGAACAGATCCAAATCAAAAGATTTTATACACATCCATTTACA-GCAGTGCCGATATGATTGTCATGAATTACTT
SEQ: 002 (439) GGAACAGATCCAAATCAAAAGATTTTATACACATCCATTTACA-GCAGTGCCGATATGATTGTCATAAATTACTT
SEQ: 003 (439) GGAACAGATCCAAATCAAAAGATTTTATACACATCCATTTACA-GCAGTGCCGATATGATTGTCATGAATTACTT
SEQ: 004 (439) GGAACAGATCCAAATCAAAAGATTTTATACACATCCATTTACA-GCAGTGCCGATATGTCATGAATTACTT
SEQ: 005 (439) GGAACAGATCCAAATCAAAAGATTTTATACACATCCATTTACA-GCAGTGCCGATATGATTGTCATGAATTACTT
SEQ: 006 (439) GGAACAGATCCAAATCAAAAGATTTTATACACATCCATTTACA-GCAGTGCCGATATGATTGTCATGAATTACTT
SEQ: 007 (439) GGAACAGATCCAAATCAAAAGATTTTATACACATCCATTTACA-GCAGTGCCAATATGATTGTCATGAATTACTT
SEQ: 008 (439) GGAACAGATCCAAATCAAAAGATTTTATACACATCCATTTACA-GCAGTGCCGATATGATTGTCATGAATTACTT
SEQ: 009 (439) GGAACAGATCCAAATCAAAAGATTTTATACACATCCATTTACA-GCAGTGCCGATATGATTGTCATGAATTATTT
SEQ: 010 (439) GGCACAGATCCAAATCAAAAATTCTTTACACATCCGTCTGTCTATA-GCTCAGCCGATCTTATTGTCGTCAACAGCCT
SEQ: 011 (448) GGCACCGATCCAAATCAAAAATTCTTTACACATCCGTCTGTCTATA-GCTCAGCCGATCTCATTGTCGTCAACAGCCT
SEQ: 012 (448) GGCACCGATCCAAATCAAAAATCCTTTACACATCCGTCTACA-GCTCAGCCGATCTTATCGTCGTCAACAGCCT
SEQ: 013 (448) GGCACAGATCCAAATCAAAAATCCTTTACACATCCGTCTATA-GCTCAGCCAGATCTTATTGTCGTCAACAGCCT
SEQ: 014 (439) GGTACTGATGCAACCAAACCAAAAGATCTGTGTACACATCCGTTTACA-GTAGTGCTGATATGATTGTTATGAATTACTT
SEQ: 015 (439) GGTACTGATCCAACCAAACAAAAGATATTGTACACATCCGTTTACA-GTAGTGCTGATATGATTGTTATGAATTACTT
SEQ: 016 (439) GGTACTGATCCAACCAAACAAAAGATCTGTACACATCCGTTTACA-GTAGTGCTGATATGATTGTTATGAATTACTT
SEQ: 017 (439) GGCACAGATCCAAATCAAAAATCTTTACACATCCGTCTATA-GCTCAGCAGATCTTATTGTCGTCAACAGTCT
SEQ: 018 (439) GGCACAGATCCAAATCAAAAATCTTTACACATCCGTCTATA-GCTCAGCCAGATCTTATTGTCGTCAACAGTCT
SEQ: 019 (448) GGAACAGATCCAAATCAAAAATTCTTTACACATCCGTCTACAAGCTCAGCCGATTTGATTGTCGTCAACAGTCT
SEQ: 020 (439) GGCACAGATCCAAATCAAAAATTCTTTACACATCCGTCTACAAGCTCAGCCGATCTCATTGTCGTCAACAGTCT
```

FIGURE 3g

```
                    526                                                                                600
SEQ: 001   (513)   ATCAAAAATTAGACGGT-GCTAAAAAC-GCTCAAATTCATGGCGTTGGGCACATTGGTTTATTGATGAACAGCCAA
SEQ: 002   (513)   ATCAAGATTAGATGGT-GCTAGAAAAC-GTTCAAATTCATGGCGTTGGACACATCGGCCTTGGTTTATTGATGAACAGCCAA
SEQ: 003   (513)   ATCAAAATTAGACGGT-GCTAAAAAC-GTTCAAATTCATGGCGTTGGGCGTTGGCACATTGGTTTATTGATGAACAGCCAA
SEQ: 004   (513)   ATCAAAATTAGACGGT-GCTAAAAAC-GTTCAAATTCATGGCGTTGGGCACATTGGTTTATTGATGAACAGCCAA
SEQ: 005   (513)   ATCAAAATTAGACGGT-GCTAAAAAC-GTTCAAATTCATGGCGTTGGGCACATTGGTTTATTGATGAACAGCCAA
SEQ: 006   (513)   ATCAAAATTAGACGGT-GCTAAAAAC-GTACAAATTCATGGCGTTGGGCACATTGGTTTATTGATGAACAGCCAA
SEQ: 007   (513)   ATCAAAATTAGACGGT-GCTAAAAAC-GCTCAAATTCATGGCGTTGGGCACATTGGTTTATTGATGAACAGCCAA
SEQ: 008   (513)   ATCAAAATTAGACGGT-GCTAAAAAC-GTTCAAATTCATGGCGTTGGGCACATTGGTTTATTGATGAACAGCCAA
SEQ: 009   (513)   ATCAAGATTAGATGGT-GCGAGAAAC-GTTCAAATCCATGGCGTTGGACACATCGGCCCTTCTGTACAGCAGCCAA
SEQ: 010   (513)   CTCTCGTTTAATTGGC-GCAAGAAAC-ATCCTGATCCATGGCGTTGGTCATATCGGTCTATTAACCTCAAGCCAA
SEQ: 011   (522)   TTCGC-GTTTAATTGGCGCAAGAAAC-GTCCTGATCCACGGCGTTGGTCATATCGGTCTATTAACCTCAAGCCAA
SEQ: 012   (522)   CTCGC-GTTTAATTGGCGCAAGAAAC-GTCCTCATTCACGGCGTTGGTCATATCGGTCTATTAGCTCAAGCCAA
SEQ: 013   (522)   CTCTCAGTTTAATTGGCGCAAGAAAC-ATCCTGATCCA-GGCGTTGGTCATATCGGTCTATTAACCTCGTACAGCAGCCAA
SEQ: 014   (513)   AACAAAATTAGACGGG-GCTAAAAAT-GTTCAAATTCATGGTGTCGGACATATCGGCCTTCTGTACAGCAGCCAA
SEQ: 015   (513)   ATCAAAATTAGACGGG-GCTAAAAAT-GTTCAAATTCATGGTGTCGGACATATCGGCCTTCTGTACAGCAGCCAA
SEQ: 016   (513)   ATCAAAATTAGACGGG-GCTAAAAAT-GTTCAAATTCATGGTGTCGGACATATCGGCCTTCTGTACAGCAGCCAA
SEQ: 017   (513)   CTCTCGTTTAATTGGC-GCAAGAAAC-GTCCAAATCCATGGCGTTGGACATATCGGTCTATTAACCTCAAGCCTA
SEQ: 018   (513)   CTCTCGTTTAATTGGC-GCAAGAAAC-GTCCAAATCCATGGCGTTGGACATATCGGTCTATTAACCTCAAGCCAA
SEQ: 019   (522)   TTCGC-GTTAACTGGCGCAAGAAAT-GTCCTGATCCACGGCGTTGGCCATATCGGTCTATTAACCTCAAGCCAA
SEQ: 020   (514)   CTCTCGTTTAATTGGCTGCAAGAACAGTCCAAATCCATGGCGTTGGACATATCGGTCTATTAACCTCAAGCCAA
```

FIGURE 3h

```
                                                                                    654
SEQ: 001  (586) GTCAACAGCCTGATTAAAGAAGGACTGAACGGGCGGGGGCCAAAATACGAATTAA
SEQ: 002  (586) GTCAACAGCCTGATTAAAGAAGGACTGAACGGGCGGGGGACTCAATACAAATTAG
SEQ: 003  (586) GTCAACAGCCTGATTAAAGAAGGACTGAACGGGCCACACAGGACTAAATACAAATTAA
SEQ: 004  (586) GTCAACAGCCTGATTAAAGAAGGACTGAACGGGCCGAGGACTAAATACAAATTAA
SEQ: 005  (586) GTCAACAGCCTGATTAAAGAAGGACTGAACGGGCCGGGGGCCTCAATACAAATTAA
SEQ: 006  (586) GTCAACAGCCTGATTAAAGAAGGACTGAACGGGCCGGGGGCCTAGATACAAATTAA
SEQ: 007  (586) GTCAACAGCCTGATTAAAGAAGGACTGAACGGGCCGAGCCCACAATACAAATTAA
SEQ: 008  (586) GTCAACAGCCTGATTAAAGAAGGACTGAACGGCGGAGCCCACAATACAAATTAA
SEQ: 009  (586) GTCAACAGCCTGATTAAAGAAGAAGGCTGAACGGCCTGAGCCCTCAATACAAATTAA
SEQ: 010  (586) GTGAAAGGCTATATTAAAGAAGAATGAACGGCCGAGCCTCAATACAAATTAA
SEQ: 011  (595) GTGAAAGGCTATGTGAAAGAATCAAAGAAGAATTGAATGCCGAGGCCAAAATACAAATTAA
SEQ: 012  (595) GTGAAAGGCTATATCAAAGAAGAATGAACGGCTGAACGCCGAGCCTCAATACAAATTAA
SEQ: 013  (595) GTGAAAGGCTATATTAAAGAAGAAGGACTGAACGGCCGAGCCTCAATACAAATTAA
SEQ: 014  (586) GTCAACAGCCCTGATTAAAGAAGGACTTAACGGCCGAGGCCTCAATACAAATTAA
SEQ: 015  (586) GTCAATAGCCTGATTAAAGAAGAAGGGCTTAACGGCCGGAGACTCAATACGAATTAA
SEQ: 016  (586) GTCAACAGCCCTGATTAAAGAAGAAGGGCTGAACGGCCGGGCCTGAATACGAATTAA
SEQ: 017  (586) GTCAAAGGATATATTAAAGAAGAAGGGCTGAACGGCCGAGCCCAAAATACAAATTAA
SEQ: 018  (586) GTCAAAGGATATATTAAAGAAGAAGGACTGAACGGCCGAGCCCTAAATACAAATTAA
SEQ: 019  (595) GTGAAAGGTATATTAAAGAAGAAGGACTGAACGGCGGGGCCCTAAATACAAATTAA
SEQ: 020  (589) GTCAAAGGATATATTAAAGAAGGACTGAACGGCGGGGGACTAAATACAAATTAA
```

FIGURE 3i

| | | 1 | 75 |
|---|---|---|---|
| SEQ: | 021 | (1) | TGAACACAATCCAGTTGTTGTTATGGTTCACGGTATTGGAGGGGCATCATTCATTCAATTTTGCGGGAATTAAGAGCTATCT |
| SEQ: | 022 | (1) | TGAACACAATCCAGTTGTTGTTATGGTTCACGGTATTGGAGGGGCATCATTCATTCAATTTTGCGGGAATTAAGAGCTATCT |
| SEQ: | 023 | (1) | TGAACACAATCCAGTTGTTGTTATGGTTCACGGTATTGGAGGGGCATCATTCATTCAATTTTGCGGGAATTAAGAGCTATCT |
| SEQ: | 024 | (1) | TGAACACAATCCAGTTGTTGTTATGGTTCACGGTATTGGAGGGGCATCATTCATTCAATTTTGCGGGAATTAAGAGCTATCT |
| SEQ: | 025 | (1) | TGAACACAATCCAGTTGTTGTTATGGTTCACGGTATCGGAGGGGCATCATTCATACAATTTGCGGGAATTAAGAGCTATCT |
| SEQ: | 026 | (1) | TGAACACAATCCAGTTGTTGTTATGGTTCACGGTATCGGAGGAGCTTCATACAATTTCAGTTTTGCGGGAATTAAGAGCTATCT |
| SEQ: | 027 | (1) | TGAACACAATCCAGTTGTTGTTATGGTTCACGGTATTGGAGGGGCATCATTCAGTTTTGCGGGAATTAAGAGCTATCT |
| SEQ: | 028 | (1) | TGAACACAATCCAGTTGTTGTTATGGTTCACGGTATCGGAGGGGCATCATTCAGTTTTGCGGGAATTAAGAGCTATCT |
| SEQ: | 029 | (1) | TGAACACAATCCAGTTGTTGTTATGGTTCACGGTATCGGAGGAGCTTCATACAGTTTGCGGGAATTAAGAGCTATCT |
| SEQ: | 030 | (1) | TGAACACAATCCAGTTGTTGTTATGGTTCACGGTATCGGAGGAGCTTCATACAGTTTGCGGGAATTAAGAGCTATCT |
| SEQ: | 031 | (1) | TGAACACAATCCAGTTGTTGTTATGGTTCACGGTATTGGAGGGGCATCATTCAATTTGCGGGAATTAGGAGCTATCT |
| SEQ: | 032 | (1) | TGAACACAATCCAGTCGTTGTTATGGTTCACGGTATCGGAGGGGCATCATTCAATTTGCGGGAATTAAGAGCTATCT |
| SEQ: | 033 | (1) | TGAACACAATCCAGTTGTTGTTATGGTTCACGGTATTGGAGGGGCATCATTCAATTTGCGGGAATTAAGAGCTATCT |
| SEQ: | 034 | (1) | TGAACACAATCCAGTTGTTGTTATGGTTCACGGTATTGGAGGGGCATCATTCAATTTGCGGGAATTAAGAGCTATCT |
| SEQ: | 035 | (1) | TGAACACAATCCAGTTGTTGTTATGGTTCACGGTATCGGAGGGGCATCATTCAGTTTGCGGGAATTAGGAGCTATCT |
| SEQ: | 036 | (1) | TGAACACAATCCAGTTGTTGTTATGGTTCACGGTATCGGAGGGGCATCATTCAGTTTGCGGGAATTAGGAGCTATCT |
| SEQ: | 037 | (1) | TGAACACAATCCAGTTGTTGTTATGGTTCACGGTATCGCGGGGCATCATCATTCAGTTTGCGGGAATTAGGAGCTATCT |
| SEQ: | 038 | (1) | TGAACACAATCCAGTTGTTGTTATGGTTCACGGTATCGGAGGGGCATCATCATTCAGTTTGCGGGAATTAGGAGCTATCT |
| SEQ: | 039 | (1) | TGAACACAATCCAGTTGTTATGGTTATGGTTCACGGTATCGGAGGACATGGGGCATCATCATTCAATTCAATTTGCGGGAATTAAGAGCTATCT |
| SEQ: | 040 | (1) | TGAACACAATCCAGTTGTTGTTATGGTTATGGTTCACGGTATCGGAGGGGCATCATCATTCAATTTGCGGGAATTAAGAGCTATCT |
| SEQ: | 041 | (1) | TGAACACAATCCAGTTGTTGTTATGGTTATGGTTCACGGTATCGGAGGGGCATCATCATTCAGTTTGCGGGAATTAAGAGCTATCT |
| SEQ: | 042 | (1) | TAAACACAATCCAGTTGTTGTTATGGTTATGGTTCACGGTATTGGAGGGGCATCATCATACAATTTGCGGGAATAAGAGCTATCT |
| SEQ: | 043 | (1) | TGAACACAATCCAGTTGTTGTTATGGTTATGGTTCACGGTATTGGAGGGGCATCGTCATTCAATTTGCGGGAATTAAGAGCTATCT |
| SEQ: | 044 | (1) | TGAACACAATCCAGTTGTTGTTATGGTTATGGTTCACGGTATTGGAGGGGCATCATTCATTCAATTTGCGGGAATTAAGAGCTATCT |
| SEQ: | 045 | (1) | TGAACACAATCCAGTTGTTGTTATGGTTATGGTTCACGGTATCGGAGGGGCATCATTCATTCAATTTGCGGGAATTAAGAGCTATCT |
| SEQ: | 046 | (1) | TGAACACAATCCAGTTGTTGTTATGGTTATGGTTCACGGTATTGGAGGGGCATCATTCATTCAATTTGCGGGAATTAAGAGCTATCT |
| SEQ: | 047 | (1) | TGAACACAATCCAGTTGTTGTTATGGTTATGGTTCACGGTATTGGAGGGGCATCATTCATTCAATTTGCGGGAATTAAGAGCTATCT |
| SEQ: | 048 | (1) | TGAACACAATCCAGTTGTTGTTATGGTTATGGTTCACGGTATTGGAGGGGCATCGTTCATTCAATTTGCGGGAATTAAGAGCTATCT |
| SEQ: | 049 | (1) | TGAACACAATCCAGTTGTTGTTATGGTTATGGTTCACGGTATTGGAGGGGCATCATTCATTCAATTTGCGGGAATTAAGAGCTATCT |
| SEQ: | 050 | (1) | TGAACACAATCCAGTTGTTGTTATGGTTATGGTTCACGGTATTGGAGGGGCATCATTCATTCAATTTGCGGGAATTAAGAGCTATCT |
| SEQ: | 051 | (1) | TGAACACAATCCAGTTGTTGTTATGGTTATGGTTCACGGTATTGGAGGGGCATCATTCATTCAATTTGCGGGAATAAAGAGCTATCT |
| SEQ: | 052 | (1) | TGAACACAATCCAGTTGTTGTTATGGTTATGGTTCACGGTATTGGAGGGGCATCATTCATTCAATTTGCGGGAATTAAGAGCTATCT |
| SEQ: | 053 | (1) | TAAACACAATCCAGTTGTTGTTATGGTTATGGTTCACGGTATCGGAGGGGCATCATTCAATTCAATTTGCGGGAATTAAGAGCTATCT |
| SEQ: | 054 | (1) | TGAACACAATCCAGTTGTTGTTATGGTTATGGTTCACGGTATCGGAGGGGCATCATTCATTCAATTTGCGGGAATTAAGAGCTATCT |

```
                226                                                                                             300
SEQ: 021  (226) CAGCATGGGCGGCGCGCTAACACGCTTTACTACTACATAAAAAATCTGACGGCGCGGAAATAAAGTTGAAAACGTCGTAAC
SEQ: 022  (226) CAGCATGGGGGGCGCGCGGAACACACTTTACTACACATTTACTACATAAAAATCTGACGGCGGAAATAAAATAAAACGTCGTAAC
SEQ: 023  (226) CAGCATGGTGCGCGCGAACACACTTTACTACACATTTACTACATAAAAATCTGACGGCGGAAATAAAATTGAAACGTCGTAAC
SEQ: 024  (226) CAGCATGGGGGGCGCGCGAACACACTTTACTACACACTTTACTACATAAAAATCTGACGGCGGAAATAAAATTGAAACGTCGTAAC
SEQ: 025  (226) CAGCATGGGCGGCGCGCGAACACACTTTACTACACACTTTACTACATAAAAATTTGATGCGGAAATAAAATTGAAACGTCGTAAC
SEQ: 026  (226) CAGCATGGGCGGCGCGCGAACACACTTTACTACACACTTTACTACATAAAAATCTGACGGCGGAAATAAAATTGAAACGTCGTAAC
SEQ: 027  (226) CAGTATGGGTGGCGCGCGAACACACTTTACTACACACTTTACTACATAAAAATCTGACGGCGGAAATAAAATTGAAACGTCGTAAC
SEQ: 028  (226) CAGTATGGGTGGCGCGCGAACACACTTTACTACACACTTTACTACATAAAAAATCTGACGGCGGAAATAAAATTGAAACGTCGTAAC
SEQ: 029  (226) CAGCATGGGTGGCGCGCGAACACACTTTACTACACACTTTACTACATAAAAATCTGGACGGCGGAAATAAAATTGAAACGTCGTAAC
SEQ: 030  (226) CAGCATGGGGGGCGCGCGAACACACTTTACTACACACTTTACTACATAAAAATCTGGACGGCGGAAATAAAATTGAAACGTCGTGAC
SEQ: 031  (226) CAGCATGGGTGGCGCGCGAACACACTTTACTACACACTTTACTACATAAAAAATCTGGACGGCGGAAATAAAATTGAAACGTCGTGAC
SEQ: 032  (226) CAGCATGGGTGGCGCGGCGCGCTAACACACTTTACTACACGCTTTACTACATAAAAAATCTGACGGCGGAAATAAAATTGAAACGTCGTAAC
SEQ: 033  (226) CAGCATGGGTGGCGCGGCGCGCGAACACACTTTACTACACACTTTACTACATAAAAAATCTGACGGCGGAAATAAAATTGAAACGTCGTAAC
SEQ: 034  (226) CAGCATGGGGGGGCGCGCGAACACACTTTACTACACACTTTACTACATAAAAAATCTGACGGCGGAAATAAGTTGAAAGCGTCGTAAC
SEQ: 035  (226) CAGCATGGGTGGCGCGGCGCGCGAACACACTTTACTACACACTTTACTACATAAAAAATCTGACGGCGGAAATAAAGTTGAAAACGTCGTAAC
SEQ: 036  (226) CAGCATGGGTGGCGCGGCGCGCGAACACACTTTACTACACACTTTACTACATAAAAAATCTGACGGCGGAAATAAAGTTGAAAACGTCGTGAC
SEQ: 037  (226) CAGCATGGGTGGCGCGGCGCGCGAACACACTTTACTACACACTTTACTACATAAAAAATCTGACGGCGGAAATAAAGTTGAAAACGTCGTGAC
SEQ: 038  (226) CAGCATGGGTGGCGCGGCGCGCGAACACACTTTACTACACACTTTACTACATAAAAAATCTGACGGCGCGGAAATAAAGTTGAAAACGTCGTGAC
SEQ: 039  (226) CAGCATGGGTGGCGCGGCGCGCCAACACACTTTACTACACACTTTACTACATAAAAAATCTGACGGCGGAAATAAAATTGAAAACGTCGTGAC
SEQ: 040  (226) CAGCATGGGCGGCGGGGCGCGCGAACACACTTTACTACACACTTTACTACATAAAAAATCTGACGGCGGAAATAAAATTGAAAACGTCGTGAC
SEQ: 041  (226) CAGCATGGGCGGCGGGGCGCGCGAACACACTTTACTACACACTTTACTACATAAAAAATCTGATGGCGGAAATTGAATAAAATTGAAAACGTCGTAAC
SEQ: 042  (226) CAGCATGGGCGGCGGGGCGCGCGAACACACTTTACTACACACTTTACTACATAAAAAATCTGACGGCGGTAATAAAATTGAAAACGTCGTAAC
SEQ: 043  (226) CAGCATGGGCGGCGGGGCGCGCGAACACACTTTACTACACACTTTACTACATAAAAAATCTGACGGCGGTAATAAAATTGAAAACGTCGTAAC
SEQ: 044  (226) CAGCATGGGGGGCGGGGCGCGCGAACACACTTTACTACACACTTTACTACATAAAAAATCTGACGGCGGCGGAAATAAAATTGAAAACGTCGTAAC
SEQ: 045  (226) CAGCATGGGGGGCGGGGCGCGCGAACACACTTTACTACACACTTTACTACATAAAAAATCTGACGGCGGCGGAAATAAAATTGAAAACGTCGTCAC
SEQ: 046  (226) CAGCATGGGGGGCGGGGCGCGCGAACACACTTTACTACACACTTTACTACATAAAAGAATCTGACGGCGGCGGAAATAAAATTGAAAACGTCGTAAC
SEQ: 047  (226) CAGCATGGGCGGCGCGCTAACACGCTTTACTACACGCTTTACTACATAAAAAATCTGGACGGCGCGCGATAAAATTGAAAACGTCGTAAC
SEQ: 048  (226) CAGCATGGGTGGCGCGCTAACACGCTTTACTACACGCTTTACTACATAAAAAATCTGGACGGCGGATAAATTGAGAACGTCGTAAC
SEQ: 049  (226) CAGCATGGGCGGCGGGGGAACACACTTTACTACACGCTTTACTACATAAAAAATCTGGACGGCGGTAATAAATTGAAAACGTCGTAAC
SEQ: 050  (226) CAGCATGGGCGGCGGGGGAACACACTTTACTACACGCTTTACTACATAAAAAATCTGGATGGCGGTAATAAATTGAAAACGTCGTCAC
SEQ: 051  (226) CAGCATGGGCGGCGGGGGAACACACTTTACTACACGCTTTACTACATAAAAAATCTGGACGGCGGTAATAAAATTGAAAACGTCGTAAC
SEQ: 052  (226) CAGCATGGTGGCGGAACACACTTTACTACACACTTTACTACATAAAAAATCTGGACGGCGGAAATAAATAAAATGAAAACGTCGTAAC
SEQ: 053  (226) CAGCATGGTGGCGGAACACACTTTACTACACACTTTACTACATAAAAAATCTGGACGGCGGAAATAAATAAAGTTGAAACGTCGTAAC
SEQ: 054  (226) CAGCATGGGTGGCGCGGAACACACTTTACTACACACTTTACTACATAAAAAATCTGGACGGCGGAAATAAAATTGAAAACGTCGTAAC
```

```
         451                                                                                                   525
SEQ: 021 (451) TCATGGCGTTGGGCACATTGGTTTATTGATGAACAGCCTCAAGTCAACAGCCTGATTAAAGAAGACTGAACGGCGG
SEQ: 022 (451) TCATGGCGTTGGGCACATTGGTTTATTGATGATGAACAGCCAAGTCAAGTCAACAGCCTGATTAAAGAAGACTGAACGGCGG
SEQ: 023 (451) CCATGGCGTTGGGCACATTGGTTTATTGATGATGAACAGCCAAGTCAAGTCAACAGCCTGATTAAAGAAGACTGAACGGCGG
SEQ: 024 (451) TCATGGCGTTGGGCACATTGGTTTATTGATGATGAACAGCCAAGTCAAGTCAACAGCCTGATTAAAGAAGACTGAACGGCGG
SEQ: 025 (451) CCATGGCGTTGGGCACATTGGTCTATTAACCTCAAGCAACAGCCAAGTCAAGTCAACAGCCTGATTAAAGAAGACTGAACGGCGG
SEQ: 026 (451) CCATGGCGTTGGGCACATTGGTCTATTGATGAACAGCCAAGTCAAGTCAACAGGATATATTAAAGAAGACTGAACGGCGG
SEQ: 027 (451) TCATGGCGTTGGGCACATTGGTTTATTGATGAACAGCCAAGTCAAGTCAACAGGATATATTAAAGAAGACTGAACGGCGG
SEQ: 028 (451) TCATGGCGTTGGGCACATTGGTTTATTGATGAACAGCCAAGTCAAGTCAACAGCCTGATTAAAGAAGACTGAACGGCGG
SEQ: 029 (451) TCATGGCGTCGGACATATCGCCCTTCTGTACAGCAACAGCCAAGTCAACAGCCTGATTAAAGAAGACTGAACGGCGG
SEQ: 030 (451) TCATGGCGTTGGGCACACTGGTTTATTGATGAACAGCCAAGTCAAGTCAACAGCCTGATTAAAGAAGACTGAACGGCGG
SEQ: 031 (451) TCATGGCGTTGGGCACATTGGTTTATTGATGAACAGCCCTTCTGTACAGCAACAGCCAAGTCAACAGCCTGATTAAAGAAGACTGAACGGCGG
SEQ: 032 (451) TCATGGCGTCGGACACATCGCCCTTCTGATGAACAGCCAAGTCAAGTCAACAGCCTGATTAAAGAAGACTGAACGGCGG
SEQ: 033 (451) CCATGGCGTTGGGCACATTGGTTTATTGATGAACAGCCAAGTCAAGTCAACAGCCTGATTAAAGAAGACTGAACGGCGG
SEQ: 034 (451) TCATGGCGTCGTCGGACATATCGGCCTTCTGATGAACAGCCAAGTCAAGTCAACAGCCTGATTAAAGAAGACTGAACGGCGG
SEQ: 035 (451) CCATGGCGTTGGGCACATTGGTTTATTGATGAACAGCCAAGTCAAGTCAACAGCCTGATTAAAGAAGACTGAACGGCGG
SEQ: 036 (451) TCATGGCGTTGGGCACATTGGTTTATTGATGAACAGCCAAGTCAAGTCAACAGCCTGATTAAAGAAGACTGAACGGCGG
SEQ: 037 (451) TCATGGTGTCGGCACATTGGTTTATTGATGAACAGCCAAGTCAAGTCAACAGCCTGATTAAAGAAGACTGAACGGCGG
SEQ: 038 (451) TCATGGCGTTGGGCACATTGGTTTATTGTTGATGAACAGCCAAGTCAAGTCAACAGCCTGATTAAAGAAGACTGAACGGCGG
SEQ: 039 (451) TCATGGCGTTGGGCACATTGGTTTATTGTTGATGAACAGCCAAGTCAAGTCAACAGCCTGATTAAAGAAGAGGCTTAACGGCGG
SEQ: 040 (451) TCATGGCGTTGGGCACATTGGTTTATTGATGAACAGCCAAGTCAAGTCAACAGCCTGATTAAAGAAGAGGGCTGAACGGCGG
SEQ: 041 (451) TCATGGCGTTGGGCACATTGGTTGTTGTTGATGAACAGCCAAGTCAAGTCAACAGCCTGATTAAAGAAGAGGGCTGAACGGCGG
SEQ: 042 (451) TCATGGCGTTGGGCACATTGGTTGTTGTTGATGAACAGCCAAGTCAAGTCAACAGCCTGATTAAAGAAGAGGGCTGAACGGCGG
SEQ: 043 (451) CCATGGCGTTGGGCACATTGGTTGTTGTTGATGAACAGCCAAGTCAAGTCAACAGCCTGATTAAAGAAGAGGGCTGAACGGCGG
SEQ: 044 (451) TCATGGCGTTGGGCACATTGGTTGTTGTTGATGAACAGCCAAGTCAAGTCAACAGCCTGATTAAAGAAGAGGGCTTAACGGCGG
SEQ: 045 (451) TCATGGCGTTGGGCACATTGGTTGTTGTTGATGAACAGCCAAGTCAAGTCAACAGCCTGATTAAAGAAGAGGGCTGAACGGCGG
SEQ: 046 (451) TCATGGCGTTGGGCACATTGGTTGTTGTTGATGAACAGCCAAGTCAAGTCAACAGCCTGATTAAAGAAGAGGGCTGAACGGCGG
SEQ: 047 (451) TCATGGCGTTGGGCACATTGGTTGTTGTTGATGAACAGCCAAGTCAAGTCAACAGCCTGATTAAAGAAGAGGGCTGAACGGCGG
SEQ: 048 (451) TCATGGCGTTGGGCACATTGGTTGTTGTTGATGAACAGCCAAGTCAAGTCAACAGCCTGATTAAAGAAGAGGGCTGAACGGCGG
SEQ: 049 (451) TCATGGCGTTGGGCACATTGGTTGTTGTTGATGAACAGCCAAGTCAAGTCAACAGCCTGATTAAAGAAGAGGGCTGAACGGCGG
SEQ: 050 (451) TCATGGCGTTGGGCACATTGGTTGTTGTTGATGAACAGCCAAGTCAAGTCAACAGCCTGATTAAAGAAGAGGGCTGAACGGCGG
SEQ: 051 (451) TCATGGCGTTGGGCACATTGGTTGTTGTTGATGAACAGCCAAGTCAAGTCAACAGCCTGATTAAAGAAGAGGGCTTAACGGCGG
SEQ: 052 (451) TCATGGCGTTGGGCACATTGGTTGTTGTTGATGAACAGCCAAGTCAAGTCAACAGCCTGATTAAAGAAGAGGGCTGAACGGCGG
SEQ: 053 (451) TCATGGCGTTGGGCACATTGGTTGTTGTTGATGAACAGCCAAGTCAAGTCAACAGCCTGATTAAAGAAGAGGGCTGAACGGCGG
SEQ: 054 (451) TCATGGCGTTGGGCACATTGGTTGTTGTTGATGAACAGCCAAGTCAAGTCAACAGCCTGATTAAAGAAGAGGGCTGAACGGCGG
```

FIGURE 4g

```
                526                            544
SEQ: 021  (526) GGGACTCAATACGAATTGA
SEQ: 022  (526) GGGACTCAATACGAATTGA
SEQ: 023  (526) GGGACTGAATACAAATTGA
SEQ: 024  (526) GGGACTCAATACGAATTGA
SEQ: 025  (526) GGGCCACAATACGAATTGA
SEQ: 026  (526) AGGCCTAAATACGAATTGA
SEQ: 027  (526) GGGCCTAAATACAAATTGA
SEQ: 028  (526) GGGCCTAAATACAAATTGA
SEQ: 029  (526) GGGCCAAAATACAAATTGA
SEQ: 030  (526) GGGCCACAATACAAATTGA
SEQ: 031  (526) GGGCCTGAATACAAATTGA
SEQ: 032  (526) GGGCCTCAATACGAATTGA
SEQ: 033  (526) GGGACTCAATACGAATTGA
SEQ: 034  (526) GGGACTCAATACAAATTGA
SEQ: 035  (526) GGGCCACAATACACAATTGA
SEQ: 036  (526) AGGCCACAATACACAATTGA
SEQ: 037  (526) AGGCCACAATACAAATTGA
SEQ: 038  (526) AGGCCACAATACAAATTGA
SEQ: 039  (526) AGGCCACAATACAAATTGA
SEQ: 040  (526) GGGCCACAATACAAATTGA
SEQ: 041  (526) GGGCCACAGAATACGAATTGA
SEQ: 042  (526) GGGATTAAATACGAATTGA
SEQ: 043  (526) GGGCCAGAATACGAATTGA
SEQ: 044  (526) AGGCCAGAATACGAATTGA
SEQ: 045  (526) GGGCCACAATACGAATTGA
SEQ: 046  (526) GGGCCAGAATACGAATTGA
SEQ: 047  (526) AGGCCTAAATACAAATTGA
SEQ: 048  (526) AGGCCAGAATACAAATTGA
SEQ: 049  (526) AGGCCAAAATACGAATTGA
SEQ: 050  (526) AGGCCAAAATACGAATTGA
SEQ: 051  (526) AGGCCAGAATACGAATTGA
SEQ: 052  (526) GGGCCAAAATACGAATTGA
SEQ: 053  (526) GGGCCAAAATACAAATTGA
SEQ: 054  (526) AGGACAAAATACAAATTGA
```

FIGURE 4h

| SEQ: | (Signal peptide) | -35 | -1 | 1 | (Mature region) | 40 |
|---|---|---|---|---|---|---|
| SEQ: 055 | (1) | --MKFVKRRIIALVTILVLSVTSLFAMQP | -SAKAA | EHNPVVMVHGIGGASYNFAGIKSYLVSQGWSRGKLYAVDF |
| SEQ: 056 | (1) | --MKFVKRRIIALVTILMLSVTSLFALQP | -SAKAA | EHNPVVMVHGIGGASFNFAGIKSYLVSQGWSRDKLYAVDF |
| SEQ: 057 | (1) | --MKFVKRRIIALVTILVLSVTSLFAMQP | -SAKAA | DTIQLLWFTGIGGASYNFAGIKSYLVSQGWSRGKLYAVDF |
| SEQ: 058 | (1) | --MKFVKRRIIALVTILVLSVTSLFAMQP | -SAKAA | EHNPVVMVHGIGGASYNFAGIKSYLVSQGWSRGKLYAVDF |
| SEQ: 059 | (1) | --MKFIKRRIIALVTILVLSVTSLFAMQP | -SAKAA | EHNPVVMVHGIGGASYNFAGIKSYLVSQGWSRGELYAVDF |
| SEQ: 060 | (1) | --MKFVKRRIIALVTILVLSVTSLFAMQP | -SAKAA | EHNPVVMVHGIGGASYNFAGIKSYLVSQGWSRGKLYAVDF |
| SEQ: 061 | (1) | --MKFVKRRIIALVTILVLSVTSLFALQP | -SAKAA | EHNPVVMVHGIGGASYNFAGIKSYLVSQGWSRDKLYAVDF |
| SEQ: 062 | (1) | --MKFVKRRIIALVTILVLSVTSLFAMQP | -SAKAA | EHNPVVMVHGIGGASFNFAGIKSYLVSQGWSRDKLYAVDF |
| SEQ: 063 | (1) | --MKFVKRRIIALVTILMLSVTSLFALQP | -SAKAA | EHNPVVMVHGIGGASFNFAGIKSYLVSQGWSRDKLYAVDF |
| SEQ: 064 | (1) | --MKFVKRRIIALVTILMLSVTSLFALQP | -SAKAA | EHNPVVMVHGIGGASFNFAGIKSYLVSQGWDQNQLFAIDF |
| SEQ: 065 | (1) | MKVIFVKKRSLQILVALALVLGSIAFIQP | KEAKAA | EHNPVVMVHGMGGASYNFASIKRYLVSQGWDRNQLFAIDF |
| SEQ: 066 | (1) | MKVIFVKKRSLQILVLALVLALVMGSMAFIQP | KEAKAA | EHNPVVMVHGMGGASYNFASIKSYLVSQGWDRNQLYAIDF |
| SEQ: 067 | (1) | MKVIFVKKRSLQILALALVTILMLSVTSLFALQP | KEAKAA | EHNPVVMVHGIGGASYNFFSIKSYLATQGWSRGKLYAVDF |
| SEQ: 068 | (1) | --MKFVKRRIIALVTILMLSVTSLFALQP | -SAKAA | EHNPVVMVHGIGGASFNFAGIKSYLVSQGWSRDKLYAVDF |
| SEQ: 069 | (1) | --MKFVKRRIIALVTILMLSVTSLFALQP | -SAKAA | EHNPVVMVHGIGGASFNFAGIKSYLVSQGWSRDKLYAVDF |
| SEQ: 070 | (1) | --MKFVKRRIIALVTILMLSVTSLFALQP | -SAKAA | EHNPVVMVHGIGGASYNFAGIKSYLVSQGWSRDKLYAVDF |
| SEQ: 071 | (1) | --MKFVKRRIIALVTILMLSVTSLFALQP | -SAKAA | EHNPVVMVHGIGGASYNFAGIKSYLVSQGWSRDKLYAVDF |
| SEQ: 072 | (1) | --MKFVKRRSLQILVALALVIGSMAFIQP | KEIKAA | EHNPVVMVHGIGGASFNFAGIKSYLVNQGWDRNQLFAIDF |
| SEQ: 073 | (1) | MKVIFVKKRSLQILVALALVIGSMAFIQP | KEIKAA | EHNPVVMVHGIGGASFNFAGIKSYLVNQGWDRNQLFAIDF |
| SEQ: 074 | (1) | --MKFVKRRIIALVTILMLSVTSLFALQP | -SAKAA | EHNPVVMVHGIGGASFNFAGIKSYLVSQGWSRDKLYAVDF |

FIGURE 5a

```
      41                                                                          115
SEQ: 055 (73) WDKTGTNYNNGPVLSRFVQKVLDETGAKKVDIVAHSMGGANTPYYIKNLDGGNKIENVVTLGGANRSTTSKALPG
SEQ: 056 (73) WDKTGTNYNNGPVLSRFVQKVLDETGAKKVDIVAHSMGGANTLYYIKNLDGGNKVANVVTLGGANRLTTGKALPG
SEQ: 057 (73) WDKTGTNYNNGPVLPRFVQKVLDETGAKKVDIVAHSMGGANTLYYIKNLDGGNKVDIVVTLGGANRLTTSKALPG
SEQ: 058 (73) WDKTGTNYNNGPVLSRFVQKVLDETGAKKVDIVAHSMGGANTLYYIKNLDGGNKIENVVTLGGANRLTTSKALPG
SEQ: 059 (73) WDKTGTNYNNGPVLSRFVQKVLDETGAKKVDIVAHSMGGANTLYYIKNLDGGNKIENVVTLGGANRLTTSKALPG
SEQ: 060 (73) WDKTGTNYNNGPVLSRFVQKVLDETGAKKVDIVAHSMGGANTLYYIKNLDGGNKIENVVTLGGANRLTTSKALPG
SEQ: 061 (73) WDKTGTNYNNGPVLSRFVQKVLDETGAKKVDIVAHSMGGANTLYYIKNLDGGNKIENVVTLGGANRLTTSKALPG
SEQ: 062 (73) WDKTGTNYNNGPVLSRFVQKVLDETGAKKVDIVAHSMGGANTLYYIKNLDGGNKIENVVTLGGANRLTTSKALPG
SEQ: 063 (73) KDKTGTNYNNGPVLSRFVQKVLDETGAKKVDIVAHSMGGANTLYYIKNLDGGNKVENVVTLGGANRLTTGKALPG
SEQ: 064 (73) XDKTGNNRNNGPRLSRFVKDVLDKTGAKKVDIVAHSMGGANTLYYIKNLDGGDKIENVVTLGGANGLVSLRALPG
SEQ: 065 (76) IDKTGNNLNNGPRLSRFVKDVLAKTGAKKVDIVAHSMGGANTLYYIKNLDGGDKIENVVTLGGANGLVSLRALPG
SEQ: 066 (76) IDKTGNNLNNGPRLSRFVKDVLAKTGAKKVDIVAHSMGGANTLYYIKNLDGGDKIENVVTIGGANGLVSLRALPG
SEQ: 067 (73) IDKTGNNRNNGPVLSRFVKDVLDETGAKKVDIVAHSMGGANTLYYIKNLDGGNKIENVVTLGGANRLTTGKALPG
SEQ: 068 (73) IDKTGNNLNNGPVLSRFVKKVLDETGAKKVDIVAHSMGGANTLYYIKNLDGGNKIENVVTLGGANRLTTGKALPG
SEQ: 069 (73) WDKTGNNLNNGPVLSRFVKKVLDETGAKKVDIVAHSMGGANTLYYIKNLDGGNKIENVVTLGGANRLVTGKALPG
SEQ: 070 (73) SDKTGNNLNNGPVLSRFVKDVLDETGAKKVDIVAHSMGGANTLYYIKNLDGGNKIENVVTLGGANRLVTGKALPG
SEQ: 071 (73) KDKTGNNRNNGPRLSRFVKDVLDKTGAKKVDIVAHSMGGANTLYYIKNLDGGDKIENVVTIGGANGLVSSRALPG
SEQ: 072 (73) IDKTGNNRNNGPRLSRFVKDVLDKTGAKKVDIVAHSMGGANTLYYIKNLDGGDKIENVVTIGGANGLVSLRALPG
SEQ: 073 (76) IDKTGNNRNNGPRLSRFVKDVLDKTGAKKVDIVAHSMGGANTLYYIKNLDGGDKIENVVTIGGANGLVSLRALPG
SEQ: 074 (73) RDKTGNNRNNGPRLSKFVKDVLDKTGAKKVDIVAHSMGGANTLYYIKNLDGGDKIENVVTIGGANGLVSSRALPG
```

FIGURE 5b

```
        116                                                               181
SEQ: 055  TDPNQKILYTSIYSSADMIVMN-YLSKLDGAKNAQIHGVGHIGLLMNSQVNSLIKEGLNGGQNTN
SEQ: 056  TDPNQKILYTSIYSSADMIVIN-YLSRLDGARNVQIHGVGHIGLLMNSQVNSLIKEGLNGGLNTN
SEQ: 057  TDPNQKILYTSIYSSADMIVMN-YLSKLDGAKNVQIHGVGHIGLLMNSQVNSLIKEGLNGGHNTN
SEQ: 058  TDPNQKILYTSIYSSADMIVMN-YLSKLDGAKNVQIHGVGHIGLLMNSQVNSLIKEGLNGGLNTN
SEQ: 059  TDPNQKILYTSIYSSANMIVMN-YLSKLDGAKNVQIHGVGHIGLLMNSQVNSLIKEGLNGGLNTN
SEQ: 060  TDPNQKILYTSIYSSADMIVMN-YLSKLDGAKNAQIHGVGHIGLLMNSQVNSLIKEGLNGGLDTN
SEQ: 061  TDPNQKILYTSIYSSADMIVMN-YLSKLDGAKNAQIHGVGHIGLLMNSQVNSLIKEGLNGGHNTN
SEQ: 062  TDPNQKILYTSIYSSADMIVMN-YLSKLDGAKNVQIHGVGHIGLLMNSQVNSLIKEGLNGGHNTN
SEQ: 063  TDPNQKILYTSIYSSADMIVMN-YLSRLDGARNVQIHGVGHIGLLYSSQVNSLIKEGLNGGLNTN
SEQ: 064  TDPNQKILYTSVYSSADLIVVN-SLSRLIGARNILIHGVGHIGLLTSSQVKGYIKEGLNGGLNTN
SEQ: 065  TDPNQKILYTSVYSSADLIVVN-SLSRLIGARNVLIHGVGHIGLLTSSQVKGYIKEGLNGGQNTN
SEQ: 066  TDPNQKILYTSVYSSADLIVVN-SLSRLIGARNVLIHGVGHIGLLASSQVKGYIKEGLNGGQNTN
SEQ: 067  TDPNQKILYTSVYSSADLIVVN-SLSQFNWRKKHPDPGVGHIGLLTSSQVKGYIKEGLNGGLNTN
SEQ: 068  TDPNQKILYTSVYSSADMIVMN-YLTKLDGAKNVQIHGVGHIGLLYSSQVNSLIKEGLNGGLNTN
SEQ: 069  TDPNQKILYTSVYSSADMIVMN-YLSKLDGAKNVQIHGVGHIGLLYSSQVNSLIKEGLNGGLNTN
SEQ: 070  TDPNQKILYTSVYSSADMIVMN-YLSK DGAKNVQIHGVGHIGLLYSSQVNSLIKEGLNGGLNTN
SEQ: 071  TDPNQKILYTSVYSSADLIVVN-SLSRLIGARNVQIHGVGHIGLLTSSQVKGYIKEGLNGGLNTN
SEQ: 072  TDPNQKILYTSVYSSADLIVVN-SLSRLIGARNVQIHGVGHIGLLTSSQVKGYIKEGLNGGLNTN
SEQ: 073  TDPNQKILYTSVYSSADLIVVN-SLSRLTGARNVLIHGVGHIGLLTSSQVKGYIKEGLNGGLNTN
SEQ: 074  TDPNQKILYTSVYKLSRSHCRQQSLSFNWLQETVQIHGVGHIGLLTSSQVKGYIKEGLNGGLNTN
```

```
                1                                                                              75
SEQ: 075  (1)  EHNPVVMVHGIGGASFNFAGIKSYLVSQGWSRGKLYAVDFWDKTGTNYNYNNGPVLSRFVKKVLDETGAKKVDIVAH
SEQ: 076  (1)  EHNPVVMVHGIGGASFNFAGIKSYLVSQGWSRGKLYAVDFWDKTGTNYNYNNGPVLSRFVKDVLDKTGAKKVDIVAH
SEQ: 077  (1)  EHNPVVMVHGIGGASFNFAGIKSYLVSQGWSRGKLYAVDFWDRTGTNYNYNNGPVLSRFVKKVLDETGAKKVDIVAH
SEQ: 078  (1)  EHNPVVMVHGIGGASFNFAGIKSYLVSQGWSRGKLYAVDFWDKTGTNYNYNNGPVLSRFVQKVLDETGAKKVDIVAH
SEQ: 079  (1)  EHNPVVMVHGIGGASFNFAGIKSYLVSQGWSRGKLYAVDFWDKTGTNYNYNNGPVLSRFVQKVLDETGAKKVDIVAH
SEQ: 080  (1)  EHNPVVMVHGIGGASFNFAGIKSYLVSQGWSRGKLYPVDFWDKTGTNYNYNNGPVLSRFVQKVLDETGAKKVDIVAH
SEQ: 081  (1)  EHNPVVMVHGIGGASFSFAGIKSYLVSQGWSRGKLYAVDFWDKTGTNYNYNNGPVLSRFVQKVLDETGAKKVDIVAH
SEQ: 082  (1)  EHNPVVMVHGIGGASFSFAGIKSYLVSQGWSRGKLYAVDFWDKTGTNYNYNNGPVLSRFVQKVLDETGAKKVDIVAH
SEQ: 083  (1)  EHNPVVMVHGIGGASYSFAGIKSYLVSQGWSRGKLYAVDFWDKTGTNYNYNNGPVLSRFVQKVLDETGAKKVDIVAH
SEQ: 084  (1)  EHNPVVMVHGIGGASYSFAGIKSYLVSQGWSRGKLYTVDFWDKTGTNYNYNNGPVLSRFVQKVLDETGAKKVDIVAH
SEQ: 085  (1)  EHNPVVMVHGIGGASYNFAGIKSYLVSQGWSRGKLYAVDFWDRTGTNYNYNNGPVLSRFVQKVLDETGAKKVDIVAH
SEQ: 086  (1)  EHNPVVMVHGIGGASFNFAGIRSYLVSQGWSRDKPYAVDFWDKTGTNYNYNNGPVLSRFVQKVLDETGAKKVDIVAH
SEQ: 087  (1)  EHNPVVMVHGIGGASFNFAGIRSYLVSQGWSRDKLYAVDFWDKTGTNYNYNNGPVLSRFVQKVLDKTGAKKVDIVAH
SEQ: 088  (1)  EHNPVVMVHGIGGASFNFAGIKSYLVSQGWSRDKPYAVDFWDKTGTNYNYNNGPVLSRFVQKVLDETGAKKVDIVAH
SEQ: 089  (1)  EHNPVVMVHGIGGASFNFAGIKSYLVSQGWPRDKLYAVDFWDKTGTNYNYNNGPVLSRFVQKVLDETGAKKVDIVAH
SEQ: 090  (1)  EHNPVVMVHGIGGASFSFAGIRSYLVSQGWPRDKLYAVDFWDKTGTNYNYNNGPVLSRFVQKVLDETGAKKVDIVAY
SEQ: 091  (1)  EHNPVVMVHGIGGASFSFAGIKSYLVSQGWPRDKLYAVDFWDKTGTNYNYNNGPVLSRFVQKVLDETGAKKVDIVAH
SEQ: 092  (1)  EHNPVVMVHGIGGASFSFAGIKSYLVSQGWSRDKLYAVDFWDKTGTNYNYNNGPVLSRFVQKVLDETGAKKVDIVAH
SEQ: 093  (1)  EHNPVVMVHGIGGTSFNFAGIKSYLVSQGWSRDKLYAVDFWDKTGTNYNYNNGPVLSRFVQKVLDETGAKKVDIVAH
SEQ: 094  (1)  EHNPVVMVHGIGGASFNFAGIKSYLVSQGWSRDKLYAVDFSDKTGTNYNYNNGPVLSRFVQKVLDETGAKKVDIVAH
SEQ: 095  (1)  EHNPVVMVHGIGGASFNFAGIKSYLVSQGWSRDKLYAVDFSDKTGTNYNYNNGPVLSRFVQKVLDETGAKKVDIVAH
SEQ: 096  (1)  KHNPVVMVHGIGGASFNFAGIKSYLVSQGWSRGKLYAVDFWDRTGTNYNYNNGPVLSRFVQKVLDETGAKKVDIVAH
SEQ: 097  (1)  EHNPVVMVHGIGGASFNFAGIKSYLESQGWSRGKLYAVDFWDRTGTNYNYNNGPVLSRFVQKVLDETGAKKVDIVAH
SEQ: 098  (1)  EHNPVVMVHGIGGASFNFAGIKSYLVSQGWSRGKLYAVDFWDKTGKDKTGTNYNYNNGPVLSRFVQKVLDETGAKKVDIVAH
SEQ: 099  (1)  EHNPVVMVHGIGGASFNFAGIKSYLVSQGWSRGKLYAVDFWDKTGTNYNYNNGPVLSRFVQKVLDETGAKKVDIVAH
SEQ: 100  (1)  EHNPVVMVHGIGGASFNFAGIKSYLVSQGWSRGKLYAVDFKDKTGTNYNYNNGPVLSRFVKKVLDETGAKKVDIVAH
SEQ: 101  (1)  EHNPVVMVHGIGGASFNFAGIKSYLVSQGWSRGKLYAVDFKDKTGTNYNYNNGPVLSRFVKKVLDETGAKKVDIVAH
SEQ: 102  (1)  EHNPVVMVHGIGGASFNFAGIKSYLVSQGWSRDKLYAVDFWDKTGTNYNYNNGPVLSRFVKKVLDETGAKKVDIVAH
SEQ: 103  (1)  EHNPVVMVHGIGGASFNFAGIKSYLVSQGWSRDKLYAVDFWGKTGTNYNYNNGPVLSRFVKKVLDETGAKKVDIVAH
SEQ: 104  (1)  EHNPVVMVHGIGGASFNFAGIKSYLVSQGWSRDKLYAVDFKDKTGTNYNYNNGPVLSRFVKKVLDETGAKKVDIVAH
SEQ: 105  (1)  EHNPVVMVHGIGGASFNFAGIKSYLVSQGWSRDELYAVDFWDETGTNYNYNNGPVLSRFVKKVLDETGAKKVDIVAH
SEQ: 106  (1)  KHNPVVMVHGIGGASFNFAGIKSYLVSQGWSRDKLYAVDFWDKTGTNYNYNNGPVLSRFVQKVLDETGAKKVDIVAH
SEQ: 107  (1)  EHNPVVMVHGIGGASFNFAGIKSYLVSQGWSRDKLYAVDFWDKTGTNYNYNNGPVLSRFVQKVLDETGAKKVDIVAH
SEQ: 108  (1)  EHNPVVMVHGIGGASFNFAGIKSYLVSQGWSRGKLYAVDFWDKTGTNYNYNNGPVLSRFVQKVLDETGAKKVDIVAH
```

|  |  | 151 | 180 |
|---|---|---|---|
| SEQ: 075 | (151) | HGVGHIGLLMNSQVNSLIKEGLNGGGLNTN |
| SEQ: 076 | (151) | HGVGHIGLLMNSQVNSLIKEGLNGGGLNTN |
| SEQ: 077 | (151) | HGVGHIGLLMNSQVNSLIKEGLNGGGLNTN |
| SEQ: 078 | (151) | HGVGHIGLLMNSQVNSLIKEGLNGGGLNTN |
| SEQ: 079 | (151) | HGVGHIGLLTSSQVKGYIKEGLNGGGHNTN |
| SEQ: 080 | (151) | HGVGHIGLLMNSQVKGYIKEGLNGGGLNTN |
| SEQ: 081 | (151) | HGVGHIGLLMNSQVNSLIKEGLNGGGLNTN |
| SEQ: 082 | (151) | HGVGHIGLLMNSQVNSLIKEGLNGGGLNTN |
| SEQ: 083 | (151) | HGVGHIGLLYSSQVNSLIKEGLNGGGQNTN |
| SEQ: 084 | (151) | HGVGHTGLLMNSQVNSLIKEGLNGGGHNTN |
| SEQ: 085 | (151) | HGVGHIGLLYSSQVNSLIKEGLNGGGLNTN |
| SEQ: 086 | (151) | HGVGHIGLLMNSQVNSLIKEGLNGGGHNTN |
| SEQ: 087 | (151) | HGVGHIGLLYSSQVNSLIKEGLNGGGLNTN |
| SEQ: 088 | (151) | HGVGHIGLLMNSQVNSLIKEGLNGGGLNTN |
| SEQ: 089 | (151) | HGVGHIGLLMNSQVNSLIKEGLNGGGLNTN |
| SEQ: 090 | (151) | HGVGHIGLLMNSQVNRLIKEGLNGGGHNTN |
| SEQ: 091 | (151) | HGVGHIGLLMNSQVNRLIKEGLNGGGHNTN |
| SEQ: 092 | (151) | HGVGHIGLLMNSQVNRLIKEGLNGGGHNTN |
| SEQ: 093 | (151) | HGVGHIGLLMNSQVNRLIKEGLNGGGHNTN |
| SEQ: 094 | (151) | HGVGHIGLLMNSQVNSLIKEGLNGGGHNTN |
| SEQ: 095 | (151) | HGVGHIGLLMNSQVNSLIKEGLNGGGHNTN |
| SEQ: 096 | (151) | HGVGHIGLLMNSQVNSLIKEGLNGGGLNTN |
| SEQ: 097 | (151) | HGVGHIGLLMNSQVNSLIKEGLNGGGQNTN |
| SEQ: 098 | (151) | HGVGHIGLLMNSQVNSLIKEGLNGGGQNTN |
| SEQ: 099 | (151) | HGVGHIGLLMNSQVNSLIKEGLNGGGHNTN |
| SEQ: 100 | (151) | HGVGHIGLLMNSQVNSLIKEGLNGGGLNTN |
| SEQ: 101 | (151) | HGVGHIGLLMNSQVNSLIKEGLNGGGQNTN |
| SEQ: 102 | (151) | HGVGHIGLLMNSQVNSLIKEGLNGGGQNTN |
| SEQ: 103 | (151) | HGVGHIGLLMNSQVNSLIKEGLNGGGQNTN |
| SEQ: 104 | (151) | HGVGHIGLLMNSQVNSLIKEGLNGGGQNTN |
| SEQ: 105 | (151) | HGVGHIGLLMNSQVNSLIKEGLNGGGQNTN |
| SEQ: 106 | (151) | HGVGHIGLLMNSQVNSLIKEGLNGGGQNTN |
| SEQ: 107 | (151) | HGVGHIGLLMNSQVNSLIKEGLNGGGQNTN |
| SEQ: 108 | (151) | HGVGHIGLLMNSQVNSLIKEGLNGGGQNTN |

FIGURE 6c

SEQUENCE LISTING

<160> NUMBER OF SEQ ID NOS: 111

<210> SEQ ID NO 1
<211> LENGTH: 639
<212> TYPE: DNA
<213> ORGANISM: Bacillus pumilus

<400> SEQUENCE: 1

```
atgaaatttg taaaagaag gatcattgca cttgtaacaa ttttggtgct gtcagtcaca      60
tcgctgtttg cgatgcagcc gtcagcaaaa gccgctgaac acaatccagt tgttatggtt     120
cacggtatcg gaggagcttc atacaatttt gcgggaatta agagctatct cgtatctcag    180
ggctggtcac ggggcaagct gtatgcggtt gattttttggg acaagacagg gacgaattat    240
aacaatggcc cggtattatc acgatttgtg caaaaggttt tagacgaaac gggtgcgaaa     300
aaagtggata ttgtcgctca cagtatgggt ggcgcgaaca caccttacta cataaaaaat    360
ctggacggcg gaaataaaat tgaaaacgtc gtaacgcttg gcggcgcgaa ccgttcgacg    420
acaagcaagg cgcttccggg aacagatcca aatcaaaaga ttttatacac atccatttac    480
agcagtgccg atatgattgt catgaattac ttatcaaaat tagacggtgc taaaaacgct    540
caaattcatg gcgttgggca cattggttta ttgatgaaca gccaagtcaa cagcctgatt    600
aaagaaggac tgaacggcgg gggccaaaat acgaattaa                           639
```

<210> SEQ ID NO 2
<211> LENGTH: 639
<212> TYPE: DNA
<213> ORGANISM: Bacillus subtilis

<400> SEQUENCE: 2

```
atgaaatttg taaaaagaag gatcattgca cttgtaacaa ttttgatgct gtctgttaca     60
tcgctgtttg cgttgcagcc gtcagcaaaa gccgctgaac acaatccagt cgttatggtt    120
cacggtattg gagggcatc attcaatttt gcgggaatta agagctatct cgtatctcag    180
ggctggtcgc gggacaagct gtatgcagtt gattttttggg acaagacagg cacaaattat    240
aacaatggac cggtattacc acgatttgtg caaaaggttt tagatgaaac gggtgcgaaa     300
aaagtggata ttgtcgctca cagcatgggg ggcgcgaaca cactttacta cataaaaaat    360
ctggacggcg gaaataaagt tgcaaacgtc gtgacgcttg gcggcgcgaa ccgtttgacg    420
acaggcaagg cgcttccggg aacagatcca aatcaaaaga ttttatacac atccatttac    480
agcagtgccg atatgattgt cataaattac ttatcaagat tagatggtgc tagaaacgtt    540
```

```
caaatccatg gcgttggaca catcggcctt ctgtacagca gccaagtcaa cagcctgatt    600
aaagaagggc tgaacggcgg gggactcaat acaaattag                           639
```

<210> SEQ ID NO 3
<211> LENGTH: 639
<212> TYPE: DNA
<213> ORGANISM: Bacillus megaterium

<400> SEQUENCE: 3

```
atgaaatttg taaaaagaag gatcattgca cttgtaacaa ttttggtgct gtcagtcaca     60
tcgctgtttg cgatgcagcc gtcagcaaaa gccgctgaca caatccagtt gttatggttc    120
actggtatcg gaggagcttc atacaatttt gcgggaatta agagctatct cgtatctcag    180
ggctggtcac ggggcaagct gtatgcggtt gattttggg acaagacagg gacgaattat     240
aacaatggcc cggtattatc acgatttgtg caaaaggttt tagacgaaac gggtgcgaaa    300
aaagtggata ttgtcgctca cagcatgggt ggcgcgaaca cactttacta cataaaaaat    360
ctggacggcg gaaataaaat tgaaaacgtc gtaacgcttg gcggcgcgaa ccgtttgacg    420
acaagcaagg cgcttccggg aacagatcca aatcaaaaga tttttatacac atccatttac   480 agcagtgccg atatgattgt catgaattac ttatcaaaat tagacggtgc taaaaacgtt    540
caaattcatg gcgttgggca cattggttta ttgatgaaca gccaagtcaa cagcctgatt    600
aaagaaggac tgaacggcgg gggccacaat acaaattaa                           639
```

<210> SEQ ID NO 4
<211> LENGTH: 639
<212> TYPE: DNA
<213> ORGANISM: Bacillus lentus

<400> SEQUENCE: 4

```
atgaaatttg taaaaagaag gatcattgca cttgtaacaa ttttggtgct gtcagtcaca     60
tcgctgtttg cgatgcagcc gtcagcaaaa gccgctgaac acaatccagt tgttatggtt    120
cacggtatcg gaggagcttc atacaatttt gcgggaatta agagctatct cgtatctcag    180
ggctggtcac ggggcaagct gtatgcggtt gattttggg acaagacagg gacgaattat     240
aacaatggcc cggtattatc acgatttgtg caaaaggttt tagacgaaac gggtgcgaaa    300
aaagtggata ttgtcgctca cagcatgggt ggcgcgaaca cactttacta cataaaaaat    360
ctggacggcg gaaataaaat tgaaaacgtc gtaacgcttg gcggcgcgaa ccgtttgacg    420
acaagcaagg cgcttccggg aacagatcca aatcaaaaga tttttatacac atccatttac   480 agcagtgccg atatgattgt catgaattac ttatcaaaat tagacggtgc taaaaacgtt    540
caaattcatg gcgttgggca cattggttta ttgatgaaca gccaagtcaa cagcctgatt    600
aaagaaggac tgaacggcgg aggactaaat acaaattaa                           639
```

<210> SEQ ID NO 5
<211> LENGTH: 639
<212> TYPE: DNA
<213> ORGANISM: Bacillus circulans

<400> SEQUENCE: 5

```
atgaaatttta taaaaagaag gatcattgca cttgtaacaa ttttggtgct gtcagtcaca    60
tcgctgtttg cgatgcagcc gtcagcaaaa gccgctgaac acaatccagt tgttatggtt    120
cacggtatcg gaggagcttc atacaatttt gcgggaatta agagctatct cgtatctcag    180
```

| ggctggtcac gggcaagct gtatgcggtt gattttggg acaagacagg gacgaattat | 240 |
| aacaatggcc cggtattatc acgatttgtg caaaaggttt tagacgaaac gggtgcgaaa | 300 |
| aaagtggata ttgtcgctca cagcatgggt ggcgcgaaca cactttacta cataaaaaat | 360 |
| ctggacggcg aaataaaat tgaaaacgtc gtaacgcttg gcggcgcgaa ccgtttgacg | 420 |
| acaagcaagg cgcttccggg aacagatcca aatcaaaaga ttttatacac atccatttac | 480 |
| agcagtgccg atatgattgt catgaattac ttatcaaaat tagacggtgc taaaaacgtt | 540 |
| caaattcatg gcgttgggca cattggttta ttgatgaaca gccaagtcaa cagcctgatt | 600 |
| aaagaaggac tgaacggcgg gggcctcaat acaaattaa | 639 |

<210> SEQ ID NO 6
<211> LENGTH: 639
<212> TYPE: DNA
<213> ORGANISM: Bacillus azotoformans

<400> SEQUENCE: 6

| atgaaatttg taaaagaag gatcattgca cttgtaacaa ttttggtgct gtcagtcaca | 60 |
| tcgctgtttg cgatgcagcc gtcagcaaaa gccgctgaac acaatccagt tgttatggtt | 120 |
| cacggtatcg gaggagcttc atacaatttt gcgggaatta agagctatct cgtatctcag | 180 |
| ggctggtcac ggggcgagct gtatgcggtt gattttggg acaagacagg gacgaattat | 240 |
| aacaatggcc cggtattatc acgatttgtg caaaaggttt tagacgaaac gggtgcgaaa | 300 |
| aaagtggata ttgtcgctca cagcatgggt ggcgcgaaca cactttacta cataaaaaat | 360 |
| ctggacggcg aaataaaat tgaaaacgtc gtaacgcttg gcggcgcgaa ccgtttgacg | 420 |
| acaagcaagg cgcttccggg aacagatcca aatcaaaaga ttttatacac atccatttac | 480 |
| agcagtgcca atatgattgt catgaattac ttatcaaaat tagacggtgc taaaaacgta | 540 |
| caaattcatg gcgttgggca cattggttta ttgatgaaca gccaagtcaa cagcctgatt | 600 |
| aaagaaggac tgaacggcgg gggcctagat acaaattaa | 639 |

<210> SEQ ID NO 7
<211> LENGTH: 639
<212> TYPE: DNA
<213> ORGANISM: Bacillus firmus

<400> SEQUENCE: 7

| atgaaatttg taaaagaag gatcattgca cttgtaacaa ttttggtgct gtcagtcaca | 60 |
| tcgctgtttg cgatgcagcc gtcagcaaaa gccgctgaac acaatccagt tgttatggtt | 120 |
| cacggtatcg gaggagcttc atacaatttt gcgggaatta agagctatct cgtatctcag | 180 |
| ggctggtcac gggcaagct gtatgcggtt gattttggg acaagacagg gacgaattat | 240 |
| aacaatggcc cggtattatc acgatttgtg caaaaggttt tagacgaaac gggtgcgaaa | 300 |
| aaagtggata ttgtcgctca cagcatgggt ggcgcgaaca cactttacta cataaaaaat | 360 |
| ctggacggcg aaataaaat tgaaaacgtc gtaacgcttg gcggcgcgaa ccgtttgacg | 420 |
| acaagcaagg cgcttccggg aacagatcca aatcaaaaga ttttatacac atccatttac | 480 |
| agcagtgccg atatgattgt catgaattac ttatcaaaat tagacggtgc taaaaacgct | 540 |
| caaattcatg gcgttgggca cattggttta ttgatgaaca gccaagtcaa cagcctgatt | 600 |
| aaagaaggac tgaacggcgg aggccacaat acaaattaa | 639 |

<210> SEQ ID NO 8
<211> LENGTH: 639

```
<212> TYPE: DNA
<213> ORGANISM: Bacillus badius

<400> SEQUENCE: 8
atgaaatttg taaaagaag gatcattgca cttgtaacaa ttttggtgct gtcagtcaca      60
tcgctgtttg cgatgcagcc gtcagcaaaa gccgctgaac acaatccagt tgttatggtt    120
cacggtatcg aggagcttc atacaatttt gcgggaatta agagctatct cgtatctcag     180
ggctggtcac ggggcaagct gtatgcggtt gattttggg acaagacagg gacgaattat     240
aacaatggcc cggtattatc acgatttgtg caaaaggttt tagacgaaac gggtgcgaaa    300
aaagtggata ttgtcgctca cagcatgggt ggcgcgaaca cactttacta cataaaaaat    360
ctggacggcg aaataaaat tgaaaacgtc gtaacgcttg cggcgcgaa ccgtttgacg      420
acaagcaagg cgcttccggg aacagatcca aatcaaaaga ttttatacac atccatttac    480
agcagtgccg atatgattgt catgaattac ttatcaaaat tagacggtgc taaaaacgtt    540
caaattcatg gcgttgggca cattggttta ttgatgaaca gccaagtcaa cagcctgatt    600
aaagaaggac tgaacggcgg aggccacaat acaaattaa                           639

<210> SEQ ID NO 9
<211> LENGTH: 639
<212> TYPE: DNA
<213> ORGANISM: Bacillus sp.

<400> SEQUENCE: 9
atgaaatttg taaaagaag gatcattgca cttgtaacaa ttttgatgct gtctgttaca      60
tcgctgtttg cgttgcaacc gtcagcaaaa gccgctgaac acaatccagt cgttatggtt    120
cacggtattg agggggcatc attcaatttt gcgggaatta agagctatct cgtatctcag    180
ggctggtcgc gggacaagct gtatgcagtt gatttcaagg acaagacagg cacaaattat    240
aacaatggcc cggtattatc acgatttgtg caaaaggttt tagatgaaac gggtgcgaaa    300
aaagtggata ttgtcgctca cagcatgggg ggcgcgaaca cactttacta cataaaaaat    360
ctggacggcg aaataaagt tgaaaacgtc gtgacgcttg cggcgccaa ccgtttgacg      420
acaggcaagg cgcttccggg aacagatcca aatcaaaaga ttttatacac atccatttac    480
agcagtgccg atatgattgt catgaattat ttatcaagat tagatggtgc gagaaacgtt    540
caaatccatg gcgttggaca catcggcctt ctgtacagca gccaagtcaa cagcctgatt    600
aaagaagggc tgaacggcgg gggcctcaat acaaattaa                           639

<210> SEQ ID NO 10
<211> LENGTH: 639
<212> TYPE: DNA
<213> ORGANISM: Bacillus sp.

<400> SEQUENCE: 10
atgaaatttg taaaagaag gatcattgca cttgtaacaa ttttgatgct gtctgttaca      60
tcgctgtttg cgttgcaacc gtcagcaaaa gccgctgaac acaatccagt cgttatggtt    120
cacggtattg agggggcatc attcaatttt gcgggaatta agagctacct cgtatctcag    180
ggctggtcgc gggacaagct gtatgcagtt gatttctaag acaaaacagg gaataaccgc    240
aacaatggtc cgcgtctatc gagattcgtc aaagatgtgt tagacaaaac gggtgccaaa    300
aaagtagata ttgtggctca tagtatgggg ggagcgaaca cgctatacta tatcaagaat    360
ctagatggcg gcgataaaat tgagaacgtt gtcacaattg gtggagcaaa cggactcgtt    420
```

```
tcaagcagag cattaccagg cacagatcca atcaaaaaa ttctttacac atccgtctat      480
agctcagcag atcttattgt cgtcaacagc ctctctcgtt taattggcgc aagaaacatc      540
ctgatccatg gcgttggtca tatcggtcta ttaacctcaa gccaagtgaa agggtatatt      600
aaagaaggac tgaacggcgg aggcctcaat acaaattaa                             639
```

<210> SEQ ID NO 11
<211> LENGTH: 648
<212> TYPE: DNA
<213> ORGANISM: Bacillus sp.

<400> SEQUENCE: 11

```
atgaaagtga tttttgttaa gaaaaggagt ttgcaaattc ttgttgccct tgccttagtg       60
ctaggttcaa tagccttcat ccagccgaaa gaagccaaag cggctgagca taatccggtt      120
gtaatggtgc atggcatggg tggtgcgtct tataactttg cttcgatcaa acgatactta      180
gtatcacagg gatgggatca aaaccaactt tttgcaatcg atttcataga caaacaggc       240 aataacctaa caatggccc gaggctctcg agattcgtga agacgtact agccaaaacg        300 ggcgccaaaa aagtagatat tgtggctcat agtatgggcg gtgcgaacac gttatactat      360
attaaaaacc tagacggtgg agataaaatt gaaaacgtcg tcacattagg tggagcaaac      420
ggactcgtat cactcagagc attaccaggc accgatccaa atcaaaaaat tctttacaca      480
tctgtctata gctcagccga tctcattgtc gtcaacagcc tttcgcgttt aattggcgca      540
agaaacgtcc tgatccacgg cgttggacat atcggtctat taacctcaag ccaagtcaaa      600
ggctatgtga agaaggatt gaatggcggg ggacagaata caaattaa                   648
```

<210> SEQ ID NO 12
<211> LENGTH: 648
<212> TYPE: DNA
<213> ORGANISM: Bacillus sp.

<400> SEQUENCE: 12

```
atgaaagtga tttttgttaa gaaaaggagt ttgcaaattc ttgttgtgct tgcattggtg       60
atgggttcaa tggccttcat ccagccaaaa gagatcagag cggctgagca taatccggtt      120
gtgatggtac atggcatggg cggtgcgtct tataactttg cttcgattaa agttacttg       180 gtatcacaag gatgggatcg aaaccaatta tttgctatcg atttcataga caaacaggt      240 aataaccgca acaatggtcc gcgtctatcc agattcgtca agatgtgct agccaaaaca      300 ggtgccaaaa aagttgatat tgtggctcat agtatgggcg gagcgaacac gttatactat      360
attaagaatc tagacggcgg cgataaaata gaaaacgttg ttacacttgg tggagcgaac      420
ggactcgttt cactcagagc attaccaggc accgatccaa atcaaaaat cctttacaca      480 tccgtctaca gctcagccga tcttatcgtc gtcaacagcc tctcgcgttt aattggcgca     540
agaaacgtcc tcattcacgg cgttggtcac atcggtctat tagcttcaag ccaagtcaaa     600
ggctatatca agaaggact gaatggcgga ggccaaaata caaattaa                   648
```

<210> SEQ ID NO 13
<211> LENGTH: 648
<212> TYPE: DNA
<213> ORGANISM: Bacillus sp.

<400> SEQUENCE: 13

```
atgaaagtga tttttgttaa gaaaaggagt ttgcaaattc tcattgcgct tgcattggtg      60
attggttcaa tggcgtttat ccagccgaaa gaggcgaagg cggctgagca taatccggtt     120
```

```
gtgatggtgc atggcattgg cggtgcctct tataactttt tttctattaa aagttatttg    180
gccacacaag gctgggatcg aaaccaatta tatgctattg atttcataga caaaacagga    240
aataaccgca acaatggtcc gcgtctatcg agattcgtca agatgtgtt agacaaaacg      300 ggtgccaaaa aagtagatat tgtggctcat agtatgggtg agcgaacac gctatactat      360 atcaagaatc tagatggcgg cgataaaatt gagaacgttg tcacaattgg tggagcaaac    420
ggactcgttt caagcagagc attaccaggc acagatccaa atcaaaaaat tctttacaca    480
tccgtctata gctcagcaga tcttattgtc gtcaacagcc tctctcagtt taattggcgc    540
aagaaacatc ctgatccagg cgttggtcat atcggtctat aacctcaag ccaagtgaaa      600 gggtatatta agaaggact gaacggcgga ggcctcaata caaattaa                    648

<210> SEQ ID NO 14
<211> LENGTH: 639
<212> TYPE: DNA
<213> ORGANISM: Bacillus sp.

<400> SEQUENCE: 14
atgaaatttg taaaagaag gatcattgca cttgtaacaa ttttgatgct gtctgttaca      60
tcgctgtttg cgttgcaacc gtcagcaaaa gccgctgaac acaatccagt cgttatggtt    120
cacggtattg gagggcatc attcaatttt gcgggaatta agagctatct cgtatctcaa      180
ggctggtcgc gggacaagct gtatgcagtt gatttcaggg acaagacagg caataactta    240
aacaacggtc cagtattatc gcgtttcgtg aaaaaggtat tagatgaaac cggtgcgaaa    300
aaagtggata ttgtcgctca cagcatgggc ggcgctaaca cgctttacta cataaaaaat    360
ttggatggcg gtaataaaat tgaaaacgtc gtaacacttg gcggcgcgaa tcgtcttgtg    420
acaggcaagg cgcttccggg tactgatccc aaccaaaaga tcttgtacac atccgtttac    480
agtagtgctg atatgattgt tatgaattac ttaacaaaat tagacggggc taaaaatgtt    540
caaattcatg gtgtcggaca tatcggcctt ctgtacagca gccaagtcaa cagcctgatt    600
aaagaagggc ttaacggcgg aggcctcaat acaaattaa                            639

<210> SEQ ID NO 15
<211> LENGTH: 639
<212> TYPE: DNA
<213> ORGANISM: Bacillus sp.

<400> SEQUENCE: 15
atgaaatttg taaaagaag gatcattgca cttgtaacaa ttttgatgct gtctgttaca      60
tcgctgtttg cgttgcaacc gtcagcaaaa gccgctgaac acaatccagt cgttatggtt    120
cacggtattg gagggcatc attcaatttt gcgggaatta agagctatct cgtatctcag      180
ggctggtcgc gggacaagct gtatgcagtt gatttctggg ataagacagg caataactta    240
aacaacggtc cagtattatc gcgttttgtg aaaaaggtat tagatgaaac cggtgcgaaa    300
aaagtggata ttgtcgctca cagcatgggc ggcgctaaca cgctttacta cataaaaaat    360
ttggatggcg gtaataaaat tgaaaacgtc gtaacacttg gcggcgcgaa tcgtcttgtg    420
acaggcaagg cgcttccggg tactgatccc aaccaaaaga tattgtacac atccgtttac    480
agtagtgctg atatgattgt tatgaattac ttatcaaaat tagacggggc taaaaatgtt    540
caaattcatg gtgtcggaca tatcggcctt ctgtacagca gccaagtcaa tagcctgatt    600
aaagaagggc ttaacggcgg aggactcaat acgaattaa                            639
```

<210> SEQ ID NO 16
<211> LENGTH: 639
<212> TYPE: DNA
<213> ORGANISM: Bacillus sp.

<400> SEQUENCE: 16

| | | | | | |
|---|---|---|---|---|---|
| atgaaatttg | taaaaagaag | gatcattgca | cttgtaacaa | ttttgatgct | gtctgttaca | 60 |
| tcgctgtttg | cgttgcaacc | gtcagcaaaa | gccgctgaac | acaatccagt | cgttatggtt | 120 |
| cacggtattg | gagggcatc | attcaattt | gcgggaatta | agagctatct | cgtatctcag | 180 |
| ggctggtcgc | gggacaagct | gtatgcagtt | gattttagtg | acaaaacagg | caataactta | 240 |
| aacaacggtc | cagtattatc | gcgttttgtg | aaaaaggtat | tagatgaaac | cggtgcgaaa | 300 |
| aaagtggata | ttgtcgctca | cagcatgggc | ggcgctaaca | cgctttacta | cataaaaaat | 360 |
| ttggatggcg | gtaataaaat | tgaaaacgtc | gtaacacttg | gcggcgcgaa | tcgtcttgta | 420 |
| acaggcaagg | cgcttccggg | tactgatccc | aaccaaaaga | tcttgtacac | atccgtttac | 480 |
| agtagtgctg | atatgattgt | tatgaattac | ttatcaaaat | tagacggggc | taaaaatgtt | 540 |
| caaattcatg | gtgtcggaca | tatcggcctt | ctgtacagca | gccaagtcaa | cagcctgatt | 600 |
| aaagaagggc | ttaacggcgg | gggcctgaat | acgaattaa | | | 639 |

<210> SEQ ID NO 17
<211> LENGTH: 639
<212> TYPE: DNA
<213> ORGANISM: Bacillus sp.

<400> SEQUENCE: 17

| | | | | | |
|---|---|---|---|---|---|
| atgaaatttg | taaaaagaag | gatcattgca | cttgtaacaa | ttttgatgct | gtctgttaca | 60 |
| tcgctgtttg | cgttgcaacc | gtcagcaaaa | gccgctgaac | acaatccagt | cgttatggtt | 120 |
| cacggtattg | gagggcatc | attcaattt | gcgggaatta | agagctatct | cgtatctcag | 180 |
| ggctggtcgc | gggacaagct | gtatgcagtt | gatttcaaag | acaagacagg | gaataaccgc | 240 |
| aacaatggtc | cgcgtctatc | gagattcgtc | aagatgtgt | tagacaaaac | aggagccaaa | 300 |
| aaagtagata | ttgtggctca | tagtatgggc | ggagcgaaca | cattatacta | tattaagaat | 360 |
| ctagatggtg | gcgataaaat | tgagaacgtt | gtcacaattg | gtggagcaaa | cggactcgtt | 420 |
| tcaagcagag | cattaccagg | cacagatcca | atcaaaaaa | ttctttacac | atccgtctat | 480 |
| agctcagcag | atcttattgt | cgtcaacagt | ctctctcgtt | taattggcgc | aagaaacgtc | 540 |
| caaatccatg | gcgttggaca | tatcggtcta | ttaacctcaa | gccaagtcaa | aggatatatt | 600 |
| aaagaaggac | tgaacggcgg | gggcctcaat | acaaattaa | | | 639 |

<210> SEQ ID NO 18
<211> LENGTH: 639
<212> TYPE: DNA
<213> ORGANISM: Bacillus sp.

<400> SEQUENCE: 18

| | | | | | |
|---|---|---|---|---|---|
| atgaaatttg | taaaaagaag | gatccttgca | cttgtaacaa | ttttgatgct | gtctgttaca | 60 |
| tcgctgtttg | cgttgcaacc | gtcagcaaaa | gccgctgaac | acaatccagt | cgttatggtt | 120 |
| cacggtattg | gagggcatc | attcaattt | gcgggaatta | agagctatct | cgtatctcag | 180 |
| ggctggtcgc | gggacaagct | gtatgcagtt | gatttcattg | acaagacagg | aaataaccgc | 240 |
| aacaatggtc | cgcgtctatc | gagattcgtc | aagatgtgt | tagacaaaac | aggagccaaa | 300 |
| aaagtagata | ttgtggctca | tagtatgggc | ggagcgaaca | cattatacta | tattaagaat | 360 |

-continued

```
ctagatggtg gcgataaaat tgagaacgtt gtcacaattg gtggagcaaa cggactcgtt      420
tcaagcagag cattaccagg cacagatcca aatcaaaaaa ttctttacac atccgtctat      480
agctcagcag atcttattgt cgtcaacagt ctctctcgtt taattggcgc aagaaacgtc      540
caaatccatg gcgttggaca tatcggtcta ttaacctcaa gcctagtcaa aggatatatt      600
aaagaaggac tgaacggcgg aggccaaaat acaaattaa                             639
```

<210> SEQ ID NO 19
<211> LENGTH: 648
<212> TYPE: DNA
<213> ORGANISM: Bacillus sp.

<400> SEQUENCE: 19

```
atgaaagtga ttttttgttaa gaaaaggagt ttgcaaattc ttgttgccct tgccttagtg      60
ataggttcaa tggccttcat ccagccaaaa gaaatcaaag cagctgagca caatccggtt     120
gtgatggtac atggtattgg aggagcgtct tataactttg cttcgattaa agttatttg      180 gttaaccaag gctgggatcg aaaccaatta tttgctatcg atttcataga caaaacaggg     240
aataaccgca acaatggtcc tcgtttatct agattcgtca aagatgtgct agacaaaacg     300
ggtgccaaaa aagtagatat tgtggcgcat agtatgggcg gggcgaacac gctatactat     360
attaagaatc tagatggcgg cgataaaatt gaaaacgtcg tcaccattgg tggagcaaac     420
ggactcgttt cactcagagc attaccagga acagatccaa atcaaaaaat tctctataca     480
tctgtctata gctcagccga tttgattgtc gtcaacagcc tttcgcgttt aactggcgca     540
agaaatgtcc tgatccacgg cgttggccat atcggtctat taacctcaag ccaagtgaaa     600
gggtatatta agaaggact gaacggcggg ggcctaaata caaattaa                   648
```

<210> SEQ ID NO 20
<211> LENGTH: 642
<212> TYPE: DNA
<213> ORGANISM: Bacillus sp.

<400> SEQUENCE: 20

```
atgaaatttg taaaagaag gatcattgca cttgtaacaa ttttgatgct gtctgttaca      60
tcgctgtttg cgttgcaacc gtcagcaaaa gccgctgaac acaatccagt cgttatggtt     120
cacggtattg aggggcatc attcaatttt gcgggaatta agagctatct cgtatctcag     180
ggctggtcgc gggacaagct gtatgcagtt gatttcaggg acaagacagg aaataaccgc     240
aacaatggtc cgcgtctatc taaattcgtc aaagatgtgt tagacaaaac gggtgccaaa    300
aaagtagata ttgtggctca tagtatgggc ggggcgaaca cgctatacta tattaagaat   360
ctagatggcg gcgataaaat tgagaacgtt gtcacaattg gcggagcaaa cggactcgtt     420
tcaagcagag cattaccagg cacagatcca aatcaaaaaa ttctttacac atccgtctac    480
aagctcagcc gatctcattg tcgtcaacag tctctctcgt ttaattggct gcaagaaaca     540
gtccaaatcc atggcgttgg acatatcggt ctattaacct caagccaagt caaaggatat     600 attaagaag gactgaacgg cgggggacta aatacaaatt aa                        642
```

<210> SEQ ID NO 21
<211> LENGTH: 544
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 21

```
tgaacacaat ccagttgtta tggttcacgg tattggaggg gcatcattca attttgcggg    60
aattaagagc tatctcgtat ctcagggctg gtcgcgggc aagctgtatg cggttgattt   120
ttgggacaag acaggacga attataacaa tggcccggta ttatcgcgtt ttgtgaaaaa   180
ggtattagat gaaacgggtg cgaaaaaagt ggatattgtc gctcacagca tgggcggcgc   240
taacacgctt tactacataa aaatctgga cggcggaaat aaagttgaaa acgtcgtaac   300
gcttggcggc acgaaccgtt cgacgacaag caaggcgctt ccgggaacag atccaaatca   360
aaagatttta tacacatcca tttacagcag tgccgatatg attgtcatga attacttatc   420
aaaattagac ggtgctaaaa atgttcaaat tcatggcgtt gggcacattg gtttattgat   480
gaacagccaa gtcaacagcc tgattaaaga aggactgaac ggcggggac tcaatacgaa    540
ttga                                                                544
```

<210> SEQ ID NO 22
<211> LENGTH: 544
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 22

```
tgaacacaat ccagttgtta tggttcacgg tattggaggg gcatcattca attttgcggg    60
aattaagagc tatctcgtat ctcagggctg gtcacggggc aagctgtatg cggttgattt   120
ttgggacaag acaggacga attataacaa tggcccggta ttatctagat tcgtcaaaga   180
tgtgctagac aaaacgggtg cgaaaaaagt ggatattgtc gctcacagca tggggggcgc   240
gaacacactt tactacataa aaatctgga cggcggaaat aaaattgaaa acgtcgtaac   300
gcttggcggc gcgaaccgtt cgacgacaag caaggcgctt ccgggaacag atccaaatca   360
aaagatttta tacacatcca tttacagcag tgccgatatg attgtcatga attacttatc   420
aaaattagac ggggctaaaa atgttcaaat tcatggcgtt gggcacattg gtttattgat   480
gaacagccaa gtcaacagcc tgattaaaga aggactgaac ggcggggac tcaatacgaa    540
ttga                                                                544
```

<210> SEQ ID NO 23
<211> LENGTH: 544
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 23

```
tgaacacaat ccagttgtta tggttcacgg tattggaggg gcatcattca attttgcggg    60
aattaagagc tatctcgtat ctcagggctg gtcacggggc aagctgtatg cggttgattt   120
ttgggacagg acaggacga attataacaa tggcccggta ttatcacgat ttgtgaaaaa   180
ggtattagat gaaccggtg cgaaaaaagt ggacattgtc gctcacagca tgggtggcgc   240
gaacacactt tactacataa aaatctgga cggcggaaat aaaattgaaa acgtcgtaac   300
gcttggcggc gcgaaccgtt tgacgacaag caaggcgctt ccgggaacag atccaaatca   360
aaagatttta tacacatcca tttacggcag tgccgatatg attgtcatga attacttatc   420
```

-continued

```
aaaattagac ggtgctaaaa acgttcaaat ccatggcgtt gggcacattg gtttattgat    480
gaacagccaa gtcaacagcc tgattaaaga aggactgaac ggcgggggac tgaatacaaa    540
ttga                                                                 544
```

<210> SEQ ID NO 24
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 24

```
tgaacacaat ccagttgtta tggttcacgg tatcggaggg gcatcattca attttgcggg    60
aattaagagc tatctcgtat ctcagggctg gtcacggggc aagctgtatg cggttgattt    120
ttgggacaag acaggacga attataacaa tggcccggta ttatcacgat ttgtgcaaaa    180
ggttttagac gaaacgggtg cgaaaaaagt ggatattgtc gctcacagca tgggggggcgc    240 gaacacactt tactacataa aaatctgga cggcggaaat aaaattgaaa acgtcgtaac    300
gcttggcggc gcgaaccgtt cgacgacaag caaggcgctt ccgggaacag atccaaatca    360
aaagatttta tacacatcca tttacggcag tgccgatatg attgtcatga attacttatc    420
aaaattagac ggtgctaaaa acgtacaaat tcatggcgtt gggcacattg gtttattgat    480
gaacagccaa gtcaacagcc tgattaaaga aggactgaac ggcgggggac tcaatacgaa    540
ttga                                                                 544
```

<210> SEQ ID NO 25
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 25

```
tgaacacaat ccagttgtta tggttcacgg tattggaggg gcatcattca attttgcggg    60
aattaagagc tatctcgtat ctcagggctg gtcgcggggc aagctgtatg cggttgattt    120
ttgggacaag acaggacga attataacaa tggcccggta ttatcacgat ttgtgcaaaa    180
ggttttagac gaaacggtg cgaaaaaagt ggatattgtc gctcacagca tgggcggcgc    240
gaacacactt tactacataa aaatttgga tggcggtaat aaaattgaaa acgtcgtcac    300
cattggtgga gcaaacggac tcgtttcaag cagagcatta ccaggcacag atccaaatca    360
aaaaattctt tacacatccg tctatagctc agcagatctt attgtcgtca acagtctctc    420
tcgtttaatt ggcgcaagaa acgtccaaat ccatggcgtt ggacatatcg gtctattaac    480
ctcaagccaa gtcaaaggat atattaaaga agggcttaac ggcgggggcc acaatacgaa    540
ttga                                                                 544
```

<210> SEQ ID NO 26
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 26

```
tgaacacaat ccagttgtta tggttcacgg tatcggagga gcttcataca attttgcggg      60
aattaagagc tatctcgtat ctcagggctg gtcacggggc aagctgtatg cggttgattt     120
ttgggacaag acaggggacga attataacaa tggcccggta ttatcacgat ttgtgcaaaa    180
ggttttagac gaaaccggtg cgaaaaaagt ggatattgtc gctcacagca tgggtggcgc     240
gaacacactt tactacataa aaaatctgga cggcggaaat aaaattgaaa acgtcgtaac     300
gcttggcggc gcgaaccgtt tgacgacaag cagggcgctt ccgggaacag atccaaatca    360
aaagatttta tacacatcca tttacagcag tgccgatatg attgtcatga attacttatc     420
aaaattagac ggtgctaaaa acgtacaaat tcatggcgtt gggcacattg gtttattgat     480
gaacagccaa gtcaaaggat atattaaaga aggactgaac ggcggaggcc taaatacgaa     540
ttga                                                                  544

<210> SEQ ID NO 27
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 27
tgaacacaat ccagttgtta tggttcacgg tattggaggg gcatcattca gttttgcggg     60
aattaagagc tatctcgtat ctcagggctg gtcacggggc aagctgtatc cggttgattt    120
ttgggacaag acagggacga attataacaa tggcccggta ttatcacgat ttgtgcaaaa    180
ggttttggac gaaacggggtg cgaaaaaagt ggatattgtc gctcacagta tgggtggcgc    240
gaacacactt tactacataa aaaatctgga cggcggaaat aaaattgaaa acgtcgtaac    300
gcttggcggc gcgaaccgtt tgacgacaag caaggcgctt ccgggtactg atcccaacca    360
aaagatcttg tacacatccg tttacagtag tgctgatatg attgttatga attacttatc    420
aaaattagac ggggctaaaa atgttcaaat tcatggcgtt gggcacattg gtttattgat    480
gaacagccaa gtcaacagcc tgattaaaga aggactgaac ggcgggggcc taaatacaaa    540
ttga                                                                  544

<210> SEQ ID NO 28
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 28
tgaacacaat ccagttgtta tggttcacgg tattggaggg gcatcattca gttttgcggg     60
aattaagagc tatctcgtat ctcagggctg gtcacggggc aagctgtatg cggttgattt    120
ttgggacaag acagggacga attataacaa tggcccggta ttatcacgat ttgtgcaaaa    180
ggttttggac gaaacgggtg cgaaaaaagt ggatattgtc gctcacagta tgggtggcgc    240
gaacacactt tactacataa aaaatctgga cggcggaaat aaaattgaaa acgtcgtaac    300
gcttggcggc gcgaaccgtt tgacgacaag caaggcgctt ccgggtactg atcccaacca    360
aaagatcttg tacacatccg tttacagtag tgctgatatg attgttatga attacttatc    420
aaaattagac ggggctaaaa atgttcaaat tcatggcgtt gggcacattg gtttattgat    480
gaacagccaa gtcaacagcc tgattaaaga aggactgaac ggcgggggcc taaatacaaa    540
```

```
ttga                                                                544
```

<210> SEQ ID NO 29
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 29

```
tgaacacaat ccagttgtta tggttcacgg tatcggagga gcttcataca gttttgcggg      60
aattaagagc tatctcgtat ctcagggctg gtcacggggc aagctgtatg cggttgattt     120
ttgggacaag acaggacga attataacaa tggcccggta ttatcacgat ttgtgcaaaa      180
ggttttagac gaaacgggtg cgaaaaagt ggatattgtc gctcacagca tgggtggcgc      240
gaacacactt tactacataa aaatctgga cggcggaaat aaaattgaaa acgtcgtaac      300
gcttggcggc gcgaaccgtt tgacgacaag caaggcgctt ccgggaacag atcccaacca    360
aaagatcttg tacacatccg tttacagtag tgccgatatg attgtcatga attacttatc    420
aaaattagac ggggctaaaa atgttcaaat tcatggtgtc ggacatatcg gccttctgta    480
cagcagccaa gtcaacagcc tgattaaaga aggactgaac ggcggggggcc aaaatacaaa   540 ttga                                                                544
```

<210> SEQ ID NO 30
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 30

```
tgaacacaat ccagttgtta tggttcacgg tatcggagga gcttcataca gttttgcggg      60
aattaagagc tatctcgtat ctcagggctg gtcacggggc aagctgtatg cggttgattt     120
ttgggacaag acaggacga attataacaa tggcccggta ttatcacgat ttgtgcaaaa      180
ggttttagac gaaacgggtg cgaaaaagt ggatattgtc gctcacagca tggggggcgc      240
gaacacactt tactacataa aaatctgga cggcggaaat aaaattgaaa acgtcgtaac      300
gcttggcggc gcgaaccgtt tgacgacaag caaggcgctt ccgggaactg atcccaacca    360
aaagatcttg tacacatccg tttacagtag tgctgatatg attgttatga attacttatc    420
aaaattagac ggggctaaaa atgttcaaat tcatggcgtt gggcacactg gtttattgat    480
gaacagccaa gtcaacagcc tgattaaaga aggactgaac ggcggggggcc acaatacaaa   540 ttga                                                                544
```

<210> SEQ ID NO 31
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 31

```
tgaacacaat ccagttgtta tggttcacgg tattggagga gcatcataca attttgcggg      60
aattaagagc tatctcgtat ctcagggctg gtcacggggc aagctgtata cggttgattt     120
```

```
ttgggacaag acaggcacaa attataacaa tggcccggta ttatcacgat ttgtgcaaaa    180
ggttttagac gaaacggtg cgaaaaagt ggatattgtc gctcacagca tgggtggcgc    240
gaacacactt tactacataa aaaatctgga cggcggaaat aaaattgaaa acgtcgtaac    300
gcttggcggc gcgaatcgtc ttgtaacagg caaggcgctt ccgggaacag atcccaatca    360
aaagattttg tacgcatccg tttacagcag tgccgatatg attgtcatga attacttatc    420
aaaattagac ggtgctaaaa acgttcaaat tcatggcgtt gggcacattg gtttattgat    480
gaacagccaa gtcaacagcc tgattaaaga aggactgaac ggcggggcc tgaatacaaa    540 ttga                                                                 544

<210> SEQ ID NO 32
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 32
tgaacacaat ccagtcgtta tggttcacgg tattggaggg gcatcattca attttgcggg    60
aattaggagc tatctcgtat ctcagggctg gtcacggggc aagctgtatg cggttgattt    120
ttgggacagg acaggacga attataacaa tggcccggta ttatcacgat ttgtgcaaaa    180
ggttttagat gaaaccggtg cgaaaaagt ggacattgtc gctcacagca tgggtggcgc    240
gaacacactt tactacataa aaaatctgga cggcggaaat aaaattgaaa acgtcgtaac    300
gcttggcggc gcgaaccgtt tgacgacaag caaggcgctt ccgggaacag atccaaatca    360
aaagatttta tacacatcca tttacagcag tgccgatatg attgtcatga attacttatc    420
aaaattagac ggggctaaaa atgttcaaat ccatggcgtt ggacacatcg gccttctgta    480
cagcagccaa gtcaacagcc tgattaaaga aggactgaac ggcggggcc tcaatacgaa    540 ttga                                                                 544

<210> SEQ ID NO 33
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 33
tgaacacaat ccagttgtta tggttcacgg tatcggaggg gcatcattca attttgcggg    60
aattaggagc tatctcgtat ctcagggctg gtcacggggc aagctgtatg cggttgattt    120
ttgggacaag acaggacga attataacaa tggcccggta ttatcacgat ttgtgcaaaa    180
ggttttagac gaaaccggtg cgaaaaagt ggacattgtc gctcacagca tgggcggcgc    240
taacacgctt tactacataa aaaatctgga cggcggaaat aaaattgaaa acgtcgtaac    300
gcttggcggc acgaaccgtt tgacgacaag cagggcgctt ccgggaacag atccaaatca    360
aaagatttta tacacatcca tttacagcag tgccgatatg attgtcatga attacttatc    420
aaaactagac ggtgctaaaa acgttcaaat tcatggcgtt gggcacattg gtttattgat    480
gaacagccaa gtcaacagcc tgattaaaga aggactgaac ggcgggggac tcaatacgaa    540
ttga                                                                 544
```

<210> SEQ ID NO 34
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 34

```
tgaacacaat ccagttgtta tggttcacgg tattggaggg gcatcattca attttgcggg      60
aattaagagc tatctcgtat ctcagggctg gtcgcgggac aagccgtatg cggttgattt     120
ttgggacaag acaggacga attataacaa tggcccggta ttatcacgat ttgtgcaaaa     180
ggttttagac aaaacggggtg cgaaaaaagt ggatattgtc gctcacagca tgggggcgc     240
gaacacactt tactacataa aaaatctgga cggcggaaat aaagttgaaa acgtcgtaac     300
gcttggcggc gcgaaccgtt tgacgacaag caaggcgctt ccgggaacag atccaaatca     360
aaagatttta tacacatcca tttacagcag tgccgatatg attgtcatga attacttatc     420
aaaattagac ggtgctaaaa acgttcaaat tcatggcgtt gggcacattg gtttattgat     480
gaacagccaa gtcaacagcc tgattaaaga aggactgaac ggcgggggac tcaatacgaa     540
ttga                                                                  544
```

<210> SEQ ID NO 35
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 35

```
tgaacacaat ccagttgtta tggttcacgg tattggaggg gcatcattca attttgcggg      60
aattaagagc tatctcgtgt ctcagggctg gccgcgggac aagctgtatg cagttgattt     120
ttgggacaag acaggacga attataacaa tggcccggta ttatcacgat ttgtgcaaaa     180
ggttttagac gaaacggggtg cgaaaaaagt ggatattgtc gctcacagca tgggtggcgc     240
gaacacactt tactacataa aaaatctgga cggcggaaat aaagttgaaa gcgtcgtaac     300
acttggcggc gcgaatcgtc ttgtaacagg caaggcgctt ccgggaactg atcccaacca     360
aaagatttta tacacatcca tttacagcag tgccgatatg attgtcatga attacttatc     420
aaaattagac ggtgctaaaa acgttcaaat tcatggcgtc ggacatatcg gccttctgat     480
gaacagccaa gtcaacagcc tgattaaaga aggactgaac ggcgggggcc acaatacaaa     540
ttga                                                                  544
```

<210> SEQ ID NO 36
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 36

```
tgaacacaat ccagttgtta tggttcacgg tatcggaggg gcatcattca gttttgcggg      60
aattaggagc tatctcgtat ctcagggctg gccgcgggac aagctgtatg cggttgattt     120
ttgggacaag acaggcacaa attataacaa tggcccggta ttatcacgat ttgtgcaaaa     180
```

```
ggtattagat gaaaccggtg cgaaaaaagt ggatattgtc gcccacagca tgggtggcgc     240
gaacacactt tactacataa aaaatctgga cggcggaaat aaagttgaaa acgtcgtgac     300
gcttggcggc gccaaccgtt tgacgacagg caaggcgctt ccgggtactg atcccaatca     360
aaagatttta tacacatccg tttacagcag tgccgatatg attgtcatga attacttatc     420
aaaattagac ggtgctaaaa acgttcaaat tcatggcgtt gggcacattg gtttattgat     480
gaacagccaa gtcaacaggc tgattaaaga aggactgaac ggcggaggcc acaatacaaa     540
ttga                                                                 544
```

<210> SEQ ID NO 37
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 37

```
tgaacacaat ccagttgtta tggttcacgg tatcggaggg gcatcattca gttttgcggg      60
aattaggagc tatctcgtat ctcagggctg gccgcgggac aagctgtatg cggttgattt     120
ttgggacaag acaggcacaa attataacaa tggcccggta ttatcacgat ttgtgcaaaa     180
ggtattagat gaaaccggtg cgaaaaaagt ggatattgtc gcctacagca tgggtggcgc     240
gaacacactt tactacataa aaaatctgga cggcggaaat aaagttgaaa acgtcgtgac     300
gcttggcggc gccaaccgtt tgacgacagg caaggcgctt ccgggtactg atcccaatca     360
aaagatttta tacacatccg tttacagcag tgccgatatg attgtcatga attacttatc     420
aaaattagac ggtgctaaaa acgttcaaat tcatggcgtt gggcacattg gtttattgat     480
gaacagccaa gtcaacaggc tgattaaaga aggactgaac ggcggaggcc acaatacaaa     540
ttga                                                                 544
```

<210> SEQ ID NO 38
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 38

```
tgaacacaat ccagttgtta tggttcacgg tatcggggggg gcatcattca gttttgcggg      60
aattaggagc tatctcgtat ctcagggctg gccgcgggac aagctgtatg cggttgattt     120
ttgggacaag acaggcacaa attataacaa tggcccggta ttatcacgat ttgtgcaaaa     180
ggtattagat gaaaccggtg cgaaaaaagt ggatattgtc gcccacagca tgggtggcgc     240
gaacacactt tactacataa aaaatctgga cggcggaaat aaagttgaaa acgtcgtgac     300
gcttggcggc gccaaccgtt tgacgacagg caaggcgctt ccgggtactg atcccaatca     360
aaagatttta tacacatccg tttacagcag tgccgatatg attgtcatga attacttatc     420
aaaattagac ggtgctaaaa acgttcaaat tcatggcgtt gggcacattg gtttattgat     480
gaacagccaa gtcaacaggc tgattaaaga aggactgaac ggcggaggcc acaatacaaa     540
ttga                                                                 544
```

<210> SEQ ID NO 39
<211> LENGTH: 544

```
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 39
tgaacacaat ccagttgtta tggttcacgg tatcggaggg gcatcattca gttttgcggg      60
aattaggagc tatctcgtat cccagggctg gccgcgggac aagctgtatg cggttgattt    120
ttgggacaag acaggcacaa attataacaa tggcccggta ttatcacgat ttgtgcaaaa    180
ggtattagat gaaaccggtg cgaaaaaagt ggatattgtc gcccacagca tgggtggcgc    240
gaacacactt tactacataa aaaatctgga cggcggaaat aaagttgaaa acgtcgtgac    300
gcttggcggc gccaaccgtt tgacgacagg caaggcgctt ccgggtactg atcccaatca    360
aaagatttta tacacatccg tttacagcag tgccgatatg attgtcatga attacttatc    420
aaaattagac ggtgctaaaa acgttcaaat tcatggcgtt gggcacattg gtttattgat    480
gaacagccaa gtcaacaggc tgattaaaga aggactgaac ggcggaggcc acaatacaaa    540
ttga                                                                  544

<210> SEQ ID NO 40
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 40
tgaacacaat ccagttgtta tggttcacgg tattggaggg acatcattca attttgcggg      60
aattaagagc tatctcgtat ctcagggctg gtcacgggac aagctgtatg cggttgattt    120
ttgggacaag acaggacga attataacaa tggcccggta ttatcacgat ttgtgcaaaa    180
ggttttagac gaaacggtg cgaaaaaagt ggatattgtc gctcacagca tgggcggcgc    240
caacacgctt tactacataa aaaatctgga cggcggaaat aaaattgaaa acgtcgtgac    300
gcttggcggc gcgaaccgtt tgacgacaag caaggcgctt ccgggaacag atccaaatca    360
aaagatttta tacacatcca tttacagcag tgccgatatg attgtcatga attacttatc    420
aaaattagac ggtgctaaaa acgttcaaat tcatggcgtt gggcacattg gtttattgat    480
gaacagccaa gtcaacagcc tgattaaaga aggactgaac ggcgggggcc acaatacaaa    540
ttga                                                                  544

<210> SEQ ID NO 41
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 41
tgaacacaat ccagttgtta tggttcacgg tatcggaggg gcatcattca gttttgcggg      60
aattaagagc tatctcgtat ctcagggctg gtcgcgggac aagctgtatg cagttgattt    120
tagtgacaaa acaggcacga attataacaa tggcccggta ttatcacgat ttgtgcaaaa    180
ggttttagac gaaacggtg cgaaaaaagt ggatattgtc gctcacagca tggggggcgc    240
gaacacactt tactacataa aaaatctgga tggcggtaat aaaattgaaa acgtcgtaac    300
```

```
acttggcggc gcgaaccgtt tgacgacaag caaggcgctt ccgggtactg atcccaacca      360
aaagatcttg tacacatcca tttacagcag tgccgatatg gttgtcatga attacttatc      420
aaaattagac ggggctaaaa atgttcaaat tcatggtgtc gggcacattg gtttattgat      480
gaacagccaa gtcaacagcc tgattaaaga aggactgaac ggcgggggcc acaatacgaa      540
ttga                                                                   544

<210> SEQ ID NO 42
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 42
taaacacaat ccagttgtta tggttcacgg tattggaggg gcatcataca attttgcggg      60
aataaagagc tatctcgtat ctcagggctg gtcgcgggac aagctgtatg cagttgattt     120
tagtgacaag acagggacga attataacaa tggcccggta ttatcacgat ttgtgcaaaa     180
ggttttagac gaaacggggtg cgaaaaaagt ggatattgtc gctcacagca tgggggcgc      240 gaacacactt tactacataa aaatctgga cggcggtaat aaaattgaaa acgtcgtaac      300
acttggcggc gcgaaccgtt tgacgacaag caaggcgctt ccgggaacag atccaaatca     360
aaagatttta tacacatcca tttacagcag tgccgatatg attgtcatga attacttatc     420
aaaactagac ggtgctaaaa acgttcaaat tcatggcgtt gggcacattg gtttattgat     480
gaacagccaa gtcaacagcc tgattaaaga aggactgaac ggcgggggat aaatacgaa      540 ttga                                                                   544

<210> SEQ ID NO 43
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 43
tgaacacaat ccagttgtta tggttcacgg tattggaggg gcatcattca attttgcggg      60
aattaagagc tatctcgaat ctcagggctg gtcacgggc aagctgtatg cggttgattt      120
ttgggacaag accgggacga attataacaa tggcccggta ttatcacgat tgtgcaaaa      180 ggctttagac gaaacggggtg cgaaaaaagt ggatattgtc gctcacagca tgggtggcgc    240
gaacacactt tactacataa aaatctgga cggcggaaat aaaattgaaa acgtcgtaac      300
gcttggcggc gcgaaccgtt tgacgacaag caaggcgctt ccgggaacag atccaaatca     360
aaagatttta tacacatcca tttacagcag tgccgatatg attgtcatga attacttatc     420
aaaattagac ggtgctaaaa acgttcaaat ccatggcgtt gggcacattg gtttattgat     480
gaacagccaa gtcaacagcc tgattaaaga aggactgaac ggcgggggcc agaatacgaa     540
ttga                                                                   544

<210> SEQ ID NO 44
<211> LENGTH: 544
<212> TYPE: DNA
<213> ORGANISM: Artificial Sequence
<220> FEATURE:
```

<223> OTHER INFORMATION: Description of Artificial Sequence: Synthetic
      nucleotide sequence

<400> SEQUENCE: 44

```
tgaacacaat ccagttgtta tggttcacgg tatcggaggg gcatcattca attttgcggg      60
aattaagagc tatctcgtat ctcagggctg gtcacggggc aagctgtatg cggttgattt     120
ttgggacagg acaggacga attataacaa tggcccggta ttatcacgat ttgtgaaaaa      180
ggtattagat gaaaccggtg cgaaaaaagt ggatattgtc gctcacagca tgggggcgc      240
gaacacactt tactacataa aaatctgga cggcggaaat aaaattgaaa acgtcgtcac      300
acttggcggc gcgaaccgtt cgacgacaag caaggcgctt ccgggaacag atccaaatca     360
aaagatttta tacacatcca tttacagcag tgccgatatg attgtcatga attacttatc     420
aaaattagac ggtgctaaaa acgttcaaat tcatggcgtt gggcacattg gtttattgat     480
gaacagccaa gtcaacagcc tgattaaaga agggctgaac ggcggaggcc agaatacgaa     540
ttga                                                                  544
```

<210> SEQ ID NO 45
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 45

```
tgaacacaat ccagttgtta tggttcacgg tattggaggg gcatcattca attttgcggg      60
aattaagagc tatctcgtat ctcagggctg gtcgcggggc aagctgtatg cggttgattt     120
ttgggacagg acaggacga attataacaa tggcccggta ttatcacgat ttgtgcaaaa      180
ggttttagac gaaaccgggtg cgaaaaaagt ggatattgtc gctcacagca tgggggcgc     240
gaacacactt tactacataa aaatctgga cggcggaaat aaaattgaaa acgtcgtcac      300
acttggcggc gcgaaccgtt cgacgacaag caaggcgctt ccgggaacag atccaaatca     360
aaagatttta tacacatcca tttacagcag tgccgatatg attgtcatga attacttatc     420
aaaattagac ggtgctaaaa acgttcaaat tcatggcgtt gggcacattg gtttattgat     480
gaacagccaa gtcaacagcc tgattaaaga agggcttaac ggcgggggcc acaatacgaa     540
ttga                                                                  544
```

<210> SEQ ID NO 46
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 46

```
tgaacacaat ccagtcgtta tggttcacgg tattggaggg gcatcattca attttgcggg      60
aataagagc tatctcgtat ctcagggctg gtcacggggc aagctgtatg cggttgattt      120
ttgggacagg acaggacga attataacaa tggcccggta ttatcacgat ttgtgcaaaa      180
ggttttagac gaaacggggtg cgaaaaaagt ggatattgtc gctcacagca tgggtggcgc    240
gaacacactt tactacataa agaatctgga cggcggaaat aaaattgaaa acgtcgtaac     300
gcttggcggc gcgaaccgtt cgacgacaag caaggcgctt ccgggaacag atccaaatca     360
```

```
aaagatttta tacacatcca tttacagcag tgccgatatg attgtcatga attgcttatc    420
aaaattagac ggtgctaaaa acgttcaaat tcatggcgtt gggcacattg gtttattgat    480
gaacagccaa gtcaacagcc tgattaaaga aggactgaac ggcgggggcc agaatacgaa    540
ttga                                                                544
```

<210> SEQ ID NO 47
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 47

```
tgaacacaat ccagttgtta tggttcacgg tattggaggg gcatcgttca attttgcggg     60
aattaagagc tatctcgtat ctcagggctg gtcgcgggac aagctgtatg cagttgattt    120
caaagacaag acagggacga attataacaa tggcccggta ttatcacgat ttgtgaaaaa    180
ggtattagat gaaacggtg cgaaaaagt ggatattgtc gctcacagca tgggcggcgc     240
taacacgctt tactacataa agaatctgga cggcggaaat aaaattgaaa acgtcgtaac    300
gcttggcggc gcgaaccgtt cgacgacaag caaggcgctt ccgggtactg atcccaacca    360
aaagatcttg tacacatccg tttacagtag tgctgatatg attgttatga attacttatc    420
aaaattagac ggtgctaaaa acgttcaaat tcatggcgtt gggcacattg gtttattgat    480
gaacagccaa gtcaacagcc tgattaaaga aggactgaac ggcggaggcc taaatacaaa    540
ttga                                                                544
```

<210> SEQ ID NO 48
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 48

```
tgaacacaat ccagttgtta tggttcacgg tattggaggg gcatcattca attttgcggg     60
aattaagagc tatctcgtat ctcagggctg gtcgcgggac aagctgtatg cggttgatttt   120 ttgggacaag acagggacga attataacaa tggcccggta ttatcacgat ttgtgaaaaa    180
ggtattagat gaaaccggtg cgaaaaaagt ggatattgtc gctcacagca tgggtggcgc    240
taacacgctt tactacataa aaatctgga cggcggcgat aaaattgaga acgtcgtaac     300
acttggcggc gcgaaccgtt cgacgacaag caaggcgctt ccgggaacag atccaaatca    360
aaagatcttg tacacatccg tttacagtag tgctgatatg attgtcatga attacttatc    420
aaaattagac ggtgctaaaa acgttcaaat tcatggcgtt gggcacattg gtttattgat    480
gaacagccaa gtcaacagcc tgattaaaga agggctgaac ggcggaggcc agaatacgaa    540
ttga                                                                544
```

<210> SEQ ID NO 49
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

```
<400> SEQUENCE: 49
tgaacacaat ccagttgtta tggttcacgg tattggaggg gcatcattca attttgcggg      60
aattaagagc tatctcgtat ctcagggctg gtcgcgggac aagctgtatg cagttgattt     120
ttggggcaag acaggacga  attataacaa tggcccggta ttatcgcgtt ttgtgaaaaa     180
ggtattagat gaaacggtg  cgaaaaaagt ggatattgtc gctcacagca tgggggcgc     240 gaacacactt tactacataa aaaatctgga cggcggaaat aaaattgaaa acgtcgtaac     300
acttggcggc gcgaaccgtt cgacgacaag caaggcgctt ccgggaacag atccaaatca     360
aaagatttta tacacatcca tttacagcag tgccgatatg attgtcatga attacttatc     420
aaaattagac ggggctaaaa atgttcaaat tcatggcgtt gggcacattg gtttattgat     480
gaacagccaa gtcaacagcc tgattaaaga aggactgaac ggcggaggcc aaaatacgaa     540
ttga                                                                  544

<210> SEQ ID NO 50
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 50
tgaacacaat ccagttgtta tggttcacgg tattggaggg gcatcattca attttgcggg      60
aattaagagc tatctcgtat ctcagggctg gtcacggggc aagctgtatg cagttgattt     120
ttgggacaag acaggacga  attataacaa tggcccggta ttatcgcgtt ttgtgaaaaa     180
ggtattagat gaaacggtg  cgaaaaaagt ggatattgtc gctcacagca tgggcggcgc     240
taacacgctt tactacataa aaaatctgga tggcggtaat aaaattgaaa acgtcgtcac     300
acttggcggc gcgaaccgtt cgacgacaag caaggcgctt ccgggaactg atcccaacca     360
aaagatttta tacacatcca tttacagcag tgccgatatg attgtcatga attacttatc     420
aaaattagac ggtgctaaaa acgttcaaat tcatggcgtt gggcacattg gtttattgat     480
gaacagccaa gtcaacagcc tgattaaaga aggactgaac ggcggaggcc aaaatacgaa     540
ttga                                                                  544

<210> SEQ ID NO 51
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 51
tgaacacaat ccagttgtta tggttcacgg tattggaggg gcatcattca attttgcggg      60
aattaagagc tatctcgtat ctcagggctg gtcacggggc aagctgtatg cggttgattt     120
caaggacaag acaggcacaa attataacaa tggcccggta ttatcacgat ttgtgaaaaa     180
ggtattagat gaaccggtg  cgaaaaaagt ggatattgtc gctcacagca tgggcggcgc     240
taacacgctt tactacataa aaaatctgga cggcggaaat aaaattgaaa acgtcgtaac     300
gcttggcggc gcgaaccgtt cgacgacaag caaggcgctt ccgggtactg atcccaacca     360
aaagatttta tacacatcca tttacagcag tgccgatatg attgtcatga attacttatc     420
aaaattagac ggtgctaaaa acgttcaaat tcatggcgtt gggcacattg gtttattgat     480
```
gaacagccaa gtcaacagcc tgattaaaga agggcttaac ggcgggggcc agaatacgaa    540
ttga    544

<210> SEQ ID NO 52
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 52
taaacacaat ccagttgtta tggttcacgg tattggaggg gcatcattca attttgcggg    60
aattaagagc tatctcgtat ctcagggctg gtcgcgggac gagctgtatg cggttgattt    120
ttgggacgag acaggacga attataacaa tggcccggta ttatcacgat ttgtgcaaaa    180
ggttttagac gaaaccggtg cgaaaaaagt ggatattgtc gctcacagca tgggtggcgc    240
gaacacactt tactacataa aaaatctgga cggcggaaat aaaattgaaa acgtcgtaac    300
gcttggcggc gcgaaccgtt cgacgacaag caaggcgctt ccgggtacag atccaaatca    360
aaagatttta tacacatcca tttacagcag tgccgatatg attgtcatga attacttatc    420
aaaattagac ggtgctaaaa atgttcaaat tcatggcgtt gggcacattg gtttattgat    480
gaacagccaa gtcaacagcc tgattaaaga agggctgaac ggcggaggcc aaaatacgaa    540
ttga    544

<210> SEQ ID NO 53
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 53
tgaacacaat ccagttgtta tggttcacgg tatcggaggg gcatcattca attttgcggg    60
aattaagagc tatctcgtat ctcagggctg gtcgcgggac aagctgtatg cggttgattt    120
ttgggacaag acaggacga attataacaa tggcccggta ttatcacgat ttgtgcaaaa    180
ggttttagac gaaacgggtg cgaaaaaagt ggatattgtc gctcacagca tgggtggcgc    240
gaacacactt tactacataa aaaatctgga cggcggaaat aaagttgaaa acgtcgtaac    300
acttggcggc gcgaatcgtt cgacgacaag caaggcgctt ccgggaacag atccaaatca    360
aaagatttta tacacatcca tttacagcag tgccgatatg attgtcatga attacttatc    420
aaaattagac ggtgctaaaa acgttcaaat tcatggcgtt gggcacattg gtttattgat    480
gaacagccaa gtcaacagcc tgattaaaga aggactgaac ggcgggggcc aaaatacaaa    540
ttga    544

<210> SEQ ID NO 54
<211> LENGTH: 544
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 54
tgaacacaat ccagttgtta tggttcacgg tatcggaggg gcatcattca attttgcggg    60

-continued

```
aattaagagc tatctcgtat ctcagggctg gtcacggggc aagctgtatg cggttgattt    120
ttgggacaag acagggacga attataacaa tggcccggta ttatcacgat ttgtgcaaaa    180
ggttttagac gaaacgggtg cgaaaaaagt ggatattgtc gctcacagca tgggtggcgc    240
gaacacactt tactacataa aaatctggac ggcggaaat aaaattgaaa acgtcgtaac    300
acttggcggc gcgaaccgtt cgacgacaag caaggcgctt ccgggaacag atccaaatca    360
aaagatttta tacacatcca tttacagcag tgccgatatg attgtcatga attacttatc    420
aaaattagac ggtgctaaaa atgttcaaat tcatggcgtt gggcacattg gtttattgat    480
gaacagccaa gtcaacagcc tgattaaaga agggctgaac ggcggaggac aaaatacaaa    540
ttga                                                                544
```

<210> SEQ ID NO 55
<211> LENGTH: 212
<212> TYPE: PRT
<213> ORGANISM: Bacillus pumilus

<400> SEQUENCE: 55

```
Met Lys Phe Val Lys Arg Arg Ile Ile Ala Leu Val Thr Ile Leu Val
1               5                   10                  15

Leu Ser Val Thr Ser Leu Phe Ala Met Gln Pro Ser Ala Lys Ala Ala
            20                  25                  30

Glu His Asn Pro Val Val Met Val His Gly Ile Gly Gly Ala Ser Tyr
        35                  40                  45

Asn Phe Ala Gly Ile Lys Ser Tyr Leu Val Ser Gln Gly Trp Ser Arg
    50                  55                  60

Gly Lys Leu Tyr Ala Val Asp Phe Trp Asp Lys Thr Gly Thr Asn Tyr
65                  70                  75                  80

Asn Asn Gly Pro Val Leu Ser Arg Phe Val Gln Lys Val Leu Asp Glu
                85                  90                  95

Thr Gly Ala Lys Lys Val Asp Ile Val Ala His Ser Met Gly Gly Ala
            100                 105                 110

Asn Thr Pro Tyr Tyr Ile Lys Asn Leu Asp Gly Gly Asn Lys Ile Glu
        115                 120                 125

Asn Val Val Thr Leu Gly Gly Ala Asn Arg Ser Thr Thr Ser Lys Ala
    130                 135                 140

Leu Pro Gly Thr Asp Pro Asn Gln Lys Ile Leu Tyr Thr Ser Ile Tyr
145                 150                 155                 160

Ser Ser Ala Asp Met Ile Val Met Asn Tyr Leu Ser Lys Leu Asp Gly
                165                 170                 175

Ala Lys Asn Ala Gln Ile His Gly Val Gly His Ile Gly Leu Leu Met
            180                 185                 190

Asn Ser Gln Val Asn Ser Leu Ile Lys Glu Gly Leu Asn Gly Gly Gly
        195                 200                 205

Gln Asn Thr Asn
    210
```

<210> SEQ ID NO 56
<211> LENGTH: 212
<212> TYPE: PRT
<213> ORGANISM: Bacillus subtilis

<400> SEQUENCE: 56

```
Met Lys Phe Val Lys Arg Arg Ile Ile Ala Leu Val Thr Ile Leu Met
1               5                   10                  15
```

```
Leu Ser Val Thr Ser Leu Phe Ala Leu Gln Pro Ser Ala Lys Ala Ala
             20                  25                  30

Glu His Asn Pro Val Val Met Val His Gly Ile Gly Gly Ala Ser Phe
         35                  40                  45

Asn Phe Ala Gly Ile Lys Ser Tyr Leu Val Ser Gln Gly Trp Ser Arg
 50                  55                  60

Asp Lys Leu Tyr Ala Val Asp Phe Trp Asp Lys Thr Gly Thr Asn Tyr
 65                  70                  75                  80

Asn Asn Gly Pro Val Leu Pro Arg Phe Val Gln Lys Val Leu Asp Glu
                 85                  90                  95

Thr Gly Ala Lys Lys Val Asp Ile Val Ala His Ser Met Gly Gly Ala
             100                 105                 110

Asn Thr Leu Tyr Tyr Ile Lys Asn Leu Asp Gly Gly Asn Lys Val Ala
         115                 120                 125

Asn Val Val Thr Leu Gly Gly Ala Asn Arg Leu Thr Thr Gly Lys Ala
     130                 135                 140

Leu Pro Gly Thr Asp Pro Asn Gln Lys Ile Leu Tyr Thr Ser Ile Tyr
145                 150                 155                 160

Ser Ser Ala Asp Met Ile Val Ile Asn Tyr Leu Ser Arg Leu Asp Gly
                 165                 170                 175

Ala Arg Asn Val Gln Ile His Gly Val Gly His Ile Gly Leu Leu Tyr
             180                 185                 190

Ser Ser Gln Val Asn Ser Leu Ile Lys Glu Gly Leu Asn Gly Gly Gly
         195                 200                 205

Leu Asn Thr Asn
    210

<210> SEQ ID NO 57
<211> LENGTH: 212
<212> TYPE: PRT
<213> ORGANISM: Bacillus megaterium

<400> SEQUENCE: 57

Met Lys Phe Val Lys Arg Arg Ile Ile Ala Leu Val Thr Ile Leu Val
 1               5                  10                  15

Leu Ser Val Thr Ser Leu Phe Ala Met Gln Pro Ser Ala Lys Ala Ala
             20                  25                  30

Asp Thr Ile Gln Leu Leu Trp Phe Thr Gly Ile Gly Gly Ala Ser Tyr
         35                  40                  45

Asn Phe Ala Gly Ile Lys Ser Tyr Leu Val Ser Gln Gly Trp Ser Arg
 50                  55                  60

Gly Lys Leu Tyr Ala Val Asp Phe Trp Asp Lys Thr Gly Thr Asn Tyr
 65                  70                  75                  80

Asn Asn Gly Pro Val Leu Ser Arg Phe Val Gln Lys Val Leu Asp Glu
                 85                  90                  95

Thr Gly Ala Lys Lys Val Asp Ile Val Ala His Ser Met Gly Gly Ala
             100                 105                 110

Asn Thr Leu Tyr Tyr Ile Lys Asn Leu Asp Gly Gly Asn Lys Ile Glu
         115                 120                 125

Asn Val Val Thr Leu Gly Gly Ala Asn Arg Leu Thr Thr Ser Lys Ala
     130                 135                 140

Leu Pro Gly Thr Asp Pro Asn Gln Lys Ile Leu Tyr Thr Ser Ile Tyr
145                 150                 155                 160

Ser Ser Ala Asp Met Ile Val Met Asn Tyr Leu Ser Lys Leu Asp Gly
```

```
                    165                 170                 175
Ala Lys Asn Val Gln Ile His Gly Val Gly His Ile Gly Leu Leu Met
            180                 185                 190

Asn Ser Gln Val Asn Ser Leu Ile Lys Glu Gly Leu Asn Gly Gly Gly
        195                 200                 205

His Asn Thr Asn
    210

<210> SEQ ID NO 58
<211> LENGTH: 212
<212> TYPE: PRT
<213> ORGANISM: Bacillus lentus

<400> SEQUENCE: 58

Met Lys Phe Val Lys Arg Arg Ile Ile Ala Leu Val Thr Ile Leu Val
  1               5                  10                  15

Leu Ser Val Thr Ser Leu Phe Ala Met Gln Pro Ser Ala Lys Ala Ala
             20                  25                  30

Glu His Asn Pro Val Val Met Val His Gly Ile Gly Gly Ala Ser Tyr
         35                  40                  45

Asn Phe Ala Gly Ile Lys Ser Tyr Leu Val Ser Gln Gly Trp Ser Arg
     50                  55                  60

Gly Lys Leu Tyr Ala Val Asp Phe Trp Asp Lys Thr Gly Thr Asn Tyr
 65                  70                  75                  80

Asn Asn Gly Pro Val Leu Ser Arg Phe Val Gln Lys Val Leu Asp Glu
                 85                  90                  95

Thr Gly Ala Lys Lys Val Asp Ile Val Ala His Ser Met Gly Gly Ala
            100                 105                 110

Asn Thr Leu Tyr Tyr Ile Lys Asn Leu Asp Gly Gly Asn Lys Ile Glu
        115                 120                 125

Asn Val Val Thr Leu Gly Gly Ala Asn Arg Leu Thr Thr Ser Lys Ala
    130                 135                 140

Leu Pro Gly Thr Asp Pro Asn Gln Lys Ile Leu Tyr Thr Ser Ile Tyr
145                 150                 155                 160

Ser Ser Ala Asp Met Ile Val Met Asn Tyr Leu Ser Lys Leu Asp Gly
                165                 170                 175

Ala Lys Asn Val Gln Ile His Gly Val Gly His Ile Gly Leu Leu Met
            180                 185                 190

Asn Ser Gln Val Asn Ser Leu Ile Lys Glu Gly Leu Asn Gly Gly Gly
        195                 200                 205

Leu Asn Thr Asn
    210

<210> SEQ ID NO 59
<211> LENGTH: 212
<212> TYPE: PRT
<213> ORGANISM: Bacillus circulans

<400> SEQUENCE: 59

Met Lys Phe Ile Lys Arg Arg Ile Ile Ala Leu Val Thr Ile Leu Val
  1               5                  10                  15

Leu Ser Val Thr Ser Leu Phe Ala Met Gln Pro Ser Ala Lys Ala Ala
             20                  25                  30

Glu His Asn Pro Val Val Met Val His Gly Ile Gly Gly Ala Ser Tyr
         35                  40                  45

Asn Phe Ala Gly Ile Lys Ser Tyr Leu Val Ser Gln Gly Trp Ser Arg
```

```
                50                    55                    60
Gly Lys Leu Tyr Ala Val Asp Phe Trp Asp Lys Thr Gly Thr Asn Tyr
 65                  70                  75                  80

Asn Asn Gly Pro Val Leu Ser Arg Phe Val Gln Lys Val Leu Asp Glu
                85                  90                  95

Thr Gly Ala Lys Lys Val Asp Ile Val Ala His Ser Met Gly Gly Ala
                100                 105                 110

Asn Thr Leu Tyr Tyr Ile Lys Asn Leu Asp Gly Gly Asn Lys Ile Glu
                115                 120                 125

Asn Val Val Thr Leu Gly Gly Ala Asn Arg Leu Thr Thr Ser Lys Ala
                130                 135                 140

Leu Pro Gly Thr Asp Pro Asn Gln Lys Ile Leu Tyr Thr Ser Ile Tyr
 145                 150                 155                 160

Ser Ser Ala Asp Met Ile Val Met Asn Tyr Leu Ser Lys Leu Asp Gly
                165                 170                 175

Ala Lys Asn Val Gln Ile His Gly Val Gly His Ile Gly Leu Leu Met
                180                 185                 190

Asn Ser Gln Val Asn Ser Leu Ile Lys Glu Gly Leu Asn Gly Gly Gly
                195                 200                 205

Leu Asn Thr Asn
    210

<210> SEQ ID NO 60
<211> LENGTH: 212
<212> TYPE: PRT
<213> ORGANISM: Bacillus azotoformans

<400> SEQUENCE: 60

Met Lys Phe Val Lys Arg Arg Ile Ile Ala Leu Val Thr Ile Leu Val
  1               5                   10                  15

Leu Ser Val Thr Ser Leu Phe Ala Met Gln Pro Ser Ala Lys Ala Ala
                20                  25                  30

Glu His Asn Pro Val Val Met Val His Gly Ile Gly Gly Ala Ser Tyr
                35                  40                  45

Asn Phe Ala Gly Ile Lys Ser Tyr Leu Val Ser Gln Gly Trp Ser Arg
    50                  55                  60

Gly Glu Leu Tyr Ala Val Asp Phe Trp Asp Lys Thr Gly Thr Asn Tyr
 65                  70                  75                  80

Asn Asn Gly Pro Val Leu Ser Arg Phe Val Gln Lys Val Leu Asp Glu
                85                  90                  95

Thr Gly Ala Lys Lys Val Asp Ile Val Ala His Ser Met Gly Gly Ala
                100                 105                 110

Asn Thr Leu Tyr Tyr Ile Lys Asn Leu Asp Gly Gly Asn Lys Ile Glu
                115                 120                 125

Asn Val Val Thr Leu Gly Gly Ala Asn Arg Leu Thr Thr Ser Lys Ala
                130                 135                 140

Leu Pro Gly Thr Asp Pro Asn Gln Lys Ile Leu Tyr Thr Ser Ile Tyr
 145                 150                 155                 160

Ser Ser Ala Asn Met Ile Val Met Asn Tyr Leu Ser Lys Leu Asp Gly
                165                 170                 175

Ala Lys Asn Val Gln Ile His Gly Val Gly His Ile Gly Leu Leu Met
                180                 185                 190

Asn Ser Gln Val Asn Ser Leu Ile Lys Glu Gly Leu Asn Gly Gly Gly
                195                 200                 205
```

```
Leu Asp Thr Asn
    210

<210> SEQ ID NO 61
<211> LENGTH: 212
<212> TYPE: PRT
<213> ORGANISM: Bacillus firmus

<400> SEQUENCE: 61

Met Lys Phe Val Lys Arg Arg Ile Ile Ala Leu Val Thr Ile Leu Val
  1               5                  10                  15

Leu Ser Val Thr Ser Leu Phe Ala Met Gln Pro Ser Ala Lys Ala Ala
             20                  25                  30

Glu His Asn Pro Val Val Met Val His Gly Ile Gly Gly Ala Ser Tyr
         35                  40                  45

Asn Phe Ala Gly Ile Lys Ser Tyr Leu Val Ser Gln Gly Trp Ser Arg
     50                  55                  60

Gly Lys Leu Tyr Ala Val Asp Phe Trp Asp Lys Thr Gly Thr Asn Tyr
 65                  70                  75                  80

Asn Asn Gly Pro Val Leu Ser Arg Phe Val Gln Lys Val Leu Asp Glu
                 85                  90                  95

Thr Gly Ala Lys Lys Val Asp Ile Val Ala His Ser Met Gly Gly Ala
            100                 105                 110

Asn Thr Leu Tyr Tyr Ile Lys Asn Leu Asp Gly Gly Asn Lys Ile Glu
        115                 120                 125

Asn Val Val Thr Leu Gly Gly Ala Asn Arg Leu Thr Thr Ser Lys Ala
    130                 135                 140

Leu Pro Gly Thr Asp Pro Asn Gln Lys Ile Leu Tyr Thr Ser Ile Tyr
145                 150                 155                 160

Ser Ser Ala Asp Met Ile Val Met Asn Tyr Leu Ser Lys Leu Asp Gly
                165                 170                 175

Ala Lys Asn Ala Gln Ile His Gly Val Gly His Ile Gly Leu Leu Met
            180                 185                 190

Asn Ser Gln Val Asn Ser Leu Ile Lys Glu Gly Leu Asn Gly Gly Gly
        195                 200                 205

His Asn Thr Asn
    210

<210> SEQ ID NO 62
<211> LENGTH: 212
<212> TYPE: PRT
<213> ORGANISM: Bacillus badius

<400> SEQUENCE: 62

Met Lys Phe Val Lys Arg Arg Ile Ile Ala Leu Val Thr Ile Leu Val
  1               5                  10                  15

Leu Ser Val Thr Ser Leu Phe Ala Met Gln Pro Ser Ala Lys Ala Ala
             20                  25                  30

Glu His Asn Pro Val Val Met Val His Gly Ile Gly Gly Ala Ser Tyr
         35                  40                  45

Asn Phe Ala Gly Ile Lys Ser Tyr Leu Val Ser Gln Gly Trp Ser Arg
     50                  55                  60

Gly Lys Leu Tyr Ala Val Asp Phe Trp Asp Lys Thr Gly Thr Asn Tyr
 65                  70                  75                  80

Asn Asn Gly Pro Val Leu Ser Arg Phe Val Gln Lys Val Leu Asp Glu
                 85                  90                  95
```

```
Thr Gly Ala Lys Lys Val Asp Ile Val Ala His Ser Met Gly Gly Ala
            100                 105                 110

Asn Thr Leu Tyr Tyr Ile Lys Asn Leu Asp Gly Gly Asn Lys Ile Glu
        115                 120                 125

Asn Val Val Thr Leu Gly Gly Ala Asn Arg Leu Thr Thr Ser Lys Ala
    130                 135                 140

Leu Pro Gly Thr Asp Pro Asn Gln Lys Ile Leu Tyr Thr Ser Ile Tyr
145                 150                 155                 160

Ser Ser Ala Asp Met Ile Val Met Asn Tyr Leu Ser Lys Leu Asp Gly
                165                 170                 175

Ala Lys Asn Val Gln Ile His Gly Val Gly His Ile Gly Leu Leu Met
            180                 185                 190

Asn Ser Gln Val Asn Ser Leu Ile Lys Glu Gly Leu Asn Gly Gly Gly
        195                 200                 205

His Asn Thr Asn
    210

<210> SEQ ID NO 63
<211> LENGTH: 212
<212> TYPE: PRT
<213> ORGANISM: Bacillus sp.

<400> SEQUENCE: 63

Met Lys Phe Val Lys Arg Arg Ile Ile Ala Leu Val Thr Ile Leu Met
  1               5                  10                  15

Leu Ser Val Thr Ser Leu Phe Ala Leu Gln Pro Ser Ala Lys Ala Ala
             20                  25                  30

Glu His Asn Pro Val Val Met Val His Gly Ile Gly Gly Ala Ser Phe
         35                  40                  45

Asn Phe Ala Gly Ile Lys Ser Tyr Leu Val Ser Gln Gly Trp Ser Arg
     50                  55                  60

Asp Lys Leu Tyr Ala Val Asp Phe Lys Asp Lys Thr Gly Thr Asn Tyr
 65                  70                  75                  80

Asn Asn Gly Pro Val Leu Ser Arg Phe Val Gln Lys Val Leu Asp Glu
                 85                  90                  95

Thr Gly Ala Lys Lys Val Asp Ile Val Ala His Ser Met Gly Gly Ala
            100                 105                 110

Asn Thr Leu Tyr Tyr Ile Lys Asn Leu Asp Gly Gly Asn Lys Val Glu
        115                 120                 125

Asn Val Val Thr Leu Gly Gly Ala Asn Arg Leu Thr Thr Gly Lys Ala
    130                 135                 140

Leu Pro Gly Thr Asp Pro Asn Gln Lys Ile Leu Tyr Thr Ser Ile Tyr
145                 150                 155                 160

Ser Ser Ala Asp Met Ile Val Met Asn Tyr Leu Ser Arg Leu Asp Gly
                165                 170                 175

Ala Arg Asn Val Gln Ile His Gly Val Gly His Ile Gly Leu Leu Tyr
            180                 185                 190

Ser Ser Gln Val Asn Ser Leu Ile Lys Glu Gly Leu Asn Gly Gly Gly
        195                 200                 205

Leu Asn Thr Asn
    210

<210> SEQ ID NO 64
<211> LENGTH: 212
<212> TYPE: PRT
<213> ORGANISM: Bacillus sp.
```

-continued

```
<220> FEATURE:
<221> NAME/KEY: MOD_RES
<222> LOCATION: (73)
<223> OTHER INFORMATION: Variable amino acid

<400> SEQUENCE: 64

Met Lys Phe Val Lys Arg Arg Ile Ile Ala Leu Val Thr Ile Leu Met
 1               5                  10                  15

Leu Ser Val Thr Ser Leu Phe Ala Leu Gln Pro Ser Ala Lys Ala Ala
            20                  25                  30

Glu His Asn Pro Val Val Met Val His Gly Ile Gly Gly Ala Ser Phe
        35                  40                  45

Asn Phe Ala Gly Ile Lys Ser Tyr Leu Val Ser Gln Gly Trp Ser Arg
    50                  55                  60

Asp Lys Leu Tyr Ala Val Asp Phe Xaa Asp Lys Thr Gly Asn Asn Arg
65                  70                  75                  80

Asn Asn Gly Pro Arg Leu Ser Arg Phe Val Lys Asp Val Leu Asp Lys
                85                  90                  95

Thr Gly Ala Lys Lys Val Asp Ile Val Ala His Ser Met Gly Gly Ala
            100                 105                 110

Asn Thr Leu Tyr Tyr Ile Lys Asn Leu Asp Gly Gly Asp Lys Ile Glu
        115                 120                 125

Asn Val Val Thr Ile Gly Gly Ala Asn Gly Leu Val Ser Ser Arg Ala
    130                 135                 140

Leu Pro Gly Thr Asp Pro Asn Gln Lys Ile Leu Tyr Thr Ser Val Tyr
145                 150                 155                 160

Ser Ser Ala Asp Leu Ile Val Val Asn Ser Leu Ser Arg Leu Ile Gly
                165                 170                 175

Ala Arg Asn Ile Leu Ile His Gly Val Gly His Ile Gly Leu Leu Thr
            180                 185                 190

Ser Ser Gln Val Lys Gly Tyr Ile Lys Glu Gly Leu Asn Gly Gly Gly
        195                 200                 205

Leu Asn Thr Asn
    210

<210> SEQ ID NO 65
<211> LENGTH: 215
<212> TYPE: PRT
<213> ORGANISM: Bacillus sp.

<400> SEQUENCE: 65

Met Lys Val Ile Phe Val Lys Arg Ser Leu Gln Ile Leu Val Ala
 1               5                  10                  15

Leu Ala Leu Val Leu Gly Ser Ile Ala Phe Ile Gln Pro Lys Glu Ala
            20                  25                  30

Lys Ala Ala Glu His Asn Pro Val Val Met Val His Gly Met Gly Gly
        35                  40                  45

Ala Ser Tyr Asn Phe Ala Ser Ile Lys Arg Tyr Leu Val Ser Gln Gly
    50                  55                  60

Trp Asp Gln Asn Gln Leu Phe Ala Ile Asp Phe Ile Asp Lys Thr Gly
65                  70                  75                  80

Asn Asn Leu Asn Asn Gly Pro Arg Leu Ser Arg Phe Val Lys Asp Val
                85                  90                  95

Leu Ala Lys Thr Gly Ala Lys Lys Val Asp Ile Val Ala His Ser Met
            100                 105                 110

Gly Gly Ala Asn Thr Leu Tyr Tyr Ile Lys Asn Leu Asp Gly Gly Asp
```

```
                115                 120                 125
Lys Ile Glu Asn Val Val Thr Leu Gly Gly Ala Asn Gly Leu Val Ser
    130                 135                 140

Leu Arg Ala Leu Pro Gly Thr Asp Pro Asn Gln Lys Ile Leu Tyr Thr
145                 150                 155                 160

Ser Val Tyr Ser Ser Ala Asp Leu Ile Val Val Asn Ser Leu Ser Arg
                165                 170                 175

Leu Ile Gly Ala Arg Asn Val Leu Ile His Gly Val Gly His Ile Gly
                180                 185                 190

Leu Leu Thr Ser Ser Gln Val Lys Gly Tyr Val Lys Glu Gly Leu Asn
                195                 200                 205

Gly Gly Gly Gln Asn Thr Asn
    210                 215

<210> SEQ ID NO 66
<211> LENGTH: 215
<212> TYPE: PRT
<213> ORGANISM: Bacillus sp.

<400> SEQUENCE: 66

Met Lys Val Ile Phe Val Lys Lys Arg Ser Leu Gln Ile Leu Val Val
1               5                   10                  15

Leu Ala Leu Val Met Gly Ser Met Ala Phe Ile Gln Pro Lys Glu Ile
                20                  25                  30

Arg Ala Ala Glu His Asn Pro Val Val Met Val His Gly Met Gly Gly
                35                  40                  45

Ala Ser Tyr Asn Phe Ala Ser Ile Lys Ser Tyr Leu Val Ser Gln Gly
    50                  55                  60

Trp Asp Arg Asn Gln Leu Phe Ala Ile Asp Phe Ile Asp Lys Thr Gly
65              70                  75                  80

Asn Asn Arg Asn Asn Gly Pro Arg Leu Ser Arg Phe Val Lys Asp Val
                85                  90                  95

Leu Ala Lys Thr Gly Ala Lys Lys Val Asp Ile Val Ala His Ser Met
                100                 105                 110

Gly Gly Ala Asn Thr Leu Tyr Tyr Ile Lys Asn Leu Asp Gly Gly Asp
                115                 120                 125

Lys Ile Glu Asn Val Val Thr Leu Gly Gly Ala Asn Gly Leu Val Ser
    130                 135                 140

Leu Arg Ala Leu Pro Gly Thr Asp Pro Asn Gln Lys Ile Leu Tyr Thr
145                 150                 155                 160

Ser Val Tyr Ser Ser Ala Asp Leu Ile Val Val Asn Ser Leu Ser Arg
                165                 170                 175

Leu Ile Gly Ala Arg Asn Val Leu Ile His Gly Val Gly His Ile Gly
                180                 185                 190

Leu Leu Ala Ser Ser Gln Val Lys Gly Tyr Ile Lys Glu Gly Leu Asn
                195                 200                 205

Gly Gly Gly Gln Asn Thr Asn
    210                 215

<210> SEQ ID NO 67
<211> LENGTH: 215
<212> TYPE: PRT
<213> ORGANISM: Bacillus sp.

<400> SEQUENCE: 67

Met Lys Val Ile Phe Val Lys Lys Arg Ser Leu Gln Ile Leu Ile Ala
```

```
                1               5              10              15
Leu Ala Leu Val Ile Gly Ser Met Ala Phe Ile Gln Pro Lys Glu Ala
                    20              25              30

Lys Ala Ala Glu His Asn Pro Val Val Met Val His Gly Ile Gly Gly
                    35              40              45

Ala Ser Tyr Asn Phe Phe Ser Ile Lys Ser Tyr Leu Ala Thr Gln Gly
                    50              55              60

Trp Asp Arg Asn Gln Leu Tyr Ala Ile Asp Phe Ile Asp Lys Thr Gly
 65                     70              75                  80

Asn Asn Arg Asn Asn Gly Pro Arg Leu Ser Arg Phe Val Lys Asp Val
                    85              90              95

Leu Asp Lys Thr Gly Ala Lys Lys Val Asp Ile Val Ala His Ser Met
                    100             105             110

Gly Gly Ala Asn Thr Leu Tyr Tyr Ile Lys Asn Leu Asp Gly Gly Asp
                    115             120             125

Lys Ile Glu Asn Val Val Thr Ile Gly Gly Ala Asn Gly Leu Val Ser
        130             135             140

Ser Arg Ala Leu Pro Gly Thr Asp Pro Asn Gln Lys Ile Leu Tyr Thr
145                     150             155                 160

Ser Val Tyr Ser Ser Ala Asp Leu Ile Val Val Asn Ser Leu Ser Gln
                    165             170             175

Phe Asn Trp Arg Lys Lys His Pro Asp Pro Gly Val Gly His Ile Gly
                    180             185             190

Leu Leu Thr Ser Ser Gln Val Lys Gly Tyr Ile Lys Glu Gly Leu Asn
                    195             200             205

Gly Gly Gly Leu Asn Thr Asn
        210             215

<210> SEQ ID NO 68
<211> LENGTH: 212
<212> TYPE: PRT
<213> ORGANISM: Bacillus sp.

<400> SEQUENCE: 68

Met Lys Phe Val Lys Arg Arg Ile Ile Ala Leu Val Thr Ile Leu Met
 1               5              10              15

Leu Ser Val Thr Ser Leu Phe Ala Leu Gln Pro Ser Ala Lys Ala Ala
                    20              25              30

Glu His Asn Pro Val Val Met Val His Gly Ile Gly Gly Ala Ser Phe
                    35              40              45

Asn Phe Ala Gly Ile Lys Ser Tyr Leu Val Ser Gln Gly Trp Ser Arg
        50              55              60

Asp Lys Leu Tyr Ala Val Asp Phe Arg Asp Lys Thr Gly Asn Asn Leu
 65                     70              75                  80

Asn Asn Gly Pro Val Leu Ser Arg Phe Val Lys Val Leu Asp Glu
                    85              90              95

Thr Gly Ala Lys Lys Val Asp Ile Val Ala His Ser Met Gly Gly Ala
                    100             105             110

Asn Thr Leu Tyr Tyr Ile Lys Asn Leu Asp Gly Gly Asn Lys Ile Glu
                    115             120             125

Asn Val Val Thr Leu Gly Gly Ala Asn Arg Leu Val Thr Gly Lys Ala
        130             135             140

Leu Pro Gly Thr Asp Pro Asn Gln Lys Ile Leu Tyr Thr Ser Val Tyr
145                     150             155                 160
```

```
Ser Ser Ala Asp Met Ile Val Met Asn Tyr Leu Thr Lys Leu Asp Gly
            165                 170                 175

Ala Lys Asn Val Gln Ile His Gly Val Gly His Ile Gly Leu Leu Tyr
            180                 185                 190

Ser Ser Gln Val Asn Ser Leu Ile Lys Glu Gly Leu Asn Gly Gly Gly
            195                 200                 205

Leu Asn Thr Asn
    210

<210> SEQ ID NO 69
<211> LENGTH: 212
<212> TYPE: PRT
<213> ORGANISM: Bacillus sp.

<400> SEQUENCE: 69

Met Lys Phe Val Lys Arg Arg Ile Ile Ala Leu Val Thr Ile Leu Met
  1               5                  10                  15

Leu Ser Val Thr Ser Leu Phe Ala Leu Gln Pro Ser Ala Lys Ala Ala
             20                  25                  30

Glu His Asn Pro Val Val Met Val His Gly Ile Gly Gly Ala Ser Phe
         35                  40                  45

Asn Phe Ala Gly Ile Lys Ser Tyr Leu Val Ser Gln Gly Trp Ser Arg
 50                  55                  60

Asp Lys Leu Tyr Ala Val Asp Phe Trp Asp Lys Thr Gly Asn Asn Leu
 65                  70                  75                  80

Asn Asn Gly Pro Val Leu Ser Arg Phe Val Lys Val Leu Asp Glu
             85                  90                  95

Thr Gly Ala Lys Lys Val Asp Ile Val Ala His Ser Met Gly Gly Ala
            100                 105                 110

Asn Thr Leu Tyr Tyr Ile Lys Asn Leu Asp Gly Gly Asn Lys Ile Glu
            115                 120                 125

Asn Val Val Thr Leu Gly Gly Ala Asn Arg Leu Val Thr Gly Lys Ala
        130                 135                 140

Leu Pro Gly Thr Asp Pro Asn Gln Lys Ile Leu Tyr Thr Ser Val Tyr
145                 150                 155                 160

Ser Ser Ala Asp Met Ile Val Met Asn Tyr Leu Ser Lys Leu Asp Gly
            165                 170                 175

Ala Lys Asn Val Gln Ile His Gly Val Gly His Ile Gly Leu Leu Tyr
            180                 185                 190

Ser Ser Gln Val Asn Ser Leu Ile Lys Glu Gly Leu Asn Gly Gly Gly
            195                 200                 205

Leu Asn Thr Asn
    210

<210> SEQ ID NO 70
<211> LENGTH: 212
<212> TYPE: PRT
<213> ORGANISM: Bacillus sp.

<400> SEQUENCE: 70

Met Lys Phe Val Lys Arg Arg Ile Ile Ala Leu Val Thr Ile Leu Met
  1               5                  10                  15

Leu Ser Val Thr Ser Leu Phe Ala Leu Gln Pro Ser Ala Lys Ala Ala
             20                  25                  30

Glu His Asn Pro Val Val Met Val His Gly Ile Gly Gly Ala Ser Phe
         35                  40                  45
```

-continued

```
Asn Phe Ala Gly Ile Lys Ser Tyr Leu Val Ser Gln Gly Trp Ser Arg
 50                  55                  60

Asp Lys Leu Tyr Ala Val Asp Phe Ser Asp Lys Thr Gly Asn Asn Leu
 65                  70                  75                  80

Asn Asn Gly Pro Val Leu Ser Arg Phe Val Lys Val Leu Asp Glu
                 85                  90                  95

Thr Gly Ala Lys Lys Val Asp Ile Val Ala His Ser Met Gly Gly Ala
                100                 105                 110

Asn Thr Leu Tyr Tyr Ile Lys Asn Leu Asp Gly Gly Asn Lys Ile Glu
                115                 120                 125

Asn Val Val Thr Leu Gly Gly Ala Asn Arg Leu Val Thr Gly Lys Ala
                130                 135                 140

Leu Pro Gly Thr Asp Pro Asn Gln Lys Ile Leu Tyr Thr Ser Val Tyr
145                 150                 155                 160

Ser Ser Ala Asp Met Ile Val Met Asn Tyr Leu Ser Lys Leu Asp Gly
                165                 170                 175

Ala Lys Asn Val Gln Ile His Gly Val Gly His Ile Gly Leu Leu Tyr
                180                 185                 190

Ser Ser Gln Val Asn Ser Leu Ile Lys Glu Gly Leu Asn Gly Gly Gly
                195                 200                 205

Leu Asn Thr Asn
    210
```

<210> SEQ ID NO 71
<211> LENGTH: 212
<212> TYPE: PRT
<213> ORGANISM: Bacillus sp.

<400> SEQUENCE: 71

```
Met Lys Phe Val Lys Arg Arg Ile Ile Ala Leu Val Thr Ile Leu Met
  1               5                  10                  15

Leu Ser Val Thr Ser Leu Phe Ala Leu Gln Pro Ser Ala Lys Ala Ala
                 20                  25                  30

Glu His Asn Pro Val Val Met Val His Gly Ile Gly Gly Ala Ser Phe
                 35                  40                  45

Asn Phe Ala Gly Ile Lys Ser Tyr Leu Val Ser Gln Gly Trp Ser Arg
 50                  55                  60

Asp Lys Leu Tyr Ala Val Asp Phe Lys Asp Lys Thr Gly Asn Asn Arg
 65                  70                  75                  80

Asn Asn Gly Pro Arg Leu Ser Arg Phe Val Lys Asp Val Leu Asp Lys
                 85                  90                  95

Thr Gly Ala Lys Lys Val Asp Ile Val Ala His Ser Met Gly Gly Ala
                100                 105                 110

Asn Thr Leu Tyr Tyr Ile Lys Asn Leu Asp Gly Gly Asp Lys Ile Glu
                115                 120                 125

Asn Val Val Thr Ile Gly Gly Ala Asn Gly Leu Val Ser Ser Arg Ala
                130                 135                 140

Leu Pro Gly Thr Asp Pro Asn Gln Lys Ile Leu Tyr Thr Ser Val Tyr
145                 150                 155                 160

Ser Ser Ala Asp Leu Ile Val Val Asn Ser Leu Ser Arg Leu Ile Gly
                165                 170                 175

Ala Arg Asn Val Gln Ile His Gly Val Gly His Ile Gly Leu Leu Thr
                180                 185                 190

Ser Ser Gln Val Lys Gly Tyr Ile Lys Glu Gly Leu Asn Gly Gly Gly
                195                 200                 205
```

Leu Asn Thr Asn
    210

<210> SEQ ID NO 72
<211> LENGTH: 212
<212> TYPE: PRT
<213> ORGANISM: Bacillus sp.

<400> SEQUENCE: 72

Met Lys Phe Val Lys Arg Ile Leu Ala Leu Val Thr Ile Leu Met
1               5                   10                  15

Leu Ser Val Thr Ser Leu Phe Ala Leu Gln Pro Ser Ala Lys Ala Ala
                20                  25                  30

Glu His Asn Pro Val Val Met Val His Gly Ile Gly Gly Ala Ser Phe
            35                  40                  45

Asn Phe Ala Gly Ile Lys Ser Tyr Leu Val Ser Gln Gly Trp Ser Arg
        50                  55                  60

Asp Lys Leu Tyr Ala Val Asp Phe Ile Asp Lys Thr Gly Asn Asn Arg
65                  70                  75                  80

Asn Asn Gly Pro Arg Leu Ser Arg Phe Val Lys Asp Val Leu Asp Lys
                85                  90                  95

Thr Gly Ala Lys Lys Val Asp Ile Val Ala His Ser Met Gly Gly Ala
            100                 105                 110

Asn Thr Leu Tyr Tyr Ile Lys Asn Leu Asp Gly Gly Asp Lys Ile Glu
        115                 120                 125

Asn Val Val Thr Ile Gly Gly Ala Asn Gly Leu Val Ser Ser Arg Ala
    130                 135                 140

Leu Pro Gly Thr Asp Pro Asn Gln Lys Ile Leu Tyr Thr Ser Val Tyr
145                 150                 155                 160

Ser Ser Ala Asp Leu Ile Val Val Asn Ser Leu Ser Arg Leu Ile Gly
                165                 170                 175

Ala Arg Asn Val Gln Ile His Gly Val Gly His Ile Gly Leu Leu Thr
            180                 185                 190

Ser Ser Leu Val Lys Gly Tyr Ile Lys Glu Gly Leu Asn Gly Gly Gly
        195                 200                 205

Gln Asn Thr Asn
    210

<210> SEQ ID NO 73
<211> LENGTH: 215
<212> TYPE: PRT
<213> ORGANISM: Bacillus sp.

<400> SEQUENCE: 73

Met Lys Val Ile Phe Val Lys Arg Ser Leu Gln Ile Leu Val Ala
1               5                   10                  15

Leu Ala Leu Val Ile Gly Ser Met Ala Phe Ile Gln Pro Lys Glu Ile
                20                  25                  30

Lys Ala Ala Glu His Asn Pro Val Val Met Val His Gly Ile Gly Gly
            35                  40                  45

Ala Ser Tyr Asn Phe Ala Ser Ile Lys Ser Tyr Leu Val Asn Gln Gly
        50                  55                  60

Trp Asp Arg Asn Gln Leu Phe Ala Ile Asp Phe Ile Asp Lys Thr Gly
65                  70                  75                  80

Asn Asn Arg Asn Asn Gly Pro Arg Leu Ser Arg Phe Val Lys Asp Val
                85                  90                  95

```
Leu Asp Lys Thr Gly Ala Lys Val Asp Ile Val Ala His Ser Met
            100                 105                 110
Gly Gly Ala Asn Thr Leu Tyr Tyr Ile Lys Asn Leu Asp Gly Gly Asp
        115                 120                 125
Lys Ile Glu Asn Val Val Thr Ile Gly Gly Ala Asn Gly Leu Val Ser
    130                 135                 140
Leu Arg Ala Leu Pro Gly Thr Asp Pro Asn Gln Lys Ile Leu Tyr Thr
145                 150                 155                 160
Ser Val Tyr Ser Ser Ala Asp Leu Ile Val Asn Ser Leu Ser Arg
                165                 170                 175
Leu Thr Gly Ala Arg Asn Val Leu Ile His Gly Val Gly His Ile Gly
            180                 185                 190
Leu Leu Thr Ser Ser Gln Val Lys Gly Tyr Ile Lys Glu Gly Leu Asn
        195                 200                 205
Gly Gly Gly Leu Asn Thr Asn
    210                 215

<210> SEQ ID NO 74
<211> LENGTH: 213
<212> TYPE: PRT
<213> ORGANISM: Bacillus sp.

<400> SEQUENCE: 74

Met Lys Phe Val Lys Arg Arg Ile Ile Ala Leu Val Thr Ile Leu Met
1               5                   10                  15
Leu Ser Val Thr Ser Leu Phe Ala Leu Gln Pro Ser Ala Lys Ala Ala
            20                  25                  30
Glu His Asn Pro Val Val Met Val His Gly Ile Gly Gly Ala Ser Phe
        35                  40                  45
Asn Phe Ala Gly Ile Lys Ser Tyr Leu Val Ser Gln Gly Trp Ser Arg
    50                  55                  60
Asp Lys Leu Tyr Ala Val Asp Phe Arg Asp Lys Thr Gly Asn Asn Arg
65                  70                  75                  80
Asn Asn Gly Pro Arg Leu Ser Lys Phe Val Lys Asp Val Leu Asp Lys
                85                  90                  95
Thr Gly Ala Lys Lys Val Asp Ile Val Ala His Ser Met Gly Gly Ala
            100                 105                 110
Asn Thr Leu Tyr Tyr Ile Lys Asn Leu Asp Gly Gly Asp Lys Ile Glu
        115                 120                 125
Asn Val Val Thr Ile Gly Gly Ala Asn Gly Leu Val Ser Ser Arg Ala
    130                 135                 140
Leu Pro Gly Thr Asp Pro Asn Gln Lys Ile Leu Tyr Thr Ser Val Tyr
145                 150                 155                 160
Lys Leu Ser Arg Ser His Cys Arg Gln Gln Ser Leu Ser Phe Asn Trp
                165                 170                 175
Leu Gln Glu Thr Val Gln Ile His Gly Val Gly His Ile Gly Leu Leu
            180                 185                 190
Thr Ser Ser Gln Val Lys Gly Tyr Ile Lys Glu Gly Leu Asn Gly Gly
        195                 200                 205
Gly Leu Asn Thr Asn
    210

<210> SEQ ID NO 75
<211> LENGTH: 180
<212> TYPE: PRT
```

<213> ORGANISM: Artificial Sequence
<220> FEATURE:
<223> OTHER INFORMATION: Description of Artificial Sequence: Synthetic peptide

<400> SEQUENCE: 75

```
Glu His Asn Pro Val Val Met Val His Gly Ile Gly Gly Ala Ser Phe
1               5                   10                  15

Asn Phe Ala Gly Ile Lys Ser Tyr Leu Val Ser Gln Gly Trp Ser Arg
            20                  25                  30

Gly Lys Leu Tyr Ala Val Asp Phe Trp Asp Lys Thr Gly Thr Asn Tyr
        35                  40                  45

Asn Asn Gly Pro Val Leu Ser Arg Phe Val Lys Lys Val Leu Asp Glu
    50                  55                  60

Thr Gly Ala Lys Lys Val Asp Ile Val Ala His Ser Met Gly Gly Ala
65                  70                  75                  80

Asn Thr Leu Tyr Tyr Ile Lys Asn Leu Asp Gly Gly Asn Lys Val Glu
                85                  90                  95

Asn Val Val Thr Leu Gly Gly Thr Asn Arg Ser Thr Thr Ser Lys Ala
            100                 105                 110

Leu Pro Gly Thr Asp Pro Asn Gln Lys Ile Leu Tyr Thr Ser Ile Tyr
        115                 120                 125

Ser Ser Ala Asp Met Ile Val Met Asn Tyr Leu Ser Lys Leu Asp Gly
130                 135                 140

Ala Lys Asn Val Gln Ile His Gly Val Gly His Ile Gly Leu Leu Met
145                 150                 155                 160

Asn Ser Gln Val Asn Ser Leu Ile Lys Glu Gly Leu Asn Gly Gly Gly
                165                 170                 175

Leu Asn Thr Asn
            180
```

<210> SEQ ID NO 76
<211> LENGTH: 180
<212> TYPE: PRT
<213> ORGANISM: Artificial Sequence
<220> FEATURE:
<223> OTHER INFORMATION: Description of Artificial Sequence: Synthetic peptide

<400> SEQUENCE: 76

```
Glu His Asn Pro Val Val Met Val His Gly Ile Gly Gly Ala Ser Phe
1               5                   10                  15

Asn Phe Ala Gly Ile Lys Ser Tyr Leu Val Ser Gln Gly Trp Ser Arg
            20                  25                  30

Gly Lys Leu Tyr Ala Val Asp Phe Trp Asp Lys Thr Gly Thr Asn Tyr
        35                  40                  45

Asn Asn Gly Pro Val Leu Ser Arg Phe Val Lys Asp Val Leu Asp Lys
    50                  55                  60

Thr Gly Ala Lys Lys Val Asp Ile Val Ala His Ser Met Gly Gly Ala
65                  70                  75                  80

Asn Thr Leu Tyr Tyr Ile Lys Asn Leu Asp Gly Gly Asn Lys Ile Glu
                85                  90                  95

Asn Val Val Thr Leu Gly Gly Ala Asn Arg Ser Thr Thr Ser Lys Ala
            100                 105                 110

Leu Pro Gly Thr Asp Pro Asn Gln Lys Ile Leu Tyr Thr Ser Ile Tyr
        115                 120                 125

Ser Ser Ala Asp Met Ile Val Met Asn Tyr Leu Ser Lys Leu Asp Gly
```

```
                130                 135                 140
Ala Lys Asn Val Gln Ile His Gly Val Gly His Ile Gly Leu Leu Met
145                 150                 155                 160

Asn Ser Gln Val Asn Ser Leu Ile Lys Glu Gly Leu Asn Gly Gly Gly
                165                 170                 175

Leu Asn Thr Asn
        180

<210> SEQ ID NO 77
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Glu His Asn Pro Val Val Met Val His Gly Ile Gly Gly Ala Ser Phe
1               5                   10                  15

Asn Phe Ala Gly Ile Lys Ser Tyr Leu Val Ser Gln Gly Trp Ser Arg
                20                  25                  30

Gly Lys Leu Tyr Ala Val Asp Phe Trp Asp Arg Thr Gly Thr Asn Tyr
            35                  40                  45

Asn Asn Gly Pro Val Leu Ser Arg Phe Val Lys Lys Val Leu Asp Glu
    50                  55                  60

Thr Gly Ala Lys Lys Val Asp Ile Val Ala His Ser Met Gly Gly Ala
65                  70                  75                  80

Asn Thr Leu Tyr Tyr Ile Lys Asn Leu Asp Gly Gly Asn Lys Ile Glu
                85                  90                  95

Asn Val Val Thr Leu Gly Gly Ala Asn Arg Leu Thr Thr Ser Lys Ala
            100                 105                 110

Leu Pro Gly Thr Asp Pro Asn Gln Lys Ile Leu Tyr Thr Ser Ile Tyr
        115                 120                 125

Gly Ser Ala Asp Met Ile Val Met Asn Tyr Leu Ser Lys Leu Asp Gly
    130                 135                 140

Ala Lys Asn Val Gln Ile His Gly Val Gly His Ile Gly Leu Leu Met
145                 150                 155                 160

Asn Ser Gln Val Asn Ser Leu Ile Lys Glu Gly Leu Asn Gly Gly Gly
                165                 170                 175

Leu Asn Thr Asn
        180

<210> SEQ ID NO 78
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Glu His Asn Pro Val Val Met Val His Gly Ile Gly Gly Ala Ser Phe
1               5                   10                  15

Asn Phe Ala Gly Ile Lys Ser Tyr Leu Val Ser Gln Gly Trp Ser Arg
                20                  25                  30

Gly Lys Leu Tyr Ala Val Asp Phe Trp Asp Lys Thr Gly Thr Asn Tyr
            35                  40                  45

Asn Asn Gly Pro Val Leu Ser Arg Phe Val Gln Lys Val Leu Asp Glu
```

```
                 50                  55                  60

Thr Gly Ala Lys Lys Val Asp Ile Val Ala His Ser Met Gly Gly Ala
 65                  70                  75                  80

Asn Thr Leu Tyr Tyr Ile Lys Asn Leu Asp Gly Gly Asn Lys Ile Glu
                 85                  90                  95

Asn Val Val Thr Leu Gly Gly Ala Asn Arg Ser Thr Thr Ser Lys Ala
                100                 105                 110

Leu Pro Gly Thr Asp Pro Asn Gln Lys Ile Leu Tyr Thr Ser Ile Tyr
                115                 120                 125

Gly Ser Ala Asp Met Ile Val Met Asn Tyr Leu Ser Lys Leu Asp Gly
130                 135                 140

Ala Lys Asn Val Gln Ile His Gly Val Gly His Ile Gly Leu Leu Met
145                 150                 155                 160

Asn Ser Gln Val Asn Ser Leu Ile Lys Glu Gly Leu Asn Gly Gly Gly
                165                 170                 175

Leu Asn Thr Asn
            180

<210> SEQ ID NO 79
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Glu His Asn Pro Val Val Met Val His Gly Ile Gly Gly Ala Ser Phe
 1               5                  10                  15

Asn Phe Ala Gly Ile Lys Ser Tyr Leu Val Ser Gln Gly Trp Ser Arg
                 20                  25                  30

Gly Lys Leu Tyr Ala Val Asp Phe Trp Asp Lys Thr Gly Thr Asn Tyr
             35                  40                  45

Asn Asn Gly Pro Val Leu Ser Arg Phe Val Gln Lys Val Leu Asp Glu
 50                  55                  60

Thr Gly Ala Lys Lys Val Asp Ile Val Ala His Ser Met Gly Gly Ala
 65                  70                  75                  80

Asn Thr Leu Tyr Tyr Ile Lys Asn Leu Asp Gly Gly Asn Lys Ile Glu
                 85                  90                  95

Asn Val Val Thr Ile Gly Gly Ala Asn Gly Leu Val Ser Ser Arg Ala
                100                 105                 110

Leu Pro Gly Thr Asp Pro Asn Gln Lys Ile Leu Tyr Thr Ser Val Tyr
                115                 120                 125

Ser Ser Ala Asp Leu Ile Val Val Asn Ser Leu Ser Arg Leu Ile Gly
130                 135                 140

Ala Arg Asn Val Gln Ile His Gly Val Gly His Ile Gly Leu Leu Thr
145                 150                 155                 160

Ser Ser Gln Val Lys Gly Tyr Ile Lys Glu Gly Leu Asn Gly Gly Gly
                165                 170                 175

His Asn Thr Asn
            180

<210> SEQ ID NO 80
<211> LENGTH: 180
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 80

```
Glu His Asn Pro Val Val Met Val His Gly Ile Gly Gly Ala Ser Tyr
  1               5                  10                  15

Asn Phe Ala Gly Ile Lys Ser Tyr Leu Val Ser Gln Gly Trp Ser Arg
             20                  25                  30

Gly Lys Leu Tyr Ala Val Asp Phe Trp Asp Lys Thr Gly Thr Asn Tyr
         35                  40                  45

Asn Asn Gly Pro Val Leu Ser Arg Phe Val Gln Lys Val Leu Asp Glu
     50                  55                  60

Thr Gly Ala Lys Lys Val Asp Ile Val Ala His Ser Met Gly Gly Ala
 65                  70                  75                  80

Asn Thr Leu Tyr Tyr Ile Lys Asn Leu Asp Gly Gly Asn Lys Ile Glu
                 85                  90                  95

Asn Val Val Thr Leu Gly Gly Ala Asn Arg Leu Thr Thr Ser Arg Ala
            100                 105                 110

Leu Pro Gly Thr Asp Pro Asn Gln Lys Ile Leu Tyr Thr Ser Ile Tyr
            115                 120                 125

Ser Ser Ala Asp Met Ile Val Met Asn Tyr Leu Ser Lys Leu Asp Gly
130                 135                 140

Ala Lys Asn Val Gln Ile His Gly Val Gly His Ile Gly Leu Leu Met
145                 150                 155                 160

Asn Ser Gln Val Lys Gly Tyr Ile Lys Glu Gly Leu Asn Gly Gly Gly
                165                 170                 175

Leu Asn Thr Asn
            180
```

<210> SEQ ID NO 81
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

```
Glu His Asn Pro Val Val Met Val His Gly Ile Gly Gly Ala Ser Phe
  1               5                  10                  15

Ser Phe Ala Gly Ile Lys Ser Tyr Leu Val Ser Gln Gly Trp Ser Arg
             20                  25                  30

Gly Lys Leu Tyr Pro Val Asp Phe Trp Asp Lys Thr Gly Thr Asn Tyr
         35                  40                  45

Asn Asn Gly Pro Val Leu Ser Arg Phe Val Gln Lys Val Leu Asp Glu
     50                  55                  60

Thr Gly Ala Lys Lys Val Asp Ile Val Ala His Ser Met Gly Gly Ala
 65                  70                  75                  80

Asn Thr Leu Tyr Tyr Ile Lys Asn Leu Asp Gly Gly Asn Lys Ile Glu
                 85                  90                  95

Asn Val Val Thr Leu Gly Gly Ala Asn Arg Leu Thr Thr Ser Lys Ala
            100                 105                 110

Leu Pro Gly Thr Asp Pro Asn Gln Lys Ile Leu Tyr Thr Ser Val Tyr
            115                 120                 125

Ser Ser Ala Asp Met Ile Val Met Asn Tyr Leu Ser Lys Leu Asp Gly
130                 135                 140
```

```
Ala Lys Asn Val Gln Ile His Gly Val Gly His Ile Gly Leu Leu Met
145                 150                 155                 160

Asn Ser Gln Val Asn Ser Leu Ile Lys Glu Gly Leu Asn Gly Gly Gly
                165                 170                 175

Leu Asn Thr Asn
            180

<210> SEQ ID NO 82
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Glu His Asn Pro Val Val Met Val His Gly Ile Gly Gly Ala Ser Phe
  1               5                  10                  15

Ser Phe Ala Gly Ile Lys Ser Tyr Leu Val Ser Gln Gly Trp Ser Arg
                 20                  25                  30

Gly Lys Leu Tyr Ala Val Asp Phe Trp Asp Lys Thr Gly Thr Asn Tyr
             35                  40                  45

Asn Asn Gly Pro Val Leu Ser Arg Phe Val Gln Lys Val Leu Asp Glu
         50                  55                  60

Thr Gly Ala Lys Lys Val Asp Ile Val Ala His Ser Met Gly Gly Ala
 65                  70                  75                  80

Asn Thr Leu Tyr Tyr Ile Lys Asn Leu Asp Gly Gly Asn Lys Ile Glu
                 85                  90                  95

Asn Val Val Thr Leu Gly Gly Ala Asn Arg Leu Thr Thr Ser Lys Ala
                100                 105                 110

Leu Pro Gly Thr Asp Pro Asn Gln Lys Ile Leu Tyr Thr Ser Val Tyr
            115                 120                 125

Ser Ser Ala Asp Met Ile Val Met Asn Tyr Leu Ser Lys Leu Asp Gly
        130                 135                 140

Ala Lys Asn Val Gln Ile His Gly Val Gly His Ile Gly Leu Leu Met
145                 150                 155                 160

Asn Ser Gln Val Asn Ser Leu Ile Lys Glu Gly Leu Asn Gly Gly Gly
                165                 170                 175

Leu Asn Thr Asn
            180

<210> SEQ ID NO 83
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Glu His Asn Pro Val Val Met Val His Gly Ile Gly Gly Ala Ser Tyr
  1               5                  10                  15

Ser Phe Ala Gly Ile Lys Ser Tyr Leu Val Ser Gln Gly Trp Ser Arg
                 20                  25                  30

Gly Lys Leu Tyr Ala Val Asp Phe Trp Asp Lys Thr Gly Thr Asn Tyr
             35                  40                  45

Asn Asn Gly Pro Val Leu Ser Arg Phe Val Gln Lys Val Leu Asp Glu
         50                  55                  60
```

```
Thr Gly Ala Lys Lys Val Asp Ile Val Ala His Ser Met Gly Gly Ala
 65                  70                  75                  80

Asn Thr Leu Tyr Tyr Ile Lys Asn Leu Asp Gly Gly Asn Lys Ile Glu
                 85                  90                  95

Asn Val Val Thr Leu Gly Gly Ala Asn Arg Leu Thr Thr Ser Lys Ala
            100                 105                 110

Leu Pro Gly Thr Asp Pro Asn Gln Lys Ile Leu Tyr Thr Ser Val Tyr
        115                 120                 125

Ser Ser Ala Asp Met Ile Val Met Asn Tyr Leu Ser Lys Leu Asp Gly
130                 135                 140

Ala Lys Asn Val Gln Ile His Gly Val Gly His Ile Gly Leu Leu Tyr
145                 150                 155                 160

Ser Ser Gln Val Asn Ser Leu Ile Lys Glu Gly Leu Asn Gly Gly
                165                 170                 175

Gln Asn Thr Asn
            180

<210> SEQ ID NO 84
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Glu His Asn Pro Val Val Met Val His Gly Ile Gly Gly Ala Ser Tyr
 1               5                  10                  15

Ser Phe Ala Gly Ile Lys Ser Tyr Leu Val Ser Gln Gly Trp Ser Arg
             20                  25                  30

Gly Lys Leu Tyr Ala Val Asp Phe Trp Asp Lys Thr Gly Thr Asn Tyr
         35                  40                  45

Asn Asn Gly Pro Val Leu Ser Arg Phe Val Gln Lys Val Leu Asp Glu
     50                  55                  60

Thr Gly Ala Lys Lys Val Asp Ile Val Ala His Ser Met Gly Gly Ala
 65                  70                  75                  80

Asn Thr Leu Tyr Tyr Ile Lys Asn Leu Asp Gly Gly Asn Lys Ile Glu
                 85                  90                  95

Asn Val Val Thr Leu Gly Gly Ala Asn Arg Leu Thr Thr Ser Lys Ala
            100                 105                 110

Leu Pro Gly Thr Asp Pro Asn Gln Lys Ile Leu Tyr Thr Ser Val Tyr
        115                 120                 125

Ser Ser Ala Asp Met Ile Val Met Asn Tyr Leu Ser Lys Leu Asp Gly
130                 135                 140

Ala Lys Asn Val Gln Ile His Gly Val Gly His Thr Gly Leu Leu Met
145                 150                 155                 160

Asn Ser Gln Val Asn Ser Leu Ile Lys Glu Gly Leu Asn Gly Gly Gly
                165                 170                 175

His Asn Thr Asn
            180

<210> SEQ ID NO 85
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 85

Glu His Asn Pro Val Val Met Val His Gly Ile Gly Gly Ala Ser Tyr
 1               5                  10                  15

Asn Phe Ala Gly Ile Lys Ser Tyr Leu Val Ser Gln Gly Trp Ser Arg
             20                  25                  30

Gly Lys Leu Tyr Thr Val Asp Phe Trp Asp Lys Thr Gly Thr Asn Tyr
         35                  40                  45

Asn Asn Gly Pro Val Leu Ser Arg Phe Val Gln Lys Val Leu Asp Glu
     50                  55                  60

Thr Gly Ala Lys Lys Val Asp Ile Val Ala His Ser Met Gly Gly Ala
 65                  70                  75                  80

Asn Thr Leu Tyr Tyr Ile Lys Asn Leu Asp Gly Gly Asn Lys Ile Glu
                 85                  90                  95

Asn Val Val Thr Leu Gly Gly Ala Asn Arg Leu Val Thr Gly Lys Ala
             100                 105                 110

Leu Pro Gly Thr Asp Pro Asn Gln Lys Ile Leu Tyr Ala Ser Val Tyr
         115                 120                 125

Ser Ser Ala Asp Met Ile Val Met Asn Tyr Leu Ser Lys Leu Asp Gly
     130                 135                 140

Ala Lys Asn Val Gln Ile His Gly Val Gly His Ile Gly Leu Leu Met
145                 150                 155                 160

Asn Ser Gln Val Asn Ser Leu Ile Lys Glu Gly Leu Asn Gly Gly Gly
                165                 170                 175

Leu Asn Thr Asn
            180

<210> SEQ ID NO 86
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Glu His Asn Pro Val Val Met Val His Gly Ile Gly Gly Ala Ser Phe
 1               5                  10                  15

Asn Phe Ala Gly Ile Arg Ser Tyr Leu Val Ser Gln Gly Trp Ser Arg
             20                  25                  30

Gly Lys Leu Tyr Ala Val Asp Phe Trp Asp Arg Thr Gly Thr Asn Tyr
         35                  40                  45

Asn Asn Gly Pro Val Leu Ser Arg Phe Val Gln Lys Val Leu Asp Glu
     50                  55                  60

Thr Gly Ala Lys Lys Val Asp Ile Val Ala His Ser Met Gly Gly Ala
 65                  70                  75                  80

Asn Thr Leu Tyr Tyr Ile Lys Asn Leu Asp Gly Gly Asn Lys Ile Glu
                 85                  90                  95

Asn Val Val Thr Leu Gly Gly Ala Asn Arg Leu Thr Thr Ser Lys Ala
             100                 105                 110

Leu Pro Gly Thr Asp Pro Asn Gln Lys Ile Leu Tyr Thr Ser Ile Tyr
         115                 120                 125

Ser Ser Ala Asp Met Ile Val Met Asn Tyr Leu Ser Lys Leu Asp Gly
     130                 135                 140

Ala Lys Asn Val Gln Ile His Gly Val Gly His Ile Gly Leu Leu Tyr
145                 150                 155                 160
```

```
Ser Ser Gln Val Asn Ser Leu Ile Lys Glu Gly Leu Asn Gly Gly Gly
            165                 170                 175

Leu Asn Thr Asn
            180

<210> SEQ ID NO 87
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Glu His Asn Pro Val Val Met Val His Gly Ile Gly Gly Ala Ser Phe
  1               5                  10                  15

Asn Phe Ala Gly Ile Arg Ser Tyr Leu Val Ser Gln Gly Trp Ser Arg
             20                  25                  30

Gly Lys Leu Tyr Ala Val Asp Phe Trp Asp Lys Thr Gly Thr Asn Tyr
         35                  40                  45

Asn Asn Gly Pro Val Leu Ser Arg Phe Val Gln Lys Val Leu Asp Glu
     50                  55                  60

Thr Gly Ala Lys Lys Val Asp Ile Val Ala His Ser Met Gly Gly Ala
 65                  70                  75                  80

Asn Thr Leu Tyr Tyr Ile Lys Asn Leu Asp Gly Gly Asn Lys Ile Glu
                 85                  90                  95

Asn Val Val Thr Leu Gly Gly Thr Asn Arg Leu Thr Thr Ser Arg Ala
                100                 105                 110

Leu Pro Gly Thr Asp Pro Asn Gln Lys Ile Leu Tyr Thr Ser Ile Tyr
            115                 120                 125

Ser Ser Ala Asp Met Ile Val Met Asn Tyr Leu Ser Lys Leu Asp Gly
        130                 135                 140

Ala Lys Asn Val Gln Ile His Gly Val Gly His Ile Gly Leu Leu Met
145                 150                 155                 160

Asn Ser Gln Val Asn Ser Leu Ile Lys Glu Gly Leu Asn Gly Gly Gly
            165                 170                 175

Leu Asn Thr Asn
            180

<210> SEQ ID NO 88
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Glu His Asn Pro Val Val Met Val His Gly Ile Gly Gly Ala Ser Phe
  1               5                  10                  15

Asn Phe Ala Gly Ile Lys Ser Tyr Leu Val Ser Gln Gly Trp Ser Arg
             20                  25                  30

Asp Lys Pro Tyr Ala Val Asp Phe Trp Asp Lys Thr Gly Thr Asn Tyr
         35                  40                  45

Asn Asn Gly Pro Val Leu Ser Arg Phe Val Gln Lys Val Leu Asp Lys
     50                  55                  60

Thr Gly Ala Lys Lys Val Asp Ile Val Ala His Ser Met Gly Gly Ala
 65                  70                  75                  80
```

```
Asn Thr Leu Tyr Tyr Ile Lys Asn Leu Asp Gly Gly Asn Lys Val Glu
            85                  90                  95

Asn Val Val Thr Leu Gly Gly Ala Asn Arg Leu Thr Thr Ser Lys Ala
            100                 105                 110

Leu Pro Gly Thr Asp Pro Asn Gln Lys Ile Leu Tyr Thr Ser Ile Tyr
            115                 120                 125

Ser Ser Ala Asp Met Ile Val Met Asn Tyr Leu Ser Lys Leu Asp Gly
130                 135                 140

Ala Lys Asn Val Gln Ile His Gly Val Gly His Ile Gly Leu Leu Met
145                 150                 155                 160

Asn Ser Gln Val Asn Ser Leu Ile Lys Glu Gly Leu Asn Gly Gly Gly
                165                 170                 175

Leu Asn Thr Asn
            180

<210> SEQ ID NO 89
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Glu His Asn Pro Val Val Met Val His Gly Ile Gly Gly Ala Ser Phe
1               5                   10                  15

Asn Phe Ala Gly Ile Lys Ser Tyr Leu Val Ser Gln Gly Trp Pro Arg
            20                  25                  30

Asp Lys Leu Tyr Ala Val Asp Phe Trp Asp Lys Thr Gly Thr Asn Tyr
        35                  40                  45

Asn Asn Gly Pro Val Leu Ser Arg Phe Val Gln Lys Val Leu Asp Glu
    50                  55                  60

Thr Gly Ala Lys Lys Val Asp Ile Val Ala His Ser Met Gly Gly Ala
65                  70                  75                  80

Asn Thr Leu Tyr Tyr Ile Lys Asn Leu Asp Gly Gly Asn Lys Val Glu
            85                  90                  95

Ser Val Val Thr Leu Gly Gly Ala Asn Arg Leu Val Thr Gly Lys Ala
            100                 105                 110

Leu Pro Gly Thr Asp Pro Asn Gln Lys Ile Leu Tyr Thr Ser Ile Tyr
            115                 120                 125

Ser Ser Ala Asp Met Ile Val Met Asn Tyr Leu Ser Lys Leu Asp Gly
130                 135                 140

Ala Lys Asn Val Gln Ile His Gly Val Gly His Ile Gly Leu Leu Met
145                 150                 155                 160

Asn Ser Gln Val Asn Ser Leu Ile Lys Glu Gly Leu Asn Gly Gly Gly
                165                 170                 175

His Asn Thr Asn
            180

<210> SEQ ID NO 90
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90
```

```
Glu His Asn Pro Val Val Met Val His Gly Ile Gly Gly Ala Ser Phe
1               5                   10                  15

Ser Phe Ala Gly Ile Arg Ser Tyr Leu Val Ser Gln Gly Trp Pro Arg
            20                  25                  30

Asp Lys Leu Tyr Ala Val Asp Phe Trp Asp Lys Thr Gly Thr Asn Tyr
                35                  40                  45

Asn Asn Gly Pro Val Leu Ser Arg Phe Val Gln Lys Val Leu Asp Glu
            50                  55                  60

Thr Gly Ala Lys Lys Val Asp Ile Val Ala His Ser Met Gly Gly Ala
65                  70                  75                  80

Asn Thr Leu Tyr Tyr Ile Lys Asn Leu Asp Gly Gly Asn Lys Val Glu
                85                  90                  95

Asn Val Val Thr Leu Gly Gly Ala Asn Arg Leu Thr Thr Gly Lys Ala
                100                 105                 110

Leu Pro Gly Thr Asp Pro Asn Gln Lys Ile Leu Tyr Thr Ser Val Tyr
            115                 120                 125

Ser Ser Ala Asp Met Ile Val Met Asn Tyr Leu Ser Lys Leu Asp Gly
130                 135                 140

Ala Lys Asn Val Gln Ile His Gly Val Gly His Ile Gly Leu Leu Met
145                 150                 155                 160

Asn Ser Gln Val Asn Arg Leu Ile Lys Glu Gly Leu Asn Gly Gly Gly
                165                 170                 175

His Asn Thr Asn
            180

<210> SEQ ID NO 91
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Glu His Asn Pro Val Val Met Val His Gly Ile Gly Gly Ala Ser Phe
1               5                   10                  15

Ser Phe Ala Gly Ile Arg Ser Tyr Leu Val Ser Gln Gly Trp Pro Arg
            20                  25                  30

Asp Lys Leu Tyr Ala Val Asp Phe Trp Asp Lys Thr Gly Thr Asn Tyr
                35                  40                  45

Asn Asn Gly Pro Val Leu Ser Arg Phe Val Gln Lys Val Leu Asp Glu
            50                  55                  60

Thr Gly Ala Lys Lys Val Asp Ile Val Ala Tyr Ser Met Gly Gly Ala
65                  70                  75                  80

Asn Thr Leu Tyr Tyr Ile Lys Asn Leu Asp Gly Gly Asn Lys Val Glu
                85                  90                  95

Asn Val Val Thr Leu Gly Gly Ala Asn Arg Leu Thr Thr Gly Lys Ala
                100                 105                 110

Leu Pro Gly Thr Asp Pro Asn Gln Lys Ile Leu Tyr Thr Ser Val Tyr
            115                 120                 125

Ser Ser Ala Asp Met Ile Val Met Asn Tyr Leu Ser Lys Leu Asp Gly
130                 135                 140

Ala Lys Asn Val Gln Ile His Gly Val Gly His Ile Gly Leu Leu Met
145                 150                 155                 160

Asn Ser Gln Val Asn Arg Leu Ile Lys Glu Gly Leu Asn Gly Gly Gly
```

His Asn Thr Asn
            180

<210> SEQ ID NO 92
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Glu His Asn Pro Val Val Met Val His Gly Ile Gly Gly Ala Ser Phe
  1               5                  10                  15

Ser Phe Ala Gly Ile Arg Ser Tyr Leu Val Ser Gln Gly Trp Pro Arg
                 20                  25                  30

Asp Lys Leu Tyr Ala Val Asp Phe Trp Asp Lys Thr Gly Thr Asn Tyr
             35                  40                  45

Asn Asn Gly Pro Val Leu Ser Arg Phe Val Gln Lys Val Leu Asp Glu
         50                  55                  60

Thr Gly Ala Lys Lys Val Asp Ile Val Ala His Ser Met Gly Gly Ala
 65                  70                  75                  80

Asn Thr Leu Tyr Tyr Ile Lys Asn Leu Asp Gly Gly Asn Lys Val Gly
                 85                  90                  95

Asn Val Val Thr Leu Gly Gly Ala Asn Arg Leu Thr Thr Gly Lys Ala
                100                 105                 110

Leu Pro Gly Thr Asp Pro Asn Gln Lys Ile Leu Tyr Thr Ser Val Tyr
            115                 120                 125

Ser Ser Ala Asp Met Ile Val Met Asn Tyr Leu Ser Lys Leu Asp Gly
        130                 135                 140

Ala Lys Asn Val Gln Ile His Gly Val Gly His Ile Gly Leu Leu Met
145                 150                 155                 160

Asn Ser Gln Val Asn Arg Leu Ile Lys Glu Gly Leu Asn Gly Gly Gly
                165                 170                 175

His Asn Thr Asn
            180

<210> SEQ ID NO 93
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Glu His Asn Pro Val Val Met Val His Gly Ile Gly Gly Ala Ser Phe
  1               5                  10                  15

Ser Phe Ala Gly Ile Arg Ser Tyr Leu Val Ser Gln Gly Trp Pro Arg
                 20                  25                  30

Asp Lys Leu Tyr Ala Val Asp Phe Trp Asp Lys Thr Gly Thr Asn Tyr
             35                  40                  45

Asn Asn Gly Pro Val Leu Ser Arg Phe Val Gln Lys Val Leu Asp Glu
         50                  55                  60

Thr Gly Ala Lys Lys Val Asp Ile Val Ala His Ser Met Gly Gly Ala
 65                  70                  75                  80

Asn Thr Leu Tyr Tyr Ile Lys Asn Leu Asp Gly Gly Asn Lys Val Glu

```
                85                  90                  95
Asn Val Val Thr Leu Gly Gly Ala Asn Arg Leu Thr Thr Gly Lys Ala
                100                 105                 110
Leu Pro Gly Thr Asp Pro Asn Gln Lys Ile Leu Tyr Thr Ser Val Tyr
            115                 120                 125
Ser Ser Ala Asp Met Ile Val Met Asn Tyr Leu Ser Lys Leu Asp Gly
        130                 135                 140
Ala Lys Asn Val Gln Ile His Gly Val Gly His Ile Gly Leu Leu Met
145                 150                 155                 160
Asn Ser Gln Val Asn Arg Leu Ile Lys Glu Gly Leu Asn Gly Gly Gly
                165                 170                 175
His Asn Thr Asn
            180

<210> SEQ ID NO 94
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Glu His Asn Pro Val Val Met Val His Gly Ile Gly Gly Thr Ser Phe
 1               5                  10                  15
Asn Phe Ala Gly Ile Lys Ser Tyr Leu Val Ser Gln Gly Trp Ser Arg
                20                  25                  30
Asp Lys Leu Tyr Ala Val Asp Phe Trp Asp Lys Thr Gly Thr Asn Tyr
            35                  40                  45
Asn Asn Gly Pro Val Leu Ser Arg Phe Val Gln Lys Val Leu Asp Glu
        50                  55                  60
Thr Gly Ala Lys Lys Val Asp Ile Val Ala His Ser Met Gly Gly Ala
65                  70                  75                  80
Asn Thr Leu Tyr Tyr Ile Lys Asn Leu Asp Gly Gly Asn Lys Ile Glu
                85                  90                  95
Asn Val Val Thr Leu Gly Gly Ala Asn Arg Leu Thr Thr Ser Lys Ala
                100                 105                 110
Leu Pro Gly Thr Asp Pro Asn Gln Lys Ile Leu Tyr Thr Ser Ile Tyr
            115                 120                 125
Ser Ser Ala Asp Met Ile Val Met Asn Tyr Leu Ser Lys Leu Asp Gly
        130                 135                 140
Ala Lys Asn Val Gln Ile His Gly Val Gly His Ile Gly Leu Leu Met
145                 150                 155                 160
Asn Ser Gln Val Asn Ser Leu Ile Lys Glu Gly Leu Asn Gly Gly Gly
                165                 170                 175
His Asn Thr Asn
            180

<210> SEQ ID NO 95
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Glu His Asn Pro Val Val Met Val His Gly Ile Gly Gly Ala Ser Phe
```

```
            1               5                  10                 15
Ser Phe Ala Gly Ile Lys Ser Tyr Leu Val Ser Gln Gly Trp Ser Arg
                20                  25                 30

Asp Lys Leu Tyr Ala Val Asp Phe Ser Asp Lys Thr Gly Thr Asn Tyr
            35                  40                 45

Asn Asn Gly Pro Val Leu Ser Arg Phe Val Gln Lys Val Leu Asp Glu
        50                  55                 60

Thr Gly Ala Lys Lys Val Asp Ile Val Ala His Ser Met Gly Gly Ala
65                  70                  75                 80

Asn Thr Leu Tyr Tyr Ile Lys Asn Leu Asp Gly Gly Asn Lys Ile Glu
                85                  90                  95

Asn Val Val Thr Leu Gly Gly Ala Asn Arg Leu Thr Thr Ser Lys Ala
                100                 105                110

Leu Pro Gly Thr Asp Pro Asn Gln Lys Ile Leu Tyr Thr Ser Ile Tyr
            115                 120                125

Ser Ser Ala Asp Met Val Met Asn Tyr Leu Ser Lys Leu Asp Gly
        130                 135                 140

Ala Lys Asn Val Gln Ile His Gly Val Gly His Ile Gly Leu Leu Met
145                 150                 155                 160

Asn Ser Gln Val Asn Ser Leu Ile Lys Glu Gly Leu Asn Gly Gly Gly
                165                 170                 175

His Asn Thr Asn
            180

<210> SEQ ID NO 96
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Lys His Asn Pro Val Val Met Val His Gly Ile Gly Gly Ala Ser Tyr
1               5                   10                 15

Asn Phe Ala Gly Ile Lys Ser Tyr Leu Val Ser Gln Gly Trp Ser Arg
                20                  25                 30

Asp Lys Leu Tyr Ala Val Asp Phe Ser Asp Lys Thr Gly Thr Asn Tyr
            35                  40                 45

Asn Asn Gly Pro Val Leu Ser Arg Phe Val Gln Lys Val Leu Asp Glu
        50                  55                 60

Thr Gly Ala Lys Lys Val Asp Ile Val Ala His Ser Met Gly Gly Ala
65                  70                  75                 80

Asn Thr Leu Tyr Tyr Ile Lys Asn Leu Asp Gly Gly Asn Lys Ile Glu
                85                  90                  95

Asn Val Val Thr Leu Gly Gly Ala Asn Arg Leu Thr Thr Ser Lys Ala
                100                 105                110

Leu Pro Gly Thr Asp Pro Asn Gln Lys Ile Leu Tyr Thr Ser Ile Tyr
            115                 120                125

Ser Ser Ala Asp Met Ile Val Met Asn Tyr Leu Ser Lys Leu Asp Gly
        130                 135                 140

Ala Lys Asn Val Gln Ile His Gly Val Gly His Ile Gly Leu Leu Met
145                 150                 155                 160

Asn Ser Gln Val Asn Ser Leu Ile Lys Glu Gly Leu Asn Gly Gly Gly
                165                 170                 175
```

-continued

Leu Asn Thr Asn
            180

<210> SEQ ID NO 97
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Glu His Asn Pro Val Val Met Val His Gly Ile Gly Gly Ala Ser Phe
 1               5                  10                  15

Asn Phe Ala Gly Ile Lys Ser Tyr Leu Glu Ser Gln Gly Trp Ser Arg
             20                  25                  30

Gly Lys Leu Tyr Ala Val Asp Phe Trp Asp Lys Thr Gly Thr Asn Tyr
         35                  40                  45

Asn Asn Gly Pro Val Leu Ser Arg Phe Val Gln Lys Ala Leu Asp Glu
     50                  55                  60

Thr Gly Ala Lys Lys Val Asp Ile Val Ala His Ser Met Gly Gly Ala
 65                  70                  75                  80

Asn Thr Leu Tyr Tyr Ile Lys Asn Leu Asp Gly Gly Asn Lys Ile Glu
                 85                  90                  95

Asn Val Val Thr Leu Gly Gly Ala Asn Arg Leu Thr Thr Ser Lys Ala
            100                 105                 110

Leu Pro Gly Thr Asp Pro Asn Gln Lys Ile Leu Tyr Thr Ser Ile Tyr
        115                 120                 125

Ser Ser Ala Asp Met Ile Val Met Asn Tyr Leu Ser Lys Leu Asp Gly
    130                 135                 140

Ala Lys Asn Val Gln Ile His Gly Val Gly His Ile Gly Leu Leu Met
145                 150                 155                 160

Asn Ser Gln Val Asn Ser Leu Ile Lys Glu Gly Leu Asn Gly Gly Gly
                165                 170                 175

Gln Asn Thr Asn
            180

<210> SEQ ID NO 98
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Glu His Asn Pro Val Val Met Val His Gly Ile Gly Gly Ala Ser Phe
 1               5                  10                  15

Asn Phe Ala Gly Ile Lys Ser Tyr Leu Val Ser Gln Gly Trp Ser Arg
             20                  25                  30

Gly Lys Leu Tyr Ala Val Asp Phe Trp Asp Arg Thr Gly Thr Asn Tyr
         35                  40                  45

Asn Asn Gly Pro Val Leu Ser Arg Phe Val Lys Val Leu Asp Glu
     50                  55                  60

Thr Gly Ala Lys Lys Val Asp Ile Val Ala His Ser Met Gly Gly Ala
 65                  70                  75                  80

Asn Thr Leu Tyr Tyr Ile Lys Asn Leu Asp Gly Gly Asn Lys Ile Glu
                 85                  90                  95

```
Asn Val Val Thr Leu Gly Gly Ala Asn Arg Ser Thr Thr Ser Lys Ala
            100                 105                 110

Leu Pro Gly Thr Asp Pro Asn Gln Lys Ile Leu Tyr Thr Ser Ile Tyr
        115                 120                 125

Ser Ser Ala Asp Met Ile Val Met Asn Tyr Leu Ser Lys Leu Asp Gly
    130                 135                 140

Ala Lys Asn Val Gln Ile His Gly Val Gly His Ile Gly Leu Leu Met
145                 150                 155                 160

Asn Ser Gln Val Asn Ser Leu Ile Lys Glu Gly Leu Asn Gly Gly Gly
                165                 170                 175

Gln Asn Thr Asn
            180

<210> SEQ ID NO 99
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Glu His Asn Pro Val Val Met Val His Gly Ile Gly Gly Ala Ser Phe
 1               5                  10                  15

Asn Phe Ala Gly Ile Lys Ser Tyr Leu Val Ser Gln Gly Trp Ser Arg
            20                  25                  30

Gly Lys Leu Tyr Ala Val Asp Phe Trp Asp Arg Thr Gly Thr Asn Tyr
        35                  40                  45

Asn Asn Gly Pro Val Leu Ser Arg Phe Val Gln Lys Val Leu Asp Glu
    50                  55                  60

Thr Gly Ala Lys Lys Val Asp Ile Val Ala His Ser Met Gly Gly Ala
65                  70                  75                  80

Asn Thr Leu Tyr Tyr Ile Lys Asn Leu Asp Gly Gly Asn Lys Ile Glu
                85                  90                  95

Asn Val Val Thr Leu Gly Gly Ala Asn Arg Ser Thr Thr Ser Lys Ala
            100                 105                 110

Leu Pro Gly Thr Asp Pro Asn Gln Lys Ile Leu Tyr Thr Ser Ile Tyr
        115                 120                 125

Ser Ser Ala Asp Met Ile Val Met Asn Tyr Leu Ser Lys Leu Asp Gly
    130                 135                 140

Ala Lys Asn Val Gln Ile His Gly Val Gly His Ile Gly Leu Leu Met
145                 150                 155                 160

Asn Ser Gln Val Asn Ser Leu Ile Lys Glu Gly Leu Asn Gly Gly Gly
                165                 170                 175

His Asn Thr Asn
            180

<210> SEQ ID NO 100
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Glu His Asn Pro Val Val Met Val His Gly Ile Gly Gly Ala Ser Phe
 1               5                  10                  15
```

```
Asn Phe Ala Gly Ile Lys Ser Tyr Leu Val Ser Gln Gly Trp Ser Arg
            20                  25                  30

Gly Lys Leu Tyr Ala Val Asp Phe Trp Asp Arg Thr Gly Thr Asn Tyr
        35                  40                  45

Asn Asn Gly Pro Val Leu Ser Arg Phe Val Gln Lys Val Leu Asp Glu
    50                  55                  60

Thr Gly Ala Lys Lys Val Asp Ile Val Ala His Ser Met Gly Gly Ala
65                  70                  75                  80

Asn Thr Leu Tyr Tyr Ile Lys Asn Leu Asp Gly Gly Asn Lys Ile Glu
                85                  90                  95

Asn Val Val Thr Leu Gly Gly Ala Asn Arg Ser Thr Thr Ser Lys Ala
            100                 105                 110

Leu Pro Gly Thr Asp Pro Asn Gln Lys Ile Leu Tyr Thr Ser Ile Tyr
        115                 120                 125

Ser Ser Ala Asp Met Ile Val Met Asn Cys Leu Ser Lys Leu Asp Gly
    130                 135                 140

Ala Lys Asn Val Gln Ile His Gly Val Gly His Ile Gly Leu Leu Met
145                 150                 155                 160

Asn Ser Gln Val Asn Ser Leu Ile Lys Glu Gly Leu Asn Gly Gly Gly
                165                 170                 175

Gln Asn Thr Asn
        180

<210> SEQ ID NO 101
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Glu His Asn Pro Val Val Met Val His Gly Ile Gly Gly Ala Ser Phe
1               5                   10                  15

Asn Phe Ala Gly Ile Lys Ser Tyr Leu Val Ser Gln Gly Trp Ser Arg
            20                  25                  30

Asp Lys Leu Tyr Ala Val Asp Phe Lys Asp Lys Thr Gly Thr Asn Tyr
        35                  40                  45

Asn Asn Gly Pro Val Leu Ser Arg Phe Val Lys Lys Val Leu Asp Glu
    50                  55                  60

Thr Gly Ala Lys Lys Val Asp Ile Val Ala His Ser Met Gly Gly Ala
65                  70                  75                  80

Asn Thr Leu Tyr Tyr Ile Lys Asn Leu Asp Gly Gly Asn Lys Ile Glu
                85                  90                  95

Asn Val Val Thr Leu Gly Gly Ala Asn Arg Ser Thr Thr Ser Lys Ala
            100                 105                 110

Leu Pro Gly Thr Asp Pro Asn Gln Lys Ile Leu Tyr Thr Ser Val Tyr
        115                 120                 125

Ser Ser Ala Asp Met Ile Val Met Asn Tyr Leu Ser Lys Leu Asp Gly
    130                 135                 140

Ala Lys Asn Val Gln Ile His Gly Val Gly His Ile Gly Leu Leu Met
145                 150                 155                 160

Asn Ser Gln Val Asn Ser Leu Ile Lys Glu Gly Leu Asn Gly Gly Gly
                165                 170                 175

Leu Asn Thr Asn
        180
```

<210> SEQ ID NO 102
<211> LENGTH: 180
<212> TYPE: PRT
<213> ORGANISM: Artificial Sequence
<220> FEATURE:
<223> OTHER INFORMATION: Description of Artificial Sequence: Synthetic peptide

<400> SEQUENCE: 102

```
Glu His Asn Pro Val Val Met Val His Gly Ile Gly Gly Ala Ser Phe
 1               5                  10                  15

Asn Phe Ala Gly Ile Lys Ser Tyr Leu Val Ser Gln Gly Trp Ser Arg
             20                  25                  30

Asp Lys Leu Tyr Ala Val Asp Phe Trp Asp Lys Thr Gly Thr Asn Tyr
         35                  40                  45

Asn Asn Gly Pro Val Leu Ser Arg Phe Val Lys Lys Val Leu Asp Glu
     50                  55                  60

Thr Gly Ala Lys Lys Val Asp Ile Val Ala His Ser Met Gly Gly Ala
 65                  70                  75                  80

Asn Thr Leu Tyr Tyr Ile Lys Asn Leu Asp Gly Gly Asp Lys Ile Glu
                 85                  90                  95

Asn Val Val Thr Leu Gly Gly Ala Asn Arg Ser Thr Thr Ser Lys Ala
            100                 105                 110

Leu Pro Gly Thr Asp Pro Asn Gln Lys Ile Leu Tyr Thr Ser Val Tyr
        115                 120                 125

Ser Ser Ala Asp Met Ile Val Met Asn Tyr Leu Ser Lys Leu Asp Gly
    130                 135                 140

Ala Lys Asn Val Gln Ile His Gly Val Gly His Ile Gly Leu Leu Met
145                 150                 155                 160

Asn Ser Gln Val Asn Ser Leu Ile Lys Glu Gly Leu Asn Gly Gly Gly
                165                 170                 175

Gln Asn Thr Asn
            180
```

<210> SEQ ID NO 103
<211> LENGTH: 180
<212> TYPE: PRT
<213> ORGANISM: Artificial Sequence
<220> FEATURE:
<223> OTHER INFORMATION: Description of Artificial Sequence: Synthetic peptide

<400> SEQUENCE: 103

```
Glu His Asn Pro Val Val Met Val His Gly Ile Gly Gly Ala Ser Phe
 1               5                  10                  15

Asn Phe Ala Gly Ile Lys Ser Tyr Leu Val Ser Gln Gly Trp Ser Arg
             20                  25                  30

Asp Lys Leu Tyr Ala Val Asp Phe Trp Gly Lys Thr Gly Thr Asn Tyr
         35                  40                  45

Asn Asn Gly Pro Val Leu Ser Arg Phe Val Lys Lys Val Leu Asp Glu
     50                  55                  60

Thr Gly Ala Lys Lys Val Asp Ile Val Ala His Ser Met Gly Gly Ala
 65                  70                  75                  80

Asn Thr Leu Tyr Tyr Ile Lys Asn Leu Asp Gly Gly Asn Lys Ile Glu
                 85                  90                  95

Asn Val Val Thr Leu Gly Gly Ala Asn Arg Ser Thr Thr Ser Lys Ala
            100                 105                 110
```

```
Leu Pro Gly Thr Asp Pro Asn Gln Lys Ile Leu Tyr Thr Ser Ile Tyr
            115                 120                 125

Ser Ser Ala Asp Met Ile Val Met Asn Tyr Leu Ser Lys Leu Asp Gly
        130                 135                 140

Ala Lys Asn Val Gln Ile His Gly Val Gly His Ile Gly Leu Leu Met
145                 150                 155                 160

Asn Ser Gln Val Asn Ser Leu Ile Lys Glu Gly Leu Asn Gly Gly Gly
                165                 170                 175

Gln Asn Thr Asn
            180

<210> SEQ ID NO 104
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Glu His Asn Pro Val Val Met Val His Gly Ile Gly Gly Ala Ser Phe
1               5                   10                  15

Asn Phe Ala Gly Ile Lys Ser Tyr Leu Val Ser Gln Gly Trp Ser Arg
            20                  25                  30

Gly Lys Leu Tyr Ala Val Asp Phe Trp Asp Lys Thr Gly Thr Asn Tyr
        35                  40                  45

Asn Asn Gly Pro Val Leu Ser Arg Phe Val Lys Lys Val Leu Asp Glu
    50                  55                  60

Thr Gly Ala Lys Lys Val Asp Ile Val Ala His Ser Met Gly Gly Ala
65                  70                  75                  80

Asn Thr Leu Tyr Tyr Ile Lys Asn Leu Asp Gly Gly Asn Lys Ile Glu
                85                  90                  95

Asn Val Val Thr Leu Gly Gly Ala Asn Arg Ser Thr Thr Ser Lys Ala
            100                 105                 110

Leu Pro Gly Thr Asp Pro Asn Gln Lys Ile Leu Tyr Thr Ser Ile Tyr
        115                 120                 125

Ser Ser Ala Asp Met Ile Val Met Asn Tyr Leu Ser Lys Leu Asp Gly
    130                 135                 140

Ala Lys Asn Val Gln Ile His Gly Val Gly His Ile Gly Leu Leu Met
145                 150                 155                 160

Asn Ser Gln Val Asn Ser Leu Ile Lys Glu Gly Leu Asn Gly Gly Gly
                165                 170                 175

Gln Asn Thr Asn
            180

<210> SEQ ID NO 105
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Glu His Asn Pro Val Val Met Val His Gly Ile Gly Gly Ala Ser Phe
1               5                   10                  15

Asn Phe Ala Gly Ile Lys Ser Tyr Leu Val Ser Gln Gly Trp Ser Arg
            20                  25                  30
```

```
Gly Lys Leu Tyr Ala Val Asp Phe Lys Asp Lys Thr Gly Thr Asn Tyr
        35                  40                  45

Asn Asn Gly Pro Val Leu Ser Arg Phe Val Lys Lys Val Leu Asp Glu
 50                  55                  60

Thr Gly Ala Lys Lys Val Asp Ile Val Ala His Ser Met Gly Gly Ala
 65                  70                  75                  80

Asn Thr Leu Tyr Tyr Ile Lys Asn Leu Asp Gly Gly Asn Lys Ile Glu
                 85                  90                  95

Asn Val Val Thr Leu Gly Gly Ala Asn Arg Ser Thr Thr Ser Lys Ala
                100                 105                 110

Leu Pro Gly Thr Asp Pro Asn Gln Lys Ile Leu Tyr Thr Ser Ile Tyr
            115                 120                 125

Ser Ser Ala Asp Met Ile Val Met Asn Tyr Leu Ser Lys Leu Asp Gly
        130                 135                 140

Ala Lys Asn Val Gln Ile His Gly Val Gly His Ile Gly Leu Leu Met
145                 150                 155                 160

Asn Ser Gln Val Asn Ser Leu Ile Lys Glu Gly Leu Asn Gly Gly Gly
                165                 170                 175

Gln Asn Thr Asn
            180

<210> SEQ ID NO 106
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Lys His Asn Pro Val Val Met Val His Gly Ile Gly Gly Ala Ser Phe
 1               5                  10                  15

Asn Phe Ala Gly Ile Lys Ser Tyr Leu Val Ser Gln Gly Trp Ser Arg
                20                  25                  30

Asp Glu Leu Tyr Ala Val Asp Phe Trp Asp Glu Thr Gly Thr Asn Tyr
        35                  40                  45

Asn Asn Gly Pro Val Leu Ser Arg Phe Val Gln Lys Val Leu Asp Glu
 50                  55                  60

Thr Gly Ala Lys Lys Val Asp Ile Val Ala His Ser Met Gly Gly Ala
 65                  70                  75                  80

Asn Thr Leu Tyr Tyr Ile Lys Asn Leu Asp Gly Gly Asn Lys Ile Glu
                 85                  90                  95

Asn Val Val Thr Leu Gly Gly Ala Asn Arg Ser Thr Thr Ser Lys Ala
                100                 105                 110

Leu Pro Gly Thr Asp Pro Asn Gln Lys Ile Leu Tyr Thr Ser Ile Tyr
            115                 120                 125

Ser Ser Ala Asp Met Ile Val Met Asn Tyr Leu Ser Lys Leu Asp Gly
        130                 135                 140

Ala Lys Asn Val Gln Ile His Gly Val Gly His Ile Gly Leu Leu Met
145                 150                 155                 160

Asn Ser Gln Val Asn Ser Leu Ile Lys Glu Gly Leu Asn Gly Gly Gly
                165                 170                 175

Gln Asn Thr Asn
            180
```

```
<210> SEQ ID NO 107
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107
```

Glu His Asn Pro Val Val Met Val His Gly Ile Gly Gly Ala Ser Phe
 1               5                  10                  15

Asn Phe Ala Gly Ile Lys Ser Tyr Leu Val Ser Gln Gly Trp Ser Arg
             20                  25                  30

Asp Lys Leu Tyr Ala Val Asp Phe Trp Asp Lys Thr Gly Thr Asn Tyr
         35                  40                  45

Asn Asn Gly Pro Val Leu Ser Arg Phe Val Gln Lys Val Leu Asp Glu
     50                  55                  60

Thr Gly Ala Lys Lys Val Asp Ile Val Ala His Ser Met Gly Gly Ala
 65                  70                  75                  80

Asn Thr Leu Tyr Tyr Ile Lys Asn Leu Asp Gly Gly Asn Lys Val Glu
                 85                  90                  95

Asn Val Val Thr Leu Gly Gly Ala Asn Arg Ser Thr Thr Ser Lys Ala
            100                 105                 110

Leu Pro Gly Thr Asp Pro Asn Gln Lys Ile Leu Tyr Thr Ser Ile Tyr
        115                 120                 125

Ser Ser Ala Asp Met Ile Val Met Asn Tyr Leu Ser Lys Leu Asp Gly
    130                 135                 140

Ala Lys Asn Val Gln Ile His Gly Val Gly His Ile Gly Leu Leu Met
145                 150                 155                 160

Asn Ser Gln Val Asn Ser Leu Ile Lys Glu Gly Leu Asn Gly Gly Gly
                165                 170                 175

Gln Asn Thr Asn
            180

```
<210> SEQ ID NO 108
<211> LENGTH: 180
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108
```

Glu His Asn Pro Val Val Met Val His Gly Ile Gly Gly Ala Ser Phe
 1               5                  10                  15

Asn Phe Ala Gly Ile Lys Ser Tyr Leu Val Ser Gln Gly Trp Ser Arg
             20                  25                  30

Gly Lys Leu Tyr Ala Val Asp Phe Trp Asp Lys Thr Gly Thr Asn Tyr
         35                  40                  45

Asn Asn Gly Pro Val Leu Ser Arg Phe Val Gln Lys Val Leu Asp Glu
     50                  55                  60

Thr Gly Ala Lys Lys Val Asp Ile Val Ala His Ser Met Gly Gly Ala
 65                  70                  75                  80

Asn Thr Leu Tyr Tyr Ile Lys Asn Leu Asp Gly Gly Asn Lys Ile Glu
                 85                  90                  95

Asn Val Val Thr Leu Gly Gly Ala Asn Arg Ser Thr Thr Ser Lys Ala
            100                 105                 110

Leu Pro Gly Thr Asp Pro Asn Gln Lys Ile Leu Tyr Thr Ser Ile Tyr

-continued

```
                    115                 120                 125
Ser Ser Ala Asp Met Ile Val Met Asn Tyr Leu Ser Lys Leu Asp Gly
        130                 135                 140

Ala Lys Asn Val Gln Ile His Gly Val Gly His Ile Gly Leu Leu Met
145                 150                 155                 160

Asn Ser Gln Val Asn Ser Leu Ile Lys Glu Gly Leu Asn Gly Gly Gly
                165                 170                 175

Gln Asn Thr Asn
            180

<210> SEQ ID NO 109
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Asp His Asn Pro Val Ile Met Val His Gly Met Gly Gly Ala Ser Tyr
 1               5                  10                  15

Asn Phe Ala Gly
            20

<210> SEQ ID NO 110
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Asp His Gln Pro Val Val Val Val His Gly Ile Gly Gly Ser Ser Phe
 1               5                  10                  15

Asn Phe Ser Gly
            20

<210> SEQ ID NO 111
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucletide

<400> SEQUENCE: 111
gagcataacc ccgtg                                                  15
```

LIPASE GENES

CROSS-REFERENCES TO RELATED APPLICATIONS

Pursuant to 35 USC §119(e), this application claims priority to and benefit of U.S. Provisional Patent Application Ser. No. 60/217,954, filed on Jul. 13, 2000, and 60/300,378, filed on Jun. 21, 2001, the disclosures of each of which is incorporated herein in their entirety for all purposes.

FIELD OF THE INVENTION

The present invention relates to the generation of novel lipase genes and homologues and to methods of recombination to produce novel lipase genes.

COPYRIGHT NOTIFICATION

Pursuant to 37 C.F.R. § 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

BACKGROUND OF THE INVENTION

Lipases are enzymes which are involved in the breakdown of fats. Lipases are commercially important enzymes which have many current uses, including as reagents in food preparation processes (e.g., as additives to animal feeds), industrial degradative processes, crop engineering and even as treatments for several human diseases (e.g., indigestion and heartburn (e.g., for pancreatic insufficiency), secondary cystic fibrosis, Celiac disease, Crohn's disease, obesity, etc.). The activities and sequences of several hundred lipases are known. See, e.g., the world wide web at led.uni-stuttgart.de/.

Because lipase enzymes are of considerable commercial value, the identification and development of new lipase enzymes is desirable. The present invention relates to new lipase proteins and nucleic acids, e.g., having novel sequences and activities, as well as variants thereof.

SUMMARY OF THE INVENTION

The invention provides lipase polypeptides, nucleic acids encoding the polypeptides, antibodies to the polypeptides, and uses therefor; data sets containing character strings of lipase homologue sequences and automated systems for using the character strings as well as other functions that will be apparent upon further review. The present invention also provides methods of producing modified lipase polypeptides.

Various aspects of the current invention comprise an isolated or recombinant polypeptide comprising a sequence having at least 97% amino acid sequence identity to any one of SEQ ID NO: 75 to SEQ ID NO: 108. Such polypeptide can optionally comprise or exhibit lipase activity (e.g., it can degrade geranyl butyrate or neryl butyrate or both). Additionally, such polypeptide can exhibit enantioselectivity for geranyl butyrate over neryl butyrate. Such polypeptide that exhibits enantioselectivity for geranyl butyrate can comprise a sequence selected from: SEQ ID NO:76, SEQ ID NO:79, SEQ ID NO:80, SEQ ID NO:86, SEQ ID NO:96, SEQ ID NO:97, SEQ ID NO:101, SEQ ID NO:102, SEQ ID NO:104, SEQ ID NO:107, SEQ ID NO:108, SEQ ID NO:78, SEQ ID NO:87, SEQ ID NO:100, SEQ ID NO:75, SEQ ID NO:77, SEQ ID NO:88, SEQ ID NO:98, SEQ ID NO:99, SEQ ID NO:103, or SEQ ID NO:106. Alternatively, the polypeptide can exhibit enantioselectivity for neryl butyrate over geranyl butyrate. Such polypeptide that exhibits enantioselectivity for neryl butyrate over geranyl butyrate can comprise a sequence selected from: SEQ ID NO:81, SEQ ID NO:82, SEQ ID NO:83, SEQ ID NO:85, SEQ ID NO:89, SEQ ID NO:90, SEQ ID NO:94, SEQ ID NO:95, SEQ ID NO:105, SEQ ID NO:84, SEQ ID NO:91, SEQ ID NO:92, or SEQ ID NO:93.

Furthermore, the polypeptide can comprise a polypeptide encoded by a polynucleotide sequence which hybridizes under highly stringent conditions over substantially the entire length of a polynucleotide sequence selected from SEQ ID NO:1–54 (or a complementary sequence thereof), or by a polynucleotide sequence encoding a polypeptide sequence selected from SEQ ID NO:55–108 (or a complementary sequence thereof), and wherein the polypeptide comprises one or more of: Lys at position 1; Thr at position 14; Ser at position 17; Arg at position 22; Glu at position 26; Pro at position 31; Gly at position 33; Glu at position 34; Pro at position 35: Pro or Thr at position 37; Ser or Lys at position 41; Gly at position 42; Arg or Glu at position 43; Ala at position 61; Tyr at position 75; Gly at position 96; Ser at position 97; Thr at position 104; Ser at position 107; Ala at position 125; Gly at position 129; Val at position 134; Cys at position 138; Lys at position 141; Lys at position 146; Thr at position 156; Met at position 160; Arg at position 166; or His at position 177. Alternatively, the polypeptide can comprise one or more of: Lys at position 1; Thr at position 14; Ser at position 17; Arg at position 22; Glu at position 26; Pro at position 31; Gly at position 33; Glu at position 34; Pro at position 35; Pro or Thr at position 37; Ser or Lys at position 41; Gly at position 42; Arg or Glu at position 43; Ala at position 61; Tyr at position 75; Gly at position 96; Ser at position 97; Thr at position 104; Ser at position 107; Ala at position 125; Gly at position 129; Val at position 134; Cys at position 138; Lys at position 141; Lys at position 146; Thr at position 156; Met at position 160; Arg at position 166; or His at position 177.

Such polypeptide can comprise or exhibit lipase activity or the ability to degrade geranyl butyrate, neryl butyrate, or both neryl and geranyl butyrate. The polypeptide can also exhibit enantioselectivity for geranyl butyrate over neryl butyrate. A polypeptide exhibiting enantioselectivity for geranyl butyrate over neryl butyrate can comprise one or more of: Arg at position 22; Gly at position 33; Ser or Lys at position 41; Arg at position 43; Ser at position 107; Lys at position 141; Lys at position 146; Met at position 160; or His at position 177, or can comprise one or more of: Arg at position 43; or Ser at position 107.

Such polypeptide can alternatively comprise or exhibit enantioselectivity for neryl butyrate over geranyl butyrate. Such polypeptide can comprise one or more of: Ser at position 17; Arg at position 22; Pro at position 31; Gly at position 33; Ser or Lys at position 41; Lys at position 141; Lys at position 146; Met at position 160; Arg at position 166; or His at position 177, or, can comprise one or more of: Ser at position 17; Pro at position 31; or Arg at position 166.

In another aspect, the invention can comprise an isolated or recombinant polypeptide comprising a sequence having at least 94% amino acid sequence identity to the mature region of SEQ ID NO: 55, 61, 64, 65, 67, 68,70, or 72. Alternatively, such polypeptide can comprise a sequence having at least 94% amino acid sequence identity to the mature region of SEQ ID NO: 55, e.g., the polypeptide can comprise a sequence selected from SEQ ID NO: 55, 58–62, 75–78, 80–88, or 94–108 (or the mature region thereof). Alternatively, the polypeptide can comprise a sequence having at least 94% amino acid sequence identity to the mature region of SEQ ID NO: 61, which polypeptide, e.g., can comprise a sequence selected from SEQ ID NO: 55, 57–62, 75–78, 80–90, or 93–108. Alternatively, the polypeptide can comprise a sequence having at least 94% amino acid sequence identity to the mature region of SEQ ID NO: 64, which polypeptide, e.g., can comprise a sequence selected from SEQ ID NO: 64, 71, or 72 (or the mature region thereof). Alternatively, the polypeptide can comprise a sequence having at least 94% amino acid sequence identity to the mature region of SEQ ID NO: 65, which polypeptide, e.g., can comprise a sequence selected from SEQ ID NO: 65, 66, or 73 (or a mature region thereof). Alternatively, the polypeptide can comprise a sequence having at least 94% amino acid sequence identity to the mature region of SEQ ID NO: 67, which polypeptide, e.g., can comprise the sequence SEQ ID NO: 67 (or the mature region thereof). Alternatively, the polypeptide can comprise a sequence having at least 94% amino acid sequence identity to the mature region of SEQ ID NO: 68, which polypeptide, e.g., can comprise a sequence selected from SEQ ID NO: 68 or 101 (or the mature region thereof). Alternatively, the polypeptide can comprise a sequence having at least 94% amino acid sequence identity to the mature region of SEQ ID NO: 70, which polypeptide, e.g., can comprise a sequence selected from SEQ ID NO: 63, 68–70, 82–83, 85–86, 96, or 101–102 (or the mature region thereof). Alternatively, the polypeptide can comprise a sequence having at least 94% amino acid sequence identity to the mature region of SEQ ID NO: 72, which polypeptide, e.g., can comprise a sequence selected from SEQ ID NO: 64, 71, or 72 (or a mature region thereof).

In another aspect, the invention can comprise an isolated or recombinant polypeptide comprising a sequence having at least 85% amino acid sequence identity to the mature region of SEQ ID NO: 74, which polypeptide, e.g., can comprise a sequence selected from SEQ ID NO: 63, 71–72, 74, or 79 (or a mature region thereof).

In yet another aspect, the invention can comprise an isolated or recombinant polypeptide comprising a sequence having at least 99% amino acid sequence identity to the mature region of SEQ ID NO: 56.

In other aspects, such isolated or recombinant polypeptide comprises an amino acid sequence of any one of SEQ ID NO: 55 through SEQ ID NO: 108 over a comparison window of at least 45 contiguous amino acids.

In some embodiments, the invention comprises an isolated or recombinant polypeptide that is at least 45 contiguous amino acid residues of a polypeptide encoded by a coding polynucleotide sequence wherein the polynucleotide sequence is selected from: a polynucleotide sequence from any of SEQ ID NO: 1 to SEQ ID NO: 54, a polynucleotide sequence that encodes a polypeptide selected from any of SEQ ID NO: 55 through SEQ ID NO: 108; or a polynucleotide sequence that hybridizes under stringent conditions over substantially the entire length of one of the above polynucleotide sequences or which hybridizes to a subsequence comprising at least about 100 nucleic acids, provided that the polynucleotide does not correspond to GenBank accession numbers: 1I6WA, 1I6WB, A02813, A02815, A34992, AAA22574, AAB31769, AAC12257, AAD30278, AAF40217, AAF63229, AB000617, AF134840, AF141874, AF237623, AJ297356, BAA11406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P37957, S23934, U78785, X95309, Z99105, and Z99108.

Additionally, the invention provides such isolated or recombinant polypeptide wherein the polypeptide exhibits enantioselectivity for either a cis form enantiomer or a trans form enantiomer of a substrate and optionally wherein such enantioselectivity is represented by an enantiomeric ratio of at least 2 or more, at least 5 or more, at least 10 or more, at least 50 or more, or at least 100 or more.

In one embodiment, the invention, provides isolated or recombinant polypeptides encoded by a nucleic acid selected from any of the following: a polynucleotide sequence selected from SEQ ID NO: 1 to SEQ ID NO: 54 (or a complementary sequence thereof); a polynucleotide sequence encoding a polypeptide selected from SEQ ID NO: 55 to SEQ ID NO: 108 (or a complementary polynucleotide sequence thereof); a polynucleotide sequence which hybridizes under highly stringent conditions over substantially the whole length of any of the previously described polynucleotides, or which hybridizes to a subsequence of the same comprising at least 100 residues wherein the polynucleotide sequence does not comprise a sequence corresponding to any of GenBank accession numbers: 1I6WA, 1I6WB, A02813, A02815, A34992, AAA22574, AAB31769, AAC12257, AAD30278, AAF40217, AAF63229, AB000617, AF134840, AF141874, AF237623, AJ297356, BAA11406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P37957, S23934, U78785, X95309, Z99105, and Z99108; a polynucleotide sequence which comprises all, or a fragment of, any of the above described polynucleotides and which encodes a polypeptide comprising lipase activity; or a polynucleotide sequence encoding a polypeptide which comprises an amino acid sequence that is substantially identical over at least 45 contiguous amino acid residues of any one of SEQ ID NO: 55 to SEQ ID NO: 108 wherein the polynucleotide sequence does not comprise a sequence corresponding to any of GenBank accession numbers: 1I6WA, 1I6WB, A02813, A02815,A34992, AAA22574, AAB31769, AAC12257, AAD30278, AAF40217, AAF63229, AB000617, AF134840, AF141874, AF237623, AJ297356, BAA11406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P37957, S23934, U78785, X95309, Z99105, and Z99108. Additionally, such polynucleotide as is produced by mutating or recombining one or more of the above described polynucleotide sequences, is provided. The invention also provides an isolated or recombinant polypeptide as described above which comprises an amino acid sequence of any of SEQ ID NO: 55 to SEQ ID NO: 108.

In other aspects, the invention includes, isolated or recombinant polypeptides (as described above) which can optionally exhibit: lipase activity (e.g., with respect to tributyrin, with respect to tributyrin in DMF, with respect to tributyrin after heat treatment (i.e., after the polypeptide has been heat treated); or enantioselective lipase activity (e.g., with respect to neryl-butyrate or geranyl-butyrate). Optionally, such polypeptides can comprise lipase activity against novel substrates (i.e., substrates upon which typical wild-type lipases do not act) such as, e.g., methyl esters, pentadecanolide, or oxacyclotridecan. Additionally, such polypeptides optionally are substantially identical over at least 45, at least 50, at least 75, at least 100, at least 125, at least 150, at least 175, or at least 200 contiguous amino acids of any of the above described polypeptides with the proviso that the sequence does not comprise a sequence corresponding to any of GenBank accession numbers: 1I6WA, 1I6WB, A02813, A02815,A34992, AAA22574, AAB31769, AAC12257, AAD30278, AAF40217, AAF63229, AB000617, AF134840, AF141874, AF237623, AJ297356, BAA11406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P37957, S23934, U78785, X95309, Z99105, and Z99108. Alternatively, such polypeptide is substantially identical over at least 180, at least 212, at least 213, or at least 215 contiguous amino acid residues of an above described polypeptide, again with the proviso that the sequence does not comprise a sequence corresponding to any of GenBank accession numbers: 1I6WA, 1I6WB, A02813, A02815, A34992, AAA22574, AAB31769, AAC12257, AAD30278, AAF40217, AAF63229, AB000617, AF134840, AF141874, AF237623, AJ297356, BAA11406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P37957, S23934, U78785, X95309, Z99105, and Z99108.

In various embodiments, the above described polypeptides further comprise one or more of: a leader sequence, a precursor polypeptide, a secretion signal or a localization signal, an epitope tag, a fusion protein comprising one or more additional amino acid sequences, a polypeptide purification subsequence (e.g., an epitope tag, a FLAG tag, a polyhistidine sequence, a GST fusion), an N-terminus methionine residue, or a modified amino acid (e.g., a glycosylated amino acid, a PEGylated amino acid, a farnesylated amino acid, an acetylated amino acid, a biotinylated amino acid, an amino acid conjugated to a lipid moiety or to an organic derivatizing agent).

Other aspects of the invention include, a composition of one or more modified amino acid polypeptide and a pharmaceutically acceptable excipient and/or a composition comprising one or more polypeptide of the invention with a surfactant (or with another component of a cleaning solution such as a builder, a polymer, a bleach system, a structurant, a pH adjuster, a humectant, or a neutral inorganic salt) or a pharmaceutically acceptable excipient.

Additionally, a polypeptide which comprises a unique subsequence selected from SEQ ID NO: 55 through SEQ ID NO: 108 which is unique as compared to a polypeptide sequence corresponding to an amino acid sequence (or which is encoded by a nucleic acid sequence) corresponding to any of GenBank accession numbers 1I6WA, 1I6WB, A02813, A02815,A34992, AAA22574, AAB31769, AAC12257, AAD30278, AAF40217, AAF63229, AB000617, AF134840, AF141874, AF237623, AJ297356, BAA11406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P37957, S23934, U78785, X95309, Z99105, and Z99108 is provided. Other aspects include a polypeptide which is specifically bound by a polyclonal antisera raised against at least one antigen comprising at least one amino acid sequence from SEQ ID NO: 55 to SEQ ID NO: 108 (or a fragment thereof) where the antisera is subtracted with a polypeptide corresponding to an amino acid sequence (or which is encoded by a nucleic acid sequence) corresponding to any of the above listed GenBank accession numbers.

In other aspects the invention includes an antibody or antisera produced by administering a polypeptide of the invention to a mammal and wherein the antibody or antisera specifically binds at least one antigen which comprises a polypeptide sequence (or fragment thereof) from SEQ ID NO: 55 to SEQ ID NO: 108 and which antibody or antisera does not specifically bind to a polypeptide encoded by a nucleic acid corresponding to, or an amino acid sequence corresponding to one or more of the above listed GenBank accession numbers.

In yet other aspects, the invention includes an antibody or antisera that specifically binds a polypeptide comprising an amino acid sequence (or fragment thereof) from SEQ ID NO: 55 to SEQ ID NO: 108 and which antibody or antisera does not specifically bind to a peptide encoded by a nucleic acid corresponding to, or an amino acid sequence corresponding to, one or more of the above listed GenBank accession numbers.

The invention also includes a nucleic acid comprising a sequence selected from: a polynucleotide sequence selected from SEQ ID NO: 1 to SEQ ID NO: 54 (or a complementary sequence thereof; a polynucleotide sequence encoding a polypeptide selected from SEQ ID NO: 55 to SEQ ID NO: 108 (or a complementary sequence thereof); a polynucleotide sequence which hybridizes under highly stringent conditions over substantially the entire length of such sequences or which hybridizes to a subsequence thereof of at least 100 residues, provided that the polynucleotide sequence does not correspond to or encode any of GenBank accession numbers 1I6WA, 1I6WB, A02813, A02815, A34992, AAA22574, AAB31769, AAC12257, AAD30278, AAF40217, AAF63229, AB000617, AF134840, AF141874, AF237623, AJ297356, BAA11406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P37957, S23934, U78785, X95309, Z99105, and Z99108; and a polynucleotide sequence comprising all or a fragment of any of the previous polynucleotides and which comprises lipase activity and, again, which does not correspond to or encode of the above listed GenBank accession numbers.

Other embodiments of the invention can comprise a nucleic acid which comprises a sequence which encodes a polypeptide having an amino acid sequence that is substantially identical over at least 45, at least 50, at least 75, at least 100, at least 125, at least 150, at least 175, or at least 200 contiguous amino acid residues of any of SEQ ID NO: 55 to SEQ ID NO: 108, and, again, which does not correspond to or encode of the above listed GenBank accession numbers. Additionally, the invention provides nucleic acid which comprises a sequence encoding a polypeptide having a sequence that is substantially identical over at least 180, at least 212, at least 213, or at least 215 contiguous amino acid residues of any of SEQ ID NO: 55 to SEQ ID NO: 108, and, which does not correspond to or encode of the above listed GenBank accession numbers.

Furthermore, the invention optionally provides such nucleic acids wherein the encoded polypeptide can optionally exhibit: lipase activity (e.g., against tributyrin, against tributyrin in DMF (dimethyl formamide), or against tributyrin after being heat treated (i.e., after the polypeptide has been heat treated); enantioselective lipase activity (e.g., against neryl-butyrate and/or geranyl-butyrate). Optionally, such nucleic acids can encode polypeptides which comprise lipase activity against novel substrates (i.e., substrates upon which typical wild-type lipases do not act) such as, e.g., methyl esters, pentadecanolide, or oxacyclotridecan. The invention also includes nucleic acids that comprise polynucleotide sequences encoding polypeptides comprising lipase activity and which are produced by mutating or recombining one or more polynucleotide sequence as described above (and which optionally comprises lipase activity) and/or an enantioselective lipase activity, and which do not correspond to or encode GenBank accession numbers: 1I6WA, 1I6WB, A02813, A02815,A34992, AAA22574, AAB31769, AAC12257, AAD30278, AAF40217, AAF63229, AB000617, AF134840, AF141874, AF237623, AJ297356, BAA11406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P37957, S23934, U78785, X95309, Z99105, and Z99108. The invention additionally provides any of the above described nucleic acids wherein the encoded polypeptide comprises: a leader sequence; a precursor peptide, an epitope tag sequence; or a fusion protein comprising one or more additional nucleic acid.

A composition comprising two or more nucleic acids of the invention, as well as such compositions that comprise a library (e.g., of at least about 2, 5, 10, 50, or more nucleic acids) is also a feature of the invention. Such compositions are optionally produced by cleaving of one or more nucleic acid (e.g., by mechanical, chemical or enzymatic (e.g., a restriction endonuclease, an RNAse, a DNAse, etc.) means) of any of the above described nucleic acids. Compositions produced by incubating one or more of any of the above described polynucleotides in the presence of deoxyribonucleotide triphosphates and a nucleic acid polymerase (e.g., a thermostable polymerase) are also aspects of the current invention. Additionally, the invention provides a cell comprising at least one nucleic acid as described above (or a cleaved or amplified fragment or product thereof), which cell optionally expresses a polypeptide encoded by the nucleic acid. Vectors and/or expression vectors (e.g., plasmids, cosmids, phages, viruses, virus fragments, etc.) comprising any nucleic acid of the invention, as well as any cell transduced by such vectors are also provided. Compositions comprising any nucleic acid of the invention and a surfactant (or with another component of a cleaning solution such as a builder, a polymer, a bleach system, a structurant, a pH adjuster, a humectant, or a neutral inorganic salt) and/or compositions comprising an excipient (optionally a pharmaceutically acceptable excipient) are also provided in the invention.

In one aspect, the invention provides a nucleic acid which comprises a unique subsequence selected from SEQ ID NO:1 to SEQ ID NO:54. The unique subsequence is unique as compared to a nucleic acid corresponding to any of the sequences represented, e.g., by GenBank accession numbers: 1I6WA, 1I6WB, A02813, A02815,A34992, AAA22574, AAB31769, AAC12257, AAD30278, AAF40217, AAF63229, AB000617, AF134840, AF141874, AF237623, AJ297356, BAA1 1406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P37957, S23934, U78785, X95309, Z99105, and Z99108, or related sequences present in GenBank as of the filing of this application. Additionally, a target nucleic acid which hybridizes under stringent conditions to a unique coding oligonucleotide which encodes a unique subsequence in a polypeptide selected from SEQ ID NO: 55 to SEQ ID NO: 108, wherein the unique subsequence is unique as compared to an amino acid sequence or to a polypeptide encode by a nucleic acid sequence corresponding to any of the above GenBank accession numbers is also provided in the invention. Furthermore, in some embodiments the stringent conditions are selected such that a perfectly complementary oligonucleotide to the coding oligonucleotide hybridizes to the coding oligonucleotide with at least a 5× higher signal to noise ratio than for hybridization of the perfectly complementary oligonucleotide to a control nucleic acid corresponding to any of the above GenBank accession numbers and wherein the target nucleic acid hybridizes to the unique coding oligonucleotide with at least about a 2× higher signal to noise ratio as compared to hybridization of the control nucleic acid to the coding oligonucleotide.

In some embodiments, the current invention provides a database of one or more character strings corresponding to sequences selected from SEQ ID NO: 1 to SEQ ID NO: 108. Such database optionally comprises one or more character string recorded in a computer readable medium (e.g., internal or external to a computer). The invention also provides: a method for manipulating a sequence record in a computer system by reading a character string (optionally selected by a user, e.g., from a database or inputted by the user into the computer system) corresponding to a sequence selected from SEQ ID NO: 1 to SEQ ID NO: 108 (or a subsequence thereof); performing an operation on the character string; and returning a result of the operation (optionally comprising transmitting the selected character string to an output device). The operations performed in such computer system optionally comprise any of the following: a local sequence comparison, a sequence alignment, a sequence identity or similarity search, a structural similarity search, a sequence identity or similarity determination, a structure determination, a nucleic acid motif determination, an amino acid motif determination, a hypothetical translation, a determination of a restriction map, a sequence recombination, or a BLAST determination. In some aspects the method can comprise: aligning the selected character string with one or more additional character strings corresponding to a polynucleotide or polypeptide sequence; translating one or more character strings from SEQ ID NO: 1 to SEQ ID NO: 54 into a character string corresponding to an amino acid sequence or translating a character string selected from SEQ ID NO: 55 to SEQ ID NO: 108, into a character string corresponding to a polynucleotide sequence; determining sequence identity or similarity between the selected character string and one or more additional character strings by evaluating codon usage (optionally determining optimal codon usage); and obtaining the result of the operation on a user output device (e.g., optionally selected from a display monitor, a printer, and an audio output). The method also comprises transmitting the character string to a device (e.g., an oligonucleotide synthesizer or peptide synthesizer) capable of producing a physical embodiment of the character string (e.g., a physical embodiment comprising a nucleic acid or polypeptide or peptide corresponding to a character string or a sub-portion thereof)

In some embodiments the invention provides methods of producing modified or recombinant nucleic acids comprising mutating or recombining (including through recursive recombination) a nucleic acid of the invention (or a fragment thereof), as well as the modified or recombinant nucleic acids that are produced by such method. Optionally, the one or more additional nucleic acid encodes a polypeptide comprising lipase activity and/or enantioselective lipase activity (or an amino acid subsequence or fragment thereof). The recombination (e.g., recursive recombination) is optionally done in vitro or in vivo and optionally produces at least one library of recombinant nucleic acids, which comprises at least one polypeptide comprising lipase activity and/or enantioselective lipase activity (or a homologue thereof). Both the nucleic acid library produced and a population of cells comprising the library are provided by the invention, as are the modified or recombinant nucleic acids produced by the mutation/recombination (and cells which comprise such nucleic acids). In some aspects, the invention also provides a method of producing a polypeptide by introducing a nucleic acid of the invention (or a fragment thereof), which is operably linked to a regulatory sequence capable of directing expression of such nucleic acid, into a population of cells and then expressing the polypeptide. The polypeptide produced from such method is also part of the current invention. Such method optionally includes isolating the polypeptide from the cells and optionally includes expressing the polypeptide by culturing the population in a nutrient medium under conditions where the regulatory sequence directs expression of the polypeptide (again, wherein the polypeptide is optionally isolated or recovered from the cells and/or from the nutrient media (such culturing is optionally done in a bulk fermentation vessel)). The cells used in such methods are optionally bacterial, eukaryotic (e.g., fungal cells, yeast cells, plant cells, insect cells, or mammalian cells (e.g., fertilized oocytes, embryonic stem cells, pluripotent stem cells, etc.)). If mammalian cells are utilized, a transgenic animal is optionally regenerated from the cells and the polypeptide is optionally recovered from the transgenic animal or from a by-product of the transgenic animal such as milk.

In other aspects, the current invention provides methods/compositions for a cleaning solution (e.g., detergent) comprising the lipase homologues. Additional components (e.g., surfactants, proteolytic enzymes, humectants, neutral inorganic salts, sudsing agent, fragrance, structurants, etc.) can be included, individually, or multiply, in such compositions.

In yet other aspects, the current invention provides methods to therapeutically or prophylactically treat a gastrointestinal lipid related condition/disease/disorder by hydrolyzing a lipid through expressing a polypeptide in a target cell or contacting a target cell with an effective amount of polypeptide of the invention (or a fragment thereof) such target cell optionally is in culture or is within a subject to be treated. The current invention also provides a method of therapeutic or prophylactic treatment of a gastrointestinal lipid related condition/disease/disorder in a subject wherein the subject is administered a polypeptide of the invention in an amount effect to treat the condition/disease/disorder, including wherein the subject is a mammal (e.g., a human), and wherein the polypeptide is administered in vivo, in vitro, or ex vivo (or a combination of such) to one or more cells of the subject. Such polypeptides include compositions of the polypeptide and a pharmaceutically acceptable excipient, which is administered to a subject in an amount effective to treat a gastrointestinal lipid related condition/disease/disorder (e.g., cystic fibrosis, celiac disease, Crohn's disease, indigestion, and obesity Another provision of the invention is a method of hydrolyzing a lipid to therapeutically or prophylactically treat a gastrointestinal lipid related condition/disease/disorder by introducing into a target cell a nucleic acid of the invention, or a fragment thereof, which is operably linked to a regulatory sequence active in the target cell such that introduction of the polynucleotide results in expression of the nucleic acid in an amount sufficient to hydrolyze the lipid. Such method optionally comprises directly administering the nucleic acid to a subject in an amount sufficient to introduce the nucleic acid into one or more cells. The subject optionally comprises a mammal (or a human) and the nucleic acid optionally comprises a vector. Yet another provision of the invention is a method of therapeutically or prophylactically treating a gastrointestinal lipid related condition/disease/disorder by expressing in a target cell (or contacting a target cell with an effective amount of) a polynucleotide of the invention, or a fragment thereof, or of a polypeptide encoded thereby (or a fragment thereof). Such method can include wherein the target cell is in culture or wherein the target cell is within a subject. Additionally, the invention provides a method of therapeutically or prophylactically treating a gastrointestinal lipid related condition/disease/disorder in a subject by administering to the subject a polynucleotide of the invention (or a fragment thereof) or a polypeptide encoded thereby (or a fragment thereof) in an amount effective to treat the gastrointestinal lipid related condition/disease/disorder. Such method comprises optional embodiments wherein the subject is a mammal or a human and wherein the polynucleotide and/or polypeptide is administered in vivo, in vitro, or ex vivo (or a combination of such) to one or more cells of, the subject and wherein a composition of the polynucleotide and/or polypeptide and a pharmaceutically acceptable excipient is administered to the subject in an amount effective to treat the gastrointestinal lipid related condition/disease/disorder (e.g., cystic fibrosis, celiac disease, Crohn's disease, indigestion, or obesity).

BRIEF DESCRIPTION OF THE FIGURES

FIG. 1: Enantiomer Selectivity of Exemplary Lipase Homologues

FIG. 2: Enantiomeric Ratio for Exemplary Lipase Homologues.

FIGS. 3a–3i: Alignment of Exemplary Novel Lipase Polynucleotides (SEQ ID NO: 1–20).

FIGS. 4a–4h: Alignment of Exemplary Novel Lipase Polynucleotides (SEQ ID NO: 21–54).

FIGS. 5a–5c: Alignment of Exemplary Novel Lipase Polypeptides (SEQ ID NO: 55–74).

FIGS. 6a–6c: Alignment of Exemplary Novel Lipase Polypeptides (SEQ ID NO: 75–108).

DETAILED DESCRIPTION OF THE INVENTION

Definitions

Unless otherwise defined herein or below in the remainder of the specification, all technical and scientific terms used herein have the same meaning as commonly understood by those of ordinary skill in the art to which the present invention belongs.

A "polynucleotide sequence" is a nucleic acid (which is a polymer of nucleotides (A,C,T,U,G, etc. or naturally occurring nucleotide analogues, artificial nucleotide analogues, etc.) or a character string representing a nucleic acid, depending on context. Either the given nucleic acid or the complementary nucleic acid can be determined from any specified polynucleotide sequence.

Similarly, an "amino acid sequence" is a polymer of amino acids (a protein, polypeptide, etc.) or a character string representing an amino acid polymer, depending on context.

A "subsequence" or "fragment" is any portion of an entire sequence, up to and including the complete sequence.

"Substantially an entire length of a polynucleotide or amino acid sequence" refers to at least about 50%, at least about 60%, generally at least about 70%, generally at least about 80%, or typically at least about 90%, 95%, 96%, 97%, 98%, or 99% or more of a length of an amino acid sequence or nucleic acid sequence.

Numbering of a given amino acid or nucleotide polymer "corresponds to numbering" of a selected amino acid polymer or nucleic acid when the position of any given polymer component (amino acid residue, incorporated nucleotide, etc.) is designated by reference to the same residue position in the selected amino acid or nucleotide, rather than by the actual position of the component in the given polymer.

"Naturally occurring," as applied to an object, refers to the fact that the object can be found in nature. For example, a polypeptide or polynucleotide sequence that is present in an organism, including viruses, that can be isolated from a source in nature and which has not been intentionally modified by humankind in the laboratory is naturally occurring. In one aspect, a "naturally occurring" nucleic acid (e.g., DNA or RNA) molecule is a nucleic acid molecule that exists in the same state as it exists in nature; that is, the nucleic acid molecule is not isolated, recombinant, or cloned.

A nucleic acid, protein, peptide, polypeptide, or other component is "isolated" when it is partially or completely separated from components with which it is normally associated (such as, other peptides, polypeptides, proteins (including complexes, e.g., polymerases and ribosomes which may accompany a native sequence), nucleic acids, cells, synthetic reagents, cellular contaminants, cellular components, etc.), e.g., such as from other components with which it is normally associated in the cell from which it was originally derived. A nucleic acid, polypeptide, or other component is substantially pure when it is partially or completely recovered or separated from other components of its natural environment such that it is the predominant species present in a composition, mixture, or collection of components (i.e., on a molar basis it is more abundant than any other individual species in the composition). In preferred embodiments, the preparation consists of more than 70%, typically more than 80%, or preferably more than 90% of the isolated species.

In one aspect, a "substantially pure" or "isolated" nucleic acid (e.g., RNA or DNA), polypeptide, protein, or composition also means wherein the object species (e.g., nucleic acid or polypeptide) comprises at least about 50, 60, or 70 percent by weight (on a molar basis) of all macromolecular species present. A substantially pure or isolated composition can also comprise at least about 80, 90, 95, 96, 97, 98, or 99 or more percent by weight of all macromolecular species present in the composition. An isolated object species can also be purified to essential homogeneity (contaminant species cannot be detected in the composition by conventional detection methods) wherein the composition consists essentially of derivatives of a single macromolecular species.

The term "isolated nucleic acid" can also refer to a nucleic acid (e.g., DNA or RNA) that is not immediately contiguous with both of the coding sequences with which it is immediately contiguous (i.e., one at the 5' and one at the 3' end) in the naturally occurring genome of the organism from which the nucleic acid of the invention is derived. Thus, this term includes, e.g., a cDNA or a genomic DNA fragment produced by polymerase chain reaction (PCR) or restriction endonuclease treatment, whether such cDNA or genomic DNA fragment is incorporated into a vector, integrated into the genome of the same or a different species than the organism, including, e.g., a virus, from which it was originally derived, linked to an additional coding sequence to form a hybrid gene encoding a chimeric polypeptide, or independent of any other DNA sequences. The DNA may be double-stranded or single-stranded, sense or antisense.

A nucleic acid or polypeptide is "recombinant" when it is artificial or engineered, or derived from an artificial or engineered protein or nucleic acid. The term "recombinant" when used with reference e.g., to a cell, nucleotide, vector, or polypeptide typically indicates that the cell, nucleotide, or vector has been modified by the introduction of a heterologous (or foreign) nucleic acid or the alteration of a native nucleic acid, or that the polypeptide has been modified by the introduction of a heterologous amino acid, or that the cell is derived from a cell so modified. Recombinant cells express nucleic acid sequences (e.g., genes) that are not found in the native (non-recombinant) form of the cell or express native nucleic acid sequences (e.g., genes) that would be abnormally expressed, under-expressed, or not expressed at all.

The term "recombinant nucleic acid" (e.g., DNA or RNA) molecule means, for example, a nucleotide sequence that is not naturally occurring or is made by the combination (for example, artificial combination) of at least two segments of sequence that are not typically included together, not typically associated with one another, or are otherwise typically separated from one another. A recombinant nucleic acid can comprise a nucleic acid molecule formed by the joining together or combination of nucleic acid segments from different sources and/or artificially synthesized. The term "recombinantly produced" refers to an artificial combination usually accomplished by either chemical synthesis means, recursive sequence recombination of nucleic acid segments or other diversity generation methods of nucleotides, or manipulation of isolated segments of nucleic acids, e.g., by genetic engineering techniques known to those of ordinary skill in the art. "Recombinantly expressed" typically refers to techniques for the production of a recombinant nucleic acid in vitro and transfer of the recombinant nucleic acid into cells in vivo, in vitro, or ex vivo where it may be expressed or propagated. A "recombinant polypeptide" or "recombinant protein" usually refers to polypeptide or protein, respectively, that results from a cloned or recombinant gene or nucleic acid.

A "vector" is a composition for facilitating cell transduction by a selected nucleic acid, or expression of the nucleic acid in the cell. Vectors include, e.g., plasmids, cosmids, viruses, YACs, bacteria, poly-lysine, etc. An "expression vector" is a nucleic acid construct, generated recombinantly or synthetically, with a series of specific nucleic acid elements that permit transcription of a particular nucleic acid in a host cell. The expression vector can be part of a plasmid, virus, or nucleic acid fragment. The expression vector typically includes a nucleic acid to be transcribed operably linked to a promoter.

The term "homology" generally refers to the degree of similarity between two or more structures. The term "homologous sequences" refers to regions in macromolecules that have a similar order of monomers. When used in relation to nucleic acid sequences, the term "homology" refers to the degree of similarity between two or more nucleic acid sequences (e.g., genes) or fragments thereof. Typically, the degree of similarity between two or more nucleic acid sequences refers to the degree of similarity of the composition, order, or arrangement of two or more nucleotide bases (or other genotypic feature) of the two or more nucleic acid sequences. The term "homologous nucleic acids" generally refers to nucleic acids comprising nucleotide sequences having a degree of similarity in nucleotide base composition, arrangement, or order. The two or more nucleic acids may be of the same or different species or group. The term "percent homology" when used in relation to nucleic acid sequences, refers generally to a percent degree of similarity between the nucleotide sequences of two or more nucleic acids.

When used in relation to polypeptide (or protein) sequences, the term "homology" refers to the degree of similarity between two or more polypeptide (or protein) sequences (e.g., genes) or fragments thereof. Typically, the degree of similarity between two or more polypeptide (or protein) sequences refers to the degree of similarity of the composition, order, or arrangement of two or more amino acids of the two or more polypeptides (or proteins). The two or more polypeptides (or proteins) may be of the same or different species or group. The term "percent homology" when used in relation to polypeptide (or protein) sequences, refers generally to a percent degree of similarity between the amino acid sequences of two or more polypeptide (or protein) sequences. The term "homologous polypeptides" or "homologous proteins" generally refers to polypeptides or proteins, respectively, that have amino acid sequences and functions that are similar. Such homologous polypeptides or proteins may be related by having amino acid sequences and functions that are similar, but are derived from, or evolved from, different or the same species using the techniques described herein.

The term "subject" as used herein includes, but is not limited to, an organism; mammal, including, e.g., human, non-human primate (e.g., monkey), mouse, pig, cow, goat, rabbit, rat, guinea pig, hamster, horse, monkey, sheep, or other non-human mammal; a non-mammal, including, e.g., a non-mammalian vertebrate, such as a bird (e.g., chicken or duck) or a fish; and a non-mammalian invertebrate.

The term "pharmaceutical composition" means a composition suitable for pharmaceutical use in a subject, including an animal or human. A pharmaceutical composition generally comprises an effective amount of an active agent and a pharmaceutically acceptable carrier.

The term "effective amount" means a dosage or amount sufficient to produce a desired result. The desired result may comprise an objective or subjective improvement in the recipient which receives the dosage or amount.

A "prophylactic treatment" is a treatment administered to a subject who does not display signs or symptoms of a disease, pathology, or medical disorder, or displays only early signs or symptoms of a disease, pathology, or disorder, such that treatment is administered for the purpose of diminishing, preventing, or decreasing the risk of developing the disease, pathology, or medical disorder. A prophylactic treatment functions as a preventative treatment against a disease or disorder. A "prophylactic activity" is an activity of an agent, such as a nucleic acid, vector, gene, polypeptide, protein, substance, or composition thereof that, when administered to a subject who does not display signs or symptoms of pathology, disease or disorder, or who displays only early signs or symptoms of pathology, disease, or disorder, diminishes, prevents, or decreases the risk of the subject developing a pathology, disease, or disorder. A "prophylactically useful" agent or compound (e.g., nucleic acid or polypeptide) refers to an agent or compound that is useful in diminishing, preventing, treating, or decreasing development of pathology, disease or disorder.

A "therapeutic treatment" is a treatment administered to a subject who displays symptoms or signs of pathology, disease, or disorder, in which treatment is administered to such subject for the purpose of diminishing or eliminating those signs or symptoms of pathology, disease, or disorder. A "therapeutic activity" is an activity of an agent, such as a nucleic acid, vector, gene, polypeptide, protein, substance, or composition thereof, that eliminates or diminishes signs or symptoms of pathology, disease or disorder, when administered to a subject suffering from such signs or symptoms. A "therapeutically useful" agent or compound (e.g., nucleic acid or polypeptide) indicates that an agent or compound is useful in diminishing, treating, or eliminating such signs or symptoms of a pathology, disease or disorder.

The term "gene" broadly refers to any segment of DNA associated with a biological function. Genes include coding sequences and/or regulatory sequences required for their expression. Genes also include non-expressed DNA nucleic acid segments that, e.g., form recognition sequences for other proteins (e.g., promoter, enhancer, or other regulatory regions).

Generally, the nomenclature used herein, and the laboratory procedures in cell culture, molecular genetics, molecular biology, nucleic acid chemistry, and protein chemistry described below, are those well known and commonly employed by those of ordinary skill in the art. Standard techniques, such as described in Sambrook et al., *Molecular Cloning—A Laboratory Manual* (2nd Ed.), Vols. 1–3, Cold Spring Harbor Laboratory, Cold Spring Harbor, New York, 1989 (hereinafter "Sambrook") and *Current Protocols in Molecular Biology*, F. M. Ausubel et al., eds., Current Protocols, a joint venture between Greene Publishing Associates, Inc. and John Wiley & Sons, Inc. (supplemented through 2000) (hereinafter "Ausubel"), are used for recombinant nucleic acid methods, nucleic acid synthesis, cell culture methods, and transgene incorporation, e.g., electroporation, injection, and lipofection. Generally, oligonucleotide synthesis and purification steps are performed according to specifications. The techniques and procedures are generally performed according to conventional methods in the art and various general references which are provided throughout this document. The procedures herein are believed to be well known to those of ordinary skill in the art and are provided for the convenience of the reader.

As used herein, an "antibody" refers to a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (e.g., antibody) structural unit comprises a tetramer. Each tetramer is composed of two identical pairs of polypeptide chains, each pair having one "light" chain (about 25 kD) and one "heavy" chain (about 50–70 kD). The N-terminus of each chain defines a variable region of about 100 to 110 or more amino acids primarily responsible for antigen recognition. The terms variable light chain (VL) and variable heavy chain (VH) refer to these light and heavy chains, respectively. Antibodies exist as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Antibodies include single chain antibodies, including single chain Fv (sFv) antibodies in which a variable heavy and a variable light chain are joined together (directly or through a peptide linker) to form a continuous polypeptide.

The term "lipase activity" refers herein to the ability of a lipase enzyme to hydrolyze a lipid, oil, or fat molecule, detected by, for example, any of the lipase activity assays described herein or known to those having ordinary skill in the art (see, e.g., EXAMPLE I and the references cited therein).

"Enantioselective lipase activity" refers herein to the ability of a lipase enzyme to preferentially hydrolyze a specific enantiomer of a lipid, oil, or fat molecule, detected by, for example, any of the enantioselective lipase activity assays described herein (see, e.g., EXAMPLE II and the references cited therein).

A "mature region" as used herein refers to the mature coding region of a polypeptide, i.e., it does not include the signal peptide coding region. For example, FIGS. 3 and 5 depict the mature coding regions of exemplary lipases of the current invention.

An "equivalent amino acid position" is defined herein as an amino acid position of a test polypeptide which aligns with an amino acid position of SEQ ID NO:75 using an alignment algorithm as described herein. The equivalent amino acid position of the test polypeptide need not be the same as the linear amino acid sequence position of the test polypeptide. As an example, amino acid number 2 of the polypeptide SEQ ID NO:75 is considered to be the equivalent amino acid position to amino acid number 35 of the polypeptide SEQ ID NO:55 and to amino acid number 38 of SEQ ID NO:65, since amino acid number 2 of SEQ ID NO:75 aligns with amino acid number 35 of SEQ ID NO:55 and with amino acid number 38 of SEQ ID NO:65 using an alignment algorithm described herein, e.g., the CLUSTALW alignment program using default parameters. Therefore, "amino acid position 2 or an equivalent position to that of SEQ ID NO:75" is meant to correspond, e.g., to amino acid 35 of SEQ ID NO:55, amino acid 38 of SEQ ID NO:65, etc.

A variety of additional terms are defined or otherwise characterized herein.

Polynucleotides

Novel Lipase Sequences

The invention provides isolated or recombinant lipase polypeptides and homologues thereof (optionally collectively referred to as lipase polypeptides), and isolated or recombinant polynucleotides encoding the polypeptides.

Novel Lipase Molecules and Lipase Variants

The present invention relates to the isolation of newly discovered lipase polynucleotides from different strains of *Bacillus* as well as creation of novel lipase polynucleotides.

A number of *Bacillus* species (both known *Bacillus* species and un-typed *Bacillus* species) were screened to identify lipase activity while in colonies. Plate screens were used to identify those colonies expressing lipase activity. See, "EXAMPLE I" below, and, e.g., Dartois, V. et al., "Cloning, nucleotide sequence and expression in *Escherichia coli* of a lipase gene from *Bacillus subtilis* 168," *Biochimica et Biophysica Acta* 1131 (1992) 253–260 and references cited therein.

DNA from colonies which displayed lipase activity was used in PCR reactions with degenerate lipase primers designed to a known lipase gene from *Bacillus subtilis*. For reactions that did not readily produce amplified lipase genes, the DNA isolates were amplified using internal degenerative primers designed to anneal to more conserved regions, thus producing lipase gene fragments which were spliced into *B. subtilis* to generate chimeric full-length genes. The techniques used for amplification, etc. are well known to those of skill in the art and references teaching such are replete herein. The lipase genes discovered through this process (SEQ ID NO: 1 through SEQ ID NO: 20) correspond to lipase homologue polypeptides shown in SEQ ID NO: 55 through SEQ ID NO: 74. Novel lipase polynucleotides were isolated from cultures of *B. pumilus, B. subtilis, B. megaterium, B. lentus, B. circulans, B. azotoformans, B. firmus*, and *B. badius* (see, SEQ ID NO: 1 through SEQ ID NO: 8 and SEQ ID NO: 55 through SEQ ID NO: 62) as well as from undetermined Bacillus species (see, SEQ ID NO: 9 through SEQ ID NO: 20 and SEQ ID NO: 63 through SEQ ID NO: 74). See, FIGS. 3 and 5.

The newly isolated *Bacillus* lipase polynucleotides were then recombined to create libraries of novel lipase homologues which were screened for lipase activity and enantioselectivity (see, "EXAMPLE I" and infra). A number of homologues were chosen for further analysis (i.e., the novel lipase homologues of the invention). Methods and protocols for generation of nucleic acid libraries and of nucleic acid recombination are well known to those of skill in the art and can be found in numerous references cited herein. The nucleic acids for both the discovered *Bacillus* lipases and the newly created lipases were cloned into *E. coli* expression vectors, transformed in to *E. coli*, and screened for lipase activity (see, below for screening).

Figure 4B:
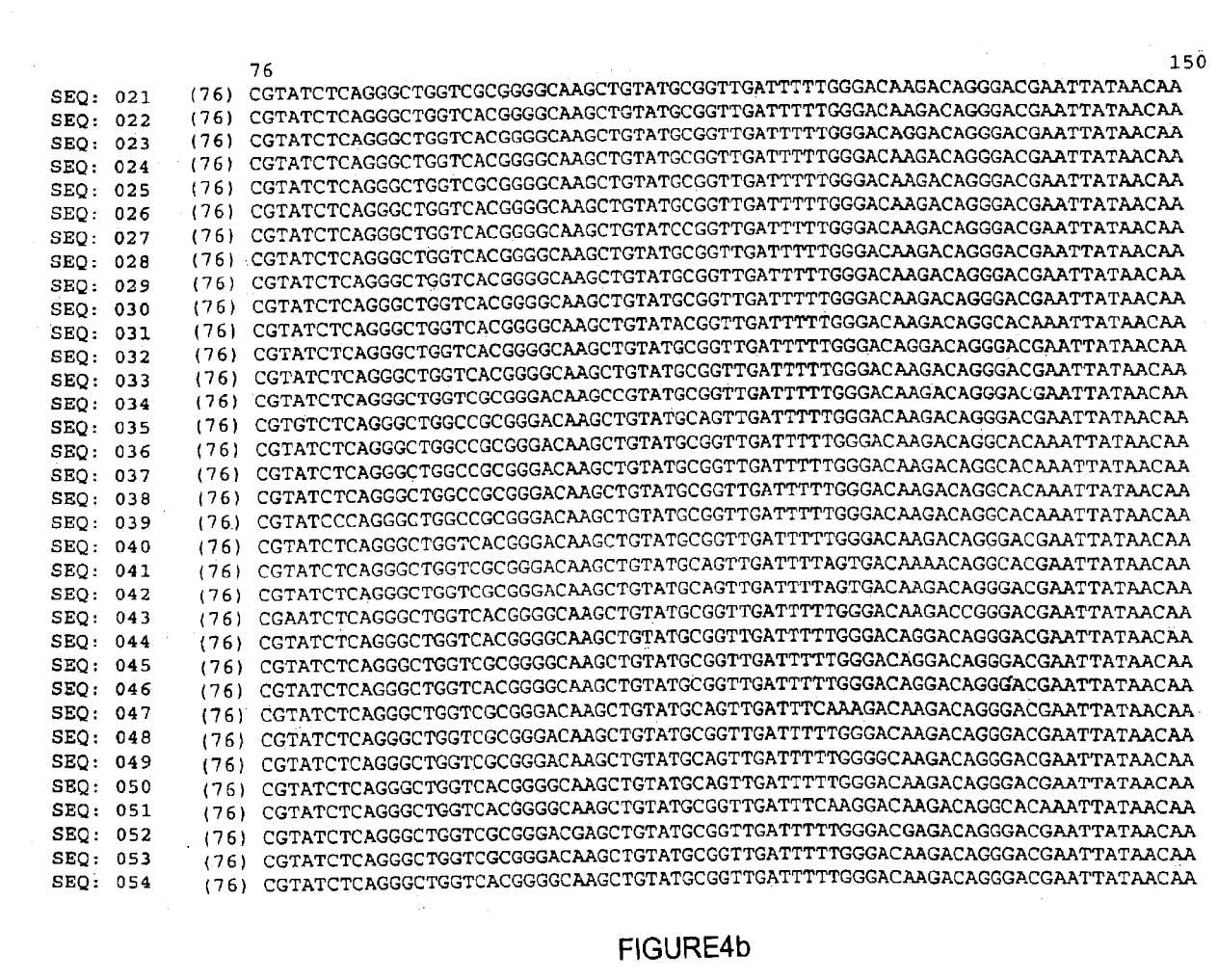

Sequences of the newly created lipase polynucleotides (i.e., those created through recombination of the newly isolated lipase genes) are shown in SEQ ID NO: 21 through SEQ ID NO: 54 (with the corresponding amino acid sequences being SEQ ID NO: 75 through SEQ ID NO: 108). It should be noted that the nucleic acid sequences of the created lipase homologues (SEQ ID NO: 21 through SEQ ID NO: 54) are present in the sequence listing table herein with an introductory 5' 'T' and an ending 3' 'TGA,' used for, e.g., construction of vector attachment sites, etc. and which, in many embodiments of the invention, are optionally removed or are not present. See, FIGS. 4 and 6

The newly created lipase homologues of the invention (i.e., SEQ ID NO: 21 through SEQ ID NO: 54 and SEQ ID NO: 75 through SEQ ID NO: 108) were also examined for enantioselectivity. Enantioselectivity as used herein, refers to the preference of an enzyme (e.g., lipase) to selectively utilize one substrate enantiomer over another enantiomer. Enantiomers are stereoisomers that are non-superimposable mirror images of each other. For example, neryl-butyrate and geranyl-butyrate are enantiomers of one another. It will be appreciated that while the screen was for enantioselectivity against neryl or geranyl butyrate, the novel lipase homologues herein optionally show lipase activity and/or enantioselective lipase activity against other substrates, e.g., neryl or geranyl acetate, other cis/trans lipids or lipid esters, etc.

While enantiomers have the same basic structure, they can vary in some specifics. For example the cis/trans enantiomers neryl-butyrate and geranyl-butyrate are used for different processes in the perfume/fragrance industry. Thus, enzymatic pathways that specifically produce one or the other (i.e., either neryl or geranyl butyrate) would be a welcome addition. Of course, myriad other enantiomers (both known and unknown) are also useful in numerous processes/applications and neryl/geranyl butyrate is only a non-limiting example of possible enantiomeric substrates for the lipase homologues of the invention.

The present invention also provides enantioselective lipases. Enantioselectivity can be readily determined as described below by comparing the conversion of such substrate enantiomers. For example, enantioselectivity was detected by growing clones expressing lipases of the present invention on media containing neryl-butyrate and geranyl-butyrate. The neryl-butyrate and geranyl-butyrate created a hazy appearance in the media on which the library constituents were grown. If an individual colony of a library produced active lipase (either secreted lipase or lipase from lysed cells) that utilized the neryl and/or geranyl butyrate in the media, it would break it down and clear that area of the plate. In other words, the colonies containing active lipase (which could breakdown the neryl-butyrate and/or geranyl-butyrate) produced a clear ring or halo around the colony. Such colonies were isolated and further analyzed to check for enantioselectivity. The protocol followed corresponded to that found in "SCREENING FOR ENZYME STEREO-SELECTIVITY UTILIZING MASS SPECTROMETRY," by Davis et al., U.S. S No. 60/278934 filed Mar. 26, 2001. While all the sequences used to create the libraries (i.e., SEQ ID NO: 1–20 (nucleic acid) and SEQ ID NO: 55–74 (polypeptide)) displayed enantioselectivity for geranyl-butyrate, a number of the novel lipase homologues of the invention surprisingly display enantioselectivity for neryl-butyrate while other lipase homologue polypeptides displayed greater geranyl enantioselective lipase activity than the parental clones. See, FIGS. 1 and 2 which list the enantioselectivity (i.e., either for geranyl butyrate or neryl butyrate) and selected enantiomeric ratio values for selected lipase homologues.

As described in U.S. S No. 60/278934, the phrase "enzyme stereoselectivity" refers to the preference for one substrate stereoisomer or pseudo-stereoisomer (if one form is labeled) over another or others in a chemical reaction catalyzed by an enzyme. When the stereoisomers are enantiomers, the phenomenon is referred to as "enzyme enantioselectivity" and is quantitatively expressed by the enantiomeric excess or the enantiomeric ratio. "Enantiomeric excess" refers to the absolute difference between the mole or weight fractions of major ($F_{(+)}$) and minor ($F_{(-)}$) enantiomers (i.e., $|F_{(+)}-F_{(-)}|$), where $F_{(+)}+F_{(-)}=1$. The percent enantiomer excess is $100|F_{(+)}-F_{(-)}|$. The enantiomeric ratio is determined by the following equation:

$$E = \frac{\ln[1 - c(1 + DE(p)]}{\ln[1 - c(1 - DE(p)]}$$

where c=the percent total substrate conversion (expressed as a decimal), and DE(p) is the diastereomeric excess (i.e., the percent product of isomer "1" less the percent product of isomer "2").

Employing the methods described herein and in U.S. S No. 60/278934, it was determined that polypeptide sequences SEQ ID NOS: 55 to 74 displayed enantioselectivity for geranyl butyrate versus neryl butyrate. As an example, an E (Enantiomeric ratio) value for an exemplary newly discovered lipase homologue has a geranyl enantiomer of about 2. See, FIG. 2.

A number of novel lipase homologues of the invention displayed enantioselectivity for geranyl butyrate versus neryl butyrate greater than that of the parental sequences. For example, 2 exemplary homologues having a preference for the geranyl enantiomer have E values of at least about 3 or more.

Surprisingly, none of SEQ ID NO: 1–20 (SEQ NO ID 55–74 for corresponding polypeptides) displayed enantioselectivity for neryl butyrate, yet a number of the other lipases of the present invention did displayed enantioselectivity for neryl butyrate versus geranyl butyrate, with E values for the neryl enantiomer of at least about 1.4 up to about 2.2 for selected homologues. See, FIG. 2.

Novel Substitutions

Certain lipase homologues of the invention (e.g., SEQ ID NOS: 75 to 108) contain one or more of the following amino acid substitutions: Lys at position 1, Thr at position 14, Ser at position 17, Arg at position 22, Glu at position 26, Pro at position 31, Gly at position 33, Glu at position 34, Pro at position 35, Pro or Thr at position 37, Ser or Lys at position 41, Gly at position 42, Arg or Glu at position 43, Ala at position 61, Tyr at position 75, Gly at position 96, Ser at position 97, Thr at position 104, Ser at position 107, Ala at position 125, Gly at position 129, Val at position 134, Cys at position 138, Lys at position 141, Lys at position 146, Thr at position 156, Met at position 160, Arg at position 166, or His at position 177, which are not found in equivalent amino acid positions of related lipase sequences having GenBank Protein Accession Nos. AAA22574, CAB95850, CAB12664, BAA11406, CAA02196, CAA00273, CAB12064, BAA22231, and CAA00274. An equivalent amino acid position is defined supra as an amino acid position of a test polypeptide which aligns with an amino acid position of SEQ ID NO:75 (see, supra).

Preferred amino acid substitutions include those which are observed in a number of the lipase homologues of the invention which display enantioselectivity for geranyl butyrate versus neryl butyrate (e.g., having E values of at least about 3 for the geranyl enantiomer): Arg at position 22, Gly at position 33, Ser or Lys at position 41, Arg at position 43, Ser at position 107, Lys at position 141, Lys at position 146, Met at position 160, and His at position 177. More preferred substitutions include those which are observed only in lipase homologues of the invention which display enantioselectivity for geranyl enantiomer: Arg at position 43 and Ser at position 107.

Preferred amino acid substitutions also include those which are observed in a number of the lipase homologues of the invention which display enantioselectivity for neryl butyrate versus geranyl butyrate (e.g., having E values of at least about 1.4 for the neryl enantiomer): Ser at position 17, Arg at position 22, Pro at position 31, Gly at position 33, Ser or Lys at position 41, Lys at position 141, Lys at position 146, Met at position 160, Arg at position 166, or His at position 177. More preferred substitutions include those which are observed only in lipase homologues of the invention which display enantioselectivity for the neryl enantiomer: Ser at position 17, Pro at position 31, and Arg at position 166.

The nucleic acid sequences of the current invention (i.e., SEQ ID NO: 1 through SEQ D NO: 54) can be recombined (or further recombined) in accordance with the methods described herein and expressed in, e.g., *E. coli* to generate additional lipase variants. Lipase activity can be screened for on, e.g., tributyrin and further parameters such as, e.g. thermostability, lipase activity on novel substrates (i.e., on substrates on which known lipase variants do not have activity, etc.) can be selected for.

Making Polynucleotides

Polynucleotides and oligonucleotides of the invention can be prepared by standard solid-phase methods, according to known synthetic methods. Typically, fragments of up to about 100 bases are individually synthesized, then joined (e.g., by enzymatic or chemical ligation methods, or polymerase mediated recombination methods) to form essentially any desired continuous sequence. For example, the polynucleotides and oligonucleotides of the invention can be prepared by chemical synthesis using, e.g., the classical phosphoramidite method described by Beaucage et al., (1981) *Tetrahedron Letters* 22:1859–69, or the method described by Matthes et al., (1984) *EMBO J* 3: 801–05, e.g., as is typically practiced in automated synthetic methods. According to the phosphoramidite method, oligonucleotides are synthesized, e.g., in an automatic DNA synthesizer, purified, annealed, ligated and cloned in appropriate vectors.

In addition, essentially any nucleic acid can be custom ordered from any of a variety of commercial sources, such as The Midland Certified Reagent Company (mcrc@oligos.com), The great American Gene Company (world wide web at genco.com), ExpressGen Inc. (the world wide web at expressgen.com), Operon Technologies Inc. (Alameda, Calif.) and many others. Similarly, peptides and antibodies can be custom ordered from any of a variety of sources, such as PeptidoGenic (pkim@ccnet.com), HTI Bioproducts, Inc. (the world wide web at htibio.com), BMA Biomedicals Ltd. (U.K.), Bio.Synthesis, Inc., and many others.

Certain polynucleotides of the invention may also obtained by screening cDNA libraries (e.g., libraries generated by recombining homologous nucleic acids as in typical recursive recombination methods) using oligonucleotide probes which can hybridize to, or PCR-amplify, polynucleotides which encode the novel lipase polypeptides and fragments of those polypeptides. Procedures for screening and isolating cDNA clones are well-known to those of skill in the art. Such techniques are described in, for example, Sambrook et al. (1989) supra, and Ausubel F M et al. (1989; supplemented through 2000) supra.

As described in more detail herein, the polynucleotides of the invention include sequences which encode novel lipase homologues and sequences complementary to the coding sequences, and novel fragments of coding sequence and complements thereof. The polynucleotides can be in the form of RNA or in the form of DNA, and include mRNA, cRNA, synthetic RNA and DNA, and cDNA. The polynucleotides can be double-stranded or single-stranded, and if single-stranded, can be the coding strand or the non-coding (anti-sense, complementary) strand. The polynucleotides optionally include the coding sequence of a novel lipase homologue (i) in isolation, (ii) in combination with additional coding sequence, so as to encode, e.g., a fusion protein, a precursor protein, a protein comprising a leader sequence, or the like, (iii) in combination with non-coding sequences, such as introns (including artificial introns), control elements such as a promoter, a terminator element, or 5' and/or 3' untranslated regions effective for expression of the coding sequence in a suitable host, and/or (iv) in a vector or host environment in which the novel lipase coding sequence is a heterologous gene. Sequences can also be found in combination with typical compositional formulations of nucleic acids, including in the presence of carriers, buffers, adjuvants, excipients and the like.

Using Polynucleotides

The polynucleotides (and polypeptides) of the invention have a variety of uses including, but not limited to, for example: recombinant production (i.e., expression) of the recombinant lipase polypeptides of the invention for industrial and other uses (e.g., especially as components of cleaning solutions such as laundry detergents, dish detergents, industrial cleansers (e.g., for septic systems, grease traps, machinery parts, etc.)); as therapeutic and prophylactic agents in methods of in vivo and ex vivo treatment of a variety of diseases, disorders, and conditions; for use in in vitro methods, such as diagnostic and screening methods, to detect, diagnose, and treat a variety of diseases, disorders, and conditions (e.g., pancreatic disorders) in a variety of subjects (e.g., mammals); as immunogens; in gene therapy methods and DNA- or RNA-based delivery methods to deliver or administer in vivo, ex vivo, or in vitro, biologically active polypeptides of the invention to a tissue, population of cells, organ, graft, bodily system of a subject (e.g., organ system, lymphatic system, blood system, etc.); as diagnostic probes for the presence of complementary or partially complementary nucleic acids (including for detection of natural lipase coding nucleic acids); as substrates for further reactions, e.g., recursive recombination reactions, mutation reactions, or other diversity generation reactions to produce new and/or improved lipase homologues, and new lipase nucleic acids encoding such homologues, e.g., to evolve novel therapeutic, prophylactic, or industrial properties, and the like; for polymerase chan reactions (PCR) or cloning methods, e.g., including digestion or ligation reactions, to identify new and/or improved naturally-occurring or non-naturally occurring lipase nucleic acids and polypeptides encoded therefrom. Polynucleotides which encode a lipase homologue of the invention, or complements of the polynucleotides, are optionally administered to a cell to accomplish a therapeutically or prophylactically useful process or to express a therapeutically useful product in vivo, ex vivo, or in vitro.

The present invention provides an isolated or recombinant nucleic acid comprising a polynucleotide sequence selected from: a polynucleotide sequence selected from SEQ ID NO: 1 to SEQ ID NO: 54 (or a complementary polynucleotide sequence thereof; a polynucleotide sequence encoding a polypeptide selected from SEQ ID NO: 55 to SEQ ID NO: 108 (or a complementary polynucleotide thereof); a polynucleotide sequence which hybridizes under highly stringent conditions over substantially the entire length of such polynucleotide sequences or which hybridizes to a subsequence thereof of at least 100 residues provided that the polynucleotide sequence does not correspond to or encode any of GenBank accession numbers 1I6WA, 1I6WB, A02813, A02815, A34992, AAA22574, AAB31769, AAC12257, AAD30278, AAF40217, AAF63229, AB000617, AF134840, AF141874, AF237623, AJ297356, BAA11406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P37957, S23934, U78785, X95309, Z99105, and Z99108; and a polynucleotide sequence comprising all or a fragment of any of the previous polynucleotides and which comprises lipase activity and which does not correspond to or encode any of the above GenBank accession numbers.

Other embodiments of the invention can comprise an isolated or recombinant nucleic acid which comprises a polynucleotide sequence which encodes a polypeptide having an amino acid sequence that is substantially identical over at least 45, at least 50, at least 75, at least 100, at least 125, at least 150, at least 175, or at least 200 contiguous amino acid residues of any of SEQ ID NO: 55 to SEQ ID NO: 108 provided that the polynucleotide sequence does not correspond to or encode any of GenBank accession numbers 1I6WA, 1I6WB, A02813, A02815,A34992, AAA22574, AAB31769, AAC12257, AAD30278, AAF40217, AAF63229, AB000617, AF134840, AF141874, AF237623, AJ297356, BAA1 1406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P37957, S23934, U78785, X95309, Z99105, and Z99108. Additionally, the invention provides an isolated or recombinant nucleic acid which comprises a polynucleotide sequence which encodes a polypeptide having an amino acid sequence that is substantially identical over at least 180, at least 212, at least 213, or at least 215 contiguous amino acid residues of any of SEQ ID NO: 55 to SEQ ID NO: 108, provided that the sequence does not correspond to or encode any of the GenBank accession numbers listed above.

Furthermore, the invention provides such nucleic acids as described wherein the encoded polypeptide comprises lipase activity (e.g., against tributyrin, against tributyrin in DMF (dimethyl formamide), against tributyrin after being heat treated (i.e., after the polypeptide has been heat treated); and/or comprises enantioselective lipase activity (e.g., against neryl-butyrate or geranyl-butyrate). Optionally, such nucleic acids as described can encode polypeptides which comprise lipase activity against novel substrates (i.e., substrates upon which typical wild-type lipases do not act) such as, e.g., methyl esters, pentadecanolide, or oxacyclotridecan. The invention also includes isolated or recombinant nucleic acids that comprise a polynucleotide sequence which encodes a polypeptide comprising lipase activity and which is produced by mutating or recombining one or more polynucleotide sequence as described above (and which optionally comprises lipase activity) providing that the sequence does not correspond to or encode any of the GenBank accession sequences above. The invention additionally provides any of the above described nucleic acids wherein the encoded polypeptide comprises: a leader sequence; a precursor peptide, an epitope tag sequence; or a fusion protein comprising one or more additional nucleic acid.

A composition comprising two or more nucleic acids as described above, as well as such compositions that comprise a library (e.g., of at least about 2, 5, 10, 50, or more nucleic acids) is also a feature of the invention. Such compositions are optionally produced by cleaving of one or more nucleic acid (e.g., by mechanical, chemical or enzymatic (e.g., a restriction endonuclease, an RNAse, a DNAse, etc.) means) of any of the above described nucleic acids. Compositions produced by incubating one or more of any of the above described polynucleotides in the presence of deoxyribonucleotide triphosphates and a nucleic acid polymerase (e.g., a thermostable polymerase) are also provided in the current invention. Additionally, the invention provides a cell (which optionally expresses a polypeptide encoded by the nucleic acid) comprising at least one nucleic acid as described above (or a cleaved or amplified fragment or product thereof). Vectors and/or expression vectors (e.g., plasmids, cosmids, phages, viruses, virus fragments, etc.) comprising any nucleic acid as described above, as well as any cell transduced by such vectors are also provided. Compositions comprising any nucleic acid as described above and an excipient (optionally a pharmaceutically acceptable excipient are also provided in the invention).

Expression of Polypeptides

In accordance with the present invention, polynucleotide sequences which encode novel lipase homologues (including mature lipase homologues), fragments of lipase proteins, related fusion proteins, or functional equivalents thereof, collectively referred to herein, e.g., as "lipase homologue polypeptides," "novel lipase polypeptides," or "lipase polypeptides" are used in recombinant DNA molecules that direct the expression of the lipase homologue polypeptides in appropriate host cells. Due to the inherent degeneracy of the genetic code, other nucleic acid sequences which encode substantially the same or a functionally equivalent amino acid sequence are also used to clone and express the lipase homologues.

Modified Coding Sequences

As will be understood by those of skill in the art, it can be advantageous to modify a coding sequence to enhance its expression in a particular host. The genetic code is redundant with 64 possible codons, but most organisms preferentially use a subset of these codons. The codons that are utilized most often in a species are called optimal codons, and those not utilized very often are classified as rare or low-usage codons (see, e.g., Zhang S P et al. (1991) *Gene* 105:61–72). Codons can be substituted to reflect the preferred codon usage of the host, a process called "codon optimization" or "controlling for species codon bias."

Optimized coding sequence containing codons preferred by a particular prokaryotic or eukaryotic host (see also, Murray, E. et al. (1989) *Nuc Acids Res* 17:477–508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, preferred stop codons for *S. cerevisiae* and mammals are UAA and UGA respectively. The preferred stop codon for monocotyledonous plants is UGA, whereas insects and *E. coli* prefer to use UAA as the stop codon (Dalphin M E et al. (1996) *Nuc Acids Res* 24: 216–218).

The polynucleotide sequences of the present invention can be engineered in order to alter lipase homologue coding sequences for a variety of reasons, including but not limited to, alterations which modify the cloning, processing and/or expression of the gene product. For example, alterations may be introduced using techniques which are well known in the art, e.g., site-directed mutagenesis, to insert new restriction sites, to alter glycosylation patterns or other conjugation patterns, to change codon preference, to introduce splice sites, to introduce or remove introns, etc.

Vectors, Promoters and Expression Systems

The present invention also includes recombinant constructs comprising one or more of the nucleic acid sequences as broadly described above. The constructs comprise a vector, such as, a plasmid, a cosmid, a phage, a virus, a bacterial artificial chromosome (BAC), a yeast artificial chromosome (YAC), and the like, into which a nucleic acid sequence of the invention has been inserted, e.g., a polynucleotide encoding a lipase homologue, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available.

General texts which describe molecular biological techniques useful herein, including the use of vectors, promoters and many other relevant topics, include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1–3, Cold Spring Harbor Laboratory, Cold Spring Harbor, N.Y., 1989 ("Sambrook") and *Current Protocols in Molecular Biology*, Ausubel et al., eds., Current Protocols, a joint venture between Greene Publishing Associates, Inc. and John Wiley & Sons, Inc., (supplemented through 2000) ("Ausubel")). Examples of techniques sufficient to direct persons of skill through in vitro amplification methods, including the polymerase chain reaction (PCR) the ligase chain reaction (LCR), Qβ-replicase amplification and other RNA polymerase mediated techniques (e.g., NASBA), e.g., for the production of the homologous nucleic acids of the invention are found in Berger, Sambrook, and Ausubel, as well as Mullis et al., (1987) U.S. Pat. No. 4,683,202; *PCR Protocols A Guide to Methods and Applications* (Innis et al. eds.) Academic Press Inc. San Diego, Calif. (1990) (Innis); Arnheim & Levinson (Oct. 1, 1990) *C&EN* 36–47; *The Journal Of NIH Research* (1991) 3, 81–94; (Kwoh et al. (1989) *Proc Natl Acad Sci USA* 86, 1173; Guatelli et al. (1990) *Proc Natl Acad Sci USA* 87, 1874; Lomeli et al. (1989) *J Clin Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426,039. Improved methods of amplifying large nucleic acids by PCR are summarized in Cheng et al. (1994) *Nature* 369: 684–685 and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra.

The present invention also relates to host cells which are transduced with vectors of the invention, and the production of polypeptides of the invention by recombinant techniques. Host cells are genetically engineered (i.e., transduced, transformed or transfected) with the vectors of this invention, which can be, for example, a cloning vector or an expression vector. The vector can be, for example, in the form of a plasmid, a viral particle, a phage, etc. The engineered host cells can be cultured in conventional nutrient media modified as appropriate for activating promoters, selecting transformants, or amplifying the lipase homologue gene. The culture conditions, such as temperature, pH and the like, are those previously used with the host cell selected for expression, and will be apparent to those skilled in the art and in the references cited herein, including, e.g., Freshney (1994) *Culture of Animal Cells, a Manual of Basic Technique*, third edition, Wiley-Liss, New York and the references cited therein.

The lipase homologue proteins of the invention can also be produced in non-animal cells such as plants, yeast, fungi, bacteria and the like. In addition to Sambrook, Berger and Ausubel, details regarding cell culture can be found in Payne et al. (1992) *Plant Cell and Tissue Culture in Liquid Systems* John Wiley & Sons, Inc. New York, N.Y.; Gamborg and Phillips (eds.) (1995) *Plant Cell, Tissue and Organ Culture*; Fundamental Methods Springer Lab Manual, Springer-Verlag (Berlin Heidelberg New York) and Atlas and Parks (eds.) *The Handbook of Microbiological Media* (1993) CRC Press, Boca Raton, Fla.

The polynucleotides of the present invention may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adeno-associated virus, retroviruses and many others. Any vector that transducers genetic material into a cell, and, if replication is desired, which is replicable and viable in the relevant host can be used.

The nucleic acid sequence in the expression vector is operatively linked to an appropriate transcription control sequence (promoter) to direct mRNA synthesis. Examples of such promoters include: LTR or SV40 promoter, *E. coli* lac or trp promoter, phage lambda $P_L$ promoter, and other promoters known to control expression of genes in prokaryotic or eukaryotic cells or their viruses. The expression vector also contains a ribosome binding site for translation initiation, and a transcription terminator. The vector optionally includes appropriate sequences for amplifying expression. In addition, the expression vectors optionally comprise one or more selectable marker genes to provide a phenotypic trait for selection of transformed host cells, such as dihydrofolate reductase or neomycin resistance for eukaryotic cell culture, or such as tetracycline or ampicillin resistance in, e.g., *E. coli.*

The vector containing the appropriate DNA sequence as described above, as well as an appropriate promoter or control sequence, may be employed to transform an appropriate host to permit the host to express the protein. Examples of appropriate expression hosts include: bacterial cells, such as *E. coli, Streptomyces*, and *Salmonella typhimurium;* fungal cells, such as *Saccharomyces cerevisiae, Pichia pastoris,* and *Neurospora crassa;* insect cells such as *Drosophila* and *Spodoptera frugiperda;* mammalian cells such as CHO, COS, BHK, HEK 293 or Bowes melanoma; plant cells, etc. It is understood that not all cells or cell lines need to be capable of producing fully functional lipase homologues; for example, antigenic fragments of lipase can be produced in a bacterial or other expression system. The invention is not limited by the host cells employed.

In bacterial systems, a number of expression vectors may be selected depending upon the use intended for the lipase homologue. For example, when large quantities of lipase homologue, or fragments thereof, are needed for the induction of antibodies, vectors which direct high level expression of fusion proteins that are readily purified may be desirable. Such vectors include, but are not limited to, multifunctional *E. coli* cloning and expression vectors such as BLUE-SCRIPT (Stratagene), in which the novel lipase coding sequence can be ligated into the vector in-frame with sequences for the amino-terminal Met and the subsequent 7 residues of beta-galactosidase so that a hybrid (or fusion) protein is produced; pIN vectors (Van Heeke & Schuster (1989) *J Biol Chem* 264:5503–5509); pET vectors (Novagen, Madison Wis.); and the like.

Similarly, in the yeast *Saccharomyces cerevisiae* a number of vectors containing constitutive or inducible promoters such as alpha factor, alcohol oxidase and PGH may be used for production of the lipase homologue proteins of the invention. For reviews, see Ausubel et al. (supra) and Grant et al. (1987; *Methods in Enzymology* 153:516–544).

In mammalian host cells, a number expression systems, such as viral-based systems, can be utilized. In cases where an adenovirus is used as an expression vector, a coding sequence is optionally ligated into an adenovirus transcription/translation complex consisting of the late promoter and tripartite leader sequence. Insertion in a nonessential E1 or E3 region of the viral genome will result in a viable virus capable of expressing lipase homologues in infected host cells (Logan and Shenk (1984) *Proc Natl Acad Sci* 81:3655–3659). In addition, transcription enhancers, such as the rous sarcoma virus (RSV) enhancer, can be used to increase expression in mammalian host cells.

Additional Expression Elements

Specific initiation signals can aid in efficient translation of a lipase homologue coding sequence. These signals can include, e.g., the ATG initiation codon and adjacent sequences. In cases where lipase homologue coding sequence, its initiation codon and upstream sequences are inserted into the appropriate expression vector, no additional translational control signals may be needed. However, in cases where only coding sequence (e.g., a mature protein coding sequence), or a portion thereof, is inserted, exogenous translational control signals including the ATG initiation codon must be provided. Furthermore, the initiation codon must be positioned in the correct reading frame to ensure translation of the entire insert to generate the desired polypeptide. Exogenous transcriptional and/or translational elements and initiation codons can be of various origins, both natural and synthetic. The efficiency of expression can be enhanced by the inclusion of enhancers appropriate to the cell system in use (Scharf D et al. (1994) *Results Probl Cell Differ* 20:125–62; Bittner et al. (1987) *Methods in Enzymol* 153:516–544).

Secretion/Localization Sequences

Polynucleotides of the invention can also be fused, for example, in-frame to nucleic acid encoding a secretion/localization sequence, to target polypeptide expression to a desired cellular compartment, membrane, or organelle, or to direct polypeptide secretion to the periplasmic space or into the cell culture media. Such sequences are known to those of skill, and include secretion leader peptides, organelle targeting sequences (e.g., nuclear localization sequences, ER retention signals, mitochondrial transit sequences, chloroplast transit sequences), membrane localization/anchor sequences (e.g., stop transfer sequences, GPI anchor sequences), and the like.

Expression Hosts

In a further embodiment, the present invention relates to host cells containing the above-described constructs, e.g., vectors comprising lipase homologues. The host cell can be a eukaryotic cell, such as a mammalian cell, a yeast cell, or a plant cell, or the host cell can be a prokaryotic cell, such as a bacterial cell (e.g., an *E. coli* cell). Introduction of the construct into the host cell can be effected by calcium phosphate transfection, DEAE-Dextran mediated transfection, electroporation, or other common techniques (Davis, L., Dibner, M., and Battey, I. (1986) *Basic Methods in Molecular Biology*, Sambrook and Ausubel, supra.).

A host cell strain is optionally chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Post-translational processing which cleaves a precursor form into a mature form of the protein may also be important for correct insertion, folding and/or function. Different host cells such as COS, CHO, HeLa, BHK, MDCK, 293, WI38, etc. have specific cellular machinery and characteristic mechanisms for such post-translational activities and can be chosen to ensure the correct modification and processing of the introduced, foreign protein.

For long-term, high-yield production of recombinant proteins, stable expression can be used. For example, cell lines which stably express a polypeptide of the invention are transduced using expression vectors which contain viral origins of replication or endogenous expression elements and a selectable marker gene. Following the introduction of the vector, cells can be allowed to grow for 1–2 days in an enriched media before they are switched to selective media. The purpose of the selectable marker is to confer resistance to selection, and its presence allows growth and recovery of cells which successfully express the introduced sequences. For example, resistant clumps of stably transformed cells can be proliferated using tissue culture techniques appropriate to the cell type.

Host cells transformed with a nucleotide sequence encoding a polypeptide of the invention are optionally cultured under conditions suitable for the expression and recovery of the encoded protein from cell culture. The protein or fragment thereof produced by a recombinant cell can be secreted, membrane-bound, or contained intracellularly, depending on the sequence and/or the vector used. As will be understood by those of skill in the art, expression vectors containing polynucleotides encoding lipase homologues of the invention can be designed with signal sequences which direct secretion of the polypeptides through a prokaryotic or eukaryotic cell membrane.

Additional Polypeptide Sequences

The polynucleotides of the present invention may also comprise a coding sequence fused in-frame to a marker sequence which, e.g., facilitates purification of the encoded polypeptide. Such purification facilitating domains include, but are not limited to, metal chelating peptides such as histidine-tryptophan modules that allow purification on immobilized metals, a sequence which binds glutathione (e.g., GST), a hemagglutinin (HA) tag (corresponding to an epitope derived from the influenza hemagglutinin protein; Wilson, I., et al. (1984) *Cell* 37:767), maltose binding protein sequences, the FLAG epitope utilized in the FLAGS extension/affinity purification system (Immunex Corp, Seattle, Wash.), and the like. The inclusion of a protease-cleavable polypeptide linker sequence between the purification domain and the lipase homologue sequence is useful to facilitate purification.

For example, one expression vector contemplated for use in the compositions and methods described herein provides for expression of a fusion protein comprising a polypeptide of the invention fused to a polyhistidine region separated by an enterokinase cleavage site. The histidine residues facilitate purification on IMIAC (immobilized metal ion affinity chromatography, as described in Porath et al. (1992) *Protein Expression and Purification* 3:263–281) while the enterokinase cleavage site provides a means for separating the lipase homologue polypeptide from the fusion protein. pGEX vectors (Promega; Madison, Wis.) can also be used to express foreign polypeptides as fusion proteins with glutathione S-transferase (GST). In general, such fusion proteins are soluble and can easily be purified from the culture medium or from lysed cells by adsorption to ligand-agarose beads (e.g., glutathione-agarose in the case of GST-fusions) followed by elution in the presence of free ligand.

Polypeptide Production and Recovery

Following transduction of a suitable host cell line or strain and growth of the host strain to an appropriate cell density, the selected promoter is induced by appropriate means (e.g., temperature shift or chemical induction) and cells are cultured for an additional period. The secreted polypeptide product is then recovered from the culture medium. Alternatively, cells can be harvested by centrifugation, disrupted by physical or chemical means, and the resulting crude extract retained for further purification. Eukaryotic or microbial cells employed in expression of proteins can be disrupted by any convenient method, including freeze-thaw cycling, sonication, mechanical disruption, or use of cell lysing agents, or other methods, which are well know to those skilled in the art.

As noted, many references are available for the culture and production of many cells, including cells of bacterial, plant, animal (especially mammalian) and archebacterial origin. See, e.g., Sambrook, Ausubel, and Berger (all supra), as well as Freshney (1994) *Culture of Animal Cells, a Manual of Basic Technique,* third edition, Wiley-Liss, New York and the references cited therein; Doyle and Griffiths (1997) *Mammalian Cell Culture: Essential Techniques* John Wiley and Sons, NY; Humason (1979) *Animal Tissue Techniques,* fourth edition W.H. Freeman and Company; and Ricciardelli, et al., (1989) *In vitro Cell Dev Biol* 25:1016–1024. For plant cell culture and regeneration, see, e.g., Payne et al. (1992) *Plant Cell and Tissue Culture in Liquid Systems* John Wiley & Sons, Inc. New York, N.Y.; Gamborg and Phillips (eds.) (1995) *Plant Cell, Tissue and Organ Culture;* Fundamental Methods Springer Lab Manual, Springer-Verlag (Berlin Heidelberg New York) and *Plant Molecular Biology* (1993) R. R. D. Croy, Ed. Bios Scientific Publishers, Oxford, U.K. ISBN 0 12 198370 6. Cell culture media in general are set forth in Atlas and Parks (eds.) *The Handbook of Microbiological Media* (1993) CRC Press, Boca Raton, Fla. Additional information for cell culture is found in available commercial literature such as the *Life Science Research Cell Culture Catalogue* (1998) from Sigma-Aldrich, Inc (St Louis, Mo.) ("Sigma-LSRCCC") and, e.g., the *Plant Culture Catalogue* and supplement (1997) also from Sigma-Aldrich, Inc (St Louis, Mo.) ("Sigma-PCCS").

Polypeptides of the invention can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems noted herein), hydroxylapatite chromatography, and lectin chromatography. Protein refolding steps can be used, as desired, in completing configuration of the mature protein. Finally, high performance liquid chromatography (HPLC) can be employed in the final purification steps. In addition to the references noted above, a variety of purification methods are well known in the art, including, e.g., those set forth in Sandana (1997) *Bioseparation of Proteins,* Academic Press, Inc.; and Bollag et al. (1996) *Protein Methods, 2$^{nd}$ Edition* Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice* 3$^{rd}$ *Edition* Springer Verlag, NY; Janson and Ryden (1998) *Protein Purification: Principles, High Resolution Methods and Applications,* Second Edition Wiley-VCH, NY; and Walker (1998) *Protein Protocols on CD-ROM* Humana Press, NJ In vitro Expression Systems Cell-free transcription/translation systems can also be employed to produce polypeptides comprising lipase homologues, and fragments thereof, using DNAs or RNAs of the present invention. Several such systems are commercially available. A general guide to in vitro transcription and translation protocols is found in Tymms (1995) *In vitro Transcription and Translation Protocols: Methods in Molecular Biology* Volume 37, Garland Publishing, NY Modified Amino Acids Polypeptides of the invention can contain one or more modified amino acid. The presence of modified amino acids can be advantageous in, for example, (a) increasing polypeptide serum half-life, (b) reducing polypeptide antigenicity, and (c) increasing polypeptide storage stability. Amino acid (s) are modified, for example, co-translationally or post-translationally during recombinant production (e.g., N-linked glycosylation at N-X-S/T motifs during expression in mammalian cells) or modified by synthetic means.

Non-limiting examples of a modified amino acid include a glycosylated amino acid, a sulfated amino acid, a prenlyated (e.g., farnesylated, geranylgeranylated) amino acid, an acetylated amino acid, an acylated amino acid, a PEGylated amino acid, a biotinylated amino acid, a carboxylated amino acid, a phosphorylated amino acid, and the like, as well as amino acids modified by conjugation to, e.g., lipid moieties or other organic derivatizing agents. References adequate to guide one of skill in the modification of amino acids are replete throughout the literature. Example protocols are found in Walker (1998) *Protein Protocols on CD-ROM* Human Press, Towata, N.J.

In Vivo Uses

Polynucleotides which encode a lipase homologue of the invention, or complements of the polynucleotides (i.e., antisense polynucleotides), are optionally administered to a cell to accomplish a therapeutically useful process or to express a therapeutically useful product. These in vivo applications, including gene therapy, include a multitude of techniques by which gene expression can be altered in cells. Such methods include, for instance, the introduction of genes for expression of, e.g., therapeutically and/or prophylactically useful polypeptides, such as the lipase homologues of the present invention to, e.g., hydrolyze ester bonds of lipids, e.g., in the treatment of, e.g., Crohn's disease, etc.

In Vivo Polypeptide Expression

Polynucleotides encoding lipase homologue polypeptides of the invention are useful for in vivo therapeutic applications, including prophylactic applications, using techniques well known to those skilled in the art. For example, cultured cells are engineered of ex vivo with a polynucleotide (DNA or RNA), with the engineered cells then being returned to the patient. Cells may also be engineered in vivo for expression of a polypeptide in vivo. As noted, and as described in more detail below, lipase production is also useful for a variety of industrial processes, including lipid degradation, and regio- or stereo-selective reaction with lipids.

A number of viral vectors suitable for organismal in vivo transduction and expression are known. Such vectors include retroviral vectors (see, Miller (1992) *Curr Top Microbiol Immunol* 158:1–24; Salmons and Gunzburg (1993) Human Gene Therapy 4:129–141; Miller et al. (1994) *Methods in Enzymology* 217: 581–599) and adeno-associated vectors (reviewed in Carter (1992) *Curr Opinion Biotech* 3: 533–539; Muzcyzka (1 992) *Curr Top Microbiol Immunol* 158: 97–129). Other viral vectors that are used include adenoviral vectors, herpes viral vectors and Sindbis viral vectors, as generally described in, e.g., Jolly (1994)

Cancer Gene Therapy 1:51–64; Latchman (1994) Molec Biotechnol 2:179–195; and Johanning et al. (1995) Nucl Acids Res 23:1495–1501.

Gene therapy provides methods for combating chronic infectious diseases (e.g., HIV infection, viral hepatitis), as well as non-infectious diseases including cancer and some forms of congenital defects such as enzyme deficiencies. Several approaches for introducing nucleic acids into cells in vivo, ex vivo and in vitro have been used. These include liposome based gene delivery (Debs and Zhu (1993) WO 93/24640 and U.S. Pat. No. 5,641,662; Mannino and Gould-Fogerite (1988) BioTechniques 6(7): 682–691; Rose, U.S. Pat No. 5,279,833; Brigham (1991) WO 91/06309; and Felgner et al. (1987) Proc Natl Acad Sci USA 84: 7413–7414); Brigham et al. (1989) Am J Med Sci, 298:278–281; Nabel et al. (1990) Science, 249:1285–1288; Hazinski et al. (1991) Am J Resp Cell Molec Biol, 4:206–209; and Wang and Huang (1987) Proc Natl Acad Sci USA, 84:7851–7855); adenoviral vector mediated gene delivery, e.g., to treat cancer (see, e.g., Chen et al. (1994) Proc Natl Acad Sci USA 91: 3054–3057; Tong et al. (1996) Gynecol Oncol 61: 175–179; Clayman et al. (1995) Cancer Res 5: 1–6; O'Malley et al. (1995) Cancer Res 55: 1080–1085; Hwang et al. (1995) Am J Respir Cell Mol Biol 13: 7–16; Haddada et al. (1995) Curr Top Microbiol Immunol 199 (Pt. 3): 297–306; Addison et al. (1995) Proc Natl Acad Sci USA 92: 8522–8526; Colak et al. (1995) Brain Res 691: 76–82; Crystal (1995) Science 270: 404–410; Elshami et al. (1996) Human Gene Ther 7: 141–148; Vincent et al. (1996) J Neurosurg 85: 648–654), and many other diseases. Replication-defective retroviral vectors harboring therapeutic polynucleotide sequence as part of the retroviral genome have also been used, particularly with regard to simple MuLV vectors. See, e.g., Miller et al. (1990) Mol Cell Biol 10:4239 (1990); Kolberg (1992) J NIH Res 4:43, and Cornetta et al. (1991) Hum Gene Ther 2:215). Nucleic acid transport coupled to ligand-specific, cation-based transport systems (Wu and Wu (1988) J Biol Chem, 263:14621–14624) have also been used. Naked DNA expression vectors have also been described (Nabel et al. (1990), supra); Wolff et al. (1990) Science, 247:1465–1468). In general, these approaches can be adapted to the invention by incorporating nucleic acids encoding the lipase homologues herein into the appropriate vectors.

General texts which describe gene therapy protocols, which can be adapted to the present invention by introducing the nucleic acids of the invention into patients, include Robbins (1996) Gene Therapy Protocols, Humana Press, NJ, and Joyner (1993) Gene Targeting: A Practical Approach, IRL Press, Oxford, England.

Antisense Technology

In addition to expression of the nucleic acids of the invention as gene replacement nucleic acids, the nucleic acids are also useful for sense and antisense suppression of expression, e.g., to down-regulate expression of a nucleic acid of the invention, once expression of the nucleic acid is no longer desired in the cell. Similarly, the nucleic acids of the invention, or subsequences or antisense sequences thereof, can also be used to block expression of naturally occurring homologous nucleic acids. A variety of sense and anti-sense technologies are known in the art, e.g., as set forth in Lichtenstein and Nellen (1997) Antisense Technology: A Practical Approach IRL Press at Oxford University, Oxford, England, and in Agrawal (1996) Antisense Therapeutics Humana Press, NJ, and the references cited therein.

Pharmaceutical Compositions

The polynucleotides of the invention may be employed for therapeutic uses in combination with a suitable pharmaceutical carrier. Such compositions comprise a therapeutically effective amount of the compound, and a pharmaceutically acceptable carrier or excipient. Such a carrier or excipient includes, but is not limited to, saline, buffered saline, dextrose, water, glycerol, ethanol, and combinations thereof. The formulation should suit the mode of administration. Methods of administering nucleic acids and proteins are well known in the art, and further discussed below.

Use as Probes

Also contemplated are uses of polynucleotides, also referred to herein as oligonucleotides, typically having at least 12 bases, preferably at least 15, more preferably at least 20, 30, or 50 bases, which hybridize under highly stringent conditions to lipase a polynucleotide sequence described above. The polynucleotides may be used as probes, primers, sense and antisense agents, and the like.

Sequence Variations

Silent Variations

It will be appreciated by those skilled in the art that due to the degeneracy of the genetic code, a multitude of nucleic acids sequences encoding novel lipase polypeptides of the invention may be produced, some which may bear minimal sequence homology to the nucleic acid sequences explicitly disclosed herein.

TABLE 1

Codon Table

| Amino acids | | | Codon | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

For instance, inspection of the codon table (Table 1) shows that codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence.

Using, as an example, the nucleic acid sequence of clone 1f15(g2) corresponding to nucleotides 2–16 of SEQ ID NO: 21, GAA CAC AAT CCA GTT, a silent variation of this sequence includes GAG CAT AAC CCC GTG, both of which sequences encode the amino acid sequence EHNPV, which corresponds to amino acids 1–5 of SEQ ID NO: 75.

Such "silent variations" are one species of "conservatively modified variations", discussed below. One of skill will recognize that each codon in a nucleic acid (except AUG and UGG, which are ordinarily the only codons for methionine and tryptophan respectively) can be modified by standard techniques to encode a functionally identical polypeptide. Accordingly, each silent variation of a nucleic acid which encodes a polypeptide is implicit in any described sequence. The invention provides each and every possible variation of nucleic acid sequence encoding a polypeptide of the invention that could be made by selecting combinations based on possible codon choices. These combinations are made in accordance with the standard triplet genetic code (e.g., as set forth in Table 1) as applied to the nucleic acid sequence encoding a lipase homologue polypeptide of the invention. All such variations of every nucleic acid herein are specifically provided and described by consideration of the sequence in combination with the genetic code. One of skill is fully able to generate or select such variations based upon knowledge of the genetic code as well as considerations such as codon preferences of a specific organism chosen for expression of a polypeptide encoded by the nucleic acid.

Conservative Variations

"Conservatively modified variations" or, simply, "conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid.

Conservative substitution tables providing functionally similar amino acids are well known in the art. Table 2 sets forth six groups which contain amino acids that are "conservative substitutions" for one another.

TABLE 2

Conservative Substitution Groups

| 1 | Alanine (A) | Serine (S) | Threonine (T) | |
|---|---|---|---|---|
| 2 | Aspartic acid (D) | Glutamic acid (E) | | |
| 3 | Asparagine (N) | Glutamine (Q) | | |
| 4 | Arginine (R) | Lysine (K) | | |
| 5 | Isoleucine (I) | Leucine (L) | Methionine (M) | Valine (V) |
| 6 | Phenylalanine (F) | Tyrosine (Y) | Tryptophan (W) | |

Thus, "conservatively substituted variations" of a listed polypeptide sequence of the present invention include substitutions of a small percentage, typically less than 5%, more typically less than 4%, 3%, 2% or 1%, of the amino acids of the polypeptide sequence, with a conservatively selected amino acid of the same conservative substitution group.

For example, a conservatively substituted variation of the polypeptide identified herein as SEQ ID NO: 75 will contain "conservative substitutions," according to the six groups defined herein, in up to 9 residues (i.e., 5% of the amino acids) in the 180 amino acid polypeptide.

In a further example, if four conservative substitutions were localized in the region corresponding to amino acids 1–20 of SEQ ID NO: 75, examples of conservatively substituted variations of this region, EHNPV VMVHG IGGAS FNFAG, include:

DHNPV IMVHG MGGAS YNFAG and

DHQPV VVVHG IGGSS FNFSG

And the like, in accordance with the conservative substitutions listed in Table 2 (in the above example, conservative substitutions are underlined). Listing of a protein sequence herein, in conjunction with the above substitution table, provides an express listing of all conservatively substituted proteins.

Finally, the addition of sequences which do not alter the encoded activity of a nucleic acid molecule, such as the addition of a non-functional sequence, is a conservative variation of the basic nucleic acid.

One of skill will appreciate that many conservative variations of the nucleic acid constructs which are disclosed yield a functionally identical construct. For example, as discussed above, owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the present invention.

Nucleic Acid Hybridization

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes,* part I, chapter 2, "Overview of principles of hybridization and the strategy of nucleic acid probe assays," (Elsevier New York), as well as in Ausubel, supra, Hames and Higgins (1995) *Gene Probes* 1, IRL Press at Oxford University Press, Oxford, England (Hames and Higgins 1) and Hames and Higgins (1995) *Gene Probes* 2, IRL Press at Oxford University Press, Oxford, England (Hames and Higgins 2) provide details on the synthesis, labeling, detection and quantification of DNA and RNA, including oligonucleotides.

"Stringent hybridization wash conditions" in the context of nucleic acid hybridization experiments, such as Southern and northern hybridizations, are sequence dependent, and are different under different environmental parameters. An extensive guide to the hybridization of nucleic acids is found in Tijssen (1993), supra, and in Hames and Higgins 1 and Hames and Higgins 2, supra.

For purposes of the present invention, generally, "highly stringent" hybridization and wash conditions are selected to be about 5° C. or less lower than the thermal melting point ($T_m$) for the specific sequence at a defined ionic strength and pH (as noted below, highly stringent conditions can also be referred to in comparative terms). The $T_m$ is the temperature (under defined ionic strength and pH) at which 50% of the test sequence hybridizes to a perfectly matched probe. Very stringent conditions are selected to be equal to the $T_m$ for a particular probe.

The $T_m$ temperature of the nucleic acid duplexes indicates the temperature at which the duplex is 50% denatured under the given conditions and represents a direct measure of the stability of the nucleic acid hybrid. Thus, the $T_m$ corresponds to the temperature corresponding to the midpoint in transition from helix to random coil; it depends on length, nucleotide composition, and ionic strength for long stretches of nucleotides.

After hybridization, unhybridized nucleic acid material can be removed by a series of washes, the stringency of which can be adjusted depending upon the desired results. Low stringency washing conditions (e.g., using higher salt and lower temperature) increases sensitivity, but can produce nonspecific hybridization signals and high background signals. Higher stringency conditions (e.g., using lower salt and higher temperature that is closer to the hybridization temperature) lowers the background signal, typically with only the specific signal remaining. See, Rapley, R. and Walker, J. M. eds., *Molecular Biomethods Handbook* (Humana Press, Inc. 1998) (hereinafter "Rapley and Walker"), which is incorporated herein by reference in its entirety for all purposes.

The $T_m$ of a DNA-DNA duplex can be estimated using the following equation:

$$T_m(°C.) = 81.5° C. + 16.6 (\log_{10} M) + 0.41 (\%G+C) - 0.72(\%f) - 500/n,$$

where M is the molarity of the monovalent cations (usually Na+), (%G+C) is the percentage of guanosine (G) and cytosine (C) nucleotides, (%f) is the percentage of formamide and n is the number of nucleotide bases (i.e., length) of the hybrid. See, Rapley and Walker, supra.

The $T_m$ of an DNA-DNA duplex can be estimated as follows:

$$T_m(°C.) = 79.8° C. + 18.5(\log_{10} M) + 0.58 (\%G+C) - 11.8(\%G+C)^2 - 0.56$$

(%f)–820/n, where M is the molarity of the monovalent cations (usually Na+), (%G+C) is the percentage of guanosine (G) and cytosine (C) nucleotides, (%f) is the percentage of formamide and n is the number of nucleotide bases (i.e., length) of the hybrid. Id. Equations 1 and 2 are typically accurate only for hybrid duplexes longer than about 100–200 nucleotides. Id.

The $T_m$ of nucleic acid sequences shorter than 50 nucleotides can be calculated as follows:

$$T_m(° C.) = 4(G+C) + 2(A+T),$$

where A (adenine), C, T (thymine), and G are the numbers of the corresponding nucleotides.

An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of stringent wash conditions is a 0.2×SSC wash at 65° C. for 15 minutes (see Sambrook, supra for a description of SSC buffer). Often the high stringency wash is preceded by a low stringency wash to remove background probe signal. An example low stringency wash is 2×SSC at 40° C. for 15 minutes.

In general, a signal to noise ratio of 2.5×5× (or higher) than that observed for an unrelated probe in the particular hybridization assay indicates detection of a specific hybridization. Detection of at least stringent hybridization between two sequences in the context of the present invention indicates relatively strong structural similarity or homology to, e.g., the nucleic acids of the present invention provided in the sequence listings herein.

As noted, "highly stringent" conditions are selected to be about 5° C. or less lower than the thermal melting point ($T_m$) for the specific sequence at a defined ionic strength and pH. Target sequences that are closely related or identical to the nucleotide sequence of interest (e.g., "probe") can be identified under highly stringency conditions. Lower stringency conditions are appropriate for sequences that are less complementary. See, e.g., Rapley and Walker, supra.

Comparative hybridization can be used to identify nucleic acids of the invention, and this comparative hybridization method is a preferred method of distinguishing nucleic acids of the invention. Detection of highly stringent hybridization between two nucleotide sequences in the context of the present invention indicates relatively strong structural similarity/homology to, e.g., the nucleic acids provided in the sequence listing herein. Highly stringent hybridization between two nucleotide sequences demonstrates a degree of similarity or homology of structure, nucleotide base composition, arrangement or order that is greater than that detected by stringent hybridization conditions. In particular, detection of highly stringent hybridization in the context of the present invention indicates strong structural similarity or structural homology (e.g., nucleotide structure, base composition, arrangement or order) to, e.g., the nucleic acids provided in the sequence listings herein. For example, it is desirable to identify test nucleic acids which hybridize to the exemplar nucleic acids herein under stringent conditions.

Thus, one measure of stringent hybridization is the ability to hybridize to one of the listed nucleic acids (e.g., nucleic acid sequences SEQ ID NO:1 to SEQ ID NO:54, and complementary polynucleotide sequences thereof) under highly stringent conditions (or very stringent conditions, or ultra-high stringency hybridization conditions, or ultra-ultra high stringency hybridization conditions). Stringent hybridization (including, e.g., highly stringent, ultra-high stringency, or ultra-ultra high stringency hybridization conditions) and wash conditions can easily be determined empirically for any test nucleic acid.

For example, in determining highly stringent hybridization and wash conditions, the hybridization and wash conditions are gradually increased (e.g., by increasing temperature, decreasing salt concentration, increasing detergent concentration and/or increasing the concentration of organic solvents, such as formamide, in the hybridization or wash), until a selected set of criteria are met. For example, the hybridization and wash conditions are gradually increased until a probe comprising one or more nucleic acid sequences selected from SEQ ID NO:1 to SEQ ID NO:54, and complementary polynucleotide sequences thereof, binds to a perfectly matched complementary target (again, a nucleic acid comprising one or more nucleic acid sequences selected from SEQ ID NO:1 to SEQ ID NO:54, and complementary polynucleotide sequences thereof), with a signal to noise ratio that is at least 2.5×, and optionally 5× or more as high as that observed for hybridization of the probe to an unmatched target. In this case, the unmatched target is a nucleic acid corresponding to, e.g., a known lipase homologue, e.g., a lipase homologue nucleic acid (other than those in the accompanying sequence listing) that is present in a public database such as GenBank™ at the time of filing of the subject application Examples of such unmatched target nucleic acids include, e.g., those represented by or which encode the following GenBank accession numbers: 1I6WA, 1I6WB, A02813, A02815, A34992, AAA22574, AAB31769, AAC12257, AAD30278, AAF40217, AAF63229, AB000617, AF134840, AF141874, AF237623, AJ297356, BAA11406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P37957, S23934, U78785, X95309, Z99105, and Z99108. It will be appreciated that the above GenBank accession numbers represent both amino acid and nucleic acid sequences. In the present application, such sequences should be read in context, e.g., when the context indicates an amino acid is to be considered, then the accession numbers that represent a nucleic acid should be interpreted as their amino acid translations and when the context indicates that a nucleic acid is intended, then the accession numbers representing amino acids should be interpreted as representing their corresponding nucleic acid. Additional such sequences can be identified in GenBank by one of skill.

A test nucleic acid is said to specifically hybridize to a probe nucleic acid when it hybridizes at least ½ as well to the probe as to the perfectly matched complementary target, i.e., with a signal to noise ratio at least ½ as high as hybridization of the probe to the target under conditions in which the perfectly matched probe binds to the perfectly matched complementary target with a signal to noise ratio that is at least about 5×–10× as high as that observed for hybridization to any of the unmatched target nucleic acids, e.g., represented by or which encode the following GenBank accession numbers: 1I6WA, 1I6WB, A02813, A02815, A34992, AAA22574, AAB31769, AAC12257, AAD30278, AAF40217, AAF63229, AB000617, AF134840, AF141874, AF237623, AJ297356, BAA11406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P37957, S23934, U78785, X95309, Z99105, and Z99108.

Ultra high-stringency hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids, e.g., represented by or which encode the following GenBank accession numbers: 1I6WA, 1I6WB, A02813, A02815,A34992, AAA22574, AAB31769, AAC12257, AAD30278, AAF40217, AAF63229, AB000617, AF134840, AF141874, AF237623, AJ297356, BAA11406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P37957, S23934, U78785, X95309, Z99105, and Z99108. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids represented by or which encode the following GenBank accession numbers: 1I6WA, 1I6WB, A02813, A02815,A34992, AAA22574, AAB31769, AAC12257, AAD30278, AAF40217, AAF63229, AB000617, AF134840, AF141874, AF237623, AJ297356, BAA11406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P37957, S23934, U78785, X95309, Z99105, and Z99108. A target nucleic acid which hybridizes to a probe under such conditions, with a signal to noise ratio of at least ½ that of the perfectly matched complementary target nucleic acid is said to bind to the probe under ultra-ultra-high stringency conditions.

Target nucleic acids which hybridize to the nucleic acids represented by SEQ ID NO:1 to SEQ ID NO:54 under high, ultra-high and ultra-ultra high stringency conditions are a feature of the invention. Examples of such nucleic acids include those with one or a few silent or conservative nucleic acid substitutions as compared to a given nucleic acid sequence.

Nucleic acids, such as man-made nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code, or when antisera generated against one or more of SEQ ID NO:55 to SEQ ID NO:108, which has been subtracted using the polypeptides represented by or which encode the following lipase related sequences in GenBank: 1I6WA, 1I6WB, A02813, A02815, A34992, AAA22574, AAB31769, AAC12257, AAD30278, AAF40217, AAF63229, AB000617, AF134840, AF141874, AF237623, AJ297356, BAA11406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P37957, S23934, U78785, X95309, Z99105, and Z99108. Further details on immunological identification of polypeptides of the invention are found below.

In one aspect, the invention provides a nucleic acid which comprises a unique subsequence in a nucleic acid selected from SEQ ID NO:1 to SEQ ID NO:54. The unique subsequence is unique as compared to a nucleic acid corresponding to any of the sequences represented or which encode, e.g., by GenBank accession numbers: 1I6WA, 1I6WB, A02813, A02815, A34992, AAA22574, AAB31769, AAC12257, AAD30278, AAF40217, AAF63229, AB000617, AF134840, AF141874, AF237623, AJ297356, BAA11406, BAA2223 1, BAB05967, C69652, CAA00273, CAA00274, CAA02196, CAA6462 1, CAB12064, CAB12664, CAB51971, CAB92662, CAB95850, D78508, E01340, E01903, E02083, E05047, JW0068, M74010, P37957, S23934, U78785, X95309, Z99105, and Z99108, or related sequences present in GenBank as of the filing of this application. Alignment can be performed using the BLAST algorithm set to default parameters. Any unique subsequence is useful, e.g., as a probe to identify the nucleic acids of the invention.

Similarly, the invention includes a polypeptide which comprises a unique subsequence in a polypeptide selected from: SEQ ID NO:55 to SEQ ID NO:108. Here, the unique subsequence is unique as compared to a polypeptide corresponding to any of the sequences represented by or which encode GenBank accession numbers: 1I6WA, 1I6WB, A02813, A02815,A34992, AAA22574, AAB31769, AAC12257, AAD30278, AAF40217, AAF63229, AB000617, AF134840, AF141874, AF237623, AJ297356, BAA11406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P37957, S23934, U78785, X95309, Z99105, and Z99108. Such unique subsequences can be determined by aligning any of SEQ ID NO:55 to SEQ ID NO:108 against the complete set of polypeptides represented by or which encode GenBank accession numbers: 1I6WA, 1I6WB, A02813, A02815,A34992, AAA22574, AAB31769, AAC12257, AAD30278, AAF40217, AAF63229, AB000617, AF134840, AF141874, AF237623, AJ297356, BAA11406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P7957, A23934, U78785, X95309, Z99105, and Z99108 (the control polypeptides) (note that where the sequence corresponds to a non-translated sequence such as a pseudo gene, the corresponding polypeptide is generated simply by in silico translation of the nucleic acid sequence into an amino acid sequence, where the reading frame is selected to correspond to the reading frame of lipase nucleic acids.

The invention also provides for target nucleic acids which hybridizes under stringent conditions to a unique coding oligonucleotide which encodes a unique subsequence in a polypeptide selected from: SEQ ID NO:55 to SEQ ID NO:108, wherein the unique subsequence is unique as compared to a polypeptide corresponding to any of the control polypeptides (i.e., the above listed GenBank accession numbers). Unique sequences are determined as noted above.

In one example, the stringent conditions are selected such that a perfectly complementary oligonucleotide to the coding oligonucleotide hybridizes to the coding oligonucleotide with at least about a 5–10× higher signal to noise ratio than for hybridization of the perfectly complementary oligonucleotide to a control nucleic acid corresponding to any of the control polypeptides. Conditions can be selected such that higher ratios of signal to noise are observed in the particular assay which is used, e.g., about 15×, 20×, 30×, 50× or more. In this example, the target nucleic acid hybridizes to the unique coding oligonucleotide with at least a 2× higher signal to noise ratio (i.e., stringent conditions) as compared to hybridization of the control nucleic acid to the coding oligonucleotide. Again, higher signal to noise ratios can be selected, e.g., about 5×, 10×, 20×, 30×, 50× or more. The particular signal will depend on the label used in the relevant assay, e.g., a fluorescent label, a colorimetric label, a radio active label, or the like.

Percent Sequence identity—Sequence Similarity

As noted above, the peptides employed in the subject invention need not be identical, but can be substantially identical, to the corresponding sequence of a lipase molecule or related molecule. The peptides can be subject to various changes, such as insertions, deletions, and substitutions, either conservative or non-conservative, where such changes might provide for certain advantages in their use. The polypeptides of the invention can be modified in a number of ways so long as they comprise a sequence substantially identical (as defined below) to a sequence in a lipase molecule.

Alignment and comparison of relatively short amino acid sequences (less than about 30 residues) is typically straightforward. Comparison of longer sequences can require more sophisticated methods to achieve optimal alignment of two sequences. Optimal alignment of sequences for aligning a comparison window can be conducted by the local homology algorithm of Smith and Waterman (1981) *Adv Appl Math* 2:482, by the homology alignment algorithm of Needleman and Wunsch (1970) *J Mol Biol* 48:443, by the search for similarity method of Pearson and Lipman (1988) *Proc Natl Acad Sci USA* 85:2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, with the best alignment (i.e., resulting in the highest percentage of sequence similarity over the comparison window) generated by the various methods being selected.

The term sequence identity means that two polynucleotide sequences are identical (i.e., on a nucleotide-by-nucleotide basis) over a window of comparison. The term "percentage of sequence identity" is calculated by comparing two optimally aligned sequences over the window of comparison, determining the number of positions at which the identical residues occur in both sequences to yield the number of matched positions, dividing the number of matched positions by the total number of positions in the window of comparison (i.e., the window size), and multiplying the result by 100 to yield the percentage of sequence identity.

As applied to polypeptides, the term substantial identity means that two peptide sequences, when optimally aligned, such as by the programs GAP or BESTFIT using default gap weights (described in more detail below), share at least about 70 percent sequence identity, or at least about 75 percent sequence identity, frequently at least about 80 percent sequence identity, often at least about 85 percent sequence identity, preferably at least about 90 percent sequence identity, more preferably at least about 95, 96, 97, 98 percent sequence identity or more (e.g., 99 percent or more sequence identity) over a designated comparison window, e.g., of at least 45 contiguous amino acids up to the entire length of the polypeptide sequence. Alternatively, parameters are set such that one or more sequences of the invention, e.g., SEQ ID NO:55 to SEQ ID NO:108 are identified by alignment to a query sequence selected from among SEQ ID NO:55 to SEQ ID NO:108, while sequences corresponding to unrelated polypeptides, e.g., corresponding to GenBank accession numbers: 1I6WA, 1I6WB, A02813, A02815,A34992, AAA22574, AAB31769, AAC12257, AAD30278, AAF40217, AAF63229, AB000617, AF134840, AF141874, AF237623, AJ297356, BAA11406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P37957, S23934, U78785, X95309, Z99105, and Z99108, are not identified.

Preferably, residue positions which are not identical differ by conservative amino acid substitutions. Conservative amino acid substitution refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

A preferred example of an algorithm that is suitable for determining percent sequence identity and sequence similarity is the FASTA algorithm, which is described in Pearson, W. R. & Lipman, D. J., (1988) *Proc Natl Acad Sci USA* 85:2444. See also, W. R. Pearson, (1996) *Methods*

*Enzymology* 266:227–258. Preferred parameters used in a FASTA alignment of DNA sequences to calculate percent identity are optimized, BL50 Matrix 15: −5, k-tuple=2; joining penalty=40, optimization=28; gap penalty −12, gap length penalty=−2; and width=16.

Other preferred examples of algorithm that are suitable for determining percent sequence identity and sequence similarity are the BLAST and BLAST 2.0 algorithms, which are described in Altschul et al., (1977) *Nuc Acids Res* 25:3389–3402 and Altschul et al., (1990) *J Mol Biol* 215:403–410, respectively. BLAST and BLAST 2.0 are used, with the parameters described herein, to determine percent sequence identity for the nucleic acids and proteins of the invention. Software for performing BLAST analyses is publicly available through the National Center for Biotechnology Information (the world wide web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=4 and a comparison of both strands. For amino acid sequences, the BLASTP program uses as defaults a wordlength of 3, and expectation (E) of 10, and the BLOSUM62 scoring matrix (see, Henikoff & Henikoff, (1989) *Proc Natl Acad Sci USA* 89:10915) uses alignments (B) of 50, expectation (E) of 10, M=5, N=−4, and a comparison of both strands.

The BLAST algorithm also performs a statistical analysis of the similarity between two sequences (see, e.g., Karlin & Altschul, (1993) *Proc Natl Acad Sci USA* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, (1987) *J Mol Evol* 35:351–360. The method used is similar to the method described by Higgins & Sharp, (1989) *CABIOS* 5:151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., (1984) *Nuc Acids Res* 12:387–395).

Another preferred example of an algorithm that is suitable for multiple DNA and amino acid sequence alignments is the CLUSTALW program (Thompson, J. D. et al., (1994) *Nuc Acids Res* 22:4673–4680). CLUSTALW performs multiple pairwise comparisons between groups of sequences and assembles them into a multiple alignment based on homology. Gap open and Gap extension penalties were 10 and 0.05 respectively. For amino acid alignments, the BLOSUM algorithm can be used as a protein weight matrix (Henikoff and Henikoff, (1992) *Proc Natl Acad Sci USA* 89:10915–10919).

It will be understood by one of ordinary skill in the art, that the above discussion of search and alignment algorithms also applies to identification and evaluation of polynucleotide sequences, with the substitution of query sequences comprising nucleotide sequences, and where appropriate, selection of nucleic acid databases.

Substrates and Formate for Sequence Recombination

A variety of diversity generating protocols are available and described in the art. The procedures can be used separately, and/or in combination to produce one or more variants of a nucleic acid or set of nucleic acids, as well variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids with or which confer desirable properties, or that encode proteins with or which confer desirable properties. Following diversification by one or more of the methods herein, or otherwise available to one of skill, any nucleic acids that are produced can be selected for a desired activity or property, e.g. Lipase activity and/or enantioselective lipase activity or lipase activity against particular substrates. This can include identifying any activity that can be detected, for example, in an automated or automatable format, by any of the assays in the art, e.g., by any lipase activity assay (see, infra, for examples of lipase activity assays). A variety of related (or even unrelated) properties can be evaluated, in serial or in parallel, at the discretion of the practitioner.

Descriptions of a variety of diversity generating procedures for generating modified nucleic acid sequences encoding lipase homologues are found in the following publications and the references cited therein: Soong, N. et al. (2000) "Molecular breeding of viruses" *Nat Genet* 25(4):436–439; Stemmer, et al. (1999) "Molecular breeding of viruses for targeting and other clinical properties" *Tumor Targeting* 4:1–4; Ness et al. (1999) "DNA Shuffling of subgenomic sequences of subtilisin" *Nature Biotechnology* 17:893–896; Chang et al. (1999) "Evolution of a cytokine using DNA family shuffling" *Nature Biotechnology* 17:793–797; Minshull and Stemmer (1999) "Protein evolution by molecular breeding" *Current Opinion in Chemical Biology* 3:284–290; Christians et al. (1999) "Directed evolution of thymidine kinase for AZT phosphorylation using DNA family shuffling" *Nature Biotechnology* 17:259–264; Crameri et al. (1998) "DNA shuffling of a family of genes from diverse species accelerates directed evolution" *Nature* 391:288–291; Crameri et al. (1997) "Molecular evolution of an arsenate detoxification pathway by DNA shuffling," *Nature Biotechnology* 15:436–438; Zhang et al. (1997) "Directed evolution of an effective fucosidase from a galactosidase by DNA shuffling and screening" *Proc Natl Acad Sci USA* 94:4504–4509; Patten et al. (1997) "Applications of DNA Shuffling to Pharmaceuticals and Vaccines" *Current Opinion in Biotechnology* 8:724–733; Crameri et al. (1996) "Construction and evolution of antibody-phage libraries by DNA shuffling" *Nature Medicine* 2:100–103; Crameri et al. (1996) "Improved green fluorescent protein by molecular evolution using DNA shuffling" *Nature Biotechnology* 14:315–319; Gates et al. (1996) "Affinity selective isolation of ligands from peptide libraries through display on a lac repressor 'headpiece dimer'" *Journal of Molecular Biology* 255:373–386; Stemmer (1996) "Sexual PCR and Assembly PCR" In: *The Encyclopedia of Molecular Biology.* VCH Publishers, New York. pp.447–457; Crameri and Stemmer (1995) "Combinatorial multiple cassette mutagenesis creates all the permutations of mutant and wildtype cassettes" *BioTechniques* 18:194–195; Stemmer et al., (1995) "Single-step assembly of a gene and entire plasmid form large numbers of oligodeoxyribonucleotides" *Gene,* 164:49–53; Stemmer (1995) "The Evolution of Molecular Computation" *Science* 270: 1510; Stemmer (1995) "Searching Sequence Space" *Bio/Technology* 13:549–553; Stemmer (1994) "Rapid evolution of a protein in vitro by DNA shuffling" *Nature* 370:389–391; and Stemmer (1994) "DNA shuffling by random fragmentation and reassembly: In vitro recombination for molecular evolution." *Proc Natl Acad Sci USA* 91:10747–10751.

Mutational methods of generating diversity include, for example, site-directed mutagenesis (Ling et al. (1997) "Approaches to DNA mutagenesis: an overview" *Anal Biochem* 254(2): 157–178; Dale et al. (1996) "Oligonucleotide-directed random mutagenesis using the phosphorothioate method" *Methods Mol Biol* 57:369–374; Smith (1985) "In vitro mutagenesis" *Ann Rev Genet* 19:423–462; Botstein & Shortle (1985) "Strategies and applications of in vitro mutagenesis" *Science* 229:1193–1201; Carter (1986) "Site-directed mutagenesis" *Biochem J* 237:1–7; and Kunkel (1987) "The efficiency of oligonucleotide directed mutagenesis" in *Nucleic Acids & Molecular Biology* (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" *Proc Natl Acad Sci USA* 82:488–492; Kunkel et al. (1987) "Rapid and efficient site-specific mutagenesis without phenotypic selection" *Methods in Enzymol* 154, 367–382; and Bass et al. (1988) "Mutant Trp repressors with new DNA-binding specificities" *Science* 242:240–245); oligonucleotide-directed mutagenesis (*Methods in Enzymol* 100: 468–500 (1983); *Methods in Enzymol* 154: 329–350 (1987); Zoller & Smith (1982) "Oligonucleotide-directed mutagenesis using M13-derived vectors: an efficient and general procedure for the production of point mutations in any DNA fragment" *Nucleic Acids Res* 10:6487–6500; Zoller & Smith (1983) "Oligonucleotide-directed mutagenesis of DNA fragments cloned into M13 vectors" *Methods in Enzymol* 100:468–500; and Zoller & Smith (1987) "Oligonucleotide-directed mutagenesis: a simple method using two oligonucleotide primers and a single-stranded DNA template" *Methods in Enzymol* 154:329–350); phosphorothioate-modified DNA mutagenesis (Taylor et al. (1985) "The use of phosphorothioate-modified DNA in restriction enzyme reactions to prepare nicked DNA" *Nucl. Acids Res.* 13: 8749–8764; Taylor et al. (1985) "The rapid generation of oligonucleotide-directed mutations at high frequency using phosphorothioate-modified DNA" *Nucl. Acids Res.* 13: 8765–8787 (1985); Nakamaye & Eckstein (1986) "Inhibition of restriction endonuclease Nci I cleavage by phosphorothioate groups and its application to oligonucleotide-directed mutagenesis" *Nucl Acids Res* 14: 9679–9698; Sayers et al. (1988) "Y-T Exonucleases in phosphorothioate-based oligonucleotide-directed mutagenesis" Nucl Acids Res 16:791–802; and Sayers et al. (1988) "Strand specific cleavage of phosphorothioate-containing DNA by reaction with restriction endonucleases in the presence of ethidium bromide" *Nucl Acids Res* 16: 803–814); mutagenesis using gapped duplex DNA (Kramer et al. (1984) "The gapped duplex DNA approach to oligonucleotide-directed mutation construction" *Nucl Acids Res* 12: 9441–9456; Kramer & Fritz (1987) *Methods in Enzymol* "Oligonucleotide-directed construction of mutations via gapped duplex DNA" 154:350–367; Kramer et al. (1988) "Improved enzymatic in vitro reactions in the gapped duplex DNA approach to oligonucleotide-directed construction of mutations" *Nucl Acids Res* 16: 7207; and Fritz et al. (1988) "Oligonucleotide-directed construction of mutations: a gapped duplex DNA procedure without enzymatic reactions in vitro" *Nucl Acids Res* 16: 6987–6999).

Additional suitable methods include point mismatch repair (Kramer et al. (1984) "Point Mismatch Repair" *Cell* 38:879–887), mutagenesis using repair-deficient host strains (Carter et al. (1985) "Improved oligonucleotide site-directed mutagenesis using M13 vectors" *Nucl Acids Res* 13: 4431–4443; and Carter (1987) "Improved oligonucleotide-directed mutagenesis using M13 vectors" *Methods in Enzymol* 154: 382–403), deletion mutagenesis (Eghtedarzadeh & Henikoff (1986) "Use of oligonucleotides to generate large deletions" *Nucl Acids Res* 14: 5115), restriction-selection and restriction-purification (Wells et al. (1986) "Importance of hydrogen-bond formation in stabilizing the transition state of subtilisin" *Phil. Trans. R. Soc. Lond.* A317: 415–423), mutagenesis by total gene synthesis (Nambiar et al. (1984) "Total synthesis and cloning of a gene coding for the ribonuclease S protein" *Science* 223: 1299–1301; Sakamar and Khorana (1988) "Total synthesis and expression of a gene for the a-subunit of bovine rod outer segment guanine nucleotide-binding protein (transducin)" *Nucl Acids Res* 14: 6361–6372; Wells et al. (1985) "Cassette mutagenesis: an efficient method for generation of multiple mutations at defined sites" *Gene* 34:315–323; and Grundström et al. (1985) "Oligonucleotide-directed mutagenesis by microscale 'shot-gun' gene synthesis" *Nucl Acids Res* 13: 3305–3316), double-strand break repair (Mandecki (1986) "Oligonucleotide-directed double-strand break repair in plasmids of *Escherichia coli:* a method for site-specific mutagenesis" *Proc Natl Acad Sci USA,* 83:7177–7181; and Arnold (1993) "Protein engineering for unusual environments" *Current Opinion in Biotechnology* 4:450–455). Additional details on many of the above methods can be found in *Methods in Enzymology* Volume 154, which also describes useful controls for trouble-shooting problems with various mutagenesis methods.

Additional details regarding various diversity generating methods can be found in the following U.S. patents, PCT publications and applications, and EPO publications: U.S. Pat. No. 5,605,793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/27230 by Stemmer et al., "Methods for Optimization of Gene Therapy by Recursive Sequence Shuffling and Selection," WO 00/00632, "Methods for Generating Highly Diverse Libraries," WO 00/09679, "Methods for Obtaining in Vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in Vitro Method for Construction of a DNA Library," WO 98/41622 by Borchert et al., "Method for Constructing a Library Using DNA Shuffling," and WO 98/42727 by Pati and Zarling, "Sequence Alterations using Homologous Recombination;" WO 00/18906 by Patten et al., "Shuffling of Codon-Altered Genes;" WO 00/04190 by del Cardayre et al. "Evolution of Whole Cells and Organisms by Recursive Recombination;" WO 00/42561 by Crameri et al., "Oligonucleotide Mediated Nucleic Acid Recombination;" WO 00/42559 by Selifonov and Stemmer "Methods of Populating Data Structures for Use in Evolutionary Simulations;" WO 00/42560 by Selifonov et al., "Methods for Making Character Strings, Polynucleotides & Polypeptides Having Desired Characteristics;" WO 01/23401 by Welch et al., "Use of Codon-Varied Oligonucleotide Synthesis for Synthetic Shuffling;" and PCT/US01/06775 "Single-Stranded Nucleic Acid Template-Mediated Recombination and Nucleic Acid Fragment Isolation" by Affholter.

In brief, several different general classes of sequence modification methods, such as mutation, recombination, etc. are applicable to the production of lipase homologue nucleic acids encoding polypeptides with desired properties, and are set forth, e.g., in the references above. The following exemplify some of the different types of preferred formats for diversity generation in the context of the present invention, including, e.g., certain recombination based diversity generation formats.

Nucleic acids can be recombined in vitro by any of a variety of techniques discussed in the references above, including e.g., DNAse digestion of nucleic acids to be recombined followed by ligation and/or PCR reassembly of the nucleic acids. For example, sexual PCR mutagenesis can be used in which random (or pseudo random, or even non-random) fragmentation of the DNA molecule is followed by recombination, based on sequence similarity, between DNA molecules with different but related DNA sequences, in vitro, followed by fixation of the crossover by extension in a polymerase chain reaction. This process and many process variants is described in several of the references above, e.g., in Stemmer (1994) *Proc Natl Acad Sci USA* 91:10747–10751. Thus, one or more in vitro recombination procedure can be employed to generate a diverse set of lipase nucleic acids suitable for evaluation in any of a variety of assays designed to identify lipase nucleic acids encoding lipase polypeptides with desired properties. See, e.g., the lipase activity assays described infra.

Similarly, nucleic acids can be recursively recombined in vivo, e.g., by allowing recombination to occur between nucleic acids in cells. Many such in vivo recombination formats are set forth in the references noted above. Such formats optionally provide direct recombination between nucleic acids of interest, or provide recombination between vectors, viruses, plasmids, etc., comprising the nucleic acids of interest, as well as other formats. Details regarding such procedures are found in the references noted above. Thus, lipase nucleic acids can also be diversified in vivo prior to, or in concert with, screening and/or selection procedures to identify lipase polypeptides with desired properties.

Whole genome recombination methods can also be used in which whole genomes of cells or other organisms are recombined, optionally including spiking of the genomic recombination mixtures with desired library components (e.g., genes corresponding to the pathways of the present invention). These methods have many applications, including those in which the identity of a target gene is not known. Details on such methods are found, e.g., in WO 98/31837 by del Cardayre et al. "Evolution of Whole Cells and Organisms by Recursive Sequence Recombination;" and in, e.g., WO 00/04190 by del Cardayre et al., also entitled "Evolution of Whole Cells and Organisms by Recursive Sequence Recombination."

Synthetic recombination methods can also be used, in which oligonucleotides corresponding to targets of interest are synthesized and reassembled in PCR or ligation reactions which include oligonucleotides which correspond to more than one parental nucleic acid, thereby generating new recombined nucleic acids. Oligonucleotides can be made by standard nucleotide addition methods, or can be made, e.g., by tri-nucleotide synthetic approaches. Details regarding such approaches are found in the references noted above, including, e.g., WO 00/42561 by Crameri et al., "Oligonucleotide Mediated Nucleic Acid Recombination;" WO 01/23401 by Welch et al., "Use of Codon-Varied Oligonucleotide Synthesis for Synthetic Shuffling;" WO 00/42560 by Selifonov et al., "Methods for Making Character Strings, Polynucleotides and Polypeptides Having Desired Characteristics;" and WO 00/42559 by Selifonov and Stemmer "Methods of Populating Data Structures for Use in Evolutionary Simulations."

In silico methods of recombination can be effected in which genetic algorithms are used in a computer to recombine sequence strings which correspond to homologous (or even non-homologous) nucleic acids. The resulting recombined sequence strings are optionally converted into nucleic acids by synthesis of nucleic acids which correspond to the recombined sequences, e.g., in concert with oligonucleotide synthesis/gene reassembly techniques. This approach can generate random, partially random, or designed variants. Many details regarding in silico recombination, including the use of genetic algorithms, genetic operators and the like in computer systems, combined with generation of corresponding nucleic acids (and/or proteins), as well as combinations of designed nucleic acids and/or proteins (e.g., based on cross-over site selection) as well as designed, pseudo-random, or random recombination methods are described in WO 00/42560 by Selifonov et al., "Methods for Making Character Strings, Polynucleotides and Polypeptides Having Desired Characteristics" and WO 00/42559 by Selifonov and Stemmer "Methods of Populating Data Structures for Use in Evolutionary Simulations." Extensive details regarding in silico recombination methods are found in these applications. This methodology is generally applicable to the present invention in providing for recombination of character strings corresponding to lipase homologues in silico and/or the generation of corresponding nucleic acids or proteins.

Many methods of accessing natural diversity, e.g., by hybridization of diverse nucleic acids or nucleic acid fragments to single-stranded templates, followed by polymerization and/or ligation to regenerate full-length sequences, optionally followed by degradation of the templates and recovery of the resulting modified nucleic acids can be similarly used. In one method employing a single-stranded template, the fragment population derived from the genomic library(ies) is annealed with partial, or, often approximately full length ssDNA or RNA corresponding to the opposite strand. Assembly of complex chimeric genes from this population is then mediated by nuclease-base removal of non-hybridizing fragment ends, polymerization to fill gaps between such fragments and subsequent single stranded ligation. The parental polynucleotide strand can be removed by digestion (e.g., if RNA or uracil-containing), magnetic separation under denaturing conditions (if labeled in a manner conducive to such separation) and other available separation/purification methods. Alternatively, the parental strand is optionally co-purified with the chimeric strands and removed during subsequent screening and processing steps. Additional details regarding this approach are found, e.g., in "Single-Stranded Nucleic Acid Template-Mediated Recombination and Nucleic Acid Fragment Isolation" by Affholter, PCT/US01/06775.

In another approach, single-stranded molecules are converted to double-stranded DNA (dsDNA) and the dsDNA molecules are bound to a solid support by ligand-mediated binding. After separation of unbound DNA, the selected DNA molecules are released from the support and introduced into a suitable host cell to generate a library enriched sequences which hybridize to the probe. A library produced in this manner provides a desirable substrate for further diversification using any of the procedures described herein.

Any of the preceding general recombination formats can be practiced in a reiterative fashion (e.g., one or more cycles of mutation/recombination or other diversity generation methods, optionally followed by one or more selection methods) to generate a more diverse set of recombinant nucleic acids.

Mutagenesis employing polynucleotide chain termination methods have also been proposed (see e.g., U.S. Pat. No. 5,965,408, "Method of DNA reassembly by interrupting synthesis" to Short, and the references above), and can be applied to the present invention. In this approach, double stranded DNAs corresponding to one or more genes sharing regions of sequence similarity are combined and denatured, in the presence or absence of primers specific for the gene. The single stranded polynucleotides are then annealed and incubated in the presence of a polymerase and a chain terminating reagent (e.g., ultraviolet, gamma or X-ray irradiation; ethidium bromide or other intercalators; DNA binding proteins, such as single strand binding proteins, transcription activating factors, or histones; polycyclic aromatic hydrocarbons; trivalent chromium or a trivalent chromium salt; or abbreviated polymerization mediated by rapid thermocycling; and the like), resulting in the production of partial duplex molecules. The partial duplex molecules, e.g., containing partially extended chains, are then denatured and reannealed in subsequent rounds of replication or partial replication resulting in polynucleotides which share varying degrees of sequence similarity and which are diversified with respect to the starting population of DNA molecules. Optionally, the products, or partial pools of the products, can be amplified at one or more stages in the process. Polynucleotides produced by a chain termination method, such as described above, are suitable substrates for any other described recombination format.

Diversity also can be generated in nucleic acids or populations of nucleic acids using a recombinational procedure termed "incremental truncation for the creation of hybrid enzymes" ("ITCHY") described in Ostermeier et al. (1999) "A combinatorial approach to hybrid enzymes independent of DNA homology" *Nature Biotech* 17:1205. This approach can be used to generate an initial library of variants which can optionally serve as a substrate for one or more in vitro or in vivo recombination methods. See also, Ostermeier et al. (1999) "Combinatorial Protein Engineering by Incremental Truncation," *Proc Natl Acad USA*, 96: 3562–67; Ostermeier et al. (1999), "Incremental Truncation as a Strategy in the Engineering of Novel Biocatalysts," *Biological and Medicinal Chemistry*, 7: 213–944.

Mutational methods which result in the alteration of individual nucleotides or groups of contiguous or non-contiguous nucleotides can be favorably employed to introduce nucleotide diversity. For example, mutagenesis procedures resulting in changes of one or more nucleotide can be used to produce any number of lipase variants of the present invention. Many mutagenesis methods are found in the above-cited references; additional details regarding mutagenesis methods can be found in following, which can also be applied to the present invention.

For example, error-prone PCR can be used to generate nucleic acid variants. Using this technique, PCR is performed under conditions where the copying fidelity of the DNA polymerase is low, such that a high rate of point mutations is obtained along the entire length of the PCR product. Examples of such techniques are found in the references above and, e.g., in Leung et al. (1989) *Technique* 1:11–15 and Caldwell et al. (1992) *PCR Methods Applic* 2:28–33. Similarly, assembly PCR can be used, in a process which involves the assembly of a PCR product from a mixture of small DNA fragments. A large number of different PCR reactions can occur in parallel in the same reaction mixture, with the products of one reaction priming the products of another reaction.

Oligonucleotide directed mutagenesis can be used to introduce site-specific mutations in a nucleic acid sequence of interest. Examples of such techniques are found in the references above and, e.g., in Reidhaar-Olson et al. (1988) *Science*, 241:53–57. Similarly, cassette mutagenesis can be used in a process that replaces a small region of a double stranded DNA molecule with a synthetic oligonucleotide cassette that differs from the native sequence. The oligonucleotide can contain, e.g., completely and/or partially randomized native sequence(s).

Recursive ensemble mutagenesis is a process in which an algorithm for protein mutagenesis is used to produce diverse populations of phenotypically related mutants, members of which differ in amino acid sequence. This method uses a feedback mechanism to monitor successive rounds of combinatorial cassette mutagenesis. Examples of this approach are found in Arkin & Youvan (1992) *Proc Natl Acad Sci USA* 89:7811–7815.

Exponential ensemble mutagenesis can be used for generating combinatorial libraries with a high percentage of unique and functional mutants. Small groups of residues in a sequence of interest are randomized in parallel to identify, at each altered position, amino acids which lead to functional proteins. Examples of such procedures are found in Delegrave & Youvan (1993) *Biotechnology Research* 11:1548–1552.

In vivo mutagenesis can be used to generate random mutations in any cloned DNA of interest by propagating the DNA, e.g., in a strain of *E. coli* that carries mutations in one or more of the DNA repair pathways. These "mutator" strains have a higher random mutation rate than that of a wild-type parent. Propagating the DNA in one of these strains will eventually generate random mutations within the DNA. Such procedures are described in the references noted above.

Other procedures for introducing diversity into a genome, e.g. a bacterial, fungal, animal or plant genome can be used in conjunction with the above described and/or referenced methods. For example, in addition to the methods above, techniques have been proposed which produce nucleic acid multimers suitable for transformation into a variety of species (see, e.g., Schellenberger U.S. Pat. No. 5,756,316 and the references above). Transformation of a suitable host with such multimers, consisting of genes that are divergent with respect to one another, (e.g., derived from natural diversity or through application of site directed mutagenesis, error prone PCR, passage through mutagenic bacterial strains, and the like), provides a source of nucleic acid diversity for DNA diversification, e.g., by an in vivo recombination process as indicated above.

Alternatively, a multiplicity of monomeric polynucleotides sharing regions of partial sequence similarity can be transformed into a host species and recombined in vivo by the host cell. Subsequent rounds of cell division can be used to generate libraries, members of which, include a single, homogenous population, or pool of monomeric polynucleotides. Alternatively, the monomeric nucleic acid can be recovered by standard techniques, e.g., PCR and/or cloning, and recombined in any of the recombination formats, including recursive recombination formats, described above.

Methods for generating multispecies expression libraries have been described (in addition to the reference noted above, see, e.g., Peterson et al. (1998) U.S. Pat. No. 5,783,431 "Methods for Generating and Screening Novel Metabolic Pathways," and Thompson, et al. (1998) U.S. Pat. No. 5,824,485 Methods for Generating and Screening Novel Metabolic Pathways) and their use to identify protein activities of interest has been proposed (In addition to the references noted above, see, Short (1999) U.S. Pat. No. 5,958,672 "Protein Activity Screening of Clones Having DNA from Uncultivated Microorganisms"). Multispecies expression libraries include, in general, libraries comprising cDNA or genomic sequences from a plurality of species or strains, operably linked to appropriate regulatory sequences, in an expression cassette. The cDNA and/or genomic sequences are optionally randomly ligated to further enhance diversity. The vector can be a shuttle vector suitable for transformation and expression in more than one species of host organism, e.g., bacterial species, eukaryotic cells. In some cases, the library is biased by preselecting sequences which encode a protein of interest, or which hybridize to a nucleic acid of interest. Any such libraries can be provided as substrates for any of the methods herein described.

The above described procedures have been largely directed to increasing nucleic acid and/or encoded protein diversity. However, in many cases, not all of the diversity is useful, e.g., functional, and contributes merely to increasing the background of variants that must be screened or selected to identify the few favorable variants. In some applications, it is desirable to preselect or prescreen libraries (e.g., an amplified library, a w genomic library, a cDNA library, a normalized library, etc.) or other substrate nucleic acids prior to diversification, e.g., by recombination-based mutagenesis procedures, or to otherwise bias the substrates towards nucleic acids that encode functional products. For example, in the case of antibody engineering, it is possible to bias the diversity generating process toward antibodies with functional antigen binding sites by taking advantage of in vivo recombination events prior to manipulation by any of the described methods. For example, recombined CDRs derived from B cell cDNA libraries can be amplified and assembled into framework regions (e.g., Jirholt et al. (1998) "Exploiting sequence space: shuffling in vivo formed complementarity determining regions into a master framework" *Gene* 215: 471) prior to diversifying according to any of the methods described herein.

Libraries can be biased towards nucleic acids which encode proteins with desirable enzyme activities. For example, after identifying a clone from a library which exhibits a specified activity, the clone can be mutagenized using any known method for introducing DNA alterations. A library comprising the mutagenized homologues is then screened for a desired activity, which can be the same as or different from the initially specified activity. An example of such a procedure is proposed in Short (1999) U.S. Pat. No. 5,939,250 for "Production of Enzymes Having Desired Activities by Mutagenesis." Desired activities can be identified by any method known in the art. For example, WO 99/10539 proposes that gene libraries can be screened by combining extracts from the gene library with components obtained from metabolically rich cells and identifying combinations which exhibit the desired activity. It has also been proposed (e.g., WO 98/58085) that clones with desired activities can be identified by inserting bioactive substrates into samples of the library, and detecting bioactive fluorescence corresponding to the product of a desired activity using a fluorescent analyzer, e.g., a flow cytometry device, a CCD, a fluorometer, or a spectrophotometer.

Libraries can also be biased towards nucleic acids which have specified characteristics, e.g., hybridization to a selected nucleic acid probe. For example, application WO 99/10539 proposes that polynucleotides encoding a desired activity (e.g., an enzymatic activity, for example: a lipase, an esterase, a protease, a glycosidase, a glycosyl transferase, a phosphatase, a kinase, an oxygenase, a peroxidase, a hydrolase, a hydratase, a nitrilase, a transaminase, an amidase or an acylase) can be identified from among genomic DNA sequences in the following manner. Single stranded DNA molecules from a population of genomic DNA are hybridized to a ligand-conjugated probe. The genomic DNA can be derived from either a cultivated or uncultivated microorganism, or from an environmental sample. Alternatively, the genomic DNA can be derived from a multi-cellular organism, or a tissue derived therefrom. Second strand synthesis can be conducted directly from the hybridization probe used in the capture, with or without prior release from the capture medium or by a wide variety of other strategies known in the art. Alternatively, the isolated single-stranded genomic DNA population can be fragmented without further cloning and used directly in, e.g., a recombination-based approach, that employs a single-stranded template, as described above.

"Non-Stochastic" methods of generating nucleic acids and polypeptides are alleged in Short "Non-Stochastic Generation of Genetic Vaccines and Enzymes" WO 00/46344. These methods, including proposed non-stochastic polynucleotide reassembly and site-saturation mutagenesis methods can be applied to the present invention as well. Random or semi-random mutagenesis using doped or degenerate oligonucleotides is also described in, e.g., Arkin and Youvan (1992) "Optimizing nucleotide mixtures to encode specific subsets of amino acids for semi-random mutagenesis" *Biotechnology* 10:297–300; Reidhaar-Olson et al. (1991) "Random mutagenesis of protein sequences using oligonucleotide cassettes" *Methods Enzymol* 208:564–86; Lim and Sauer (1991) "The role of internal packing interactions in determining the structure and stability of a protein" *J Mol Biol* 219:359–76; Breyer and Sauer (1989) "Mutational analysis of the fine specificity of binding of monoclonal antibody 51F to lambda repressor" *J Biol Chem* 264:13355–60); and "Walk-Through Mutagenesis" (Crea, R; U.S. Pat. Nos. 5,830,650 and 5,798,208, and EP Patent 0527809 B1.

It will readily be appreciated that any of the above described techniques suitable for enriching a library prior to diversification can also be used to screen the products, or libraries of products, produced by the diversity generating methods.

Kits for mutagenesis, library construction and other diversity generation methods are also commercially available. For example, kits are available from, e.g., Stratagene (e.g., QuickChange™ site-directed mutagenesis kit; and Chameleon™ double-stranded, site-directed mutagenesis kit), Bio/Can Scientific, Bio-Rad (e.g., using the Kunkel method described above), Boehringer Mannheim Corp., Clonetech Laboratories, DNA Technologies, Epicentre Technologies (e.g., 5 prime 3 prime kit); Genpak Inc, Lemargo Inc, Life Technologies (Gibco BRL), New England Biolabs, Pharmacia Biotech, Promega Corp., Quantum Biotechnologies, Amersham International plc (e.g., using the Eckstein method above), and Anglian Biotechnology Ltd. (e.g., using the Carter/Winter method above).

The above references provide many mutational formats, including recombination, recursive recombination, recursive mutation and combinations or recombination with other forms of mutagenesis, as well as many modifications of these formats. Regardless of the diversity generation format that is used, the nucleic acids of the invention can be recombined (with each other, or with related (or even unrelated) sequences) to produce a diverse set of recombinant nucleic acids, including, e.g., sets of homologous nucleic acids, as well as corresponding polypeptides.

The current invention provides methods of producing modified or recombinant nucleic acids comprising mutating or recombining (including recursive recombination with one or more additional nucleic acid) a nucleic acid of the invention (or a fragment thereof), as well as the modified or recombinant nucleic acids that are produced by such method. The method optionally includes wherein the one or more additional nucleic acid encodes a polypeptide comprising lipase activity and/or enantioselective lipase activity (or an amino acid subsequence or fragment thereof). The recombination (e.g., recursive recombination) is optionally done in vitro or in vivo and optionally produces at least one library of recombinant nucleic acids, which comprises at least one polypeptide comprising lipase activity and/or enantioselective lipase activity (or a homologue thereof). Both the nucleic acid library produced and a population of cells comprising the library are provided by the invention, as are the modified or recombinant nucleic acids produced by the mutation/recombination and the cells which comprise such nucleic acids. The invention also includes a method of producing a polypeptide by introducing a nucleic acid of the invention (or a fragment thereof), which is operably linked to a regulatory sequence capable of directing expression of such nucleic acid into a polypeptide in at least a subset of a population of cells or their progeny and then expressing the polypeptide in the subset of the population (or their progeny). The polypeptide produced from such method is also part of the current invention. Such method optionally includes isolating the polypeptide from the cells and optionally includes expressing the polypeptide by culturing the population (or subset) in a nutrient medium under conditions where the regulatory sequence directs expression of the polypeptide encoded by the nucleic acid (again, wherein the polypeptide is optionally isolated or recovered from the cells and/or from the nutrient media (such culturing is optionally done in a bulk fermentation vessel). The cells used in such methods are optionally bacterial, eukaryotic (e.g., fungal cells, yeast cells, plant cells, insect cells, or mammalian cells (e.g., fertilized oocytes, embryonic stem cells, pluripotent stem cells, etc.)). If mammalian cells are utilized, a transgenic animal is optionally regenerated from the cells and the polypeptide is optionally recovered from the transgenic animal or from a by-product of the transgenic animal such as milk.

High Throughput Screening

High throughput screening formats are typically those formats which enable the efficient evaluation of a large number of samples, such as are associated with a library of nucleic acid or polypeptide sequences. Typically, a high throughput screening assay enables the evaluation of greater than 100, more commonly greater than 500, often greater than 1000 or more samples in an efficient manner. A number of types of assays can be adapted to a high throughput format. For example, the throughput associated with a nucleic hybridization assay can be increased by adapting the assay from, e.g., electrophoretic separation of the subject nucleic acids followed by transfer to a nylon or nitrocellulose membrane and subsequent hybridization, to a "dot blot" format based on direct application of the subject nucleic acids to a membrane in an array with subsequent hybridization to a probe. The throughput can be further increased by robotic assistance, e.g., of the nucleic acid preparation and/or membrane application steps of the procedure. Similarly, many cell based assays can be reduced in scale, and increased in processing efficiency.

In addition to the nucleic acid screening methods indicated above, high throughput assays are used in the context of the present invention to measure functional activity of the nucleic acid and polypeptides described herein. One common format for cell based screening assays in a high throughput format is the multiwell microtiter plate although other formats are also suitably adapted to the present invention (e.g., microfluidic devices such as the HP/Agilent Technologies HP2100 and the Caliper HTS system: Caliper Technologies, Mountain View, Calif.).

Standard microtiter plates are available with 96, 384 or 1536 wells, although even higher numbers of wells are also available. Well construction and materials can be selected according to the precise application. For example, well dimensions vary in shape, cross sectional area, depth and volume the choice of which can be influenced by such parameters as minimizing reagent use, or maximizing product recovery. Common materials include a myriad of plastics, including polystyrene, polypropylene and the like. For some cell culture applications, it is desirable to use microtiter plates that have been pre-treated with agents that improve cell adherence or survival, e.g., poly-lysine, gelatin, etc.

Typically the plate dimensions are selected for compatibility with robotic loading and handling devices. Suitable robotic plate handling devices include, e.g., Multimek from Beckman Coulter; Q-BOTIII from Genetix; and the BioRobot #9600/9604 from Qiagen.

Other Polynucleotide Compositions

The invention also includes compositions comprising two or more polynucleotides of the invention (e.g., as substrates for recombination). The composition can comprise a library of recombinant nucleic acids, where the library contains at least 2, 3, 5, 10, 20, 50, 100, 1,000 or 5,000 or more nucleic acids. The nucleic acids are optionally cloned into expression vectors, providing expression libraries.

The invention also includes compositions produced by digesting one or more polynucleotide of the invention with a restriction endonuclease, an RNAse, or a DNAse (e.g., as is performed in certain of the recombination formats noted above); and compositions produced by fragmenting or shearing one or more polynucleotide of the invention by mechanical means (e.g., sonication, vortexing, and the like), or by chemical cleavage (e.g., by incorporating nucleotide analogues subject to, e.g., photo-activated or other cleavage) which can also be used to provide substrates for recombination in the methods above. Similarly, compositions comprising sets of oligonucleotides corresponding to more than one nucleic acid of the invention are useful as recombination substrates and are a feature of the invention. For convenience, these fragmented, sheared, or synthesized oligonucleotide mixtures are referred to as fragmented nucleic acid sets.

Also included in the invention are compositions produced by incubating one or more of the fragmented nucleic acid sets in the presence of ribonucleotide- or deoxyribonucleotide triphosphates and a nucleic acid polymerase. This resulting composition forms a recombination mixture for many of the recombination formats noted above. The nucleic acid polymerase may be an RNA polymerase, a DNA polymerase, or an RNA-directed DNA polymerase (e.g., a "reverse transcriptase"); the polymerase can be, e.g., a thermostable DNA polymerase (such as, VENT, TAQ, or the like).

Lipase Homologue Polypeptides

Figure 4C:
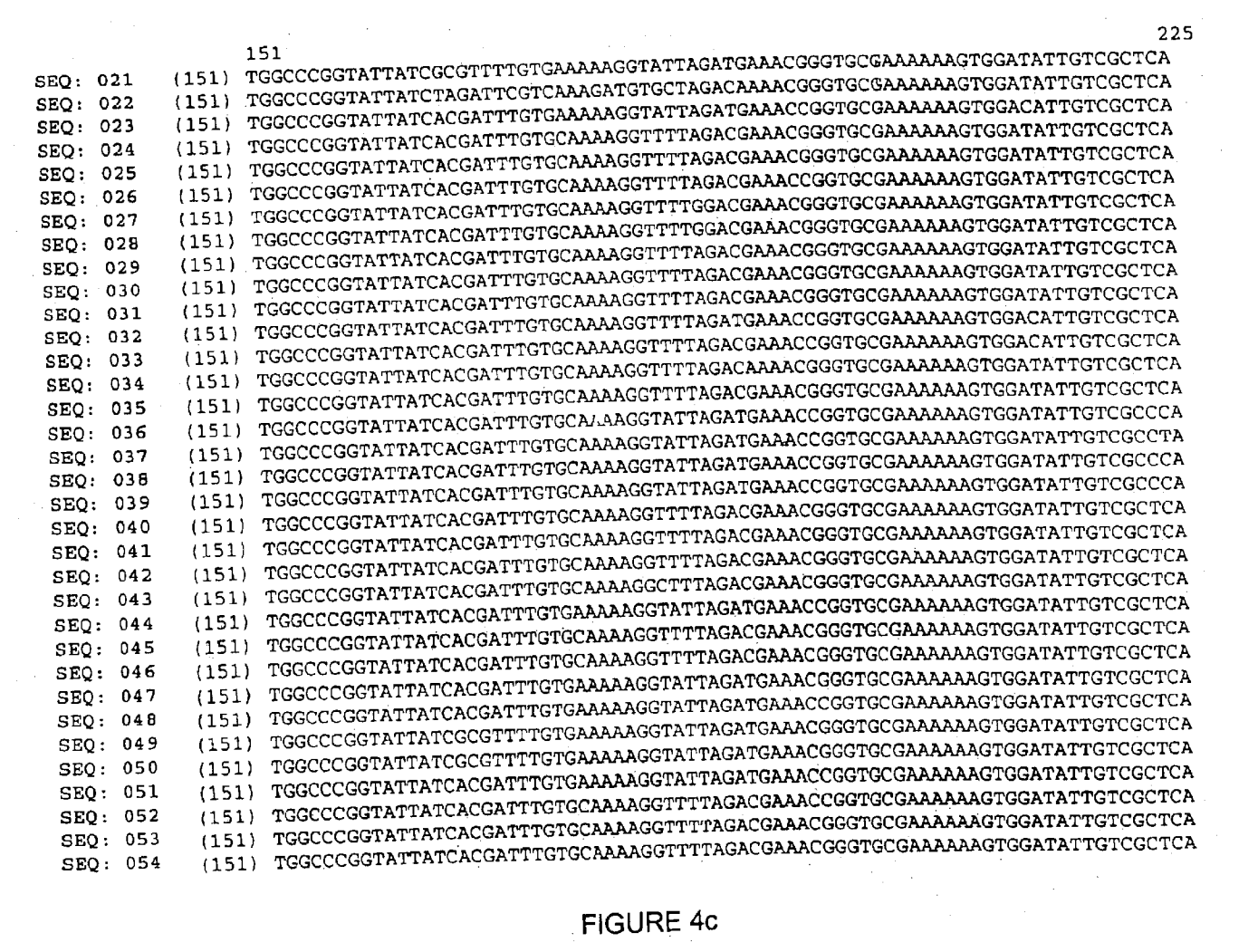
Figure 4E:
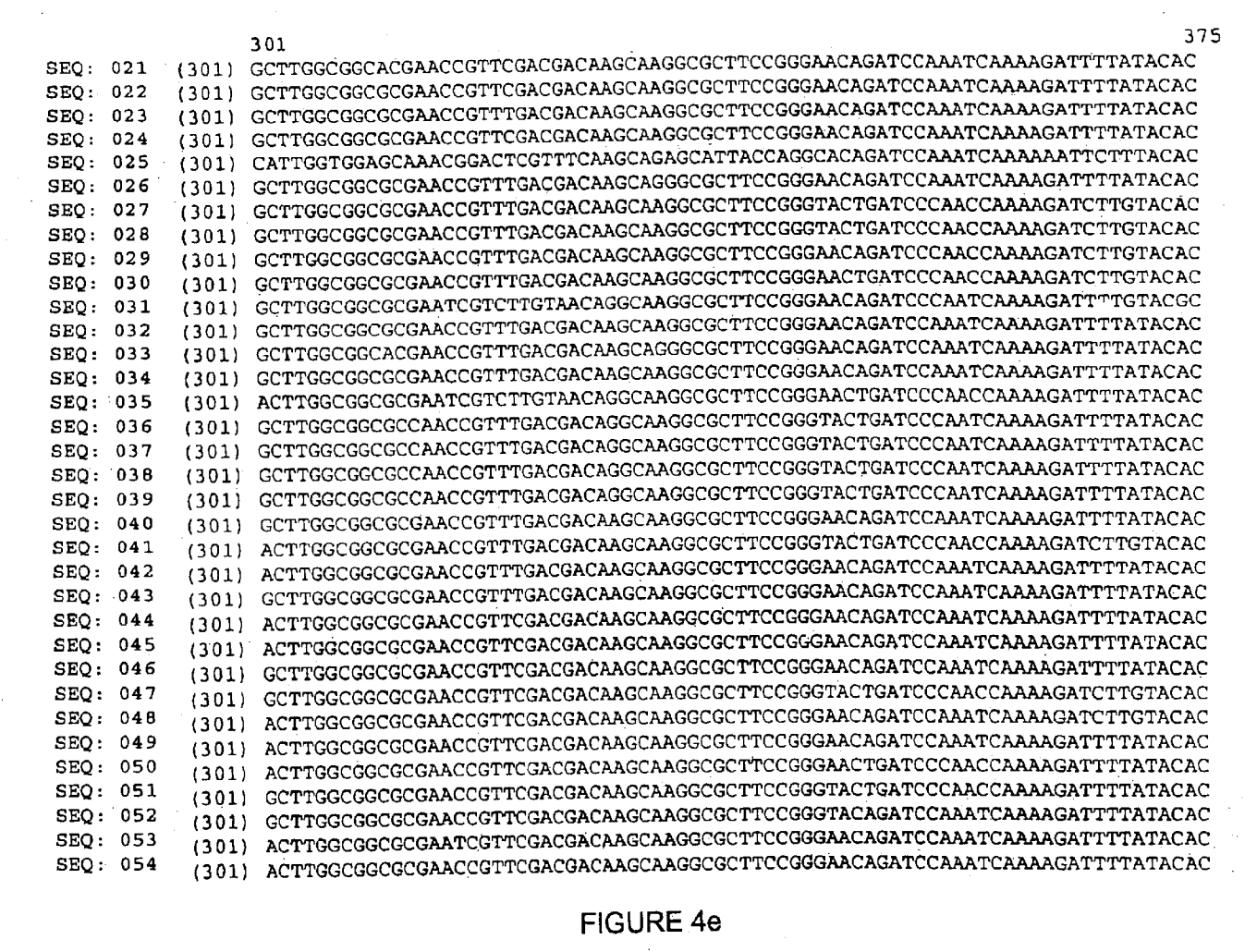
Figure 4F:
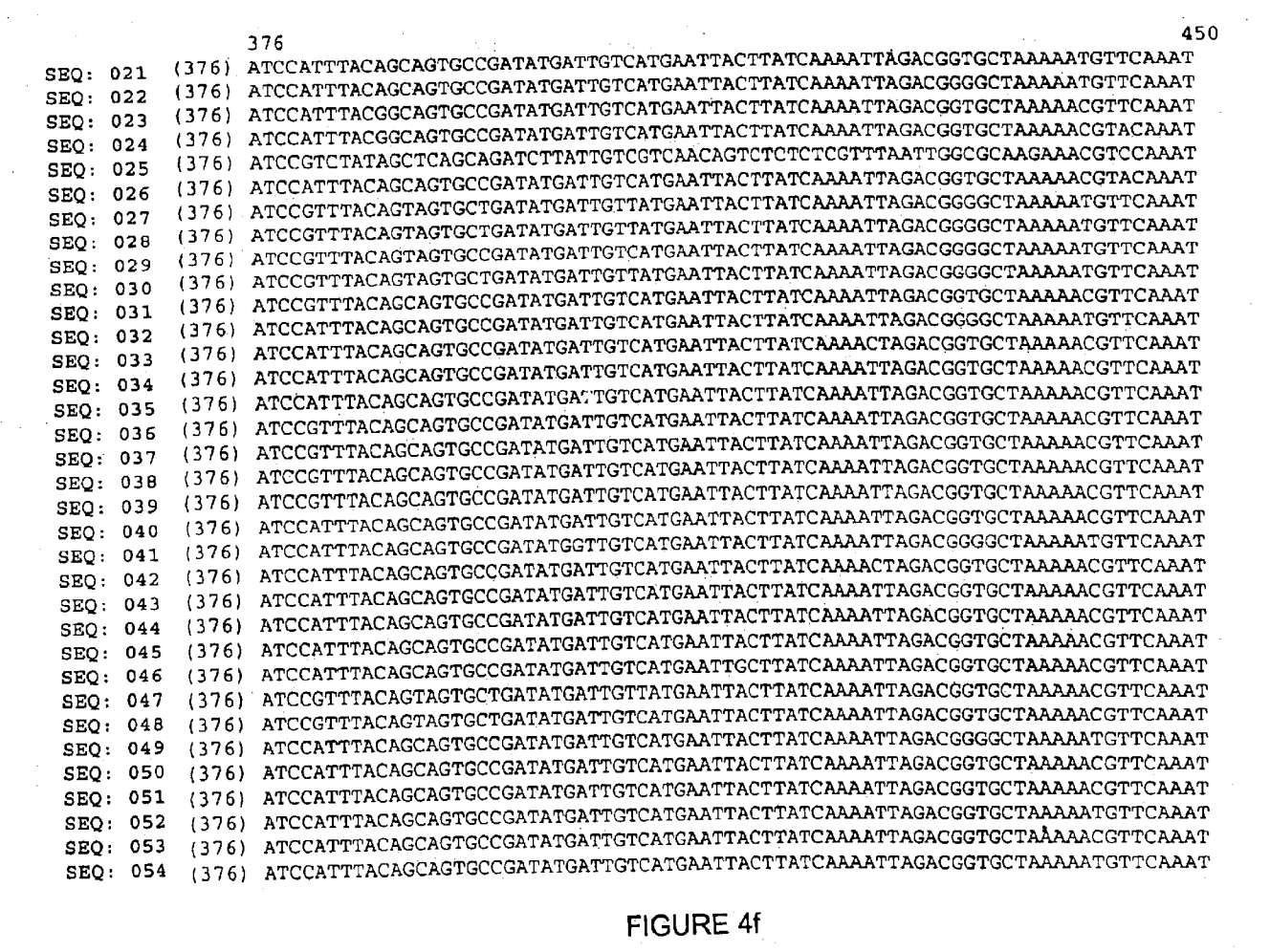
Figure 6B:
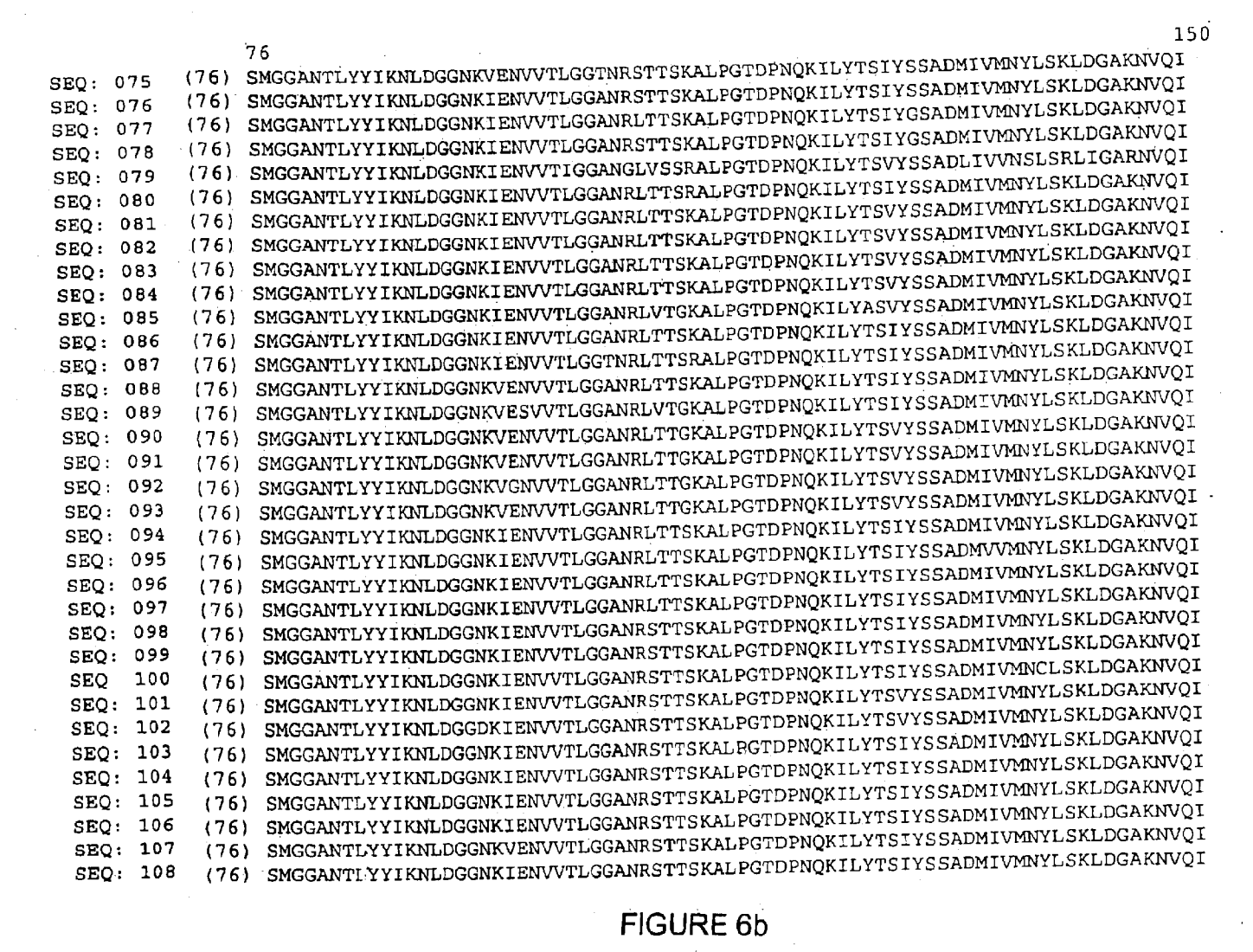

The invention provides isolated or recombinant lipase homologue polypeptides, referred to herein as "novel lipase polypeptides," "lipase homologue polypeptides," "lipase homologues," or simply "novel lipases." For example, an isolated or recombinant lipase homologue polypeptide of the invention includes a polypeptide comprising a sequence selected from SEQ ID NO: 55 to SEQ ID NO: 108, and conservatively modified variations thereof (as well as a fragment of such, which fragment can comprise lipase activity and/or enantioselective lipase activity) Additionally, the invention provides a polypeptide encoded by a polynucleotide sequence selected from SEQ ID NO: 1 through SEQ ID NO: 54 or a complementary polynucleotide sequence thereof, etc. Alignments of both nucleic acid and amino acid exemplary lipase homologue polypeptide sequences (for both newly isolated homologues and for newly created homologues) according to the invention are provided in FIGS. 3 through 6. FIG. 3 depicts an alignment of exemplary novel lipase polynucleotides of the invention (SEQ ID NOS:1–20). The predicted boundary between the signal peptide coding region and the mature coding region is indicated by the arrow. Thus, a mature coding region or mature polypeptide, either as a polypeptide or as its encoding nucleic acid, of the invention comprises such an area as is delineated in, e.g., FIG. 3, i.e., it does not include signal peptide regions, introductory 5' regions or tailing 3' regions such as a TGA stop, etc. FIG. 4 depicts an alignment of exemplary novel lipase polynucleotides of the invention (SEQ ID NOS:21–54). The nucleotide sequences depicted in the figure represent predicted mature coding regions, each with an introductory 5' 'T' just prior to the start of the mature coding region, and ending with a 3' "TGA" stop codon. FIG. 5 depicts an alignment of exemplary novel lipase polypeptides of the invention (SEQ ID NOS:55–74). The predicted boundary between the signal peptide and the mature region is indicated by the arrow. The position numbering along the top of the alignments indicate the position relative to the start of the mature region. FIG. 6 depicts an alignment of exemplary novel lipase polypeptides of the invention (SEQ ID NOS:75–108). The sequences shown represent the predicted mature region. The alignments shown in FIGS. 3–6 were prepared using the CLUSTALW multiple sequence alignment program, a part of the Vector NTI version 6 sequence analysis software package (Informax, Bethesda, Md.), using default parameters.

Another feature of the invention is an isolated or recombinant polypeptide encoded by a polynucleotide sequence which hybridizes under highly stringent conditions over substantially the entire length, or to a subsequence thereof comprising at least 100 residues or more, of a polynucleotide sequence selected from SEQ ID NO: 1 to SEQ ID NO: 54 (or a complementary sequence thereof) or a polynucleotide sequence encoding a polypeptide selected from SEQ ID NO: 55 to SEQ ID NO: 108 (or a complementary sequence thereof) or a fragment thereof (from either SEQ ID NO:

1–54 or SEQ ID NO: 55–108 which fragment can comprise lipase activity and/or enantioselective lipase activity) provided that the sequences do not correspond to or encode any of GenBank accession numbers: 1I6WA, 1I6WB, A02813, A02815,A34992, AAA22574, AAB31769, AAC12257, AAD30278, AAF40217, AAF63229, AB000617, AF134840, AF141874, AF237623, AJ297356, BAA11406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P37957, S23934, U78785, X95309, Z99105, and Z99108.

Various aspects of the current invention comprise an isolated or recombinant polypeptide comprising a sequence having at least 97% amino acid sequence identity to any one of SEQ ID NO: 75 to SEQ ID NO: 108. Such polypeptide can optionally comprise or exhibit lipase activity (e.g., it can degrade geranyl butyrate or neryl butyrate or both). Additionally, such polypeptide can exhibit enantioselectivity for geranyl butyrate over neryl butyrate. Such polypeptide that exhibits enantioselectivity for geranyl butyrate can comprise a sequence selected from: SEQ ID NO:76, SEQ ID NO:79, SEQ ID NO:80, SEQ ID NO:86, SEQ ID NO:96, SEQ ID NO:97, SEQ ID NO:101, SEQ ID NO:102, SEQ ID NO:104, SEQ ID NO:107, SEQ ID NO:108, SEQ ID NO:78, SEQ ID NO:87, SEQ ID NO:100, SEQ ID NO:75, SEQ ID NO:77, SEQ ID NO:88, SEQ ID NO:98, SEQ ID NO:99, SEQ ID NO:103, or SEQ ID NO:106. Alternatively, the polypeptide can exhibit enantioselectivity for neryl butyrate over geranyl butyrate. Such polypeptide that exhibits enantioselectivity for neryl butyrate over geranyl butyrate can comprise a sequence selected from: SEQ ID NO:81, SEQ ID NO:82, SEQ ID NO:83, SEQ ID NO:85, SEQ ID NO:89, SEQ ID NO:90, SEQ ID NO:94, SEQ ID NO:95, SEQ ID NO:105, SEQ ID NO:84, SEQ ID NO:91, SEQ ID NO:92, or SEQ ID NO:93.

Furthermore, the polypeptide can comprise a polypeptide encoded by a polynucleotide sequence which hybridizes under highly stringent conditions over substantially the entire length of a polynucleotide sequence selected from SEQ ID NO:1–54 (or a complementary sequence thereof), or by a polynucleotide sequence encoding a polypeptide sequence selected from SEQ ID NO: 55–108 (or a complementary sequence thereof), and wherein the polypeptide comprises one or more of: Lys at position 1; Thr at position 14; Ser at position 17; Arg at position 22; Glu at position 26; Pro at position 31; Gly at position 33; Glu at position 34; Pro at position 35; Pro or Thr at position 37; Ser or Lys at position 41; Gly at position 42; Arg or Glu at position 43; Ala at position 61; Tyr at position 75; Gly at position 96; Ser at position 97; Thr at position 104; Ser at position 107; Ala at position 125; Gly at position 129; Val at position 134; Cys at position 138; Lys at position 141; Lys at position 146; Thr at position 156; Met at position 160; Arg at position 166; or His at position 177. Alternatively, the polypeptide can comprise one or more of: Lys at position 1; Thr at position 14; Ser at position 17; Arg at position 22; Glu at position 26; Pro at position 31; Gly at position 33; Glu at position 34; Pro at position 35; Pro or Thr at position 37; Ser or Lys at position 41; Gly at position 42; Arg or Glu at position 43; Ala at position 61; Tyr at position 75; Gly at position 96; Ser at position 97; Thr at position 104; Ser at position 107; Ala at position 125; Gly at position 129; Val at position 134; Cys at position 138; Lys at position 141; Lys at position 146; Thr at position 156; Met at position 160; Arg at position 166; or His at position 177 (or an equivalent position to that of SEQ ID NO: 75).

Such polypeptide can comprise or exhibit lipase activity or the ability to degrade geranyl butyrate, neryl butyrate, or both neryl and geranyl butyrate. The polypeptide can also exhibit enantioselectivity for geranyl butyrate over neryl butyrate. A polypeptide exhibiting enantioselectivity for geranyl butyrate over neryl butyrate can comprise one or more of: Arg at position 22; Gly at position 33; Ser or Lys at position 41; Arg at position 43; Ser at position 107; Lys at position 141; Lys at position 146; Met at position 160; or His at position 177, or can comprise one or more of: Arg at position 43; or Ser at position 107.

Such polypeptide can alternatively comprise or exhibit enantioselectivity for neryl butyrate over geranyl butyrate. Such polypeptide can comprise one or more of: Ser at position 17; Arg at position 22; Pro at position 31; Gly at position 33; Ser or Lys at position 41; Lys at position 141; Lys at position 146; Met at position 160; Arg at position 166; or His at position 177, or, can comprise one or more of: Ser at position 17; Pro at position 31; or Arg at position 166.

In another aspect, the invention can comprise an isolated or recombinant polypeptide comprising a sequence having at least 94% amino acid sequence identity to the mature region of SEQ ID NO: 55, 61, 64, 65, 67, 68, 70, or 72. Alternatively, such polypeptide can comprise a sequence having at least 94% amino acid sequence identity to the mature region of SEQ ID NO: 55, which polypeptide also can comprise a sequence selected from SEQ ID NO: 55, 58–62, 75–78, 80–88, or 94–108 (or the mature region thereof). Alternatively, the polypeptide can comprise a sequence having at least 94% amino acid sequence identity to the mature region of SEQ ID NO: 61, which polypeptide also can comprise a sequence selected from SEQ ID NO: 55, 57–62, 75–78, 80–90, or 93–108. Alternatively, the polypeptide can comprise a sequence having at least 94% amino acid sequence identity to the mature region of SEQ ID NO: 64, which polypeptide also can comprise a sequence selected from SEQ ID NO: 64, 71, or 72 (or the mature region thereof). Alternatively, the polypeptide can comprise a sequence having at least 94% amino acid sequence identity to the mature region of SEQ ID NO: 65, which polypeptide can also comprise a sequence selected from SEQ ID NO: 65, 66, or 73 (or a mature region thereof). Alternatively, the polypeptide can comprise a sequence having at least 94% amino acid sequence identity to the mature region of SEQ ID NO: 67, which polypeptide can also comprise the sequence SEQ ID NO: 67 (or the mature region thereof). Alternatively, the polypeptide can comprise a sequence having at least 94% amino acid sequence identity to the mature region of SEQ ID NO: 68, which polypeptide can also comprise a sequence selected from SEQ ID NO: 68 or 101 (or the mature region thereof). Alternatively, the polypeptide can comprise a sequence having at least 94% amino acid sequence identity to the mature region of SEQ ID NO: 70, which polypeptide can also comprise a sequence selected from SEQ ID NO: 63, 68–70, 82–83, 85–86, 96, or 101–102 (or the mature region thereof). Alternatively, the polypeptide can comprise a sequence having at least 94% amino acid sequence identity to the mature region of SEQ ID NO: 72, which polypeptide can also comprise a sequence selected from SEQ ID NO: 64, 71, or 72 (or a mature region thereof).

In another aspect, the invention can comprise an isolated or recombinant polypeptide comprising a sequence having at least 85% amino acid sequence identity to the mature region of SEQ ID NO: 74, which polypeptide can also comprise a sequence selected from SEQ ID NO: 63, 71–72, 74, or 79 (or a mature region thereof).

In yet another aspect, the invention can comprise an isolated or recombinant polypeptide comprising a sequence having at least 99% amino acid sequence identity to the mature region of SEQ ID NO: 56.

The extent of the region of identity or similarity can extend from a comparison window of at least 45 amino acids to the entire length of the lipase homologue polypeptide. In an embodiment, such polypeptides are identified by performing a sequence alignment with any one or more of SEQ ID NO: 55 to SEQ ID NO: 108 using BLASTP with default parameters set to the desired percentage identity. Alternatively, the default parameters can be set to identify polypeptide sequences with greater identity to one or more of SEQ ID NO: 55 to SEQ ID NO: 108.

Alternatively, polypeptides of the invention can be encoded by polynucleotides that correspond to any one, or part of SEQ ID NO: 1 to SEQ ID NO: 54 (or complementary polynucleotides thereof) and or a fragment thereof, which fragment can comprise lipase activity. The polypeptides of the invention can, likewise, be encoded by polynucleotides that hybridize under stringent or highly stringent conditions over substantially the entire length of such polynucleotides, with the proviso that such sequences do not correspond to or encode any of the GenBank accession 1I6WA, 1I6WB, A02813, A02815,A34992, AAA22574, AAB31769, AAC12257, AAD30278, AAF40217, AAF63229, AB000617, AF134840, AF141874, AF237623, AJ297356, BAA11406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P37957, S23934, U78785, X95309, Z99105, and Z99108. Similarly, polypeptides that are encoded by subsequences of any such polynucleotides, e.g., a subsequence comprising at least about 45 contiguous amino acid residues, sometimes comprising at least about 45 contiguous amino acid residues, and in some cases comprising 45 contiguous amino acid residues of the polypeptide are also a feature of the invention. In some instances, such polypeptides are substantially identical to one or more of SEQ ID NO: 55 to SEQ ID NO: 108 over at least 45 contiguous amino acid residues with the proviso that such sequences do not correspond to or encode any of the GenBank accession numbers listed above. In other cases, the polypeptides, regardless of length, display lipase activity and/or enantioselective lipase activity.

The invention provides isolated or recombinant polypeptides encoded by a nucleic acid comprising a polynucleotide sequence selected from any of the following: a polynucleotide sequence selected from SEQ ID NO: 1 to SEQ ID NO: 54 (or a complementary polynucleotide sequence thereof); a polynucleotide sequence encoding a polypeptide selected from SEQ ID NO: 55 to SEQ ID NO: 108 (or a complementary polynucleotide sequence thereof); a polynucleotide sequence which hybridizes under highly stringent conditions over substantially the whole length of any of the previous described polynucleotides, or which hybridizes to a subsequence of the same, comprising at least 100 residues, again, with the proviso that none of the sequences corresponds to or is encoded by any of the GenBank accession numbers listed above; a polynucleotide sequence which comprises all, or a fragment of, any of the above described polynucleotides and which encodes a polypeptide comprising lipase activity and/or lipase enantioselective activity; a polynucleotide sequence encoding a polypeptide which comprises an amino acid sequence that is substantially identical over at least 45 contiguous amino acid residues of any one of SEQ ID NO: 55 to SEQ ID NO: 108, with the proviso that none of the sequences corresponds to or is encoded by any of the GenBank accession numbers listed above; or a polynucleotide sequence encoding a polypeptide comprising lipase activity and that is produced by mutating or recombining one or more of the polynucleotide sequences described above, yet again, with the proviso that none of the sequences corresponds to or is encoded by any of the GenBank accession numbers listed above. The invention also provides an isolated or recombinant polypeptide as described above which comprises an amino acid sequence of any of SEQ ID NO: 55 to SEQ ID NO: 108.

Isolated or recombinant polypeptides as described above wherein the encoded polypeptide comprises lipase activity (e.g., against tributyrin, against tributyrin in DMF, against tributyrin after heat treatment (i.e., after the polypeptide has been heat treated); and/or enantioselective lipase activity (e.g., against neryl-butyrate or geranyl-butyrate) are also provided. Optionally, such polypeptides as described can comprise lipase activity against novel substrates (i.e., substrates upon which typical wild-type lipases do not act) such as, e.g., methyl esters, pentadecanolide, or oxacyclotridecan. Optionally the isolated or recombinant nucleic acid can encode a polypeptide which comprises enantioselective activity as well as comprising a polynucleotide sequence encoding a polypeptide with enantioselective lipase activity. Additionally, such isolated or recombinant polypeptides optionally are substantially identical over at least 45, at least 50, at least 75, at least 100, at least 125, at least 150, at least 175, or at least 200 contiguous amino acids of any of the above described polypeptides. Alternatively, such isolated or recombinant polypeptides is substantially identical over at least 180, at least 212, at least 213, or at least 215 contiguous amino acid residues of the above described polypeptide.

In various embodiments, the above described polypeptides comprise one or more of: a leader sequence, a precursor polypeptide, a secretion signal or a localization signal, an epitope tag, a fusion protein comprising one or more additional amino acid sequences, a polypeptide purification subsequence (e.g., an epitope tag, a FLAG tag, a polyhistidine sequence, a GST fusion), an N-terminus methionine residue, or a modified amino acid (e.g., a glycosylated amino acid, a PEGylated amino acid, a farnesylated amino acid, an acetylated amino acid, a biotinylated amino acid, an amino acid conjugated to a lipid moiety or to an organic derivatizing agent).

A composition comprising one or more polypeptide comprising a modified amino acid and pharmaceutically acceptable excipient and a composition comprising one or more above described polypeptide with a pharmaceutically acceptable excipient are also provided. Additionally, the invention provides a polypeptide which comprises a unique subsequence in a polypeptide selected from SEQ ID NO: 55 through SEQ ID NO: 108 wherein such subsequence is unique as compared to a polypeptide sequence which corresponds to an amino acid sequence (or which is encoded by a nucleic acid sequence) corresponding to any of GenBank accession numbers 1I6WA, 1I6WB, A02813, A02815, A34992, AAA22574, AAB31769, AAC12257, AAD30278, AAF40217, AAF63229, AB000617, AF134840, AF141874, AF237623, AJ297356, BAA11406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P37957, S23934, U78785, X95309, Z99105, and Z99108. Also provided is a polypeptide which is specifically bound by a polyclonal antisera raised against at least one antigen comprising at least one amino acid sequence from SEQ ID NO: 55 to SEQ ID NO: 108 (or a fragment thereof) where the antisera is subtracted with a polypeptide corresponding to an amino acid sequence (or which is encoded by a nucleic acid sequence) corresponding to any of GenBank accession numbers 1I6WA, 1I6WB, A02813, A02815,A34992, AAA22574, AAB31769, AAC12257, AAD30278, AAF40217, AAF63229, AB000617, AF134840, AF141874, AF237623, AJ297356, BAA11406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P37957, S23934, U78785, X95309, Z99105, and Z99108.

In other aspects the invention includes an antibody or antisera produced by administering an above described polypeptide of the invention to a mammal and wherein the antibody or antisera specifically binds at least one antigen which comprises a polypeptide sequence (or fragment thereof) from SEQ ID NO: 55 to SEQ ID NO: 108 and which antibody or antisera does not specifically bind to a polypeptide encoded by a nucleic acid corresponding to, or an amino acid sequence corresponding to one or more of GenBank accession numbers 1I6WA, 1I6WB, A02813, A02815, A34992, AAA22574, AAB31769, AAC12257, AAD30278, AAF40217, AAF63229, AB000617, AF134840, AF141874, AF237623, AJ297356, BAA11406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P37957, S23934, U78785, X95309, Z99105, and Z99108. In yet other aspects, the invention includes an antibody or antisera that specifically binds a polypeptide which comprises an amino acid sequence (or fragment thereof) from SEQ ID NO: 55 to SEQ ID NO: 108 and which antibody or antisera does not specifically bind to a peptide encoded by a nucleic acid corresponding to, or an amino acid sequence corresponding to one or more of GenBank accession numbers: 1I6WA, 1I6WB, A02813, A02815,A34992, AAA22574, AAB31769, AAC12257, AAD30278, AAF40217, AAF63229, AB000617, AF134840, AF141874, AF237623, AJ297356, BAA11406, BAA22231, BAB05967, C69652, CAA00273, CAA00274, CAA02196, CAA6462 1, CAB12064, CAB12664, CAB51971, CAB92662, CAB95850, D78508, E01340, E01903, E02083, E05047, JW0068, M74010, P37957, S23934, U78785, X95309, Z99105, and Z99108.

Making Polypeptides

Recombinant methods for producing and isolating lipase homologue polypeptides of the invention are described above. In addition to recombinant production, the polypeptides can be produced by direct peptide synthesis using solid-phase techniques (see, e.g., Stewart et al. (1969) *Solid-Phase Peptide Synthesis,* WH Freeman Co, San Francisco; Merrifield J (1963) *J Am Chem So.* 85:2149–2154). Peptide synthesis can be performed using manual techniques or by automation. Automated synthesis can be achieved, for example, using Applied Biosystems 431A Peptide Synthesizer (Perkin Elmer, Foster City, Calif.) in accordance with the instructions provided by the manufacturer. For example, subsequences can be chemically synthesized separately and combined using chemical methods to provide full-length lipase homologues. Fragments of the lipase polypeptides of the invention, as discussed herein, are also a feature of the invention and can be synthesized by using the procedures described above.

Polypeptides of the invention can be produced by introducing into a population of cells a nucleic acid of the invention, wherein the nucleic acid is operatively linked to a regulatory sequence effective to produce the encoded polypeptide, culturing the cells in a culture medium to produce the polypeptide, and optionally isolating the polypeptide from the cells or from the culture medium.

In another aspect, polypeptides of the invention can be produced by introducing into a population of cells a recombinant expression vector comprising at least one nucleic acid of the invention, wherein the at least one nucleic acid is operatively linked to a regulatory sequence effective to produce the encoded polypeptide, culturing the cells in a culture medium under suitable conditions to produce the polypeptide encoded by the expression vector, and optionally isolating the polypeptide from the cells or from the culture medium.

Using Polypeptides

Antibodies

In another aspect of the invention, a lipase homologue polypeptide of the invention is used to produce antibodies which have, e.g., diagnostic and/or therapeutic uses, e.g., related to the activity, distribution, and expression of lipase homologues.

Antibodies to lipase homologues of the invention can be generated by methods well known in the art. Such antibodies can include, but are not limited to, polyclonal, monoclonal, chimeric, humanized, single chain, Fab fragments and fragments produced by an Fab expression library. Antibodies, i.e., those which block receptor binding, are especially preferred for therapeutic use.

Lipase homologue polypeptides for antibody induction do not require biological activity; however, the polypeptide or oligopeptide must be antigenic. Peptides used to induce specific antibodies can have an amino acid sequence consisting of at least 10 amino acids, preferably at least 15 or 20 amino acids. Short stretches of a lipase polypeptide can be fused with another protein, such as keyhole limpet hemocyanin (KLH), and antibody produced against the chimeric molecule.

Methods of producing polyclonal and monoclonal antibodies are known to those of skill in the art, and many antibodies are available. See, e.g., Coligan (1991) *Current Protocols in Immunology* Wiley/Greene, NY; and Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) *Nature* 256: 495–497. Other suitable techniques for antibody preparation include selection of libraries of recombinant antibodies in phage or similar vectors. See, Huse et al. (1989) *Science* 246: 1275–1281; and Ward, et al. (1989) *Nature* 341: 544–546. Specific monoclonal and polyclonal antibodies and antisera will usually bind with a $K_D$ of at least about 0.1 µM, preferably at least about 0.01 µM or better, and most typically and preferably, 0.001 µM or better.

Detailed methods for preparation of chimeric (humanized) antibodies can be found in U.S. Pat. No. 5,482,856. Additional details on humanization and other antibody production and engineering techniques can be found in Borrebaeck (ed.) (1995) *Antibody Engineering, $2^{nd}$ Edition* Freeman and Company, NY (Borrebaeck); McCafferty et al. (1996) *Antibody Engineering, A Practical Approach* IRL at Oxford Press, Oxford, England (McCafferty), and Paul (1995) *Antibody Engineering Protocols* Humana Press, Towata, N.J. (Paul).

In one useful embodiment, this invention provides for fully humanized antibodies against the lipase homologues of the invention. Humanized antibodies are especially desirable in applications where the antibodies are used as therapeutics in vivo in human patients. Human antibodies consist of characteristically human immunoglobulin sequences. The human antibodies of this invention can be produced using a wide variety of methods (see, e.g., Larrick et al., U.S. Pat. No. 5,001,065, and Borrebaeck McCafferty and Paul, supra, for a review). In one embodiment, the human antibodies of the present invention are produced initially in trioma cells. Genes encoding the antibodies are then cloned and expressed in other cells, such as nonhuman mammalian cells. The general approach for producing human antibodies by trioma technology is described by Ostberg et al. (1983), *Hybridoma* 2: 361–367, Ostberg, U.S. Pat. No. 4,634,664, and Engelman et al., U.S. Pat. No. 4,634,666. The antibody-producing cell lines obtained by this method are called triomas because they are descended from three cells; two human and one mouse. Triomas have been found to produce antibody more stably than ordinary hybridomas made from human cells.

Sequence Variations

Conservatively Modified Variations

Lipase homologue polypeptides of the present invention include conservatively modified variations of the sequences disclosed herein as SEQ ID NO: 55 to SEQ ID NO: 108. Such conservatively modified variations comprise substitutions, additions or deletions which alter, add or delete a single amino acid or a small percentage of amino acids (typically less than about 5%, more typically less than about 4%, 3%, 2%, or 1%, or less) in any of SEQ ID NO: 55 to SEQ ID NO: 108.

For example, a conservatively modified variation (e.g., deletion) of the 180 amino acid polypeptide identified herein as SEQ ID NO: 75 will have a length of at least 171 amino acids, preferably at least 173 amino acids, preferably at least 175 amino acids, more preferably at least 177 amino acids, and still more preferably at least 179 amino acids, corresponding to a deletion of less than about 5%, 4%, 3%, 2%, or 1% or less of the polypeptide sequence.

Another example of a conservatively modified variation (e.g., a "conservatively substituted variation") of the polypeptide identified herein as SEQ ID NO: 75 will contain "conservative substitutions" according to the six substitution groups set forth in Table 2 (supra), in up to about 9 residues (i.e., less than about 5%) of the 180 amino acid polypeptide.

The lipase polypeptide sequence homologues of the invention, including conservatively substituted sequences, can be present as part of larger polypeptide sequences such as occur upon the addition of one or more domains for purification of the protein (e.g., poly his segments, FLAG tag segments, etc.), e.g., where the additional functional domains have little or no effect on the activity of the lipase portion of the protein, or where the additional domains can be removed by post synthesis processing steps such as by treatment with a protease.

In various embodiments, the polypeptide comprises at least about 45, 50, 75, 100, 125, 150, 175, 200 or at least about 215, or more contiguous amino acid residues of any of SEQ ID NO: 55 to SEQ ID NO: 108. Alternatively, the polypeptide comprises at least about 180 contiguous amino acids residues, at least about 212 contiguous amino acid residues, at least about 213 contiguous amino acid residues, or at least about 215 amino acid residues of any of SEQ ID NO: 55 to SEQ ID NO: 108.

Defining Polypeptides by Immunoreactivity

Because the polypeptides of the invention provide a variety of new polypeptide sequences as compared to other lipases, the polypeptides also provide new structural features which can be recognized, e.g., in immunological assays. The generation of antisera which specifically binds the polypeptides of the invention, as well as the polypeptides which are bound by such antisera, are a feature of the invention.

The invention includes lipase homologue proteins that specifically bind to or that are specifically immunoreactive with an antibody or antisera generated against an immunogen comprising an amino acid sequence selected from one or more of SEQ ID NO: 55 to SEQ ID NO: 108. To eliminate cross-reactivity with other lipases, the antibody or antisera is subtracted with available homologues such as those found in GenBank represented by or encoded by GenBank accession numbers 1I6WA, 1I6WB, A02813, A02815,A34992, AAA22574, AAB31769, AAC12257, AAD30278, AAF40217, AAF63229, AB000617, AF134840, AF141874, AF237623, AJ297356, BAA1I406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P37957, S23934, U78785, X95309, Z99105, and Z99108 (i.e., the "control" lipase homologue polypeptides). Proteins that can bind specifically as described above can be determined by aligning any of SEQ ID NO: 55 to SEQ ID NO: 108 against the complete set of nucleic acids corresponding or encoded by: 1I6WA, 1I6WB, A02813, A02815,A34992, AAA22574, AAB31769, AAC12257, AAD30278, AAF40217, AAF63229, AB000617, AF134840, AF141874, AF237623, AJ297356, BAA11406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P37957, S23934, U78785, X95309, Z99105, and Z99108. Where the GenBank sequence corresponds to a nucleic acid, a polypeptide encoded by the nucleic acid is generated and used for antibody/antisera subtraction purposes. Where the nucleic acid corresponds to a non-coding sequence, e.g., a pseudo gene, an amino acid which corresponds to the reading frame of the nucleic acid is generated (e.g., synthetically), or is minimally modified to include a start codon for recombinant production.

In one typical format, the immunoassay uses a polyclonal antiserum which was raised against one or more polypeptide comprising one or more of the sequences corresponding to one or more of SEQ ID NO: 55 to SEQ ID NO: 108, or a substantial subsequence thereof (i.e., at least about 30% of the full length sequence provided). The full set of potential polypeptide immunogens derived from SEQ ID NO: 55 to SEQ ID NO: 108 are collectively referred to below as "the immunogenic polypeptides." The resulting antisera is optionally selected to have low cross-reactivity against the control lipase homologues and any other known homologues and any such cross-reactivity is removed by immunoabsorbtion with one or more of the control lipase homologues, or other known homologues, prior to use of the polyclonal antiserum in the immunoassay.

In order to produce antisera for use in an immunoassay, one or more of the immunogenic polypeptides is produced and purified as described herein. For example, recombinant protein may be produced in a mammalian cell line. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, Harlow and Lane (1988) *Antibodies, A Laboratory Manual*, Cold Spring Harbor Publications, New York, for a standard description of antibody generation, immunoassay formats and conditions that can be used to determine specific immunoreactivity). Alternatively, one or more synthetic or recombinant polypeptide derived from the sequences disclosed herein is conjugated to a carrier protein and used as an immunogen.

Polyclonal sera are collected and titered against the immunogenic polypeptide in an immunoassay, for example, a solid phase immunoassay with one or more of the immunogenic proteins immobilized on a solid support. Polyclonal antisera with a titer of $10^6$ or greater are selected, pooled and subtracted with the control lipase homologue polypeptides to produce subtracted pooled titered polyclonal antisera.

The subtracted pooled titered polyclonal antisera are tested for cross reactivity against the control lipase homologues (e.g., as enumerated herein). Preferably at least two of the immunogenic lipase homologues are used in this determination, preferably in conjunction with at least two of the control lipase homologues, to identify antibodies which are specifically bound by the immunogenic protein(s).

In this comparative assay, discriminatory binding conditions are determined for the subtracted titered polyclonal antisera which result in at least about a 5–10 fold higher signal to noise ratio for binding of the titered polyclonal antisera to the immunogenic lipase molecules as compared to binding to any control homologues. That is, the stringency of the binding reaction is adjusted by the addition of non-specific competitors such as albumin or non-fat dry milk, or by adjusting salt conditions, temperature, or the like. These binding conditions are used in subsequent assays for determining whether a test polypeptide is specifically bound by the pooled subtracted polyclonal antisera. In particular, test polypeptides which show at least a 2–5× higher signal to noise ratio than the control polypeptides under discriminatory binding conditions, and at least about a ½ signal to noise ratio as compared to the immunogenic polypeptide(s), shares substantial structural similarity with the immunogenic polypeptide as compared to control polypeptides, and is, therefore a polypeptide of the invention.

In another example, immunoassays in the competitive binding format are used for detection of a test polypeptide. For example, as noted, cross-reacting antibodies are removed from the pooled antisera mixture by immunoabsorbtion with the control lipase polypeptides. The immunogenic lipase homologue polypeptide(s) are then immobilized to a solid support which is exposed to the subtracted pooled antisera. Test proteins are added to the assay to compete for binding to the pooled subtracted antisera. The ability of the test protein(s) to compete for binding to the pooled subtracted antisera as compared to the immobilized protein(s) is compared to the ability of the immunogenic polypeptide(s) added to the assay to compete for binding (the immunogenic polypeptides compete effectively with the immobilized immunogenic polypeptides for binding to the pooled antisera). The percent cross-reactivity for the test proteins is calculated, using standard calculations.

In a parallel assay, the ability of the control proteins to compete for binding to the pooled subtracted antisera is determined as compared to the ability of the immunogenic polypeptide(s) to compete for binding to the antisera. Again, the percent cross-reactivity for the control polypeptides is calculated, using standard calculations. Where the percent cross-reactivity is at least 5–10× as high for the test polypeptides, the test polypeptides are said to specifically bind the pooled subtracted antisera.

In general, the immunoabsorbed and pooled antisera can be used in a competitive binding immunoassay as described herein to compare any test polypeptide to the immunogenic polypeptide(s). In order to make this comparison, the two polypeptides are each assayed at a wide range of concentrations and the amount of each polypeptide required to inhibit 50% of the binding of the subtracted antisera to the immobilized protein is determined using standard techniques. If the amount of the test polypeptide required is less than twice the amount of the immunogenic polypeptide that is required, then the test polypeptide is said to specifically bind to an antibody generated to the immunogenic protein, provided the amount is at least about 5–10× as high as for a control polypeptide.

As a final determination of specificity, the pooled antisera is optionally fully immunosorbed with the immunogenic polypeptide(s) (rather than any control polypeptides) until little or no binding of the resulting immunogenic polypeptide subtracted pooled antisera to the immunogenic polypeptide(s) used in the immunosorbtion is detectable. This fully immunosorbed antisera is then tested for reactivity with the test polypeptide. If little or no reactivity is observed (i.e., no more than 2× the signal to noise ratio observed for binding of the fully immunosorbed antisera to the immunogenic polypeptide), then the test polypeptide is specifically bound by the antisera elicited by the immunogenic protein.

Enantioselective Lipase Activity

As described previously, enantiomers are non-superimposable stereoisomers of a molecule. In other words, they are mirror images of each other. Enantiomers of a molecule have identical melting points, boiling points, densities, refractive indexes, etc. However one form rotates plane-polarized light to the right while the other enantiomer rotates it to the left. In fact, enantiomers are often designated as (+) or (−) forms of the molecule. Alternatively, the forms can be labeled as cis and trans forms of the molecule.

Even though enantiomers share many identical properties, when they interact with other molecules that are also stereochemically specific, differing results (e.g., products) can result, depending upon which form (cis or trans) interacts with the other molecule. Most enzymes and many other molecules in biological systems are stereochemically specific. Thus, the proper enantiomeric form of a molecule can be important if a desired result is to be achieved. This is true both in biological/pharmacological situations as well as in industrial settings.

For example (+) glucose is a commonly metabolized sugar and is extremely important in, e.g., industrial yeast fermentation. However, (−) glucose (i.e., the opposite enantiomeric form of glucose) is not commonly metabolized in animals or yeast, etc. Numerous other examples of such differences exist, such as: (+) glutamic acid/(−) glutamic acid (only one is used as a flavor enhancer); (+) carvone/(−) carvone (one smells of spearmint while the other smells of caraway); and (+) chloromycetin/(−) chloromycetin (only one has antibiotic properties), etc.

Not only can opposing enantiomers be selectively useful or have different uses, but in some situations one enantiomer can interfere with the usage of its opposing form. For example, (+) ephedrine has no drug activity and also interferes with the action of its opposing enantiomer (i.e., (−) ephedrine).

Thus, enzymes specific for interaction with a specific enantiomeric form of a substrate would be extremely useful in a myriad of chemical/industrial and clinical settings. For example, a degradative enzyme that was enantioselective for (+) ephedrine could be used to aid in purification of (−) ephedrine from a mixed population (racemic) of the 2 enantiomers.

The lipase homologue polypeptides of the current invention were screened for enantioselective lipase activity on neryl butyrate and geranyl butyrate. Again, while the current assays screened with respect to neryl/geranyl butyrate (see, EXAMPLE II), it will be appreciated that the lipase homologues of the invention optionally display lipase and/or enantioselective lipase activity with respect to a number of different substrates (e.g., neryl/geranyl acetate, tributyrin, methyl esters, etc.). Geranyl butyrate is the trans isomer of 3,7-dimethyl-2,6-octadien-1-yl butyrate while nerylbutyrate is the cis isomer of the same compound. Both neryl and geranyl butyrate have industrial uses, e.g., as precursors, etc. in the perfume/fragrance industry.

The enantioselectivity of the lipase homologue polypeptides of the invention was determined by measuring the enantiomeric ratio or "E." The enantiomeric ratio is determined by the equation:

$$E = \frac{\ln[1 - c(1 + DE(p)]}{\ln[1 - c(1 - DE(p)]}$$

in which c=the percent total substrate conversion (expressed as a decimal) and DE(p) is the diastereomeric excess (i.e., the percent product of a first isomer minus the percent product of a second isomer) of the products.

FIG. 1 shows the enantioselectivity of the newly created lipase homologue polypeptides of the invention for neryl and geranyl butyrate. As can be seen, specific clones created had specificity for either neryl butyrate or geranyl butyrate.

In other aspects, such isolated or recombinant polypeptide comprises an amino acid sequence of any one of SEQ ID NO: 55 through SEQ ID NO: 108 over a comparison window of at least 45 contiguous amino acids.

In some embodiments, the invention comprises such an isolated or recombinant polypeptide that is at least 45 contiguous amino acid residues of a polypeptide encoded by a coding polynucleotide sequence wherein the polynucleotide sequence is selected from: a polynucleotide sequence from any of SEQ ID NO: 1 to SEQ ID NO: 54, a polynucleotide sequence that encodes a polypeptide selected from any of SEQ ID NO: 55 through SEQ ID NO: 108; or a polynucleotide sequence that hybridizes under stringent conditions over substantially the entire length of the above polynucleotide sequence or which hybridizes to a subsequence comprising at least about 100 nucleic acids, provided that none of the sequences corresponds to or encodes any of GenBank accession numbers: 1I6WA, 1I6WB, A02813, A02815,A34992, AAA22574, AAB31769, AAC12257, AAD30278, AAF40217, AAF63229, AB000617, AF134840, AF141874, AF237623, AJ297356, BAA11406, BAA22231, BAB05967, C69652, CAA00273, CAA00274, CAA02196, CAA64621, CAB12064, CAB12664, CAB51971, CAB92662, CAB95850, D78508, E01340, E01903, E02083, E05047, JW0068, M74010, P37957, S23934, U78785, X95309, Z99105, and Z99108.

Additionally, the invention provides such isolated or recombinant polypeptide wherein the polypeptide is enantioselective for either a cis form substrate enantiomer or for a trans form substrate enantiomer and optionally wherein the enantiomeric ratio is at least 2 or more, at least 5 or more, at least 10 or more, at least 50 or more, or at least 100 or more.

The invention also provides such isolated or recombinant polypeptide wherein the identity is determined by a sequence alignment performed using BLASTP with default parameters set to measure a desired identity (see above). Additionally, which polypeptide comprises an amino acid sequence of any of SEQ ID NO: 55 through SEQ ID NO: 108 and/or wherein the identity is determined by a sequence alignment using BLASTP with default parameters set to measure a desired identity.

Additionally the invention comprises an isolated or recombinant polypeptide that is at least 90, at least 94, at least 95, at least 96, at least 97, at least 98, at least 99 or percent identical over a comparison window of 45 contiguous amino acids (or 50, 75, 100, 125, 150, 175, 200, 180, 212, 213, or 215 contiguous amino acids) of one or more of SEQ ID NO: 55 through SEQ ID NO: 108. Also, the invention provides an isolated or recombinant polypeptide identified by performing a sequence alignment with any one or more of SEQ ID NO: 55 through SEQ ID NO: 108 using BLASTP with default parameters set to measure a desired identity.

Commercial/Industrial Methods and Compositions

The lipase homologues of the invention are optionally used in compositions to accomplish numerous commercial and industrial procedures. The lipases of the invention are optionally used in the synthesis and/or degradation of specific lipids (i.e., to break down longer lipids and thus synthesize more desirable lipid molecules).

Other non-limiting examples of commercial/industrial uses of the current lipase homologues include: use as supplements in animal feeds, as agents of flavor modification and fat modification in human foodstuffs (e.g., cheese), as agents in the creation of food emulsifiers such as distilled monoglyceride, as agents in the production of fatty acid esters for texturing agents (e.g., for use in cosmetics), as aids in fractionation of fats, as means to remove unwanted types of lipids from lipid mixtures thus effectively concentrating the remaining lipid types (e.g., as a means to increase the percentage of "healthful" fish oils in mixtures such as dietary supplements), as agents in tanning/processing leather, and as cleaning agents (see, below).

The lipases of the invention are also optionally immobilized on substrates, e.g., cellulose fibers, capillary tubes, various microchip structures, etc. during use, thus, optionally permitting increased reaction periods, multiple reuse of the lipase molecules, avoidance of the need to purify out lipase molecules once they are no longer needed, etc.

Cleaning Solutions

The lipase homologues of the invention are favorably used in compositions that serve as cleaning solutions in wide variety of applications, including laundry detergents, contact lens cleansing solutions, and dry cleaning, among others.

For example, the present invention provides the use of the novel lipase homologues of the invention in cleaning and detergent compositions, as well as such compositions containing mutant lipase enzymes. Such cleaning and detergent compositions can in principle have any physical form, but the lipase homologues are preferably incorporated in liquid detergent compositions or in detergent compositions in the form of bars, tablets, sticks and the like for direct application, wherein they exhibit improved enzyme stability or performance.

Among the liquid compositions of the present invention are aqueous liquid detergents having for example a homogeneous physical character, e.g. they can consist of a micellar solution of surfactants in a continuous aqueous phase, so-called isotropic liquids. Alternatively, they can have a heterogeneous physical phase and they can be structured, containing suspended solid particles such as particles of builder materials e.g. of the kinds mentioned below. In addition, the liquid detergents according to the present invention can include an enzyme stabilization system, comprising calcium ion, boric acid, propylene glycol and/or short chain carboxylic acids. Optionally, the detergents include additional enzyme components including, e.g., cellulase, amylase, subtilisin, or proteases.

In addition, powder detergent compositions can include, in addition to any one or more of the lipase homologues of the invention as described herein, such components as builders (such as phosphate or zeolite builders), surfactants (such as anionic, cationic, non-ionic or zwitterionic type surfactants), polymers (such as acrylic or equivalent polymers), bleach systems (such as perborate- or amino-containing bleach precursors or activators), structurants (such as silicate structurants), alkali or acid to adjust pH (i.e., a pH adjuster), humectants, and/or neutral inorganic salts. Furthermore, a number of other ingredients are normally present in the compositions of the invention, such as co-surfactants, tartrate succinate builder, neutralization system, suds suppressor, other enzymes and other optional components.

Therapeutic and Prophylactic Methods and Compositions

Lipases, including the lipase homologue polypeptides and their encoding nucleic acids, are optionally used in the therapeutic and/or prophylactic treatment of a number of medical diseases/disorders/conditions.

For example, lipase treatment of subjects is optionally useful in conditions such as, but not limited to: Crohn's disease, cystic fibrosis, celiac disease, pancreatic abnormalities (e.g., chronic pancreatitis), nonspecific indigestion, and other gastrointestinal mal-absorption problems.

The amount of lipase polypeptide given in current treatments of such conditions is variable (as is the normal level of intrinsic lipase) and is preferably adjusted by a physician to a subject's specific medical condition. In some clinical situations lipase supplements are given in combination with supplements of other enzymes (e.g., amylases, proteolytic enzymes, etc.) to help in treatment. As detailed below, the nucleic acids of the current invention are also optionally utilized in treatment of medical conditions.

The present invention also includes methods of therapeutically or prophylactically treating a disease or disorder by administering, in vivo or ex vivo, one or more nucleic acids or fragments thereof or polypeptides or fragments thereof of the invention described above (or compositions comprising a pharmaceutically acceptable excipient and one or more such nucleic acids or polypeptides) to a subject, including, e.g., a mammal, including, e.g., a human, primate, mouse, pig, cow, goat, rabbit, rat, guinea pig, hamster, horse, sheep; or a non-mammalian vertebrate such as a bird (e.g., a chicken or duck) or a fish, or invertebrate.

In one aspect of the invention, in ex vivo methods, one or more cells, or a population of cells of interest of the subject (e.g., tumor cells, tumor tissue sample, organ cells, blood cells, cells of the skin, lung, heart, muscle, brain, mucosae, liver, intestine, spleen, stomach, lymphatic system, cervix, vagina, prostate, mouth, tongue, etc.) are obtained or removed from the subject and contacted with an amount of a polypeptide of the invention that is effective in prophylactically or therapeutically treating a disease, disorder, or other condition. The contacted cells are then returned or delivered to the subject to the site from which they were obtained or to another site (e.g., including those defined above) of interest in the subject to be treated. If desired, the contacted cells may be grafted onto a tissue, organ, or system site (including all described above) of interest in the subject using standard and well-known grafting techniques or, e.g., delivered to the blood or lymph system using standard delivery or transfusion techniques.

The invention also provides in vivo methods in which one or more cells or a population of cells of interest of the subject are contacted directly or indirectly with an amount of a polypeptide of the invention effective in prophylactically or therapeutically treating a disease, disorder, or other condition. In direct contact/administration formats, the polypeptide is typically administered or transferred directly to the cells to be treated or to the tissue site of interest (e.g., tumor cells, tumor tissue sample, organ cells, blood cells, cells of the skin, lung, heart, muscle, brain, mucosae, liver, intestine, spleen, stomach, lymphatic system, cervix, vagina, prostate, mouth, tongue, etc.) by any of a variety of formats, including topical administration, injection (e.g., by using a needle and/or syringe), or vaccine or gene gun delivery, pushing into a tissue, organ, or skin site. The polypeptide can be delivered, for example, intramuscularly, intradermally, subdermally, subcutaneously, orally, intraperitoneally, intrathecally, intravenously, or placed within a cavity of the body (including, e.g., during surgery), or by inhalation or vaginal or rectal administration.

In in vivo indirect contact/administration formats, the polypeptide is typically administered or transferred indirectly to the cells to be treated or to the tissue site of interest, including those described above (such as, e.g., skin cells, organ systems, lymphatic system, or blood cell system, etc.), by contacting or administering the polypeptide of the invention directly to one or more cells or population of cells from which treatment can be facilitated. For example, specific cells (e.g., tumor cells) within the body of the subject can be treated by contacting cells of the blood or lymphatic system, skin, or an organ with a sufficient amount of the polypeptide such that delivery of the polypeptide to the site of interest (e.g., tissue, organ, or cells of interest or blood or lymphatic system within the body) occurs and effective prophylactic or therapeutic treatment results. Such contact, administration, or transfer is typically made by using one or more of the routes or modes of administration described above.

In another aspect, the invention provides ex vivo methods in which one or more cells of interest or a population of cells of interest of the subject (e.g., tumor cells, tumor tissue sample, organ cells, blood cells, cells of the skin, lung, heart, muscle, brain, mucosae, liver, intestine, spleen, stomach, lymphatic system, cervix, vagina, prostate, mouth, tongue, etc.) are obtained or removed from the subject and transformed by contacting said one or more cells or population of cells with a polynucleotide construct comprising a target nucleic acid sequence of the invention or fragments thereof, that encodes a biologically active polypeptide of interest (e.g., a polypeptide of the invention) that is effective in prophylactically and/or therapeutically treating the disease, disorder, or other condition. The one or more cells or population of cells is contacted with a sufficient amount of the polynucleotide construct and a promoter controlling expression of said nucleic acid sequence such that uptake of the polynucleotide construct (and promoter) into the cell(s) occurs and sufficient expression of the target nucleic acid sequence of the invention results to produce an amount of the biologically active polypeptide effective to prophylactically and/or. therapeutically treat the disease, disorder, or condition. The polynucleotide construct may include a promoter sequence (e.g., CMV promoter sequence) that controls expression of the nucleic acid sequence of the invention and/or, if desired, one or more additional nucleotide sequences encoding at least one or more of another polypeptide of the invention, a cytokine, adjuvant, or co-stimulatory molecule, or other polypeptide of interest.

Following transfection, the transformed cells are returned, delivered, or transferred to the subject to the tissue site or system from which they were obtained or to another site (e.g., tumor cells, tumor tissue sample, organ cells, blood cells, cells of the skin, lung, heart, muscle, brain, mucosae, liver, intestine, spleen, stomach, lymphatic system, cervix, vagina, prostate, mouth, tongue, etc.) to be treated in the subject. If desired, the cells may be grafted onto a tissue, skin, organ, or body system of interest in the subject using standard and well-known grafting techniques or delivered to the blood or lymphatic system using standard delivery or transfusion techniques. Such delivery, administration, or transfer of transformed cells is typically made by using one or more of the routes or modes of administration described above. Expression of the target nucleic acid occurs naturally or can be induced (as described in greater detail below) and an amount of the encoded polypeptide is expressed sufficient and effective to treat the disease or condition at the site or tissue system (or at another site within the subject).

In another aspect, the invention provides in vivo methods in which one or more cells of interest or a population of cells of the subject (e.g., including those cells and cell(s) systems and subjects described above) are transformed in the body of the subject by contacting the cell(s) or population of cells with (or administering or transferring to the cell(s) or population of cells using one or more of the routes or modes of administration described above) a polynucleotide construct comprising a nucleic acid sequence of the invention that encodes a biologically active polypeptide of interest (e.g., a polypeptide of the invention) that is effective in prophylactically and/or therapeutically treating the disease, disorder, or other condition.

The polynucleotide construct can be directly administered or transferred to cell(s) suffering from the disease or disorder (e.g., by direct contact using one or more of the routes or modes of administration described above). Alternatively, the polynucleotide construct can be indirectly administered or transferred to cell(s) suffering from the disease or disorder by first directly contacting non-diseased cell(s) or other diseased cells using one or more of the routes or modes of administration described above with a sufficient amount of the polynucleotide construct comprising the nucleic acid sequence encoding the biologically active polypeptide, and a promoter controlling expression of the nucleic acid sequence, such that uptake of the polynucleotide construct (and promoter) into the cell(s) occurs and sufficient expression of the nucleic acid sequence of the invention results to produce an amount of the biologically active polypeptide effective to prophylactically and/or therapeutically treat the disease or disorder, and whereby the polynucleotide construct or the resulting expressed polypeptide is transferred naturally or automatically from the initial delivery site, system, tissue or organ of the subject's body to the diseased site, tissue, organ or system of the subject's body (e.g., via the blood or lymphatic system). Expression of the target nucleic acid occurs naturally or can be induced (as described in greater detail below) such that an amount of the encoded polypeptide expressed is sufficient and effective to treat the disease or condition at the site or tissue system. The polynucleotide construct may include a promoter sequence (e.g., CMV promoter sequence) that controls expression of the nucleic acid sequence and/or, if desired, one or more additional nucleotide sequences encoding at least one or more of another polypeptide of the invention, a cytokine, adjuvant, or co-stimulatory molecule, or other polypeptide of interest.

In each of the in vivo and ex vivo treatment methods as described above, a composition comprising an excipient and the polypeptide or nucleic acid of the invention can be administered or delivered. In one aspect, a composition comprising a pharmaceutically acceptable excipient and a polypeptide or nucleic acid of the invention is administered or delivered to the subject as described above in an amount effective to treat the disease or disorder.

In another aspect, in each in vivo and ex vivo treatment method described above, the amount of polynucleotide administered to the cell(s) or subject can be an amount sufficient that uptake of said polynucleotide into one or more cells of the subject occurs and sufficient expression of said nucleic acid sequence results to produce an amount of a biologically active polypeptide effective to enhance an immune response in the subject, including an immune response induced by an immunogen (e.g., antigen). In another aspect, for each such method, the amount of polypeptide administered to cell(s) or subject can be an amount sufficient to enhance an immune response in the subject, including that induced by an immunogen (e.g., antigen).

In yet another aspect, in each in vivo and ex vivo treatment method described above, the amount of polynucleotide administered to the cell(s) or subject can be an amount sufficient that uptake of said polynucleotide into one or more cells of the subject occurs and sufficient expression of said nucleic acid sequence results to produce an amount of a biologically active polypeptide effective to produce a tolerance or anergy response in the subject. In another aspect, for each such method, the amount of polypeptide administered to cell(s) or subject can be an amount sufficient to produce a tolerance or anergy response in the subject.

In yet another aspect, in an in vivo or in vivo treatment method in which a polynucleotide construct (or composition comprising a polynucleotide construct) is used to deliver a physiologically active polypeptide to a subject, the expression of the polynucleotide construct can be induced by using an inducible on- and off-gene expression system. Examples of such on- and off-gene expression systems include the TET-ON™ Gene Expression System and TET-OFF™ Gene Expression System (see, e.g., Clontech Catalog 2000, pg. 110–111 for a detailed description of each such system), respectively. Other controllable or inducible on- and off-gene expression systems are known to those of ordinary skill in the art. With such system, expression of the target nucleic acid of the polynucleotide construct can be regulated in a precise, reversible, and quantitative manner. Gene expression of the target nucleic acid can be induced, for example, after the stable transfected cells containing the polynucleotide construct comprising the target nucleic acid are delivered or transferred to or made to contact the tissue site, organ or system of interest. Such systems are of particular benefit in treatment methods and formats in which it is advantageous to delay or precisely control expression of the target nucleic acid (e.g., to allow time for completion of surgery and/or healing following surgery; to allow time for the polynucleotide construct comprising the target nucleic acid to reach the site, cells, system, or tissue to be treated; to allow time for the graft containing cells transformed with the construct to become incorporated into the tissue or organ onto or into which it has been spliced or attached, etc.).

Therapeutic compositions comprising one or more lipase homologue polypeptide of the invention are tested in appropriate in vitro and in vivo animal models of disease, to confirm efficacy, tissue metabolism, and to estimate dosages, according to methods well known in the art.

Administration is by any of the routes normally used for introducing a molecule into ultimate contact with blood or tissue cells. The lipase homologues of the invention are administered in any suitable manner, preferably with pharmaceutically acceptable carriers. Suitable methods of administering such lipase homologues in the context of the present invention to a patient are available, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

Polypeptide compositions can be administered by a number of routes including, but not limited to oral, intravenous, intraperitoneal, intramuscular, transdermal, subcutaneous, topical, sublingual, or rectal means. Lipase homologue polypeptide compositions can also be administered via liposomes. Such administration routes and appropriate formulations are generally known to those of skill in the art.

The lipase homologue, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of packaged nucleic acid can be presented in unit-dose or multi-dose sealed containers, such as ampules and vials.

Parenteral administration and intravenous administration are preferred methods of administration. In particular, the routes of administration already in use for lipase related therapeutic agents, along with formulations in current use, are preferred routes of administration and formulation for the lipase polypeptides of the invention.

Cells transduced with the lipase homologue nucleic acids as described above in the context of ex vivo therapy can also be administered intravenously or parenterally as described above. It will be appreciated that the delivery of cells to patients is routine, e.g., delivery of cells to the blood via intravenous or intraperitoneal administration.

The dose administered to a patient, in the context of the present invention is sufficient to effect a beneficial therapeutic response in the patient over time, depending on the application. The dose will be determined by the efficacy of the particular vector, or formulation, and the activity lipase homologue employed and the condition of the patient, as well as the body weight or surface area of the patient to be treated. The size of the dose also will be determined by the existence, nature, and extent of any adverse side-effects that accompany the administration of a particular vector, formulation, transduced cell type or the like in a particular patient.

In determining the effective amount of the vector, cell type, or formulation to be administered in the treatment or prophylaxis of a disease/condition/etc., the physician evaluates circulating plasma levels, vector/cell/formulation/lipase homologue toxicities, progression of the disease, and the production of anti-vector/lipase homologue antibodies.

The dose administered, e.g., to a 70 kilogram patient will be in the range equivalent to dosages of currently-used lipase related therapeutic proteins, and doses of vectors or cells which produce lipase homologue sequences are calculated to yield an equivalent amount of lipase homologue nucleic acid or expressed protein. The vectors of this invention can supplement the treatment of cancers and virally-mediated conditions by any known conventional therapy, including cytotoxic agents, nucleotide analogues (e.g., when used for treatment of HIV infection), biologic response modifiers, and the like.

For administration, lipase homologues and transduced cells of the present invention can be administered at a rate determined by the LD-50 of the lipase homologue, vector, or transduced cell type, and the side-effects of the lipase homologues, vector or cell type at various concentrations, as applied to the mass and overall health of the patient. Administration can be accomplished via single or divided doses.

For example, in the therapeutic and prophylactic treatment methods of the invention described herein, an effective amount of a lipase nucleic acid (e.g., DNA or mRNA) of the invention (e.g., nucleic acid dosage) will generally be in the range of, e.g., from about 0.05 microgram/kilogram (kg) to about 50 mg/kg, usually about 0.005–5 mg/kg. However, as will be understood, the effective amount of the nucleic acid (e.g., nucleic acid dosage) and/or polypeptide (e.g., polypeptide dosage) will vary in a manner apparent to those of ordinary skill in the art according to a number of factors, including the activity or potency of the polypeptide, the activity or potency of any nucleic acid construct (e.g., vector, promoter, expression system) to be administered, the disease or condition to be treated, and the subject to which or whom the nucleic acid is delivered.

For delivery of some polypeptides, e.g., by delivering nucleic acids encoding such polypeptides, for example, adequate levels of translation and/or expression are achieved with a nucleic acid dosage of, e.g., about 0.005 mg/kg to about 5 mg/kg. Dosages for other polypeptides (and nucleic acids encoding them) having a known biological activity can be readily determined by those of skill in the art according to the factors noted above. Dosages used for other known lipase related nucleic acids and polypeptides for particular diseases provide guidelines for determining dosage and treatment regimen for a nucleic acid or polypeptide of the invention. An effective amount of a lipase homologue polypeptide may be in the range of from about 1 microgram to about 1 milligram, and more typically from about 1 microgram to about 100 micrograms.

A composition for use in therapeutic and prophylactic treatment methods of the invention described herein may comprise, e.g., a concentration of a lipase homologue nucleic acid (e.g., DNA or mRNA) of the invention of from about 0.1 microgram/milliliter (ml) to about 20 mg/ml and a pharmaceutically acceptable carrier (e.g., aqueous carrier).

A composition for use in therapeutic and/or prophylactic treatment methods of the invention described herein may comprise, e.g., a concentration of a lipase homologue polypeptide of the invention in an amount as described above and herein and a pharmaceutically acceptable carrier (e.g., aqueous carrier).

For introduction of recombinant lipase nucleic acid transduced cells into a patient, blood samples are obtained prior to infusion, and saved for analysis. Between $1\times10^6$ and $1\times10^{12}$ transduced cells are infused intravenously over 60–200 minutes. Vital signs and oxygen saturation by pulse oximetry are closely monitored. Blood samples are obtained 5 minutes and 1 hour following infusion and saved for subsequent analysis. Leukopheresis, transduction and reinfusion are optionally repeated every 2 to 3 months for a total of 4 to 6 treatments in a one year period. After the first treatment, infusions can be performed on a outpatient basis at the discretion of the clinician. If the reinfusion is given as an outpatient, the participant is monitored for at least 4, and preferably 8 hours following the therapy. Transduced cells are prepared for reinfusion according to established methods. See, Abrahamsen et al. (1991) *J Clin Apheresis* 6:48–53; Carter et al. (1988) *J Clin Apheresis* 4:113–117; Aebersold et al. (1988), *J Immunol Methods* 112: 1–7; Muul et al. (1987) *J Immunol Methods* 101:171–181 and Carter et al. (1987) *Transfusion* 27:362–365. After a period of about 2–4 weeks in culture, the cells should number between $1\times10^6$ and $1\times10^{12}$. In this regard, the growth characteristics of cells vary from patient to patient and from cell type to cell type. About 72 hours prior to reinfusion of the transduced cells, an aliquot is taken for analysis of phenotype, and percentage of cells expressing the therapeutic agent.

If a patient undergoing infusion of a vector or transduced cell or protein formulation develops fevers, chills, or muscle aches, he/she receives the appropriate dose of aspirin, ibuprofen, acetaminophen or other pain/fever controlling drug. Patients who experience reactions to the infusion such as fever, muscle aches, and chills are premedicated 30 minutes prior to the future infusions with either aspirin, acetaminophen, or, e.g., diphenhydramine. Meperidine is used for more severe chills and muscle aches that do not quickly respond to antipyretics and antihistamines. Cell infusion is slowed or discontinued depending upon the severity of the reaction.

The current invention provides methods to therapeutically or prophylactically treat a gastrointestinal lipid related condition/disease/disorder by hydrolyzing a lipid through expressing in a target cell, or contacting a target cell, with an effective amount of polypeptide of the invention (or a fragment thereof) both wherein such target cell is in culture and wherein such target cell is within a subject to be treated. The current invention also provides a method of therapeutic or prophylactic treatment of a gastrointestinal lipid related condition/disease/disorder in a subject wherein the subject is administered a polypeptide of the invention in an amount effect to treat the condition/disease/disorder, including wherein the subject is a mammal or more specifically, a human, and wherein the polypeptide is administered in vivo, in vitro, or ex vivo (or a combination of such) to one or more cells of the subject. Such polypeptides include compositions of polypeptides comprising the polypeptide and a pharmaceutically acceptable excipient, which is administered to a subject in an amount effective to treat a gastrointestinal lipid related condition/disease/disorder (e.g., cystic fibrosis, celiac disease, Crohn's disease, indigestion, and obesity Another provision of the invention is a method of hydrolyzing a lipid to therapeutically or prophylactically treat a gastrointestinal lipid related condition/disease/disorder by introducing into a target cell a nucleic acid of the invention, or a fragment thereof, which is operably linked to a regulatory sequence active in a target cell such that introduction of the polynucleotide results in expression of the nucleic acid in an amount sufficient to hydrolyze the lipid. Such method optionally comprises directly administering the nucleic acid to a subject in an amount sufficient to introduce the nucleic acid into one or more cells and wherein the subject comprises a mammal (or a human) and wherein the nucleic acid optionally comprises a vector. Yet another provision of the invention is a method of therapeutically or prophylactically treating a gastrointestinal lipid related condition/disease/disorder by expressing in a target cell (or contacting a target cell with an effective amount of) a polynucleotide of the invention, or a fragment thereof, or of a polypeptide encoded thereby (or a fragment thereof). Such method can comprise wherein the target is in culture or wherein the target cell is within a subject. Additionally, the invention provides a method of therapeutically or prophylactically treating a gastrointestinal lipid related condition/disease/disorder in a subject by administering to the subject a polynucleotide of the invention (or a fragment thereof) or a polypeptide encoded thereby (or a fragment thereof) in an amount effective to treat the gastrointestinal lipid related condition/disease/disorder. Such method comprises optional embodiments wherein the subject is a mammal or a human and wherein the polynucleotide and/or polypeptide is administered in vivo, in vitro, or ex vivo (or a combination of such) to one or more cells of the subject and wherein a composition of the polynucleotide and/or polypeptide and a pharmaceutically acceptable excipient is administered to the subject in an amount effective to treat the gastrointestinal lipid related condition/disease/disorder (e.g., cystic fibrosis, celiac disease, Crohn's disease, indigestion, or obesity).

Integrated Systems

The present invention provides computers, computer readable media and integrated systems comprising character strings corresponding to the sequence information herein for the polypeptides and nucleic acids herein, including, e.g., those sequences listed herein and the various silent substitutions and conservative substitutions thereof.

Various methods and genetic algorithms (GAs) known in the art can be used to detect homology or similarity between different character strings, or can be used to perform other desirable functions such as to control output files, provide the basis for making presentations of information including the sequences and the like. Examples include BLAST, discussed supra. Extensive examples of the use of sequences in silico are found in, e.g., PCT/US00/01202 "METHODS FOR MAKING CHARACTER STRINGS, POLYNUCLEOTIDES AND POLYPEPTIDES HAVING DESIRED CHARACTERISTICS" by Selifonov et al., filed Jan. 18, 2000; PCT/US00/01230 "OLIGONUCLEOTIDE MEDIATED NUCLEIC ACID RECOMBINATION" by Crameri et al., filed Jan. 18, 2000; and PCT/US00/01138 "METHODS OF POPULATING DATA STRUCTURES FOR USE IN EVOLUTIONARY SIMULATIONS" by Selifonov and Stemmer, filed Jan. 18, 2000.

Thus, different types of homology and similarity of various stringency and length can be detected and recognized in the integrated systems herein. For example, many homology determination methods have been designed for comparative analysis of sequences of biopolymers, for spell-checking in word processing, and for data retrieval from various databases. With an understanding of double-helix pair-wise complement interactions among principal nucleobases in natural polynucleotides, models that simulate annealing of complementary homologous polynucleotide strings can also be used as a foundation of sequence alignment or other operations typically performed on the character strings corresponding to the sequences herein (e.g., word-processing manipulations, construction of figure comprising sequence or subsequence character strings, output tables, etc.). An example of a software package with GAs for calculating sequence similarity is BLAST, which can be adapted to the present invention by inputting character strings corresponding to the sequences herein.

Similarly, standard desktop applications such as word processing software (e.g., Microsoft WORD™ or Corel WORDPERFECT™) and database software (e.g., spreadsheet software such as Microsoft EXCEL™ Corel QUATTRO PRO™, or database programs such as Microsoft ACCESS™ or PARADOX™) can be adapted to the present invention by inputting a character string corresponding to the lipase homologues of the invention (either nucleic acids or proteins, or both). For example, the integrated systems can include the foregoing software having the appropriate character string information, e.g., used in conjunction with a user interface (e.g., a GUI in a standard operating system such as a Windows, Macintosh or LINUX system) to manipulate strings of characters. As noted, specialized alignment programs such as BLAST can also be incorporated into the systems of the invention for alignment of nucleic acids or proteins (or corresponding character strings).

Integrated systems for analysis in the present invention typically include a digital computer with GA software for aligning sequences, as well as data sets entered into the software system comprising any of the sequences herein. The computer can be, e.g., a PC (Intel x86 or Pentium chip-compatible DOSE, OS2™ WINDOWS™ WINDOWS NT™, WINDOWS95™, WINDOWS98™ LINUX based machine, a MACINTOSH™, Power PC, or a UNIX based (e.g., SUN™ work station) machine) or other commercially common computer which is known to one of skill. Software for aligning or otherwise manipulating sequences is available, or can easily be constructed by one of skill using a standard programming language such as Visualbasic, Fortran, Basic, Java, or the like.

Any controller or computer optionally includes a monitor which is often a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of, e.g., fluid direction and transport controllers to carry out the desired operation.

The software can also include output elements for controlling nucleic acid synthesis (e.g., based upon a sequence or an alignment of a sequences herein) or other operations which occur downstream from an alignment or other operation performed using a character string corresponding to a sequence herein.

In one embodiment, the invention provides an integrated system comprising a computer or computer readable medium comprising a database having one or more sequence records. Each of the sequence records comprises one or more character strings corresponding to a nucleic acid or polypeptide or protein sequence selected from SEQ ID NO: 1 to SEQ ID NO: 108. The integrated system further comprises a user input interface allowing a user to selectively view the one or more sequence records. In one such integrated system, the computer or computer readable medium comprises an alignment instruction set that aligns the character strings with one or more additional character strings corresponding to a nucleic acid or polypeptide or protein sequence.

One such integrated system includes an instruction set that comprises at least one of the following: a local sequence comparison or a local homology comparison determination, a sequence alignment or a homology alignment determination, a sequence identity or similarity search or a search for similarity determination, a sequence identity or similarity determination, a structural similarity search, a structure determination, a nucleic acid motif determination, an amino acid motif determination, a hypothetical translation, a determination of a restriction map, a sequence recombination and a BLAST determination. In some embodiments, the system further comprises a readable output element that displays an alignment produced by the alignment instruction set. In another embodiment, the computer or computer readable medium further comprises an instruction set that translates at least one nucleic acid sequence which comprises a sequence selected from SEQ ID NO: 1 to SEQ ID NO: 54 into an amino acid sequence. The instruction set may select the nucleic acid by applying a codon usage instruction set or an instruction set which determines sequence identity to a test nucleic acid sequence.

Methods of using a computer system to present information pertaining to at least one of a plurality of sequence records stored in a database are also provided. Each of the sequence records comprises at least one character string corresponding to SEQ ID NO: 1 to SEQ ID NO: 108. The method comprises determining at least one character string corresponding to one or more of SEQ ID NO: 1 to SEQ ID NO: 108 or a subsequence thereof; determining which of the at least one character string of the list are selected by a user; and displaying each of the selected character strings, or aligning each of the selected character strings with an additional character string. The method may further comprise displaying an alignment of each of the selected character strings with an additional character string and/or displaying the list.

The current invention provides a database of one or more character strings corresponding to polynucleotide sequences selected from SEQ ID NO: 1 to SEQ ID NO: 54 or a polypeptide sequence selected from SEQ ID NO: 55 to SEQ ID NO: 108. Such database optionally comprises wherein one or more character string is recorded in a computer readable medium (e.g., that resides internal or external to a computer). The invention also provides a method for manipulating a sequence record in a computer system by reading a character string corresponding (optionally selected by a user or wherein the user selects the character string from a database or inputs the character string into the computer system) to a polynucleotide sequence selected from SEQ ID NO: 1 to SEQ ID NO: 54 or a polypeptide sequence selected from SEQ ID NO: 55 to SEQ ID NO: 108 (or a subsequence thereof), performing an operation on the character string, and returning a result of the operation (optionally comprising transmitting the selected character string to an output device). The operations performed in such computer system optionally comprise any of the following: a local sequence comparison, a sequence alignment, a sequence identity or similarity search, a structural similarity search, a sequence identity or similarity determination, a structure determination, a nucleic acid motif determination, an amino acid motif determination, a hypothetical translation, a determination of a restriction map, a sequence recombination, or a BLAST determination. Such method can comprise aligning the selected character string with one or more additional character strings corresponding to a polynucleotide or polypeptide sequence; translating one or more character strings from SEQ ID NO: 1 to SEQ ID NO: 54 into a character string corresponding to an amino acid sequence or translating a character string selected from SEQ ID NO: 55 to SEQ ID NO: 108, into a character string corresponding to a polynucleotide sequence; determining sequence identity or similarity between the selected character string and one or more additional character strings by evaluating codon usage (optionally determining optimal codon usage); and obtaining the result of the operation on a user output device (e.g., optionally selected from a display monitor, a printer, and an audio output). The method of the invention for manipulating a sequence record in a computer system also comprises wherein the operation transmits the character string to a device (e.g., an oligonucleotide synthesizer or peptide synthesizer) capable of producing a physical embodiment of the character string (e.g., a physical embodiment comprising a nucleic acid or polypeptide or peptide corresponding to a character string or a sub-portion thereof)

Kits

In an additional aspect, the present invention provides kits embodying the methods, composition, systems and apparatus herein. Kits of the invention optionally comprise one or more of the following: (1) an apparatus, system, system component or apparatus component as described herein; (2) instructions for practicing the methods described herein, and/or for operating the apparatus or apparatus components herein and/or for using the compositions herein, (3) one or more lipase composition or component, (4) a container for holding components or compositions, and, (5) packaging materials.

In a further aspect, the present invention provides for the use of any apparatus, apparatus component, composition or kit herein, for the practice of any method or assay herein, and/or for the use of any apparatus or kit to practice any assay or method herein.

EXAMPLES

Example I

Detection of Lipase Secreting Bacteria

As described above, the nucleic acid and amino acid sequence of SEQ ID NO: 1 through SEQ ID NO: 20 and SEQ ID NO: 55 through SEQ ID NO: 74 were discovered and isolated in a number of *Bacillus* species (both species-typed and un-typed species). In order to choose *Bacillus* cultures that expressed lipase activity, two types of plate assays were preformed.

The first type of plate assay comprised a rhodane B assay (see, e.g., Kouker, G. et al., Specific and sensitive plate assay for bacterial lipases, *Appl Environ Microbiol*, (1987) 53:211–213. The assay entails preparing TGY media plates, onto which various *Bacillus* colonies were patched. The TGY media plates were prepared by mixing 5 g tryptone, 5 g yeast extract, 5 g dextrose, and 1 g K$_2$HPO$_4$ per liter of media. The media was autoclaved and cooled to approximately 60° C. before 30 milliliters of filtered sterilized soybean oil and 2 milliliters of filtered sterilized rhodamine B solution (0.1%) was vigorously mixed in. The media was then plated into petri dishes.

If the *Bacillus* colonies that were patched onto the TGY plates secreted active lipase enzymes, such enzymes would act upon the soybean oil in the plates, thus releasing free fatty acids. The free fatty acids would then react with the rhodamine B to create a visible fluorescent orange compound. Thus, *Bacillus* colonies that expressed active lipase could be visually detected (after 24–48 hours) by the fluorescent orange halo around the colonies.

The second type of plate based assay used to detect the presence of lipase activity was used to check for lipase activity of *E. coli* bacterial colonies. *E. coli* cultures were transformed with expression vectors containing either the newly discover *Bacillus* lipase variants (e.g., as detected above) or with newly created (i.e., recombined) lipase homologue variants. The transformed *E. coli* colonies were grown on plates containing LB media supplemented with tributyrin at a final concentration of 1%. Colonies expressing an active lipase, secreted such lipase into the surrounding media (which was hazy due to the tributyrin), thus, degrading the tributyrin and producing a clear media ring around the lipase active colonies.

Example II

Screening Lipase Homologues for Enantioselectivity

A. Substrate Synthesis

All materials were purchased from Sigma or Aldrich unless noted. Neryl butyrate was prepared by from nerol and butyryl chloride in methylene chloride/pyridine. Geranyl deuterobutyrate was prepared from geraniol and deuterobutyric acid (Isotec) using DCC coupling in methylene chloride. Both compounds were purified by flash chromatography (ether/hexanes) and gave satisfactory analysis by mass spectrometry and NMR.

B. Library Pre-Selection and Enzyme Preparation

Transformants were robotically picked to 386-well microtiter plates containing 70 µL growth medium (2×YT, 0.5% glucose to suppress induction, 30 µg/ml chloramphenicol) and grown 12–20 hours at 37° C., 300-rpm shaking speed in a Kuhner incubator. The cultures were then gridded via a Q-bot robot (Genetix, UK) to inducing agar (2×YT, 1.5% agar, 1 mM IPTG, 30 µg/ml chloramphenicol) in 22 cm×22 cm bioassay trays using 0.25 mm pins, and incubated at 30° C. for 16–20 hours. The colonies were then overlaid with substrate (1% neryl butyrate or geranyl butyrate) in 150 mL of 1.5% agar containing 2 mM Hepes, pH 7.4, and 1% Triton X-100 that had been heated to 45° C. The reaction was allowed to proceed at room temperature for 5 to 20 hours, until clearing zones around active colonies were visible. The trays were imaged against a black background with an Alpha Innotech Fluorchem imaging system, and the images were analyzed using Phoretix Array image analysis software. Active clones were identified based upon the intensity of the corresponding clearing zone, and transferred (5 µL) from the master 384-well plates to rows 1–7 of 96 well microtiter plates containing 200 µL growth medium. The final row of the 96-well plate was spiked with 5 µL cultures transformed with a plasmid that did not contain an active lipase as a negative background control. The cultures were grown overnight at 37° C. at 200–230 rpm shaking speed in a Kuhner incubator. The following day, 10 µL of each culture was dispensed into 200 µL inducing media (2×YT, 1 mM IPTG, 30 µg/ml chloramphenicol) in a second 96-well plate. The cultures were induced for 16–20 hours at 30° C., 200 rpm in a Kuhner incubator. The cells were then pelleted by centrifugation and the lipase-containing supernatant assayed as described below.

C. Reactions, Mass Spectrometrical Analysis, and Results

Ten μL of cell supernatant was added to 90 μL reaction mix that contained 2.78 mM neryl butyrate, 2.78 mM geraniol deuterobutyrate, and 1 mM morpholine acetate, pH 7.4, in a 96-well plate. The plates were sealed with plastic tape and shaken on a MicroMix (Diagnostics Products Corporation) set to mix at amplitude 4, form 20. After 8 hours, 10 μL of this reaction mix was added to 90 μL 40:50 $H_2O$:MeOH. The final row of the plate was spiked with known concentrations of butyrate and deuterobutyrate (0–50 uM) to provide calibration curves. The plates were sealed (MicroLiter Analytical polypropylene & aluminum foil film) and analyzed by LC/MS for butyrate and deuterobutyrate concentrations. Clones showing desired specificity were then re-confirmed by GC/MS.

While the foregoing invention has been described in some detail for purposes of clarity and understanding, it will be clear to one skilled in the art from a reading of this disclosure that various changes in form and detail can be made without departing from the true scope of the invention. For example, all the techniques, methods, compositions, apparatus and systems described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. An isolated or recombinant polypeptide having lipase activity and comprising a sequence having at least 98% amino acid sequence identity to the mature region of SEQ ID:55.

2. The isolated or recombinant polypeptide of claim 1, wherein said polypeptide comprises a sequence selected from SEQ ID NO: 55 or the mature region thereof.

3. The isolated or recombinant polypeptide of claim 2, wherein the polypeptide comprises the amino acid sequence of SEQ ID NO: 55.

4. The isolated or recombinant polypeptide of claim 1, wherein the polypeptide exhibits lipase activity with respect to tributyrin.

5. The isolated or recombinant polypeptide of claim 1, wherein the polypeptide exhibits lipase activity with respect to tributyrin in N,N-dimethylformamide (DMF).

6. The isolated or recombinant polypeptide of claim 1, wherein the polypeptide exhibits lipase activity with respect to neryl-butyrate.

7. The isolated or recombinant polypeptide of claim 1, wherein the polypeptide exhibits lipase activity with respect to geranyl-butyrate.

8. The isolated or recombinant polypeptide of claim 1, wherein the polypeptide exhibits lipase activity with respect to pentadecanolide.

9. The isolated or recombinant polypeptide of claim 1, further comprising a leader sequence.

10. The isolated or recombinant polypeptide of claim 1, wherein the polypeptide comprises a secretion signal or a localization signal.

11. The isolated or recombinant polypeptide of claim 1, wherein the polypeptide comprises an epitope tag.

12. The isolated or recombinant polypeptide of claim 1, wherein the polypeptide comprises a fusion protein comprising one or more additional amino acid sequences.

13. The isolated or recombinant polypeptide of claim 1, further comprising a polypeptide purification domain.

14. The isolated or recombinant polypeptide of claim 13, wherein the polypeptide purification domain is selected from the group consisting of: an epitope tag, a polyhistidine sequence, and a glutathione S-transferase (GST).

15. The isolated or recombinant polypeptide of claim 1, further comprising a methionine residue at the N-terminus.

16. The isolated or recombinant polypeptide of claim 1, wherein the polypeptide further comprises a modified amino acid selected from the group consisting of: a glycosylated amino acid, a PEGylated amino acid, a farnesylated amino acid, an acetylated amino acid, a biotinylated amino acid, and an amino acid conjugated to a lipid moiety.

17. A composition comprising the isolated or recombinant polypeptide of claim 1 and a pharmaceutically acceptable excipient.

18. A composition comprising the isolated or recombinant polypeptide of claim 1 and a surfactant.

19. The composition of claim 18, further comprising one or more of: a builder, a polymer, a bleach system, a structurant, a pH adjuster, a humectant, or a neutral inorganic salt.

20. The isolated or recombinant polypeptide of claim 1, wherein the polypeptide comprises one or more amino acid residues selected from the group consisting of Lys at position 1, Thr at position 14, Ser at position 17, Arg at position 22, Glu at position 26, Pro at position 31, Gly at position 33, Glu at position 34, Pro at position 35, Pro or Thr at position 37, Ser or Lys at position 41, Gly at position 42, Arg or Glu at position 43, Ala at position 61, Tyr at position 75, Gly at position 96, Ser at position 97, Thr at position 104, Ser at position 107, Ala at position 125, Gly at position 129, Val at position 134, Cys at position 138, Lys at position 141, Lys at position 146, Thr at position 156, Met at position 160, Arg at position 166, and His at position 177, wherein positions are equivalent amino acid positions with respect to SEQ ID NO: 75.

21. The isolated or recombinant polypeptide of claim 1, wherein the polypeptide comprises one or more amino acid residues selected from the group consisting of Arg at position 22, Gly at position 33, Ser or Lys at position 41, Arg at position 43, Ser at position 107, Lys at position 141, Lys at position 146, Met at position 160, and His at position 177.

22. The isolated or recominant polypeptide of claim 21, wherein the polypeptide comprises one or more amino acid residues selected from the group consisting of Arg at position 43 and Ser at position 107.

23. The isolated or recombinant polypeptide of claim 1, wherein the polypeptide comprises one or more amino acid selected from the group consisting of Ser at position 17, Arg at position 22, Pro at position 31, Gly at position 33, Ser or Lys at position 41, Lys at position 141, Lys at position 146, Met at position 160, Arg at position 166, and His at position 177.

24. The isolated or recombinant polypeptide of claim 23, wherein the polypeptide comprises one or more amino acid residues selected from the group consising of Ser at position 17, Pro at position 31, and Arg at position 166.

25. An isolated or recombinant polypeptide exhibiting lipase activity, wherein the polypeptide is encoded by a polynucleotide that hybridizes under stringent conditions over substantially the entire length of the mature coding region of SEQ ID NO: 1, or complement thereof, wherein stringent hybridization conditions are 42° C. overnight in 50% formamide with 1 mg heparin and a 0.2×SSC wash at 65° C. for 15 minutes, and wherein the polypeptide comprises one or more amino acid residues selected from the group consisting of Lys at position 1, Thr at position 14, Ser at position 17, Arg at position 22, Glu at position 26, Pro at position 31, Gly at position 33, Glu at position 34, Pro at position 35, Pro or Thr at position 37, Ser or Lys at position 41, Gly at position 42, Arg or Glu at position 43, Ala at position 61, Tyr at position 75, Gly at position 96, Ser at position 97, Thr at position 104, Ser at position 107, Ala at position 125, Gly at position 129, Val at position 134, Cys at position 138, Lys at position 141, Lys at position 146, Thr at position 156, Met at position 160, Arg at position 166, and His at position 177, wherein the positions are equivalent amino acid positions with respect to SEQ ID NO: 75.

26. The isolated or recombinant polypeptide of claim 25, wherein the polypeptide comprises one or more amino acid residues selected from the group consisting of Arg at position 22, Gly at position 33, Ser or Lys at position 41, Arg at position 43, Ser at position 107, Lys at position 141, Lys at position 146, Met at position 160, and His at position 177.

27. The isolated or recombinant polypeptide of claim 26, wherein the polypeptide comprise or more amino acid residues selected from the group consisting of Arg at position 43 and Ser at position 107.

28. The isolated or recombinant polypeptide of claim 25, wherein the polypeptide comprises one or more amino acid residues selected from the group consisting of Ser at position 17, Arg at position 22, Pro at position 31, Gly at position 33, Ser or Lys at position 41, Lys at position 141, Lys at position 146, Met at position 160, Arg at position 166, and His at position 177.

29. The isolated or recombinant polypeptide of claim 28, wherein the polypeptide comprises one or more amino acid residues selected from the group consisting of Ser at position 17, Pro at position 31, and Arg at position 166.

30. A composition comprising the isolated or recombinant polypeptide of claim 25 and a surfactant.

31. The composition of claim 30, further comprising one or more of: a builder, a polymer, a bleach system, a structurant, a pH adjuster, a humectant, or a neutral inorganic salt.

* * * * *